(12) United States Patent
Åsberg et al.

(10) Patent No.: US 9,359,311 B2
(45) Date of Patent: *Jun. 7, 2016

(54) SUBSTITUTED AROMATIC OLIGOMERS

(75) Inventors: Peter Åsberg, Stockholm (SE); Kristin Hammer, Sollentuna (SE); Johan Olsson, Stockholm (SE); Martin Henriksson, Solna (SE)

(73) Assignee: NEUROSCIOS GMBH, St. Radegund/Graz (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/232,442

(22) PCT Filed: Jul. 13, 2012

(86) PCT No.: PCT/SE2012/050837
§ 371 (c)(1),
(2), (4) Date: Jan. 13, 2014

(87) PCT Pub. No.: WO2013/009259
PCT Pub. Date: Jan. 17, 2013

(65) Prior Publication Data
US 2014/0135322 A1   May 15, 2014

(30) Foreign Application Priority Data

Jul. 14, 2011 (SE) ...................... 1150682

(51) Int. Cl.
| C07D 261/20 | (2006.01) |
| C07D 235/20 | (2006.01) |
| C07D 333/18 | (2006.01) |
| C07D 409/10 | (2006.01) |
| C07D 333/60 | (2006.01) |
| C07D 409/14 | (2006.01) |
| C07D 409/04 | (2006.01) |
| C07D 333/24 | (2006.01) |
| C07D 413/10 | (2006.01) |
| C07D 417/14 | (2006.01) |
| C07D 413/14 | (2006.01) |
| C07D 403/10 | (2006.01) |

(52) U.S. Cl.
CPC ............ *C07D 261/20* (2013.01); *C07D 235/20* (2013.01); *C07D 333/18* (2013.01); *C07D 333/24* (2013.01); *C07D 333/60* (2013.01); *C07D 403/10* (2013.01); *C07D 409/04* (2013.01); *C07D 409/10* (2013.01); *C07D 409/14* (2013.01); *C07D 413/10* (2013.01); *C07D 413/14* (2013.01); *C07D 417/14* (2013.01)

(58) Field of Classification Search
CPC .. C07D 413/14; C07D 333/18; C07D 333/24; C07D 261/20; C07D 235/20; C07D 409/10; C07D 333/60; C07D 403/10; C07D 409/04; C07D 409/14; C07D 413/10; C07D 417/14

USPC ........... 549/59; 514/232.2, 444, 422; 546/280
See application file for complete search history.

(56) References Cited

U.S. PATENT DOCUMENTS 8,828,992 B2 * 9/2014 Park et al. .................... 514/218

FOREIGN PATENT DOCUMENTS

| WO | WO-02/44378 | 6/2002 |
| WO | WO-2004/035570 | 4/2004 |
| WO | WO-2010/044743 | 4/2010 |
| WO | WO 2010044743 A1 * | 4/2010 |
| WO | WO-2011/102789 | 8/2011 |

OTHER PUBLICATIONS

Choi, S.H., "A three-dimensional human neural cell culture model of Alzheimer's disease," 2014 Nature 515: 274-292.*
Braidy, N., "Drug Treatments for Alzheimer's Disease: Hopes and Challenges," 2014, Handbook of Neurotoxicity, Springer Science + Business 1173-1190.*
Schaeffer, E. L., "Insights into Alzheimer disease pathogenesis from studies in transgenic animal models." Clinics 66 (2011): 45-54.*
Mangialasche, F., "Alzheimer's disease: clinical trials and drug development." The Lancet Neurology 9.7 (2010): 702-716.*
Gong, B.,"Persistent improvement in synaptic and cognitive functions in an Alzheimer mouse model after rolipram treatment." The Journal of clinical investigation 114.11 (2004): 1624-1634.*
Hammarstrom, P., "Luminescent conjugated oligothiophenes: optical dyes for revealing pathological hallmarks of protein misfolding diseases." SPIE Photonic Devices+ Applications. International Society for Optics and Photonics, 2010.*
Sakamoto, K., "Selective photoinduced energy transfer from a thiophene rotaxane to acceptor." Organic letters 13.4 (2011): 672-675.*
Henze, O., "Chiral amphiphilic self-assembled $\alpha$, $\alpha'$-linked quinque-, sexi-, septithiophenes: Synthesis, stability and odd-even effects." Journal of the American Chemical Society 128.17 (2006): 5923-5929.*

(Continued)

*Primary Examiner* — Samantha Shterengarts
*Assistant Examiner* — Matt Mauro
(74) *Attorney, Agent, or Firm* — Foley & Lardner LLP

(57) ABSTRACT

The present invention relates to novel chemical compounds formula (I) $(C)_n$—B-$(A)_m$-B—$(C)_n$ (I) wherein m is 0 or 1, and n is independently 0, 1, 2 or 3, A, each B and each C are independently selected from phenylene and five- and six-membered heteroaromatic rings, and for a terminal ring B or C also from bicyclic heteroaromatic fused rings having seven to ten ring members, wherein the bond between at least two of the rings A to C may be replaced by a carbonyl group (—CO—), wherein at least two of the rings A to C are substituted with one or two groups R, and wherein each ring A to C further optionally is substituted with one or two groups $R^1$. The compounds are useful in therapy, especially therapy of a mammal suffering from a disease involving misfolded or aggregated forms of proteins.

8 Claims, 4 Drawing Sheets

(56) References Cited

OTHER PUBLICATIONS

Zotti, G., "Electrochemical, magnetic, and electrical properties of α, ω-capped sexithiophene films. 1. Neutral-polaron and polaron-bipolaron conductivities." Chemistry of materials 17.25 (2005): 6492-6502.*

Casanovas, J., "Structural and electronic effects induced by carboxylic acid substitution in isomeric 2, 2'-bithiophenes and oligothiophenes: A computational study." Polymer 46.22 (2005): 9452-9460.*

"Desmin transgenic mice exhibit morphological features of amyloidosis," Therese Klingstedt, Linkoping University (Sweden) presentation Sep. 1, 2010, 14 pages.

Aslund A et al., "Novel Pentameric Thiophene Derivatives for in Vitro and in Vivo Optical Imaging of a Plethora of Protein Aggregates in Cerebral Amyloidoses." ACS Chemical Biology, 2009, vol. 4, No. 8, pp. 673-684.

Aslund a., et al., "Studies of Luminescent Conjugated Polythiophene Derivatives: Enhanced Spectral Discrimination of Protein Conformational States." Bioconjugate Chemistry, Nov. 1, 2007, vol. 18, No. 6, pp. 1860-1868.

Berg, I., et al., "Efficient imaging of amyloid deposits in *Drosophila* models of human amyloiodoses." Nature Protocols, 2010, vol. 5, pp. 935-944.

Bertoncini, C.W. and Soledad, M.C, "Small Molecule Fluorescent Probes for the Detection of Amyloid Self-Assembly in Vitor and in Vivo." Current Protein and Peptide Science, 2011, vol. 11, pp. 206-220.

Fazio, A., et al., Synthesis of 3,4-bis[(methoxycarbonyl)methyl]thiophene and bis- ter- and pentathiophenes with alternating 3,4-bis[(methoxycarbonyl)methyl]-substituted rings. Tetrahedron, Jan. 8, 1999, vol. 5, No. 2 pp. 485-502.

Hammarstrom, P., et al., "A Fluorescent Pentameric Thiophene Derivative Detects in Vitor-Formed Prefibrillar Protein Aggregates." Biochemistry, Aug. 17, 2010, vol. 49, No. 32, pp. 6838-6845.

International Search Report and Written Opinion on PCT/SE2012/050837, mailed Oct. 10, 2012.

Klingstedt, T., et al.,j "Synthesis of a library of oligothiophenes and their utilization as fluorescent ligands for spectral assignment of protein aggregates." Organic & Biomolecular Chemistry, 2011, vol. 9, No. 24, pp. 8356-8370.

Nilsson, K. P.R., et al., "Imaging Distinct Conformational States of Amyloiod-beta Fibrils in Alzheimer's Disease Using Novel Luminescent Probes." ACS Chemical Biology, Aug. 1, 2007, vol. 2, No. 8, pp. 553-560.

Nilsson, K., et al., Structural Typing of Systemic Amyloidoses ;by Luminescent-Conjugated Polymer Spectrscopy. The American Journal of Pathology, 2010, vol. 176, No. 2, pp. 563-574.

Schroth, W. et al., "1,2-Dithiines and precursors, XVI: Synthesis, structure and reactivity of non-anellated 1,2 dithiines." Tetrahedron, Sep. 23, 1996, vol. 52, No. 39, pp. 12677-12698.

Wigenius, J. et al. "Interactions Between a Luminescent Conjugated Oligoelectrolyte and Insulin During Early Phases of Amyloid Formation." Macromolecular Bioscience, 2011, vol. 11, No. 8, pp. 1120-1127.

* cited by examiner

SUBSTITUTED AROMATIC OLIGOMERS

CROSS REFERENCE TO RELATED APPLICATIONS

This application is a National Stage Application of PCT/SE2012/050837, filed Jul. 13, 2012, which claims priority to Swedish Application 11/50682-1, filed Jul. 14, 2011, both of which are incorporated herein by reference.

FIELD OF THE INVENTION

The present invention relates to novel chemical compounds useful in therapy, especially therapy of a mammal suffering from a disease involving misfolded or aggregated forms of proteins.

BACKGROUND OF THE INVENTION

Natural biopolymers, such as proteins, frequently have ordered conformations, such as alpha-helix and beta-sheets, which contribute to the three-dimensional ordered structure and the specific function of the biopolymer. The structure of a protein is essential for the protein's function; it has been shown by many scientists that an unfolded protein may not be functional. More important, in the last few years there is increasing awareness of the danger of protein misfolding and misassembly into for example amyloid and other pathological forms. Misfolding can change a protein from something that is useful into nonfunctional, harmful or even toxic. Human health relies on properly folded protein, and in vivo deposition of amyloid fibrils is associated with many diseases related to protein conformation, including Alzheimer's disease (AD), Huntington's disease, (HD), Amyotrophic Lateral Sclerosis (ALS), systemic amyloidoses, and the prion diseases. The prion diseases, i.e. transmissible spongiform encephalopathy (TSE), in animals [e.g. bovine spongiform encephalopathy (BSE), Scrapie and chronic wasting disease (CWD)] and in humans [Creutzfeldt Jakob disease (CJD), Gerstmann-Strä ussler-Scheinker disease (GSS), Kuru] are associated with the conformational conversion of the normal cellular prion protein, (PrP$^C$), to an infectious pathogenic disease-associated isoform denoted PrP$^{Sc}$. Proteins frequently alter their conformation due to different external stimuli and the importance of conformational changes of proteins leading to pathogenic states has been well documented. Especially under conditions that destabilize the native state, proteins can aggregate into characteristic fibrillar assemblies, known as amyloid fibrils. These beta-sheet rich protein assemblies have distinctively different conformations compared to that of the native state. The misfolded prion protein is even self-propagating (infectious), a property which is entirely encoded within the misfolded conformation.

Chronic human diseases seriously affect the healthcare system. It is well recognized that rapid and accurate diagnostic tools are necessary to afford early intervention and therapy. Only symptomatic therapy is available, like in Alzheimer's disease for example, and these have limited therapeutic efficacy. Presently there are no antemortem molecular diagnostic tests of Alzheimer's disease or transmissible spongiform encephalopathies (TSEs), and the clinical diagnostics that are performed require that disease progression is severe. Further, there are no efficient treatments available yet, and immunotherapy in for example Alzheimer's disease holds great promise. The lack of reliable methods to capture misfolded proteins, monitoring both treatment and disease progression is however a severe shortcoming in treatment of most protein misfolding related diseases.

The affinity between misfolded proteins in amyloid plaques, amyloid fibrils and amyloid like fibrils, and conjugated molecules compromised of repeating units of thiophene, ethylenedioxythiophene (EDOT), benzothiadizole, fluorene, and phenyl in homo and hetero oligomers and polymers with ionic or polar sidechains has been demonstrated in several in vitro studies. The interaction between amyloid like fibrils of insulin and anionic, zwitterionic and cationic poly- and oligo thiophenes was shown by [WO2005/109005]. Several of the mentioned oligomers and polymers have been shown to bind to amyloid, aβ and PrP deposits in histological sections [WO2007/091973]. Thiophene compounds have been suggested in therapy [WO2010/044743]. An anionic, more specifically an alkoxysulfonate derivative, polymer of EDOT showed high affinity for amyloid like fibrils [Hamedi, M. et al.;. Nano Lett.; (2008); 8,1736-1740]. Moreover a substituted polyfluorene and an alternating polyfluorene with a polyethylene oxide were demonstrated to strongly associate with amyloid like fibrils in vitro [Tanaka, H. et al.; Nano Lett.; (2008) 8,2858-2861].

SUMMARY OF THE INVENTION

In a first aspect, the present invention relates to novel compounds of formula (I)

$$(C)_n-B-(A)_m-B-(C)_n \qquad (I)$$

wherein
m is 0 or 1, and n is independently 0, 1, 2 or 3, preferably 0, 1 or 2,

A, each B and each C are independently selected from phenylene and five- and six-membered heteroaromatic rings, and for a terminal ring B or C also from bicyclic heteroaromatic fused rings having seven to ten ring members, wherein the bond between at least two of the rings A to C may be replaced by —CO—, wherein at least two of the rings A to C are substituted with one or two groups R, and wherein each ring A to C further optionally is substituted with one or two groups R$^1$, wherein each group R is independently selected from hydroxy, hydroxyalkyl, hydroxyalkoxy, hydroxyalkoxyalkyl, hydroxypolyoxyalkylene, alkoxy, alkoxyalkyl, polyoxyalkylene, carboxy, carboxyalkyl, carboxyalkoxy, carboxyalkoxyalkyl, carboxypolyoxyalkylene, alkoxycarbonyl, alkoxycarbonylalkyl, alkoxycarbonylalkoxy, alkoxycarbonylalkoxyalkyl, alkoxycarbonylpolyoxyalkylene, amino, alkylamino, dialkylamino, aminoalkyl, alkylaminoalkyl, dialkylaminoalkyl, aminoalkoxy, alkylaminoalkoxy, dialkylaminoalkoxy, aminopolyoxyalkylene, alkylaminopolyoxyalkylene, dialkylaminopolyoxyalkylene, aminoalkoxyalkyl, alkylaminoalkoxyalkyl, dialkylaminoalkoxyalkyl, (amino)(carboxy)alkyl, (alkylamino)(carboxy)alkyl, (dialkylamino)(carboxy)alkyl, (amino)(carboxy)alkoxy, (alkylamino)(carboxy)alkoxy, (dialkylamino)(carboxy)alkoxy, (amino)(carboxy)alkoxyalkyl, (alkylamino)(carboxy)alkoxyalkyl, (dialkylamino)(carboxy)alkoxyalkyl, (amino)(carboxy)polyoxyalkylene, (alkylamino)(carboxy)polyoxyalkylene, (dialkylamino)(carboxy)polyoxyalkylene, (alkoxycarbonyl)(amino)alkyl, (alkoxycarbonyl)(alkylamino)alkyl, (alkoxycarbonyl)(dialkylamino)alkyl, (alkoxycarbonyl)(amino)alkoxy, (alkoxycarbonyl)(alkylamino)alkoxy, (alkoxycarbonyl)(dialkylamino)alkoxy, (alkoxycarbonyl)(amino)alkoxyalkyl, (alkoxycarbonyl)(alkylamino)alkoxyalkyl, (alkoxycarbonyl)(dialkylamino)alkoxyalkyl, (alkoxycarbonyl)(amino)polyoxyalkylene, (alkoxycarbonyl)

(alkylamino)polyoxyalkylene, (alkoxycarbonyl)(dialkylamino)polyoxyalkylene, acylamino, acylaminoalkyl, acylaminoalkoxy, acylaminoalkoxyalkyl, acylaminopolyoxyalkylene, acylalkylamino, acylalkylaminoalkyl, acylalkylaminoalkoxy, acylalkylaminoalkoxyalkyl, acylalkylaminopolyoxyalkylene, hydrazinocarbonyl, hydrazinocarbonylalkyl, hydrazinocarbonylalkoxy, hydrazinocarbonylalkoxyalkyl, hydrazinocarbonylpolyoxyalkylene, nitro, nitroalkyl, nitroalkoxy, nitroalkoxyalkyl, nitropolyoxyalkylene, cyano, cyanoalkyl, cyanoalkoxy, cyanoalkoxyalkyl, cyanopolyoxyalkylene, sulfo, sulfoalkyl, sulfoalkoxy, sulfoalkoxyalkyl, sulfopolyoxyalkylene, alkylsulphonyl, alkylsulphinyl, alkylaminosulphonyl, acyloxyalkyl, carboxyalkenyl, pyrrolidinecarbonyl, morpholinoalkyl, cycloalkylcarbamoyl, trifluoroxy, carbamoyl, hydroxyalkylaminoalkyl, aminoalkylaminoalkyl, carboxyalkylaminoalkyl, piperidinealkyl, piperazinealkyl, and wherein each group $R^1$ is independently selected from halogen, alkyl, alkenyl, alkynyl, trifluoro, with the provisos that:

(i) when m=0, then one n is other than 0 or both B represent a bicyclic heteroaromatic fused ring, and (ii) when m=1 and each n=1, A, B and C are thienylene, and C is unsubstituted or monosubstituted with carboxy or iodo, then a substituent R on a ring B in ortho-position to A is other than carboxymethyl, methoxycarbonylmethyl and aminoethyl;

wherein any alkyl or alkylene moiety is $C_{1-6}$-alkyl or $C_{1-6}$-alkylene (preferably $C_{1-4}$-alkyl or $C_{1-4}$-alkylene), and any alkenyl and alkynyl moiety is $C_{2-6}$-alkenyl (preferably $C_{1-4}$-alkenyl) and $C_{2-6}$-alkynyl (preferably $C_{2-4}$-alkynyl), respectively;

or a pharmaceutically acceptable salt thereof.

In a second aspect, the invention relates to the compounds of formula (I) for use in therapy.

In a third aspect, the invention relates to the use of the compounds of the invention for the treatment of a mammal, especially a mammal such as a human suffering from a disease, primarily a disease involving misfolded or aggregated forms of proteins.

In a fourth aspect the present invention relates to methods for therapy of diseases involving misfolded or aggregated forms of proteins, and the use of compounds of formula ( ) in such methods.

In a further aspect the compounds of the invention interacts with Aβ including aggregated and misfolded forms of Aβ for the treatment of Alzheimer's disease (AD).

In a still further aspect the compounds of the invention may also interact with Tau and/or phosphorylated Tau (pTau) including aggregated and misfolded forms of Tau/pTau as well as neurofibrillary tangles for the treatment of AD.

In a still further aspect the compounds of the invention have a neuroprotective mechanism for the treatment of neurodegenerative diseases.

In yet another aspect of the invention a compound of the invention is used as a pharmaceutical agent developed specifically to treat a rare medical condition, the condition itself being referred to as an orphan disease, i.e. an orphan drug.

In a further aspect, the invention relates to a pharmaceutical composition comprising at least one compound according to the first aspect and optionally pharmaceutically acceptable buffers, diluents, excipients and/or carriers.

In yet a further aspect the invention relates to chemical intermediates useful for synthesizing the compounds of the invention.

DETAILED DESCRIPTION OF THE INVENTION

Definitions

Figure 1:
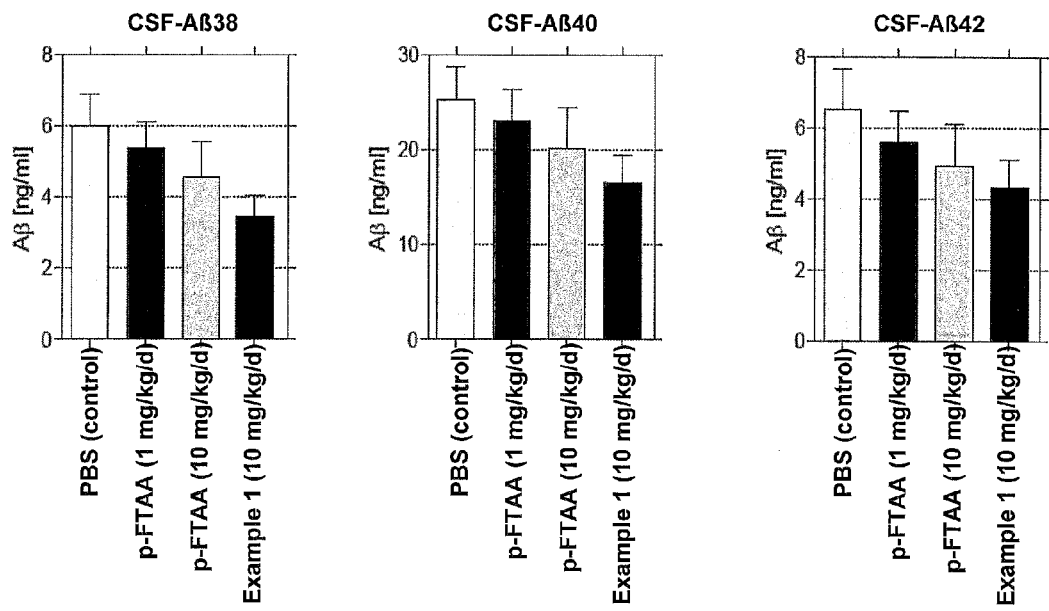
FIG. 1: Aβ8, Aβ40 and Aβ42 in CSF. Graphs represent Aβ38 (left), Aβ40 (mid), and Aβ42 (right) in CSF of APPSL Tg mice. Data are represented as group mean+SEM.

All words and abbreviations used in the present application shall be construed as having the meaning usually given to them in the relevant art, unless otherwise indicated. For clarity, some terms are however specifically defined below.

The term alkyl or alkylene moiety, as used herein, is a C1-C6 alkyl or alkylene moiety, e.g. a C1-C4 alkyl or alkylene moiety and is intended to encompass also the alkyl or alkylene portion of any functional group, e.g. an alkoxy, alkylamino or carboxypolyoxyalkylene group. Thus, for example, any alkyl in an alkoxy or alkylamino group according to the invention is a C1-C6 alkyl group, e.g. a C1-C4 alkyl group.

The term alkenyl, as used herein, is a C2-C6 alkenyl moiety, e.g. a C1-C4 alkenyl moiety, and is intended to encompass also the alkenyl portion of any functional group, The term alkynyl, as used herein, is a C2-C6 alkynyl moiety, e.g. a C2-C4 alkynyl moiety, and is intended to encompass also the alkynyl portion of any functional group, Also, any alkyl, or alkylene alkenyl or alkynyl group according to the invention may be branched or unbranched.

The term "alkyl" includes the monoradical derived from a branched or unbranched C1-C6 alkane, or C1-C4 alkane. Examples of an alkyl group are methyl ($CH_3$—), ethyl ($CH_3CH_2$—), propyl (—$CH_2CH_2CH_2$—) and isopropyl (($CH_3)_2CH$—).

The term "alkylene" includes the diradical derived from a branched or unbranched C1-C6 alkane, or C1-C4 alkane. Examples of an alkylene group are methylene (—$CH_2$—), ethylene (—$CH_2CH_2$—), propylene (—$CH_2CH_2CH_2$—) and isopropylene (—$CH(CH_3)CH_2$—).

The terms "phenylene", "pyridinylene", "pyrazinylene", "pyridazinylene", "pyrimidinylene", "thienylene", "thiazolylene", "thiadiazolylene", "oxazolylene", "furanylene", "triazolylene", "pyrazolylene", "imidazolylene", "pyrrolylene", "benzothienylene", "benzodiazolylene" and "indolylene" include diradicals derived from benzene, pyridine, pyrazine, pyridazine, pyrimidine, thiphene, thiazole, thiadiazole, oxazole, furane, triazole, pyrazole, imidazole", "pyrrolylene, benzo[c]thiophene, benzodiazole and indole, respectively.

The terms "hydroxyalkyl", "hydroxyalkoxy" "hydroxyalkoxyalkyl" and "hydroxypolyoxyalkylene", include an alkyl, alkoxy, alkoxyalkyl and polyoxyalkylene radical, respectively, carrying a hydroxy function.

The term "alkoxy" includes a group R—O—, wherein R is alkyl.

The term "alkoxyalkyl" includes an alkyl radical carrying an alkoxy function.

The term "polyoxyalkylene" includes a group of the general formula RO—(R'O)n- wherein n is an integer from 1 to 6, e.g. from 1 to 4, or 1 or 2; R is an alkyl radical and each R' is an independently selected alkylene radical.

The terms "carboxyalkyl", "carboxyalkoxy", "carboxyalkoxyalkyl" and "carboxypolyoxyalkylene" include an alkyl, alkoxy, alkoxyalkyl and polyoxyalkylene radical, respectively, carrying a carboxy function.

The term "alkoxycarbonyl" includes a radical —COOR, viz. an alkyl ester of a carboxylic acid function.

The terms "alkoxycarbonylalkyl", "alkoxycarbonylalkoxy", "alkoxycarbonylalkoxyalkyl", "alkoxycarbonylpolyoxyalkylene" include an alkyl, alkoxy, alkoxyalkyl and polyoxyalkylene radical, respectively, carrying an alkoxycarbonyl function.

The term "alkylamino" includes —NHR wherein R is alkyl.

The term "dialkylamino" includes —NRR' wherein R and R' are independently selected alkyl groups.

The terms "aminoalkyl", "alkylaminoalkyl", and "dialkylaminoalkyl" include an alkyl radical carrying an amino, alkylamino or dialkylamino function, respectively.

The terms "aminoalkoxy", "alkylaminoalkoxy", and "dialkylaminoalkoxy" include an alkoxy radical carrying an amino, alkylamino or dialkylamino function, respectively.

The terms "aminoalkoxyalkyl", "alkylaminoalkoxyalkyl", and "dialkylaminoalkoxyalkyl" include an alkoxyalkyl radical carrying an amino, alkylamino or dialkylamino function, respectively.

The terms "aminopolyoxyalkylene", "alkylaminopolyoxyalkylene", and "dialkylaminopolyoxyalkylene", include a polyoxyalkylene radical carrying an amino, alkylamino or dialkylamino function, respectively.

The term "acylamino" includes a moiety —NH—C(O)-alkyl.

The terms "acylaminoalkyl", "acylaminoalkoxy", "acylaminoalkoxyalkyl" and "acylaminopolyoxyalkylene" include an alkyl, alkoxy, alkoxyalkyl and polyoxyalkylene radical, respectively, carrying an acylamino function.

The term "acylalkylamino" includes a moiety —NR—C(O)-alkyl wherein R is alkyl.

The terms "acylalkylaminoalkyl", "acylalkylaminoalkoxy", "acylalkylaminoalkoxyalkyl" and "acylalkylaminopolyoxyalkylene" include an alkyl, alkoxy, alkoxyalkyl and polyoxyalkylene radical, respectively, carrying an acylalkylamino function.

The term "hydrazinocarbonyl" includes a moiety a —C(O)NH—NH2.

The terms "hydrazinocarbonylalkyl", "hydrazinocarbonylalkoxy", "hydrazinocarbonylalkoxyalkyl" and "hydrazinocarbonylpolyoxyalkylene", include an alkyl, alkoxy, alkoxyalkyl and polyoxyalkylene radical, respectively, carrying a hydrazinocarbonyl function.

The terms "(amino)(carboxy)alkyl", "(amino)(carboxy)alkoxy", "(amino)(carboxy)alkoxyalkyl" and "(amino)(carboxy)polyoxyalkylene" include an alkyl, alkoxy, alkoxyalkyl and polyoxyalkylene radical, respectively, carrying a carboxy and an amino function, preferably attached to the same carbon atom.

The terms "(alkylamino)(carboxy)alkyl", "(alkylamino)(carboxy)alkoxy", "(alkylamino)(carboxy)alkoxyalkyl" and "(alkylamino)(carboxy)polyoxyalkylene", include an alkyl, alkoxy, alkoxyalkyl and polyoxyalkylene radical, respectively, carrying a carboxy and an alkylamino function, preferably attached to the same carbon atom.

The terms "(dialkylamino)(carboxy)alkyl", "(dialkylamino)(carboxy)alkoxy", "(dialkylamino)(carboxy)alkoxyalkyl" and "(dialkylamino)(carboxy)polyoxyalkylene", include an alkyl, alkoxy, alkoxyalkyl and polyoxyalkylene radical, respectively, carrying a carboxy and a dialkylamino function, preferably attached to the same carbon atom.

The terms "(alkoxycarbonyl)(amino)alkyl", "(alkoxycarbonyl)(amino)alkoxy", "(alkoxycarbonyl)(amino)alkoxyalkyl" and "(alkoxycarbonyl)(amino)polyoxyalkylene", include an alkyl, alkoxy, alkoxyalkyl and polyoxyalkylene radical, respectively, carrying an alkoxycarbonyl and an amino function, preferably attached to the same carbon atom.

The terms "(alkoxycarbonyl)(alkylamino)alkyl", "(alkoxycarbonyl)(alkylamino)alkoxy", "(alkoxycarbonyl)(alkylamino)alkoxyalkyl" and "(alkoxycarbonyl)(alkylamino)-polyoxyalkylene", include an alkyl, alkoxy, alkoxyalkyl and polyoxyalkylene radical, respectively, carrying an alkoxycarbonyl and an alkylamino function, preferably attached to the same carbon atom.

The terms "(alkoxycarbonyl)(dialkylamino)alkyl", "(alkoxycarbonyl)(dialkylamino)alkoxy", "alkoxycarbonyl)(dialkylamino)alkoxyalkyl" and "(alkoxycarbonyl)(dialkylamino)-polyoxyalkylene", include an alkyl, alkoxy, alkoxyalkyl and "polyoxyalkylene" radical, respectively, carrying an alkoxycarbonyl and a dialkylamino function, preferably attached to the same carbon atom.

The terms "nitroalkyl", "nitroalkoxy", "nitroalkoxyalkyl", "nitropolyoxyalkylene" include an alkyl, alkoxy, alkoxyalkyl and polyoxyalkylene radical, respectively, carrying a nitro function.

The terms "cyanoalkyl", "cyanoalkoxy", "cyanoalkoxyalkyl", "cyanopolyoxyalkylene" include an alkyl, alkoxy, alkoxyalkyl and polyoxyalkylene radical, respectively, carrying a cyano function.

The terms "sulfoalkyl", "sulfoalkoxy", "sulfoalkoxyalkyl", "sulfopolyoxyalkylene" include an alkyl, alkoxy, alkoxyalkyl and polyoxyalkylene radical, respectively, carrying a sulfo function.

The terms "alkylsulphonyl" and "alkylaminosulphonyl" include an alkyl and alkylamino radical, respectively, carrying a sulphonyl function.

The term "alkylsulphinyl" includes an alkyl radical carrying a sulphinyl function.

It should be noted that the invention includes the compounds described herein in all possible geometric or stereomeric forms. Within the scope of the invention are cis- and trans-isomers, R and S enantiomers, diastereomers, and racemic mixtures of the mentioned compounds.

Novel Compounds

As mentioned above, in a first aspect the invention relates to novel compounds of formula (I) or a pharmaceutically acceptable salts thereof.

The compounds of formula I can be regarded as oligomers of conjugated monomers, typically trimers, tetramers, pentamers, hexamers, heptamers, octamers, and nonamers, wherein the backbone chain is formed from monomers selected from benzene and five or six-membered heteroaromatic rings, and wherein the backbone of monomers support at least two side-chains or groups of ionic or polar character (the group R in formula I above).

Optionally, one or more of the monomers may be substituted with one or more, e.g. one or two, other groups, such as, for example, halogen, e.g. chloro, iodo or bromo, trifluoro, alkyl, alkenyl or alkynyl (e.g. ethynyl) (the group $R^1$ in formula I above).

Optionally, the backbone may include one or more monomers in the form of a bicyclic fused heteroaromatic rings having 7 to 10 ring members, typically in end position of the backbone.

Examples of heteroaromatic rings include, without limitation thereto, pyridine, pyrazine, pyridazine, pyrimidine, thiophene, thiazole, isothiazole, thiadiazole, oxazole, isoxazole, furane, triazole, triazine, oxadiazole, pyrazole, imidazole and pyrrole.

Examples of bicyclic fused heteroaromatic rings include, without limitation thereto, benzothiophene, benzodiazole, indole, benzoxazole, benzothiazole, benzimidazole, benzoisothiazole, and benzofurane.

The oligomer backbone may consist of a single monomer, such as thiophenes, or of mixed monomers, and may be symmetric or asymmetric. Optionally, the backbone may include one or more carbonyl groups replacing the bond between two adjacent rings.

In some embodiments, the backbone comprises a central thiophene ring, i.e. A in formula I is thienylene. In other embodiments, the backbone comprises a central benzene ring, i.e., A in formula I is phenylene.

In some embodiments the backbone comprises a central phenylene ring surrounded by thiophene rings.

In some embodiments the backbone comprises a number of conjugated thiophene rings and benzene rings as end monomers.

Exemplary trimeric backbones include (without limitation thereto): thienylene-thienylene-thienylene phenylene-thienylene-phenylene phenylene-thienylene-thienylene phenylene-thiadiazolylene-phenylene benzothienylene-thienylene-benzothienylene benzodiazolylene-thienylene-benzodiazolylene benzothienylene-phenylene-benzothienylene benzodiazolylene-thiadiazolylene-benzodiazolylene benzodiazolylene-phenylene-benzodiazolylene.

Exemplary tetrameric backbones include (without limitation thereto): thienylene-thienylene-thienylene-thienylene thienylene-thienylene-thienylene-CO-thienylene phenylene-thienylene-thienylene-phenylene thienylene-thienylene-thienylene-CO-phenylene.

Exemplary pentameric backbones include (without limitation thereto): thienylene-thienylene-thienylene-thienylene-thienylene phenylene-thienylene-thienylene-thienylene-phenylene thienylene-thienylene-thienylene-thienylene-pyridinylene thienylene-thienylene-thienylene-thienylene-phenylene pyridinylene-thienylene-thienylene-thienylene-pyridinylene thienylene-thienylene-phenylene-thienylene-thienylene phenylene-phenylene-phenylene-thienylene-phenylene benzothienylene-thienylene-thienylene-thienylene-benzothienylene indolylene-thienylene-thienylene-thienylene-indolylene. thienylene-CO-thienylene-thienylene-thienylene-CO-thienylene phenylene-CO-thienylene-thienylene-thienylene-CO-phenylene thienylene-phenylene-thienylene-phenylene-thienylene thienylene-pyrazolylene-thienylene-pyrazolylene-thienylene phenylene-pyrazolylene-phenylene-pyrazolylene-phenylene phenylene-oxazolylene-phenylene-oxazolylene-phenylene phenylene-thiadiazolylene-phenylene-thiadiazolylene-phenylene thienylene-pyrrolylene-thienylene-pyrrolylene-thienylene thienylene-imidazolylene-thienylene-imidazolylene-thienylene phenylene-imidazolylene-phenylene-imidazolylene-phenylene thienylene-thienylene-thiadiazolylene-thienylene-thienylene phenylene-thienylene-thiadiazolylene-thienylene-phenylene pyrimidinylene-thienylene-thienylene-thienylene-pyrimidinylene thiazolylene-thiazolylene-thienylene-thiazolylene-thiazolylene thiazolylene-thienylene-thienylene-thienylene-thiazolylene thienylene-thienylene-thiazolylene-thienylene-thienylene.

Exemplary hexameric backbones include (without limitation thereto): thienylene-thienylene-thienylene-thienylene-thienylene-thienylene phenylene-thienylene-thienylene-thienylene-thienylene-phenylene.

Exemplary heptameric backbones include (without limitation thereto): thienylene-thienylene-thienylene-thienylene-thienylene-thienylene-thienylene phenylene-thienylene-thienylene-thienylene-thienylene-thienylene-phenylene thienylene-thienylene-thienylene-phenylene-thienylene-thienylene-thienylene tetrazole-thienylene-thienylene-thienylene-thienylene-thienylene-tetrazole thienylene-phenylene-thienylene-phenylene-thienylene-phenylene-thienylene thienylene-phenylene-thienylene-thienylene-thienylene-phenylene-thienylene pyridinylene-thienylene-thienylene-thienylene-thienylene-thienylene-pyridinylene imidazolylene-thienylene-thienylene-thienylene-thienylene-thienylene-imidazolylene pyrazolylene-thienylene-thienylene-thienylene-thienylene-thienylene-pyrazolylene oxazolylene-thienylene-thienylene-thienylene-thienylene-thienylene-oxazolylene pyrimidinylene-thienylene-thienylene-thienylene-thienylene-thienylene-pyrimidinylene.

When A is thienylene, it is preferably a 2,5-diradical:

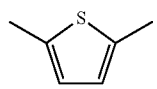

i.e. it is attached to the adjacent rings at the carbon atoms adjacent to its ring sulfur atom. This also applies when A is another five-membered heteroaromat having a single heteroatom.

When A is phenylene, it is preferably a 1,4-diradical:

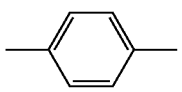

i.e. it is attached to the adjacent rings in para-position, but it may also be a 1,3-diradical

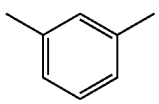

i.e. it is attached to the adjacent rings in meta-position.

In some embodiments of the compounds, ring A is unsubstituted.

In some embodiments the group R in formula I is a group $R^2$ for ring A, a group $R^3$ for ring B, and a group $R^4$ for ring C, wherein each $R^2$, $R^3$ and $R^4$ are independently selected from carboxy, carboxyalkyl, aminoalkyl, acylaminoalkyl, acyloxyalkyl, hydroxyalkyl, alkylsulphonyl, alkylsulphinyl, alkylaminosulphonyl, alkoxycarbonylalkyl, morpholinoalkyl, carboxyalkenyl, hydroxy, alkoxycarbonyl, pyrrolidinecarbonyl, morpholino, cycloalkylcarbamoyl, cyano, trifluoroxy, carbamoyl, hydroxyalkoxyalkyl, carbamoylalkyl, hydroxyalkylaminoalkyl, cyanoalkyl, alkylaminoalkyl, aminoalkylaminoalkyl, carboxyalkylaminoalkyl, piperidinealkyl, and piperazinealkyl.

In some embodiments each $R^2$, $R^3$ and $R^4$ are independently selected from carboxy, carboxyalkyl, aminoalkyl, acylaminoalkyl, acyloxyalkyl, hydroxyalkyl, alkylsulphonyl, alkylsulphinyl, alkylaminosulphonyl, alkoxycarbonylalkyl, morpholinoalkyl, carboxyalkenyl, hydroxy, alkoxycarbonyl, pyrrolidinecarbonyl, morpholino, cycloalkylcarbamoyl, cyano, trifluoroxy, and carbamoyl.

In some embodiments each $R^2$, $R^3$ and $R^4$ are independently selected from carboxy, carboxyalkyl, aminoalkyl, acylaminoalkyl, acyloxyalkyl, hydroxyalkyl, alkylsulphonyl, alkylsulphinyl, and alkylaminosulphonyl, In some embodiments each $R^2$ and $R^3$ are independently selected from carboxy, carboxyalkyl, alkoxycarbonylalkyl, morpholinoalkyl, aminoalkyl, acylaminoalkyl, hydroxyalkoxyalkyl, carbamoylalkyl, hydroxyalkylaminoalkyl, cyanoalkyl, aminoalkylaminoalkyl, carboxyalkylaminoalkyl, piperidinealkyl and piperazinealkyl.

In some embodiments each group $R^3$ is independently selected from carboxy-$C_{1-4}$-alkyl, hydroxy-$C_{1-4}$-alkyl, amino-$C_{1-4}$-alkyl, $C_{1-6}$-acylamino-$C_{1-4}$-alkyl, $C_{1-4}$-alkoxycarbonylamino-$C_{1-4}$-alkyl, and morpholino-$C_{1-4}$-alkyl.

In some embodiments each $R^4$ is independently selected from carboxy, alkylsulphonyl, alkylaminosulphonyl, hydroxyalkyl, carboxyalkenyl, hydroxy, alkoxycarbonyl, pyrrolidinoyl, morpholino, cycloalkylcarbamoyl (preferably cyclopropylcarbamoyl), cyano, trifluoroxy, and carbamoyl.

In some embodiments of the compounds, ring A is unsubstituted.

In some embodiments each $R^4$ is independently selected from carboxy, carboxy-$C_{1-4}$-alkyl, $C_{1-4}$-alkylsulphonyl, carboxy-$C_{1-4}$-alkylene, hydroxy, $C_{1-4}$-alkyl, $C_{1-4}$-alkoxycarbonyl, pyrrolidinoyl, morpholino, $C_{3-6}$-cycloalkylcarbamoyl, cyano, trifluoroxy, carbamoyl and amino-$C_{1-4}$-alkyl.

In some embodiments each $R^2$, $R^3$ and $R^4$ may be independently selected from —COOH, —CH$_2$COOH, —C$_2$H$_4$COOH, —CH$_2$COOCH$_3$, —CH$_2$NH$_2$, —C$_2$H$_4$NH$_2$, —OCH$_2$CH(NH$_2$)(COOH), and —CH$_2$CH(NH$_2$)(COOH).

When the compound of formula I is a thienyl-tetramer, wherein m=0, n=1, rings B are unsubstituted thienyl, and rings C are substituted with a group $R^3$, as defined above, especially in ortho-position to B, then $R^3$ is preferably other than carboxymethyl, and preferably other than carboxyalkyl.

When the compound of formula I is a thienyl-pentamer, wherein m=1, n=1 and ring A and rings C are unsubstituted thienyl, and rings B are disubstituted with $R^2$, as defined above, then $R^2$ is preferably other than carboxyethyl, and preferably other than carboxyalkyl.

When the compound of formula I is a thienyl-hexamer, wherein m=0, n=2, rings B are unsubstituted thienyl, both non-terminal rings C are substituted with a group $R^4$, as defined above, especially in ortho-position to ring B, and both terminal rings C are either unsubstituted or substituted with a group $R^4$, then $R^4$ on the non-terminal rings C is preferably other than carboxymethyl, preferably other than carboxyalkyl.

In some embodiments, a substituent or substituents $R^4$ on a terminal ring C is independently selected from carboxy, alkylsulphonyl (e.g. methylsulphonyl), alkylaminosulphonyl (e.g. methylaminosulphonyl), alkylsulphinyl (e.g. methylsulphinyl), carboxyalkenyl (e.g. carboxyvinyl), hydroxy, alkoxy (e.g. methoxy), cyano, alkoxycarbonyl (e.g. methoxycarbonyl), morpholino, pyrrolidinecarbonyl, trifluoroxy and carbamoyl.

In currently preferred embodiments, the compound of formula I is a heptamer. In some embodiments thereof, the compound is a heptathiophene of formula (II)

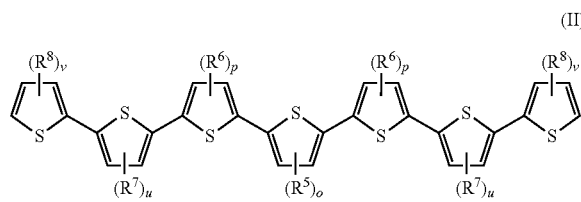

(II)

wherein
each o is independently selected from 0-2; e.g. 0 or 1, and in particular is 0;
each p is independently selected from 0-2; e.g. 0 or 1, and in particular is 1;
each u is independently selected from 0-2; e.g. 0 or 1, and in particular is 0;
each v is independently selected from 0-3; e.g. 0-2, and in particular is 0 or 1,
with the proviso that at least two of o, p, u and v are ≥1; and
each $R^5$, $R^6$, $R^7$ and $R^8$ are independently selected from carboxy, carboxyalkyl, aminoalkyl, acylaminoalkyl, acyloxyalkyl, hydroxyalkyl, alkylsulphonyl, alkylsulphinyl, alkylaminosulphonyl, alkoxycarbonylalkyl, morpholinoalkyl, carboxyalkenyl, hydroxy, alkoxycarbonyl, pyrrolidinecarbonyl, morpholino, cycloalkylcarbamoyl, cyano, trifluoroxy, carbamoyl, hydroxyalkoxyalkyl, carbamoylalkyl, hydroxyalkylaminoalkyl, cyanoalkyl, alkylaminoalkyl, aminoalkylaminoalkyl, carboxyalkylaminoalkyl, piperidinealkyl, and piperazinealkyl, and
each $R^8$ may additionally be independently selected from halogen, alkyl and trifluoro, or a pharmaceutically acceptable salt thereof.

In one embodiment, o=0, u=0, p=1 and v=1, and $R^6$ and $R^8$ are independently selected from carboxy, carboxy-$C_{1-4}$-alkyl, and amino-$C_{1-4}$-alkyl.

The group $R^8$ is preferably in 3- or 5-position on the thiophene ring.

Methods of Preparation

The compounds of the present invention may be prepared by the person of ordinary skill in the art, in the light of the general description herein and the specific illustrating examples.

Generally, ring structures, i.e. benzene, thiophene and other heteroaromates serve as basic monomer units in the inventive compounds. Substitutions of mentioned ring structures can be obtained through conventional chemistry, well known to one skilled in the art of organic synthesis and described in text books of organic synthesis, and exemplified in the synthesis examples below.

To generate dimer, trimer, tetramer, pentamer, hexamer, heptamer, octamer, nonamer, etc. structures of mentioned ring structures several methods are known to those skilled in the art; here we mention the non-limiting examples of Suzuki and Stille coupling. Another well-known method to generate polymers and oligomers of conjugated systems and some of the inventive compounds described herein is the so called Grignard Metathesis reaction, well described by McCullough. [Loewe, R. S.; Khersonsky, S. M.; McCullough, R. D. Adv. Mater. 1999, 11, 250-253.]

Stille coupling utilizes the coupling of an organotin compound with an sp²-hybridized organic halide catalyzed by a palladium, exemplified by the schematic reaction from three ring units to a trimer-block:

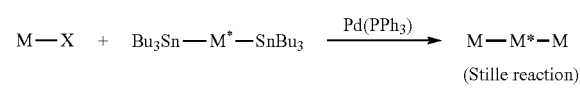

(Stille reaction)

where Bu₃Sn is tributylstannyl, M and M* symbolize arbitrary ring structure.

Suzuki coupling utilizes a reaction between an aryl- or vinyl-boronic acid or borate ester with a vinyl- or aryl-halide catalyzed by a palladium complex, exemplified by the schematic reaction:

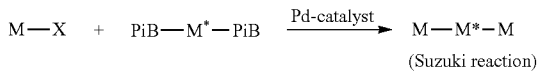

(Suzuki reaction)

wherein PiB is a borate ester.

The reaction may also be carried out with pseudo-halides such as triflates.

A representative exemplary reaction scheme is given below.

Scheme 1

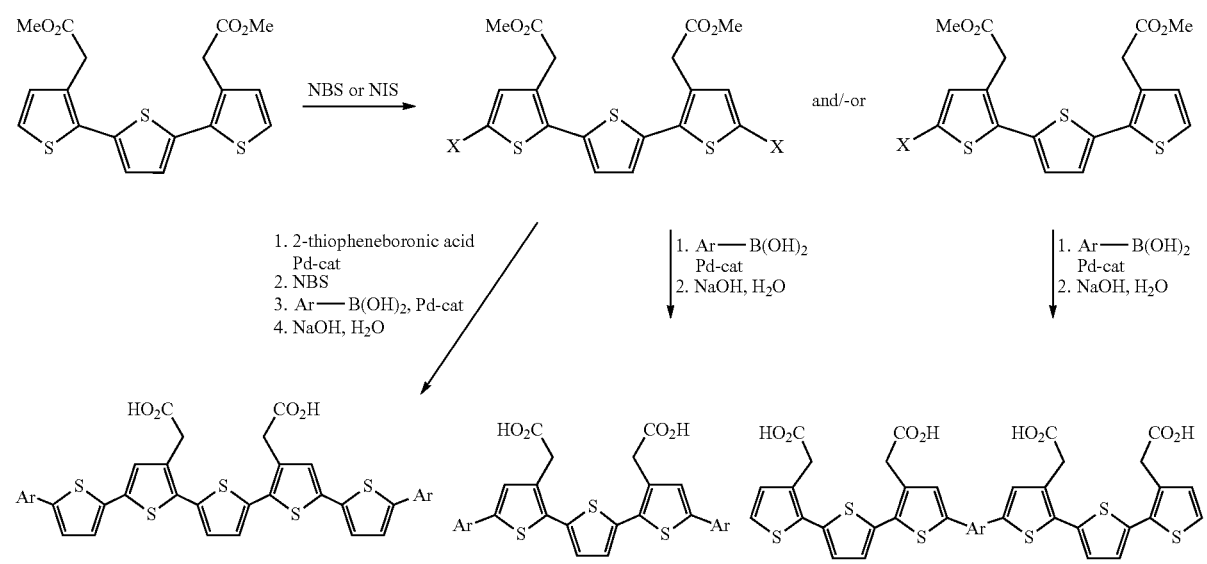

The above mentioned examples describe the preparation of symmetric compounds. To prepare asymmetric compounds, e.g. a stoichiometric approach may be used, where the amount of reagent added is equimolar to the compound to be derivatized, if this compound has several reaction sites. As is well-known to the skilled person, from any mixture of symmetrical and/or asymmetrical compounds, the individual compounds may be separated by methods of chemical separation. Non-limiting examples of separation include flash column chromatography, preparative HPLC and distillation.

In certain aspects the inventive compounds may be used in form of "pharmaceutically acceptable salts", referring to derivatives of the disclosed compounds, where the described compounds are modified by making acid and base salts thereof. Non-limiting examples of pharmaceutically acceptable salts include mineral or organic salts of basic derivatives of the mentioned R-groups such as amines and organic or inorganic, e.g. alkali salts of acidic derivatives of the mentioned R-groups such as carboxylic acids. Conventional non-toxic salts and quaternary ammonium salts are included in pharmaceutically acceptable salts.

Pharmaceutically acceptable salts disclosed in the present invention may be prepared from the inventive compounds described herein that contain a basic or acidic entity by conventional chemical methods.

Diseases

The diseases to be treated with the compounds according to the present invention are primarily diseases related to misfolded and aggregated proteins. Such diseases have also been termed proteopathies, (Walker and Levine, Curr Opin Investig Drugs. 2002 May; 3(5):782-7). Diseases featuring amyloid proteins are relevant examples for the description of diseases related to misfolded and aggregated proteins, where amyloidosis is known as a disease and may be inherited or acquired. Note that amyloidosis by default usually refers to AA amyloidosis, but any disease related to amyloid proteins, which presents amyloid deposition, is an amyloidosis. For example CJD, vCJD, Alzheimer's Disease, HD, ALS and diabetes are almost never referred to as amyloidoses.

In this paragraph some examples of amyloidosis with relevance to the present invention are named. Primary amyloidosis includes mutations in lysozyme, transthyretin, apolipoprotein B, fibrinogen and AL amyloidosis (immunoglobulin light chains, as seen with multiple myeloma). Secondary amyloidosis includes AA amyloidosis (serum amyloid A protein, an acute-phase protein due to chronic inflammation) and Gelsolin amyloidosis (plasma gelsolin fragments). Familial or hereditary amyloidosis, are most commonly caused by mutations in the transthyretin protein, but in rare occurrences can also be caused by apolipoprotein A1, gelsolin, fibrinogen, and lysozyme mutations, primarily caused by genetics, believed to be autosomal dominant, high probability of passage to offspring, Appalachian type amyloidosis and Shar Pei fever for amyloidosis in Shar Peis. Examples of organ-specific amyloidosis are Diabetes mellitus type 2 (amylin, also known as IAPP), Alzheimer's disease (Aβ39-42), Parkinson's disease (alpha-synuclein), Huntington's disease (huntingtin), Transmissible spongiform encephalopathies (prion protein, PrP), some examples are Creutzfeldt-Jakob disease (PrP in cerebrum), Kuru (diffuse PrP deposits in brain), Fatal Familial Insomnia (PrP in thalamus), Inclusion body myositis and Bovine spongiform encephalopathy (PrP in cerebrum of cows), Congophilic angiopathy (Amyloid beta). Cardiac amyloidosis includes congestive heart failure; some instances (PrP or transthyretin in heart). Another important example is the Iatrogenic conditions like insulin amyloidosis, believed to be caused by injection-administered insulin.

Some non-disease amyloids are native amyloids in organisms, Curli E. coli Protein (curlin), Yeast Prions [Sup35], Podospora Anserina Prion Het-s, Malarial coat protein, spider silk, Mammalian melanosomes (pMel), Tissue-type plasminogen activator (tPA) (a hemodynamic factor), Calcitonin and proteins and peptides engineered to make amyloid.

The prion diseases [e.g. bovine spongiform encephalopathy (BSE), and Creutzfeldt-Jakob disease (CJD)], are associated with the conformational conversion of the normal cellular prion protein, ($PrP^C$), to an infectious disease-associated isoform denoted $PrP^{Sc}$. The misfolded infectious form of the protein, $PrP^{SC}$ is the cause of a group of rare, fatal brain diseases, called prion diseases that affect humans and mammals. The prion diseases are also known as transmissible spongiform encephalopathies (TSE), and they include bovine spongiform encephalopathy (BSE, or "mad cow" disease) in cattle; scrapie in sheep; chronic wasting disease in deer and elk; and in humans [Creutzfeldt Jakob disease (CJD), Gerstmann-Strä ussler-Scheinker disease (GSS), Kuru].

The compounds of the present invention are intended to be used for methods of therapy, primarily of the above diseases.

Use of Compounds in Therapy

In general, the invention provides a compound and a method for treating a disease caused by abnormal protein folding or aggregation or amyloid formation, deposition, accumulation or persistence of misfolded proteins in a subject. The method comprises administration of one or several isolated and pure, in particular substantially pure, compounds of the invention. The present invention relates to the use of the compounds of the invention as novel therapeutic agents. A collapse of protein homeostasis may result in protein misfolding leading to the accumulation of insoluble protein fibrils and aggregates, such as amyloids. The compounds of the invention may promote protein homeostasis in vivo and/or alter amyloid pathology upon administration to an organism, i.e. act as therapeutic agents. Conditions and diseases to be treated with the compounds according to the invention are conditions and diseases related to aggregation of misfolded proteins as discussed above by administering a therapeutically effective amount of the compounds according to the invention to a subject in need thereof. The invention also relates to a method of treatment comprising administering a therapeutically effective amount of one or more compounds of the invention to a subject with symptoms of a disease characterized by amyloid deposition, for example Alzheimer's disease, producing beneficial effects, preferably sustained beneficial effects. The compounds of the invention may act by disruption of aggregated Aβ, increased inhibition of long term potentiation induced by Aβ oligomers, increase Aβ clearance, reduce cerebral accumulation of Aβ, block deposition of cerebral amyloid plaques, reduce soluble Aβ oligomers in the brain leading to maintenance of synaptic function and decrease of cognitive decline.

The compounds of the invention may act directly or indirectly with Tau or phosphorylated Tau or Tau aggregates and to the same neurofibrillary tangles (NFTs). Thus, the compounds of the present invention may also or at the same time inhibit the formation and at the same time may disaggregate the NFTs, and in consequence would be useful in the treatment and prophylaxis of the Alzheimer's disease.

The compounds of the invention may reduce neurodegeneration and may also help to maintain or increase synaptic density. Mainting and/or restoring synapses can have therapeutic benefits in the treatment of neuro-degenerative disease wherein the manifestations of the disease result in incomplete neurotransmission, thus resulting in an improvement and/or reversal of the deterioration of the nervous system of the patient under treatment. Hence, the compounds of the present invention may have a "restorative effect on synapses" and by this is meant the regeneration or reformation and refunctionalization of synapses after nerve cells have ceased to exhibit normal synapses, as a result of a neurodegenerative disease.

The compounds of the present invention can be designed in order to cross the blood brain barrier and thereby have an effect on diseases that affect the brain. This includes, but is not limited to, Abeta amyloid pathology in living organisms, i.e. influence Alzheimer's disease pathogenesis by acting as therapeutic agents.

The compounds of the invention may be included in pharmaceutical preparations adapted for injection into the blood stream, to be taken orally, intraperitoneally, intramuscularly, subcutaneously, to be inhaled, to be taken up through the skin or mucus, for distribution into other body fluids, such as cerebrospinal fluid (CSF) or lymph.

Thus, in one aspect the present invention relates to a therapeutic composition, where at least one compounds of the invention is included, suitable for therapy of diseases related to misfolded protein species and a method of preparing and use of said therapeutic composition comprising administering a pharmaceutical composition containing at least one compounds of the invention, and optionally pharmaceutically acceptable excipients, buffers and/or carriers, to a subject in need thereof.

In another aspect of the invention, a method is provided for treating in a subject a condition of the central or peripheral nervous system or systemic organ associated with a disorder in protein folding or aggregation, or amyloid formation, deposition, accumulation, or persistence, comprising administering to the subject a therapeutically effective amount of the compounds of the invention.

In another aspect, the invention provides a method involving administering to a subject a therapeutic compound of the invention which may inhibit amyloid formation, deposition, accumulation and/or persistence, and/or which cause dissolution/disruption of pre-existing amyloid and/or increase clearance of misfolded proteins. In this way the compounds and compositions of the invention may be used for inhibiting amyloidosis in disorders which are related to amyloid deposition.

In a further aspect, the invention provides a method for treating in a subject a condition associated with an amyloid interaction that may be disrupted or dissociated by using the compounds of the invention.

In an aspect, the invention provides a method for preventing or inhibiting amyloid protein assembly, enhancing clearance of amyloid deposits, or slowing deposition of amyloid deposits in a subject comprising administering a therapeutically effective amount of the compounds of the invention.

In still another aspect, the invention provides a method that may reduce or inhibit amyloid fibril formation, brain dysfunction (e.g., neurodegeneration), or cellular toxicity in a subject comprising administering to the subject a therapeutically effective amount of the compounds of the invention.

The inventive compounds may be administered by any means known to one of ordinary skill in the art. The present invention includes "pharmaceutically acceptable" compositions based on an amount of the inventive compound necessary for effective treatment of a patient together with one or more pharmaceutical carrier, such as additive and/or diluent. The inventive compounds may be formulated and administrated with other therapeutic agents. The formulation of the inventive compounds may be determined by the means of administration. The formulation for administration of the inventive compounds may be solid, liquid or in aerosol form. Formulation examples includes pills, tablets, caplets, soft and hard gelatin capsules, lozenges, sachets, cachets, vegicaps, liquid drops, elixirs, suspensions, emulsions, solutions, syrups, aerosols (as a solid or in a liquid medium) suppositories, sterile injectable solutions, and/or sterile packaged powders, which contain a compounds of the invention. Administration of the inventive compounds to an animal or human may be local or systemic accomplished parenterally, orally, by inhalation, rectally, nasally, buccally, vaginally or via an implanted reservoir. The term "parenteral" refers to administration outside the alimentary tract including subcutaneous, intravenous, intramuscular, intraarterial, intraspinal, intracranial, subdermal, intradermal by injection or infusion.

Carrier agents may be added to the pharmaceutical compositions in order to achieve the desired distribution and acceptance in the living organism. Such agents include, but are not limited to, lipids, phospholipids, cellulose membranes, sugar coatings, hyaluronic acid, detergents, peptides, proteins, ions, salts, chelators and solvents.

The administered dose of the compounds should be a dose effective for treatment of the specific patient. The specific dose level of the inventive compound(s) will be dependent on several factors, including the activity and possible toxicity of the specific compounds used; the general health state, age, sex, body weight and diet of the subject or patient, the drug combination, the time and form of administration as well as the rate of excretion. The dose administered may typically be between 0.001 mg/kg/day to 50 mg/kg/day, preferably between 0.005 mg/kg/day to 10 mg/kg/day.

Advantageously, the compositions are formulated as dosage units, each unit being adapted to supply a fixed dose of active ingredients. Tablets, coated tablets, capsules, ampoules and suppositories, sprays and patches are examples of preferred dosage forms according to the invention. It is only necessary that the active ingredient constitute an effective amount, i.e., such that a suitable effective dosage will be consistent with the dosage form employed in single or multiple unit doses. The exact individual dosages, as well as daily dosages, will, of course, be determined according to standard medical principles under the direction by someone skilled in the art.

Any of the compounds of the invention may be in the form of a prodrug that is converted in vivo to an active compound. One way to make a prodrug is to introduce a cleavable group that is cleaved after administration to a subject to provide an active (e.g. therapeutically active) compound, or an intermediate compound that subsequently yields the active compound. The cleavable group may be an ester that can be removed either enzymatically or non-enzymatically.

Recently it was demonstrated that the prior art compounds (WO2010/044743) and a few of the compounds of the present invention can be utilized as fluorescent ligands for spectral assignment of protein aggregates (Ref: Org. Biomol. Chem., 2011, 9, 8356).

The compounds of the invention can be used therapeutically or can be used prophylactically in a subject susceptible to a disease disclosed herein.

EXAMPLES

Therapeutic Effects of the Inventive Compounds

The present invention demonstrates novel anti-amyloid disease-modifying treatments based on the inventive compounds described herein. The inventive compounds can be used as anti-amyloid disease-modifying agents and, while not being bound by theory, it is suggested that these interrupt early pathological events by decreasing production of aggregated proteins or $A\beta$; by binding to existing aggregated proteins or $A\beta$; by inhibiting the formation of new aggregated protein or $A\beta$; or by increasing amyloid, aggregated proteins or $A\beta$ clearance, thereby preventing all downstream pathological processes. One plausible mechanism, related to neurological diseases, is to use the inventive compounds to rescue viable neurons to achieve some degree of symptom relief or a full reversal of the disease. Other treatments may block events occurring downstream production of aggregated proteins or $A\beta$ that affect some aspects of the disease.

Examples mentioned herein describe the first steps to show the therapeutic effects on misfolding diseases such as Alzheimer's of the inventive compounds. Both in vitro and in vivo examples will further verify these effects.

In vitro Fibrillation Inhibition Examples

An in vitro fibrillation of disease associated peptides and proteins, one non-limiting example is $A\beta$ peptides, can be performed in presence of the inventive compounds and the effect of the molecular weight distribution of the aggregated species can be evaluated to demonstrate inhibitory effects. Molecular weight of aggregated species can be determined with gel electrophoresis, size exclusion chromatography and other methods well known in the art.

In vivo Aβ Cell Assay Examples

The series of compounds of the present invention can be, but do not have to be, cell-permeable. As a model for Alzheimer's disease it is especially suitable to expose neural cells to aggregated species of Aβ peptides, where after cell responses and cell survival is studied. The therapeutic effects of the inventive compounds can in this system be studied by exposing the neural cells to aggregated species of Aβ peptides and adding the inventive compounds simultaneously, before or after, whereupon protective effects of the compounds are evaluated. It can be demonstrated that one function, but not the only one, of the inventive compounds is to protect neurons from intracellular AbO toxicity by reducing the level of intraneuronal Ab oligomers (AbO) or by merely diminishing their toxicity.

AbO can induce toxicity when applied from outside the cells. One mode of toxicity is via the strong AbO binding to synapses, resulting in severe synaptic damage. Such binding activity may also be visualized using labeled AbO or a variant of the inventive compounds. The inventive compounds will be added before or after applying AbO to neuronal cultures, or other cell cultures, in order to demonstrate their activity. The inventive compounds will also be added at the same time, together with, the application of AbO to the cell cultures to further demonstrate their activity.

In vivo Prion Assay Example

In vitro examples that are especially suitable for demonstrating therapeutic effects are cell culture or organotypic culture slide models of misfolding diseases. In the case of prion diseases the scrapie cell assay (SCA) has been known for at least five year as a model system, where prion infections can be studied via cell survival and quantification of prion protein. The therapeutic effects of the inventive compounds can be demonstrated through constant addition of these in the culture media or alternatively by a short exposure in a suitable media, whereupon cell survival and levels of prion protein would be measured. Another more in vivo like model system is the prion organotypic slice culture assay (POSCA) recently described by Aguzzi (Falsig and Aguzzi, Nat Prot, 2008, 3(4), 555-562). Brain culture slides are cultured up to 8 weeks and progression of prion infections can be monitored. In a similar fashion as with SCA, the culture slides can be constantly exposed to the inventive compounds or exposed in shorter doses, whereupon progression of the prion infection will be studied. It was recently demonstrated that the prior art compounds (WO2010/044743), p-HTAA and p-FTAA, possess a pronounced anti-prion potential. (Ref: JBC doi: 10.1074/jbc.M112.355958). These two compounds are structurally similar to some of the compounds of the present invention.

Demonstration of Efficacy In vivo

We have demonstrated that an intravenous injection of the inventive compounds rapidly passed the blood brain barrier and permeated the brain producing a fluorescently highlighted amyloid plaques in AD mouse. There are several animal models of misfolding disease, for evaluating therapeutic effects of the inventive compounds transgenic mouse models are especially suitable. Non-limiting examples of mouse models are PS-APP and 5xFAD models.

The present invention has demonstrated that the compounds of the invention recognize an amyloid conformation in AbO and in amyloid fibrils in transgenic mice. This binding can further be demonstrated in humanized mice and in humans. Being compatible with the human organism said compounds may be as therapeutics for man. The initial studies can include, but not limited to, a two week course of daily intraperitoneal injection of the inventive compounds in an AD-pathology model mice, humanized mice and later humans, in order to demonstrate the significant reduction of the quantity of amyloid lesions in the brain or in other parts of the body. No apparent toxicity should be observed. The reduction of the cerebral levels of protein or Ab aggregates by the inventive compounds might also be, but not necessarily, be confirmed by Western blot. Furthermore behavioural changes, e.g. cognitive improvements, will be studied as a response of the exposure to the inventive compounds.

The therapeutic use of known amyloid ligands, such as PIB and other derivatives of Congo red and thioflavins, is as far as the inventors of the present invention know restricted by limited ability for their synthetic modifications. The unique advantage of the inventive compounds series is that they are the first example of amyloid ligands derived from a thienyl library and that they can be oligomerized and polymerized to achieve further distinct properties. An oligomeric or polymeric structure can be of a great advantage when further modifications will be put on the core chemical structure. The inventive compound series may contain a core structure with three plus two thienyl, or other groups as described in the present invention. These are chemical unities perfectly suitable for generating new libraries and to achieve the therapeutic effect related to diseases caused by aggregated proteins.

Pharmacokinetic Profiling Study Including Investigation of BBB Crossing and Excretion of a Drug in the Rat or Other Mammal Animals are randomly distributed into groups for PK profiling, for urine and/or feces excretion Administration route: p.o. and i.v.

Test design: Single dose.

Blood Sampling: A number of collection times over an extended time period for each administration route.

Urine and/or feces collection: A number of collection times during the test period.

Tissue collection: A number of time points within the period of 0-72 hours post-dose. Blood will be also collected from these animals to correlate the systemic exposure with the levels found in the tissues and to calculate the brain/plasma ratio.

Bioanalysis of the compounds of the invention.

Study to Test the Capability of Test Compounds to Inhibit Toxic Aβ and/or Aβ Aggregates Effects In vitro This prophetic study is designed to measure the potential of compounds of the invention to inhibit toxic Aβ and/or Aβ aggregates effects in vitro. Primary chicken cortical neurons will be lesioned with 10 μM of Aβ and/or Aβ aggregates either on a number of DIV's for number of certain hours until the last DIV, when viability will be measured using for example the MTT test. In one set of experiments Aβ which needs to aggregate for a number of hours in a vial to become toxic will be co-incubated with up to 4 dosages of each test compounds of the invention (T.I.) and this solution will be added to the neuronal tissue cultures. A number stoichiometric ratios of T.I. to Aβ during aggregation will be selected. In the second set of experiments already aggregated Aβ and in parallel 4 dosages of each T.I. will be added to the neuronal tissue cultures. A number of stoichiometric ratios of T.I. to pre-aggregated Aβ will be selected. In all experiments MK801 will be applied as reference compound (R.I.) and ThioflavnS and/or Congo red as positive controls.

Microsomal Metabolic Stability

Protocol Summary: Compounds of the invention are incubated with pooled liver microsomes at a certain concentration. Compounds of the invention are incubated at a number of time points over the course of a 0-240 min experiment and the test compounds of the invention is analysed by LC-MS/MS. An intrinsic clearance value (CLint) with standard error and t1/2 value may be calculated.

EXAMPLES

Synthesis of Compounds

Synthesis of Intermediates

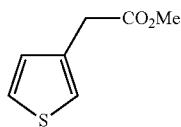

Methyl 2-(thiophen-3-yl)acetate (Intermediate A)

Acteyl chloride (7.50 ml, 106 mmol) was added dropwise to a solution of 3-thiopheneacetic acid (5.00 g, 35.3 mmol) in dry MeOH (150 ml) at 0° C. The mixture was left to slowly reach room temperature and stirred overnight. Solvents were evaporated and residue filtered through a short plug of silica gel (DCM) to give a quantitative yield of the title compound as an oil. $^1$H NMR (400 MHz, CDCl$_3$): □ 3.64 (s, 2H), 3.70 (s, 3H), 7.03-7.05 (m, 1H), 7.14-7.15 (m, 1H), 7.27-7.29 (m, 1H).

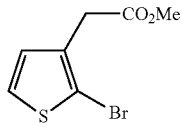 [SMILES: COC(=O)Cc1ccsc1Br]

Methyl 2-(2-bromothiophen-3-yl)acetate (Intermediate B)

NBS (6.28 g, 35.3 mmol) was added portion-wise to a solution of intermediate A (5.51 g, 35.3 mmol) in CHCl$_3$ (15 ml) and acetic acid (15 ml) at 0° C. The mixture was left to slowly reach ambient temperature and stirred for 3 d. Et$_2$O (100 ml) was added and mixture was filtered and concentrated. The residue was purified by flash chromatography using 2-10% EtOAc in iso-hexane as eluent. Yield: 5.74 g (69%); colourless oil. $^1$H NMR (400 MHz, CDCl$_3$): δ 3.64 (s, 2H), 3.72 (s, 3H), 6.93 (d, J 6 Hz, 1H), 7.24 (d, J 6 Hz, 1H).

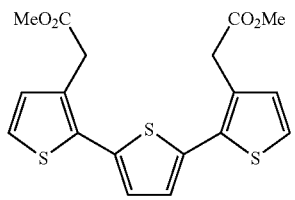 [SMILES: COC(=O)Cc1ccsc1-c1ccc(-c2sccc2CC(=O)OC)s1]

Methyl 2-(2-{5-[3-(2-methoxy-2-oxoethyl)thiophen-2-yl]thiophen-2-yl}thiophen-3-yl)acetate (Intermediate C)

Argon was bubbled through a mixture of intermediate B (16.3 g, 69.1 mmol), 2,5-thiophenediboronic acid (5.93 g, 34.5 mmol) and K$_2$CO$_3$ (28.6 g, 207 mmol) in toluene (100 ml) and MeOH (100 ml). After 10 min PEPPSI-iPr™ (475 mg, 0.70 mmol) was added and the mixture heated at 50° C. for 1.5 h. The mixture was filtered through a short plug of silica gel and concentrated. The residue was purified by flash chromatography using iso-hexane/EtOAc 9:1 and 4:1 as eluents. Yield: 9.07 g (67%); slightly yellow oil. $^1$H NMR (400 MHz, CDCl$_3$): δ 3.74 (s, 6H), 3.80 (s, 4H), 7.07 (d, J 5.3 Hz, 2H), 7.16 (s, 2H), 7.26 (d, J 5.3 Hz, 2H).

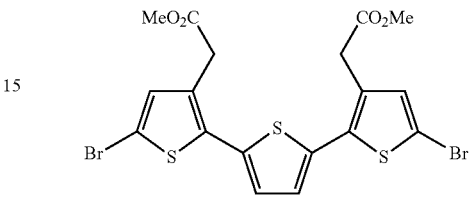

Methyl 2-(5-bromo-2-{5-[5-bromo-3-(2-methoxy-2-oxoethyl)thiophen-2-yl]thiophen-2-yl}thiophen-3-yl)acetate (Intermediate D)

NBS (2.96 g, 16.6 mmol) was added portion-wise to a solution of intermediate C (3.11 g, 7.92 mmol) in acetic acid (50 ml). The mixture was stirred at rt for 2 h. Solvent was evaporated and residue dissolved in DCM (200 ml) and water was added. The organic layer was washed with sat. NaHCO$_3$ and organic layer concentrated. The residue was purified by flash chromatography using 20% EtOAc in iso-hexane as eluent and then purified again using pet.ether/Et$_2$O 2:1 and 1:1 as eluents. Yield: 3.65 g (83%); yellow solid. $^1$H NMR (400 MHz, CDCl$_3$): δ 3.71 (s, 4H), 3.74 (s, 6H), 7.03 (s, 2H), 7.09 (s, 2H).

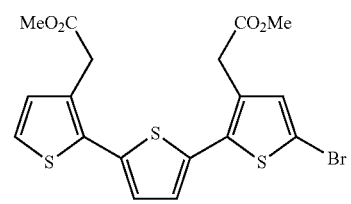 [SMILES: COC(=O)Cc1ccsc1-c1ccc(-c2sc(Br)cc2CC(=O)OC)s1]

Methyl 2-(2-{5-[5-bromo-3-(2-methoxy-2-oxoethyl)thiophen-2-yl]thiophen-2-yl}thiophen-3-yl)acetate (Intermediate E)

NBS (1.88 g, 10.5 mmol) was added portion-wise to intermediate C (4.37 g, 11.4 mmol) in CHCl$_3$ (30 ml) and AcOH (30 ml). The mixture was stirred at rt for 1 h. DCM and water was added. The organic phase was washed with water and sat. NaHCO$_3$. The organic layer was evaporated and residue purified by flash chromatography using 100% DCM and once more purification using DCM/CHCl$_3$ (2:1) as eluent. Yield: 2.02 g (38%); pale yellow oil. $^1$H NMR (400 MHz, CDCl$_3$): δ 3.74 (s, 2H), 3.75 (s, 3H), 3.76 (s, 3H), 3.80 (s, 2H), 7.05 (s, 1H), 7.08 (d, J 5.2 Hz, 1H), 7.13 (d, J 4 Hz, 1H), 7.16 (d, J 4 Hz, 1H), 7.27 (d, J 5.2 Hz, 1H).

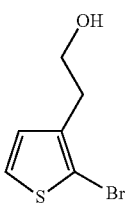

2-(2-Bromothiophen-3-yl)ethan-1-ol (Intermediate F)

NBS (9.53 g, 53.6 mmol) was added portionwise to a solution of 3-thiopheneethanol 6.87 g, 53.6 mmol) in AcOH (30 ml). The temperature was raised to 40° C. and mixture was stirred for 1 h. DCM (400 ml) and water was added. The organic layer was washed with water and sat. NaHCO$_3$. The organic layer evaporated and residue purified by flash chromatography using 25-33% EtOAc in iso-hexane. Yield: 5.39 g (49%); colourless oil. $^1$H NMR (400 MHz, CDCl$_3$): δ 2.89 (t, J 6.4 Hz, 2H), 3.85 (t, J 6.4 Hz, 2H), 6.89 (d, J 5.6 Hz, 1H), 7.26 (d, J 5.6 Hz, 1H).

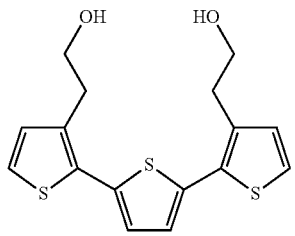 [SMILES: OCCc1ccsc1-c1ccc(-c2sccc2CCO)s1]

2-(2-{5-[3-(2-Hydroxyethyl)thiophen-2-yl]thiophen-2-yl}thiophen-3-yl)ethan-1-ol (Intermediate G)

Nitrogen was bubbled through a mixture of intermediate F (1.148 g, 5.54 mmol), 2,5-thiophenediboronic acid (476 mg, 2.77 mmol) and K$_2$CO$_3$ (1.92 g, 13.9 mmol) in toluene (8 ml) and MeOH (8 ml). PEPPSI-iPr™ (19 mg, 0.0277 mmol) was added and mixture heated at 50° C. for 45 min under nitrogen. Chloroform was added and mixture filtered. The residue after evaporation was dissolved in MeOH. Silica was added and solvent evaporated. The dry silica was applied on a flash column and product eluted using iso-hexane/EtOAc 1:1 and 1:2. Yield: 542 mg (58%); yellow oil. HPLC: R$_T$=2.49 min, 95% (254 nm, 10-90% MeCN in 3 min, XBridge). $^1$H NMR (400 MHz, CDCl$_3$): δ 3.10 (t, J 6.8 Hz, 4H), 3.92 (t, J 6.8 Hz, 4H), 7.02 (d, J 5.2 Hz, 2H), 7.13 (S, 2H), 7.27 (d, J 5.2 Hz, 2H).

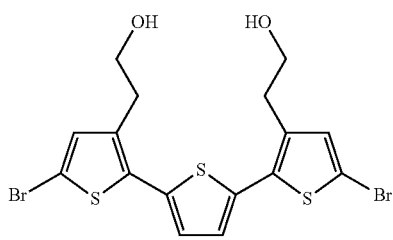 [SMILES: OCCc1cc(Br)sc1-c1ccc(-c2sc(Br)cc2CCO)s1]

2-(5-Bromo-2-{5-[5-bromo-3-(2-hydroxyethyl)thiophen-2-yl]thiophen-2-yl}thiophen-3-yl)ethan-1-ol (Intermediate H)

NBS (324 mg, 1.82 mmol) was added portion-wise to a solution of intermediate G (307 mg, 0.911 mmol) in CHCl$_3$ (8 ml) and AcOH (8 ml). The mixture was stirred at rt overnight. DCM (100 ml) and water was added. The organic layer was washed with 1 M NaOH until the aqueous layer was alkaline. The organic layer was separated and residue purified by flash chromatography using EtOAc/iso-hexane 3:2 as eluent. Yield: 254 mg (56%); yellow solid. $^1$H NMR (400 MHz, CDCl$_3$) δ 3.02 (t, J 6.8 Hz, 4H), 3.89 (d, J 6.8 Hz, 4H), 7.00 (s, 2H), 7.07 (s, 2H).

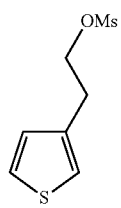 [SMILES: CS(=O)(=O)OCCc1ccsc1]

2-(Thiophen-3-yl)ethyl methanesulfonate (Intermediate I)

Methylsulfonyl chloride (2.22 ml, 28.75 mmol) was added dropwise to a solution of 3-thiopheneethanol (2.46 g, 19.2 mmol) and Et$_3$N (5.3 ml) in DCM (50 ml) as 0° C. The mixture was stirred for 15 min before DCM and water was added. Organic phase was separated and residue purified by flash chromatography using 20-25% EtOAc in iso-hexane as eluents. Yield: 3.93 g (99%); colourless oil. HPLC: R$_T$=2.20 min, 96% (254 nm, 10-90% MeCN in 0.1% TFA, 3 min ACE). $^1$H NMR (400 MHz, CDCl$_3$): δ 2.90 (s, 3H), 3.13 (t, J 6.8 Hz, 2H), 4.44 (t, J 6.8 Hz, 2H), 7.00-7.02 (m, 1H), 7.11-7.12 (m, 1H), 7.32-7.36 m, 1H).

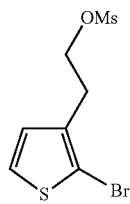 [SMILES: CS(=O)(=O)OCCc1ccsc1Br]

2-(2-Bromothiophen-3-yl)ethyl methanesulfonate (Intermediate J)

NBS (3.38 g, 19.0 mmol) was added portion-wise to a solution of intermediate I (3.92 g, 19.0 mmol) in AcOH (50 ml). The mixture was stirred at rt for 1 h. Solvent was evaporated and residue dissolved in DCM. The solution was washed with sat. NaHCO$_3$ and evaporated. The residue was purified by flash chromatography using iso-hexane:EtOAC 3:1 as eluent. Yield: 4.51 g (83%); colourless oil. HPLC: R$_T$=2.41 min, 97% (10-90% MeCN in 10 mM buffer, XBridge). $^1$H NMR (400 MHz, CDCl$_3$): δ 2.93 (s, 3H), 3.07 (t, J 6.8 Hz, 2H), 4.39 (t, J 6.8 Hz, 2H), 6.90 (d, J 4.4 Hz, 1H), 7.28 (d, J 4.4 Hz, 1H).

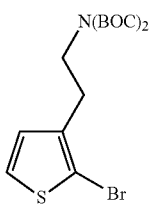

tert-Butyl N-[2-(2-bromothiophen-3-yl)ethyl]-N-[(tert-butoxy)carbonyl]carbamate (Intermediate K)

Cs$_2$CO$_3$ (7.70 g, 23.7 mmol) was added to a solution of di-t-butyl iminodicarboxylate (5.14 g, 23.7 mmol) in DMSO (100 ml) at rt and the mixture was stirred for 30 min before intermediate J (4.50 g, 15.8 mmol) in DMSO (5 ml) was added. The mixture was stirred at rt overnight. Et$_2$O and water was added. Organic phase was washed with water and then evaporated. The residue was purified by flash chromatography using 5-10% EtOAc in iso-hexane, Yield: 4.44 g (69%); colourless oil. HPLC: R$_T$=2.08 min, 100% (60-90% MeCN in 10 mM buffer, 3 min, XBridge). $^1$H NMR (400 MHz, CDCl$_3$): δ 1.51 (s, 18H), 2.88-2.92 (m, 2H), 3.78-3.81 (m, 2H), 6.83 (d, J 5.6 Hz, 1H), 7.21 (d, J 5.6 Hz, 1H).

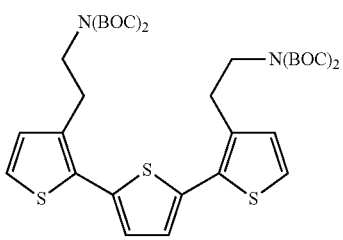

tert-Butyl N-[2-(2-{5-[3-(2-{bis[(tert-butoxy)carbonyl]amino}ethyl)thiophen-2-yl]thiophen-2-yl}thiophen-3-yl)ethyl]-N-[(tert-butoxy)carbonyl]carbamate (Intermediate L)

Nitrogen was bubbled through a mixture of intermediate K (2.10 g, 5.17 mmol), 2,5-thiophenediboronic acid (444 mg, 2.58 mmol) and K$_2$CO$_3$ (1.43 g, 10.4 mmol) in toluene (40 ml) and MeOH (20 ml). PEPPSI-iPr™ (88 mg, 0.129 mmol) was added and the mixture stirred at 60° C. for 45 min. Toluene and water were added. Aqueous layer was extracted with toluene and combined organic layers concentrated. The crude material was purified by flash chromatography using 0-5% EtOAc in toluene. Yield: 1.65 g (87%); yellow oil which solidifies. $^1$H NMR (400 MHz, CDCl$_3$): δ 1.47 (s, 36H), 3.06-3.10 (m, 4H), 3.85-3.88 (m, 4H), 6.98 (d, J 5.2 Hz, 2H), 7.14 (s, 2H), 7.22 (d, J 5.2 Hz, 2H).

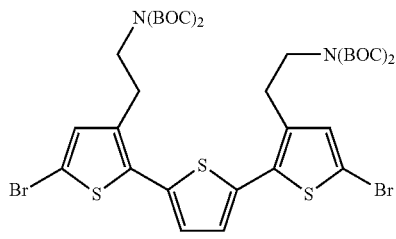

tert-Butyl N-[2-(2-{5-[3-(2-{bis[(tert-butoxy)carbonyl]amino}ethyl)-5-bromothiophen-2-yl]thiophen-2-yl}-5-bromothiophen-3-yl)ethyl]-N-[(tert-butoxy)carbonyl]carbamate (Intermediate M)

NBS (310 mg, 1.74 mmol) was added portionwise to a solution of intermediate L (642 mg, 0.873 mmol) in CHCl$_3$ (8 ml) and AcOH (8 ml). The mixture was stirred at rt for 2.5 h. CHCl$_3$ and water was added. Organic layer was washed with 1 M NaOH until aqueous layer was alkaline and then concentrated. The crude material was purified by flash chromatography using 3% EtOAc in toluene. Yield: 582 mg (75%); yellow oil which solidifies. $^1$H NMR (400 MHz, CDCl$_3$): δ 1.47 (s, 36H), 3.00 (t, J 6.8 Hz, 4H), 3.83 (t, J 6.8 Hz, 4H), 6.94 (s, 2H), 7.09 (s, 2H).

Methyl 5-(5-{5-[5-bromo-3-(2-methoxy-2-oxoethyl)thiophen-2-yl]thiophen-2-yl}-4-(2-methoxy-2-oxoethyl)thiophen-2-yl)thiophene-2-carboxylate (Intermediate N)

Acetyl chloride (0.5 ml) was added to a solution of 5-carboxy-2-thiopheneboronic acid (554 mg, 3.22 mmol) in methanol (10 ml) and the mixture was stirred at ambient temperature overnight. More acetyl chloride (0.5 ml) was added dropwise and the mixture refluxed for 3 h. Solvents were evaporated. Yield: 538 mg (90%); white solid. $^1$H NMR (400 MHz. DMSO-d$_6$): δ 3.81 (s, 3H), 7.67 (d, 3.6 Hz, 1H), 7.80 (d, J 3.6 Hz, 1H), 8.55 (s, 1H). HPLC: R$_T$=3.09 min, 98% (254 nm, 0520A3).

Argon was bubbled through a mixture of intermediate E (897 mg, 1.902 mmol), 5-(methoxycarbonyl)thiophen-2-ylboronic acid (424 mg, 2.28 mmol), potassium carbonate (788 mg, 5.71 mmol) in toluene (10 ml) and MeOH (10 ml). PEPPSI-iPr™ (24 mg, 0.035 mmol) was added and the mixture was heated at 60° C. under argon for 45 min. Water and toluene was added. The aqueous layer was extracted with toluene. Silica gel was added to the combined organic layers and solvents evaporated. The material absorbed on silica gel was applied on a flash column which was eluted with 5-10% EtOAc in toluene. Yield: 840 mg (83%); orange solid. $^1$H NMR (400 MHz, DMSO-d$_6$): δ 3.65 (s, 3H), 3.66 (s, 3H), 3.84 (bs, 5H), 3.88 (s, 2H), 7.10 (d, J 5.2 Hz, 1H), 7.25 (d, J 4.0 Hz, 1H), 7.31 (d, J 4.0 Hz, 1H), 7.43 (d, J 4.0 Hz, 1H), 7.50 (s, 1H), 7.57 (d, J 5.2 Hz, 1H), 7.77 (d, J 4.0 Hz, 1H). HPLC: R$_T$=1.90 min, 99% (254 nm, 6090×3).

NBS (278 mg, 1.56 mmol) was added portion-wise to a solution of the material from above (832 mg, 1.56 mmol) in CHCl$_3$ (5 ml) and acetic acid (5 ml). The mixture was stirred at rt for 3 h. Toluene and silica gel was added to the mixture and solvents evaporated. The material absorbed on silica was applied on a flash column and eluted with 7.5% EtOAc in toluene. Yield: 917 mg (96%); orange solid. $^1$H NMR (400 MHz, DMSO-d$_6$): δ 3.65-3.66 (m, 6H), 3.82-3.87 (m, 7H), 7.24 (s, 1H), 7.26 (d, J 4.0 Hz, 1H), 7.31 (d, J 4.0 Hz, 1H), 7.44 (d, J 4.0 Hz, 1H), 7.50 (s, 1H), 7.77 (d, J 4.0 Hz, 1H).

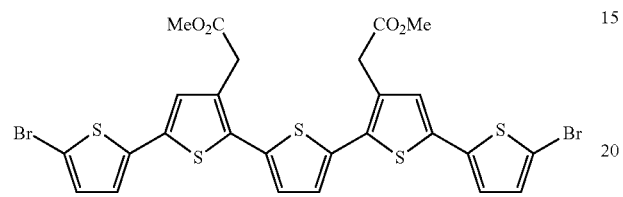

Methyl 2-[5-(5-bromothiophen-2-yl)-2-{5-[5-(5-bromothiophen-2-yl)-3-(2-methoxy-2-oxoethyl)thiophen-2-yl]thiophen-2-yl}thiophen-3-yl]acetate (Intermediate O)

Argon was bubbled through a mixture of intermediate D (2.52 g, 4.58 mmol), 2-thiopheneboronic acid (1.64 g, 11.4 mmol) and K$_2$CO$_3$ (3.16 g, 22.0 mmol) in toluene (50 ml) and MeOH (50 ml). PEPPSI-iPr™ (77 mg, 0.114 mmol) was added and the mixture heated at 60° C. for 45 under argon. Toluene and water was added. The organic layer was concentrated and residue purified by flash chromatography using 1.5-2% EtOAc in toluene as eluent. Yield: 1.86 g (73%); orange solid.

The material from above (570 mg, 1.02 mmol) was dissolved in CHCl$_3$ (20 ml) and AcOH (20 ml). NBS (364 mg, 2.05 mmol) was added portion-wise and stirring continued for 3 d at rt. DCM (50 ml) and water was added. Organic phase washed with water and sat. Na$_2$CO$_3$. Organic layer concentrated. Yield: 707 mg (97%). $^1$H NMR (400 MHz, CDCl$_3$): δ 3.75 (s, 6H), 3.77 (s, 4H), 6.93 (d, J 3.8 Hz, 2H), 6.98 (d, J 3.8 Hz, 2H), 7.06 (s, 2H), 7.18 (s, 2H).

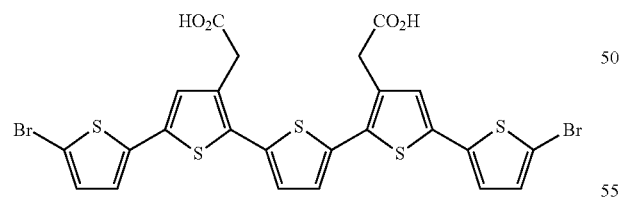

2-[5-(5-bromothiophen-2-yl)-2-{5-[5-(5-bromothiophen-2-yl)-3-(carboxymethyl)thiophen-2-yl]thiophen-2-yl}thiophen-3-yl]acetic acid (Intermediate P)

Intermediate O (707 mg, 0.989 mmol) was dissolved in dioxane (5 ml) and 2 M NaOH (5 ml) was added. The mixture was heated at 80° C. for 1 h and dioxane (10 ml) and 2 M NaOH (10 ml) was added. The mixture was stirred for 1 h at 80° C. Water was added and the mixture acidified using 6 M HCl. The precipitated material was isolated by centrifugation, washed with water and dried at high vacuum overnight. Yield: 679 mg (100%); orange solid. $^1$H NMR (400 MHz, DMSO-d$_6$): δ 3.75 (s, 4H), 7.21 (d, J 3.8 Hz, 2H), 7.25 (d, J 3.8 Hz, 2H), 7.29 (s, 2H), 7.31 (s, 2H),

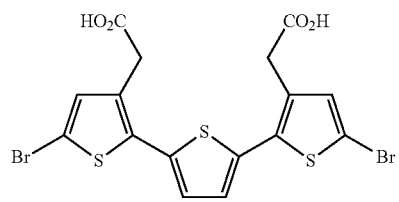 [SMILES: O=C(O)Cc1cc(Br)sc1-c1ccc(-c2sc(Br)cc2CC(=O)O)s1]

2-(5-Bromo-2-{5-[5-bromo-3-(carboxymethyl)thiophen-2-yl]thiophen-2-yl}thiophen-3-yl)acetic acid (Intermediate Q)

Intermediate D (1.10 g, 2.00 mmol) was dissolved in dioxane (5 ml) and 2 M NaOH (5 ml) was added. The mixture was heated at 80° C. for 1 h. 6 M HCl was added and the aqueous mixture extracted with EtOAc. Combined organic layers were dried (MgSO$_4$) and evaporated. Yield: 982 mg (94%); pale yellow solid. $^1$H NMR (400 MHz, DMSO-d$_6$): δ 3.77 (s, 4H), 7.30 (s, 2H), 7.31 (s, 2H).

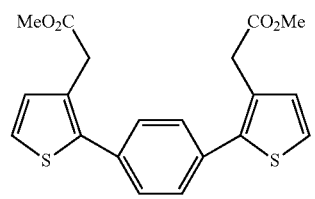 [SMILES: COC(=O)Cc1ccsc1-c1ccc(-c2sccc2CC(=O)OC)cc1]

Methyl 2-(2-{4-[3-(2-methoxy-2-oxoethyl)thiophen-2-yl]phenyl}thiophen-3-yl)acetate (Intermediate R)

Argon was bubbled through a mixture of 1,4-benzenediboronic acid (0.45 g, 2.72 mmol), intermediate B (1.34 g, 5.71 mmol) and K$_2$CO$_3$ (1.18 g, 8.57 mmol) in toluene/MeOH (1:1, 16 ml). After 15 min PEPPSI-iPr™ (57 mg, 0.08 mmol) was added and the mixture heated at 60° C. for 60 min. The reaction mixture was cooled to RT, diluted with Et$_2$O (35 ml), washed with water (40 ml), dried with MgSO$_4$ (s), filtered and evaporated to dryness to obtain the crude product. The crude product was dissolved in hot acetone (15 ml) followed by drop wise addition of iso-hexane (17 ml) and stirred at 4° C. for 20 hrs. The obtained solid was filtered, washed with iso-hexane (6 ml), washed with Et$_2$O (2×7 ml) and dried under vacuum. Yield: 0.48 g (46%); white solid. $^1$H NMR (400 MHz, CDCl$_3$): δ 3.70 (s, 4H), 3.73 (s, 6H), 7.10 (d, J 5.3 Hz, 2H), 7.30 (d, J 5.3 Hz, 2H), 7.53 (s, 4H).

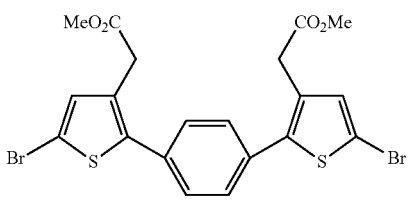 [SMILES: COC(=O)Cc1cc(Br)sc1-c1ccc(-c2sc(Br)cc2CC(=O)OC)cc1]

Methyl 2-(5-bromo-2-{4-[5-bromo-3-(2-methoxy-2-oxoethyl)thiophen-2-yl]phenyl}thiophen-3-yl)acetate (Intermediate S)

Intermediate R (0.48 g, 1.24 mmol) was dissolved in CHCl$_3$ (4.5 ml), acetic acid (4.5 ml) was added and the solution was cooled to 0° C. NBS (0.46 g, 2.54 mmol) was added and the mixture was left to slowly reach ambient temperature. After 16 hrs, the reaction mixture was diluted with CH$_2$Cl$_2$ (20 ml), washed with water (40 ml), dried with MgSO$_4$ (s), filtered and evaporated to dryness to obtain the crude product. The crude product was dissolved in hot EtOAc (15 ml) and stirred at 4° C. for 18 hrs. The obtained solid was filtered, washed with iso-hexane (6 ml), washed with Et$_2$O (6 ml) and dried under vacuum. Yield: 0.54 g (80%); off-white solid. $^1$H NMR (400 MHz, CDCl$_3$): δ 3.62 (s, 4H), 3.74 (s, 6H), 7.07 (s, 2H), 7.47 (s, 4H).

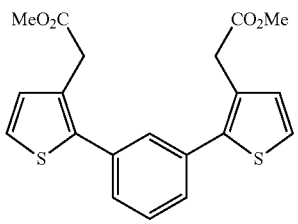 [SMILES: COC(=O)Cc1ccsc1-c1cccc(-c2sccc2CC(=O)OC)c1]

Methyl 2-(2-{3-[3-(2-methoxy-2-oxoethyl)thiophen-2-yl]phenyl}thiophen-3-yl)acetate (Intermediate T)

Argon was bubbled through a mixture of 1,3-benzenediboronic acid (0.38 g, 2.27 mmol), intermediate B (1.17 g, 4.99 mmol) and K$_2$CO$_3$ (1.00 g, 7.26 mmol) in toluene/MeOH (1:1, 12 ml). After 15 min PEPPSI-iPr™ (63 mg, 0.09 mmol) was added and the mixture heated at 60° C. for 60 min. The reaction mixture was cooled to RT, diluted with CH$_2$Cl$_2$ (40 ml), washed with water (40 ml), dried with MgSO$_4$ (s), filtered and evaporated to dryness to obtain the crude product. The residue was purified by flash chromatography using toluene/EtOAc 100:1→50:1→40:1) as eluent. Yield: 0.77 g (87%); yellowish oil. $^1$H NMR (400 MHz, CDCl$_3$): δ 3.70 (s, 10H), 7.09 (d, J 5.3 Hz, 2H), 7.29 (d, J 5.3 Hz, 2H), 7.46-7.48 (m, 3H), 7.57 (m, 1H).

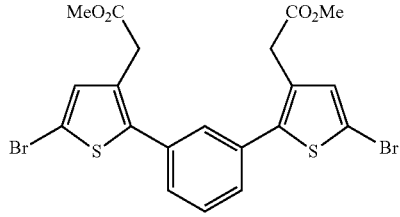 [SMILES: COC(=O)Cc1cc(Br)sc1-c1cccc(-c2sc(Br)cc2CC(=O)OC)c1]

Methyl 2-(5-bromo-2-{3-[5-bromo-3-(2-methoxy-2-oxoethyl)thiophen-2-yl]phenyl}thiophen-3-yl)acetate (Intermediate U)

Intermediate T (0.81 g, 2.10 mmol) was dissolved in CHCl$_3$ (8 ml), acetic acid (8 ml) was added and the solution was cooled to 0° C. NBS (0.77 g, 4.30 mmol) was added and the mixture was left to slowly reach ambient temperature. After 18 hrs, the reaction mixture was diluted with CH$_2$Cl$_2$ (30 ml), washed with water (40 ml), dried with MgSO$_4$ (s), filtered and evaporated to dryness to obtain the crude product. The residue was purified by flash chromatography using toluene/EtOAc 100:1→40:1) as eluent. Yield: 0.94 g (87%); off-white solid. $^1$H NMR (400 MHz, CDCl$_3$): δ 3.61 (s, 4H), 3.72 (s, 6H), 7.06 (s, 2H), 7.41-7.47 (m, 4H).

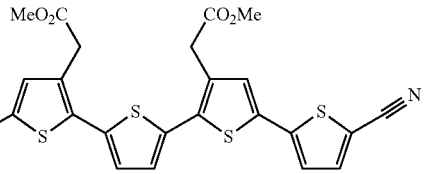

Methyl 2-[5-(5-cyanothiophen-2-yl)-2-{5-[5-(5-cyanothiophen-2-yl)-3-(2-methoxy-2-oxoethyl)thiophen-2-yl]thiophen-2-yl}thiophen-3-yl]acetate (Intermediate V)

Argon was bubbled through a mixture of intermediate D (161 mg, 0.293 mmol), 5-cyanothiophene-2-boronic acid (112 mg, 0.731 mmol) and K$_2$CO$_3$ (122 mg, 0.879 mmol) in toluenen (2 ml) and MeOH (2 ml). PEPPSI-iPr™ (8 mg, 0.0118 mmol) was added and the mixture heated at 70° C. for 10 min in a microwave reactor. Silica was added to the mixture and solvents evaporated. The dry silica was applied on a flash column which was eluted with 5-10% EtOAc in toluene. Yield: 115 mg (64%); bright orange solid. $^1$H NMR (400 MHz, CDCl$_3$): δ 3.77 (s, 6H), 3.80 (s, 4H), 7.14 (d, J 4.0 Hz, 2H), 7.23 (s, 2H), 7.25 (s, 2H), 7.54 (d, J 4.0 Hz, 2H).

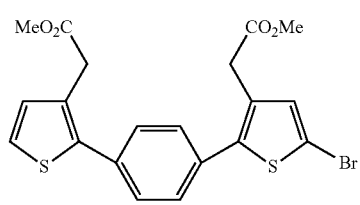 [SMILES: COC(=O)Cc1ccsc1-c1ccc(-c2sc(Br)cc2CC(=O)OC)cc1]

Methyl 2-(2-{4-[5-bromo-3-(2-methoxy-2-oxoethyl)thiophen-2-yl]phenyl}thiophen-3-yl)acetate (Intermediate X)

Intermediate R (1.13 g, 2.92 mmol) was dissolved in CHCl$_3$ (5 ml), acetic acid (5 ml) was added and the solution was cooled to 0° C. NBS (0.53 g, 2.92 mmol) was added and the mixture was left to slowly reach ambient temperature. After 14 hrs, the reaction mixture was diluted with CH$_2$Cl$_2$ (20 ml), washed with water/brine (30:1-60 ml), dried with MgSO$_4$ (s), filtered and evaporated to dryness to obtain the crude product. The residue was purified by flash chromatography using toluene/EtOAc 100:1→40:1) as eluent. Yield: 0.54 g (40%); off-white solid. $^1$H NMR (400 MHz, CDCl$_3$): δ 3.63 (s, 2H), 3.69 (s, 2H), 3.73 (s, 3H), 3.74 (s, 3H), 7.06 (s, 1H), 7.09 (d, J 5.3 Hz, 1H), 7.30 (d, J 5.3 Hz, 1H), 7.45-7.48 (m, 2H), 7.51-7.54 (m, 2H).

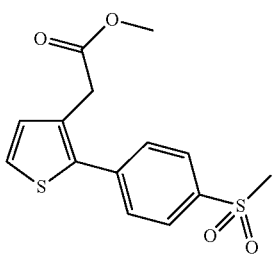 [SMILES: COC(=O)Cc1ccsc1-c1ccc(S(C)(=O)=O)cc1]

Methyl 2-[2-(4-methanesulfonylphenyl)thiophen-3-yl]acetate (Intermediate Y)

Intermediate B (2.30 g, 9.78 mmol), 4-methylsulfonylphenylboronic acid (1.96 g, 9.78 mmol), K$_2$CO$_3$ (4.15 g, 30.0 mmol), tetrakis(triphenylphosphine)palladium(0) (150 mg, 0.130 mmol), MeCN (30 ml) and water (10 ml) were heated at 70° C. for 1 hour. The organic phase was removed in vacuo and the crude material was dissolved in DCM. The mixture was purified by flash chromatography using 30% and 50% EtOAc in iso-hexane as eluent. Yield: 2.25 g (74%); white solid. $^1$H NMR (400 MHz, CDCl$_3$): δ 3.11 (s, 3H), 3.67 (s, 2H), 3.74 (s, 3H), 7.13 (d, J 5.0 Hz, 1H), 7.39 (d, J 5.0 Hz, 1H), 7.67-7.72 (m, 2H), 7.98-8.04 (m, 2H).

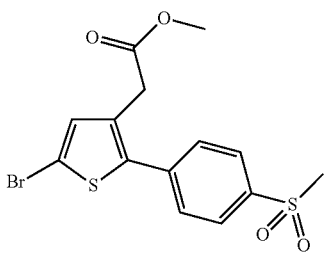 [SMILES: COC(=O)Cc1cc(Br)sc1-c1ccc(S(C)(=O)=O)cc1]

Methyl 2-[5-bromo-2-(4-methanesulfonylphenyl)thiophen-3-yl]acetate (Intermediate Z)

NBS (209 mg, 1.18 mmol) was added in small portions to a stirred solution of Intermediate Y (365 mg, 1.18 mmol) in a mixture of MeOH (10 ml) and chloroform (5 ml) at 0° C. AcOH (0.250 ml) was added and the reaction was stirred at 0° C. for 1 hour then at r.t. for 3 hours. More NBS (35 mg, 0.20 mmol) was added at 0° C. and the reaction was stirred at r.t. over night. A new reaction was also started. NBS (342 mg, 1.92 mmol) was added in small portions to a stirred solution of Intermediate Y (519 mg, 1.67 mmol) in a mixture of MeOH (15 ml) and chloroform (7 ml) at 0° C. AcOH (0.50 ml) was added and the reaction was stirred at r.t. over night.

The two reaction mixtures were combined and the solvents were removed in vacuo. The crude material was dissolved in toluene and the mixture was purified by flash chromatography using 50% EtOAc in iso-hexane as eluent. Yield: 1.03 g (93%); white solid. $^1$H NMR (400 MHz, CDCl$_3$): δ 3.10 (s, 3H), 3.60 (s, 2H), 3.75 (s, 3H), 7.10 (s, 1H), 7.62-7.66 (m, 2H), 7.98-8.03 (m, 2H)

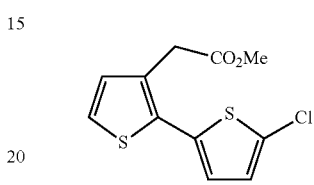

Methyl 2-[2-(5-chlorothiophen-2-yl)thiophen-3-yl]acetate (Intermediate A2)

Argon was bubbled through a mixture of intermediate B (475 mg, 2.02 mmol), 5-chloro-2-thiopheneboronic acid (395 mg, 2.42 mmol) and K$_2$CO$_3$ (838 mg, 6.06 mmol) in toluene (5 ml) and methanol (5 ml). PEPPSI-iPr™ (27 mg, 0.0396 mmol) was added and the mixture heated at 60° C. for 30 min under argon. CHCl$_3$ was added, mixture filtered and concentrated. The residue was purified by flash chromatography using 4% EtOAc in iso-hexane as eluent. Yield: 448 mg (81%); colourless oil. $^1$H NMR (400 MHz, CDCl$_3$): δ 3.72 (s, 5H), 6.89 (d, J 3.8 Hz, 1H), 6.94 (d, J 4.0 Hz, 1H), 7.03 (d, J 5.3 Hz, 1H), 7.25 (d, J 5.3 Hz, 1H).

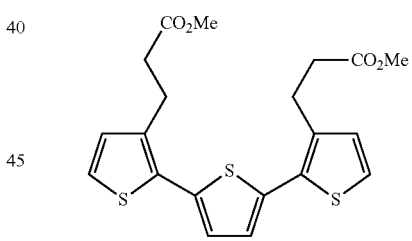

Methyl 3-(2-{5-[3-(3-methoxy-3-oxopropyl)thiophen-2-yl]thiophen-2-yl}thiophen-3-yl)propanoate (Intermediate B2)

10% Pd/C (12.5 g) was added into a solution of trans-3-(3-thienyl)acrylic acid (25.0 g, 16.2 mmol) in methanol (300 ml) and acetic acid (150 ml). The flask was evacuated and flushed with H$_2$. The reaction was stirred for 12 hrs at 50° C. then filtered through Celite. The filtrate was poured into ice water and then extracted with ethyl acetate. The organic extracts were washed with water, sat. NaHCO3, brine, dried with anhydrous Na$_2$SO$_4$, filtered, concentrated in vacuo. Yield: 25.0 g (99%); pale yellow oil.

The material from above (15.6 g, 10 mmol) was dissolved in methanol (200 ml) at 0° C., then thionyl chloride (11.8 g, 10 mmol) was added dropwise to maintain the temperature below 5° C. The reaction was warmed to RT and stirred for 3 hrs. The reaction mixture was poured into ice water and extracted with ethyl acetate. The organic extracts were washed with water, sat. NaHCO$_3$, brine, dried with anhydrous Na$_2$SO$_4$, filtered, concentrated in vacuo. Yield: 17.0 g (100%); oil.

NBS (37.5 g, 21 mmol) was added in small portions into a solution of the material from above (40.0 g, 24 mmol) in chloroform (300 ml) and acetic acid (300 ml) below 5° C. and then the reaction was stirred at RT. The completion of the reaction was indicated by the disappearance of starting material by HPLC. The reaction mixture was concentrated and ice-water was added. The mixture was extracted with dichloromethane and the organic extracts were washed with water, sat. NaHCO3, brine, dried with anhydrous Na$_2$SO$_4$, filtered and concentrated in vacuo. Yield: 52.0 g (87%); pale brown oil.

2,5-Bis(tributylstannyl)thiophene (20.0 g, 30 mmol), the bromide from above (12.5 g, 50 mmol) and toluene (200 ml) were charged into a flask, Pd(PPh$_3$)$_4$ was added and the reaction was stirred for 12 hrs at RT. The reaction mixture was poured in to ice water and extracted with ethyl acetate, washed with water, sat. NaHCO$_3$, brine, dried with anhydrous Na$_2$SO$_4$, filtered, concentrated in vacuo. The residue was purified by flash chromatography (Petroleum ether: Ethyl acetate=10:1). Yield: 2.1 g; yellow oil. $^1$H NMR (300 MHz, CDCl$_3$): δ 7.21 (d, J 5.9 Hz, 2H), 7.09 (s, 2H), 6.95 (d, J 5.9 Hz, 2H), 3.69 (s, 6H), 3.14 (t, J 7.8 Hz, 4H), 2.66 (t, J 7.8 Hz, 4H). MS (ESI, positive): 438.1 [M+NH4]+.

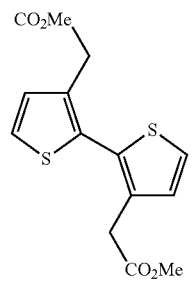

Methyl 2-{2-[3-(2-methoxy-2-oxoethyl)thiophen-2-yl]thiophen-3-yl}acetate (Intermediate D2)

Argon was flushed through a mixture of intermediate B (1.83 g, 7.78 mmol), bispinacolatodiboron (0.989 g, 3.89 mmol) and KF (2.27 g, 39.0 mmol) in toluene (10 ml) and MeOH (10 ml). 1,1'-Bis(diphenylphosphino)ferrocene-palladium(II)dichloride (171 mg, 0.234 mmol) was added and the mixture was heated in a sealed tube at 80° C. for 30 min. Toluene and water were added. The organic phase was concentrated and residue purified by flash chromatography using 15% EtOAc in iso-hexane as eluent. Yield: 591 mg (49%); colourless oil. $^1$H NMR (400 MHz, CDCl$_3$): δ 3.54 (s, 4H), 3.66 (s, 6H), 7.07 (d, J 5.3 Hz, 2H), 7.36 (d, J 5.3 Hz, 2H).

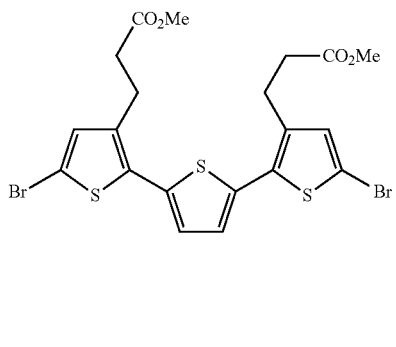 [SMILES: COC(=O)CCc1cc(Br)sc1-c1ccc(-c2sc(Br)cc2CCC(=O)OC)s1]

Methyl 3-(5-bromo-2-{5-[5-bromo-3-(3-methoxy-3-oxopropyl)thiophen-2-yl]thiophen-2-yl}thiophen-3-yl)propanoate (Intermediate C2)

NBS (3.4 g, 19 mmol) was added in small portions into a solution of intermediate B2 (4.2 g, 10 mmol) in chloroform (50 ml) and acetic acid (50 ml) below 5° C. and then the reaction was stirred at RT. The completion of the reaction was indicated by the disappearance of starting material by HPLC. The reaction mixture was concentrated and ice water was added. The mixture was extracted with dichloromethane. The organic extracts were washed with water, sat. NaHCO$_3$, brine, dried with anhydrous Na$_2$SO$_4$, filtered, concentrated in vacuo. The residue was purified by flash chromatography (Petroleum ether:Ethyl acetate=7:1). Yield: 5.3 g (92%); yellow solid. $^1$H NMR (CDCl$_3$, 300 MHz) δ: 7.03 (s, 2H), 6.92 (s, 2H), 3.69 (s, 6H), 3.05 (t, J 7.8 Hz, 4H), 2.61 (t, J 7.8 Hz, 4H). MS (ESI, positive): 595.9 [M+NH4]+.

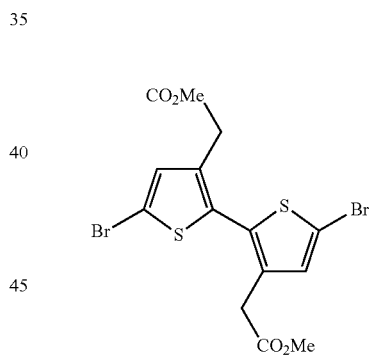

Methyl 2-{5-bromo-2-[5-bromo-3-(2-methoxy-2-oxoethyl)thiophen-2-yl]thiophen-3-yl}acetate (Intermediate E2)

NBS (170 mg, 0.960 mmol) was added portion-wise to a solution of intermediate D2 (149 mg, 0.480 mmol) in AcOH (5 ml) and CHCl$_3$ (5 ml) at ambient temperature. The mixture was stirred overnight, solvents evaporated and residue purified by flash chromatography using 10% EtOAc in iso-hexanes as eluent. Yield: 161 mg (72%); colourless oil. $^1$H NMR (400 MHz, CDCl$_3$): δ 3.49 (s, 4H), 3.68 (s, 6H), 7.04 (s, 2H).

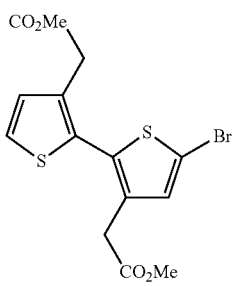 [SMILES: COC(=O)Cc1ccsc1-c1sc(Br)cc1CC(=O)OC]

Methyl 2-{5-bromo-2-[3-(2-methoxy-2-oxoethyl)thiophen-2-yl]thiophen-3-yl}acetate (Intermediate F2)

Br$_2$ (0.022 ml, 0.425 mmol) in DCM (1 ml) was added to a stirred solution of intermediate D2 (132 mg, 0.425 mmol) in DCM (3 ml) at 0° C. The reaction was stirred at this temperature for 15 min. DCM (~10 ml) was added and the mixture was extracted with saturated Na$_2$S$_2$O$_3$ and diluted K$_2$CO$_3$. The organic phase was dried over MgSO$_4$ and removed in vacuo. The crude material was purified by flash chromatography (3% iso-propanol in toluene and with 15% EtOAc in isohexane) Yield: 66 mg (40%); colourless oil. $^1$H NMR (400 MHz, CDCl$_3$): δ 3.50 (s, 2H), 3.57 (s, 2H), 3.69 (s, 6H), 7.07-7.10 (m, 2H), 7.40 (d, 1H).

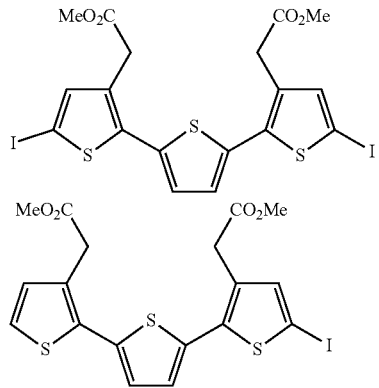

Methyl 2-(5-iodo-2-{5-[5-iodo-3-(2-methoxy-2-oxoethyl)thiophen-2-yl]thiophen-2-yl}thiophen-3-yl)acetate (Intermediate G2) and methyl 2-(5-iodo-2-{5-[3-(2-methoxy-2-oxoethyl)thiophen-2-yl]thiophen-2-yl}thiophen-3-yl)acetate (Intermediate H2)

NIS (2.31 g, 10.3 mmol) was added portion-wise to a solution of intermediate C (4.03 g, 10.3 mmol) in AcOH (15 ml) and CHCl$_3$ (15 ml) at 0° C. The mixture was allowed to slowly reach ambient temperature overnight. DCM and sat. Na$_2$CO$_3$ was added. Organic phase was evaporated and residue purified by flash chromatography using 2% EtOAc in toluene as eluent. First eluted methyl 2-(5-iodo-2-{5-[5-iodo-3-(2-methoxy-2-oxoethyl)thiophen-2-yl]thiophen-2-yl}thiophen-3-yl)acetate (G2). Yield: 1.010 g (15%); yellow oil. $^1$H NMR (400 MHz, CDCl$_3$): δ 3.75 (s, 4H), 3.76 (s, 6H), 7.11 (s, 2H), 7.23 (s, 2H).

Second eluted methyl 2-(5-iodo-2-{5-[3-(2-methoxy-2-oxoethyl)thiophen-2-yl]thiophen-2-yl}thiophen-3-yl)acetate (H2). Yield: 2.368 g (44%); yellow oil. $^1$H NMR (400 MHz, CDCl$_3$): δ 3.75 (s, 3H), 3.76 (s, 3H), 3.76 (s, 2H), 3.80 (s, 2H), 7.08 (d, J 5.3 Hz, 1H), 7.13 (d, J 4.0 Hz, 1H), 7.16 (d, J 4.0 Hz, 1H), 7.23 (s, 1H), 7.29 (d, J 5.3 Hz, 1H)

Synthesis of active compounds (LCOs)

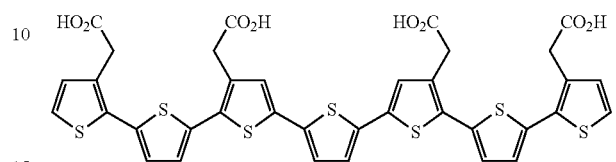

Example 1

2-(2-{5-[3-(Carboxymethyl)-5-{5-[4-(carboxymethyl)-5-{5-[3-(carboxymethyl)thiophen-2-yl]thiophen-2-yl}thiophen-2-yl]thiophen-2-yl}thiophen-2-yl]thiophen-2-yl}thiophen-3-yl)acetic acid (P9707_003)

Nitrogen was bubbled through a mixture of intermediate E (2.00 g, 4.24 mmol) and 2,5-thiophenediboronic acid (346 mg, 2.02 mmol) and K$_2$CO$_3$ (1.67 g, 12.1 mmol) in toluene (50 ml) and MeOH (50 ml). After 10 min PEPPSI-iPr™ (13.7 mg, 0.02 mmol) was added and the mixture heated at 50° C. for 1 h. Water and toluene were added. The aqueous layer was extracted with toluene and DCM. Organic layer was evaporated and residue purified by flash chromatography using 0-5% MeOH in DCM as eluent and a second time using 10-20% EtOAc in toluene as eluent. Yield: 1.22 g (70%); orange solid.

The ester from above (989 mg, 1.14 mmol) was dissolved in dioxane (60 ml) and 2 M NaOH (60 ml) was added. The mixture was stirred at rt for 1 h and at 60° C. for 2 h. The mixture was cooled and conc. HCl was added dropwise (pH 2). The red precipitate was collected by centrifugation and washed several times with water. The material was dried at high vacuum overnight. Yield: 870 mg (94%); dark orange metallic crystals. $^1$H (400 MHz, DMSO-d$_6$): δ 3.74 (s, 4H), 3.77 (s, 4H), 7.11 (d, J 5.4 Hz, 2H), 7.27 (d, J 4.4 Hz, 2H), 7.31 (d, J 4.4 Hz, 2H), 7.33 (s, 2H), 7.35 (s, 2H), 7.55 (d, J 5.4 Hz, 2H). LC-MS: m/z=807 (M−1). HPLC: R$_T$=2.48 min, 95% (254 nm, 10-40% MeCN in 10 mM buffer, 3 min, XBridge) and R$_T$=2.50 min, 95% (400 nm, 10-40% MeCN in 10 mM buffer, 3 min, XBridge).

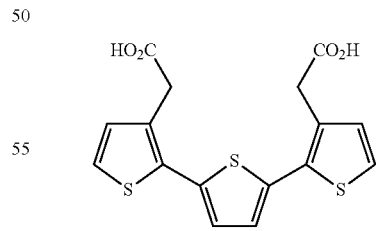

Example 2

2-(2-{5-[3-(Carboxymethyl)thiophen-2-yl]thiophen-2-yl}thiophen-3-yl)acetic acid (P9707_004)

Intermediate C (71 mg, 0.181 mmol) was dissolved in dioxane (2 ml) and 1 M NaOH (0.40 ml) and the mixture was stirred at rt overnight. The mixture was acidified by 1 M HCl and aqueous layer extracted with EtOAc. The organic layer was dried (MgSO₄) and filtered. Yield: 57 mg (87%); yellow soid. $^1$H NMR (400 HMz, DMSO-$d_6$): δ 3.73 (s, 4H), 7.09 (d, J 5.2 Hz, 2H), 7.23 (s, 2H), 7.53 (d, J 5.2 Hz, 2H), 12.52 (s, 2H).

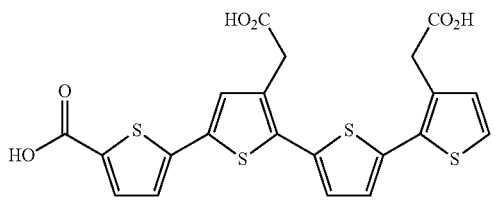 [SMILES: O=C(O)Cc1ccsc1-c1ccc(-c2sc(-c3ccc(C(=O)O)s3)cc2CC(=O)O)s1]

Example 3

5-[4-(Carboxymethyl)-5-{5-[3-(carboxymethyl) thiophen-2-yl]thiophen-2-yl}thiophen-2-yl] thiophene-2-carboxylic acid (P9707_005)

Nitrogen was bubbled through a mixture of intermediate E (172 mg, 0.37 mmol), 5-carboxythiophene-2-boronic acid (94 mg, 0.73 mmol) and K₂CO₃ (202 mg, 1.46 mmol) in toluene (2.5 ml) and MeOH (2.5 ml). PEPPSI-iPr™ (4.96 mg, 0.0073 mmol) was added and the mixture heated at 50° C. for 1 h. Toluene and 1 M HCl was added. The organic layer was separated and evaporated. The crude material was purified by flash chromatography using 2% AcOH in DCM as eluent. Yield: 156 mg. $^1$H NMR (500 MHz, CDCl₃): δ 3.65 (s, 3H), 3.68 (s, 3H), 3.70 (s, 2H), 3.71 (s, 2H), 6.97 (d, J 5.5 Hz, 1H), 7.05 (d, J 4.0 Hz, 1H), 7.09 (d, J 4.0 Hz, 1H), 7.15 (s, 1H), 7.17 (d, J 5.5 Hz, 1H), 7.67 (s, 1H).

The material from above (156 mg, 0.301 mmol) was dissolved in dioxane (10 ml) and 1 M NaOH (10 ml) was added. The mixture was stirred at rt for 2 h. Solid material precipitated upon addition of 1 M HCl which was separated by centrifugation, washed with water and dried at high vacuum to give a quantitative yield of the title compound. $^1$H NMR (400 MHz, DMSO-$d_6$): δ 3.73 (s, 2H), 3.75 (s, 2H), 7.09 (d, 1H), 7.25 (d, 1H), 7.27-7.29 (m, 2H), 7.35 (d, 1H), 7.54 (d, 1H), 7.56 (d, 1H). LC-MS: 489 (M−1).

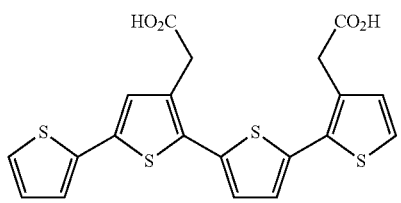 [SMILES: O=C(O)Cc1ccsc1-c1ccc(-c2sc(-c3cccs3)cc2CC(=O)O)s1]

Example 4

2-(2-{5-[3-(Carboxymethyl)thiophen-2-yl]thiophen-2-yl}-5-(thiophen-2-yl)thiophen-3-yl)acetic acid (P9707_006)

Nitrogen was bubbled through a mixture of intermediate E (58 mg, 0.12 mmol), thiophene-2-boronic acid (32 mg, 0.25 mmol) and K₂CO₃ (68 mg, 0.49 mmol) in toluene (2 ml) and MeOH (2 ml). PEPPSI-iPr™ (1.7 mg, 0.0025 mmol) was added and the mixture heated at 50° C. for 1 h under N₂. Solvents were evaporated and residue purified by flash chromatography using DCM. Yield: 58.4 mg.

The material from above (148 mg) was dissolved in dioxane (15 ml) and 1 M NaOH (15 ml) and the mixture was stirred at rt for 2 h. 1 M HCl (25 ml) was added and the precipitated material was separated by centrifugation, washed with water and dried under high vacuum. Yield: 134 mg; yellow solid. $^1$H NMR (400 MHz, DMSO-$d_6$): δ 3.77 (s, 2H), 3.78 (s, 2H), 7.10 (d, 1H), 7.27 (d, 1H), 7.35 (d, 1H), 7.40 (d, 1H), 7.46 (s, 1H), 7.54 (d, 1H). LC-MS: m/z=445 (M−1).

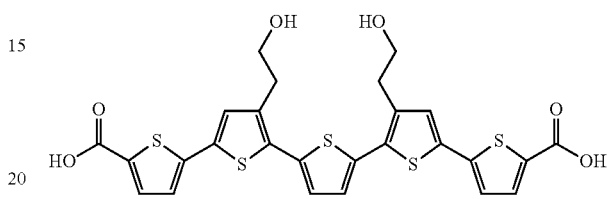

Example 5

5-(5-{5-[5-(5-Carboxythiophen-2-yl)-3-(2-hydroxyethyl)thiophen-2-yl]thiophen-2-yl}-4-(2-hydroxyethyl)thiophen-2-yl)thiophene-2-carboxylic acid (P9707_008)

Nitrogen was bubbled through a mixture of intermediate H (250 mg, 0.506 mmol), 5-carboxythiopheneboronic acid (217 mg, 1.26 mmol) and K₂CO₃ (349 mg, 2.52 mmol) in toluene (10 ml) and MeOH (10 ml). PEPPSI-iPr™ (17 mg, 0.025 mmol) was added and the mixture stirred at 60° C. for 1 h. MeOH (70 ml) was added. The suspension was acidified with 1 M HCl and a red solid precipitated, which was isolated by centrifugation. The solid material was washed with MeOH and water several times. Yield: 277 mg (93%); red solid. LC-MS: m/z=587 (M−1). HPLC: $R_T$=1.47 min, 99% (254 nm, 10-90% MeCN in 10 mM buffer, 3 min, XBridge) and $R_T$=2.13 min, 97% (400 nm, 10-40% MeCN in 10 mM buffer, 3 min, XBridge).

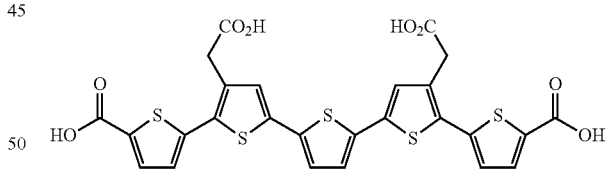

Example 6

5-[3-(Carboxymethyl)-5-{5-[4-(carboxymethyl)-5-(5-carboxythiophen-2-yl)thiophen-2-yl]thiophen-2-yl}thiophen-2-yl]thiophene-2-carboxylic acid (P9707_009)

A mixture of intermediate B (705 mg, 3.00 mmol), 2-carboxythiophene-5-boronic acid (619 mg, 3.60 mmol) and potassium carbonate (1.24 g, 9.00 mmol) in toluene (10 ml) and methanol (10 ml) was degassed by bubbling nitrogen through the mixture. PEPPSI-iPr™ (102 mg, 0.150 mmol) was added and the mixture heated at 60° C. for 45 min under nitrogen. Water and EtOAc were added. The aqueous layer was acidified using 2 M HCl (pH 2). The organic layer was separated and concentrated. The residue was purified by flash chromatography using 5% MeOH+0.1% AcOH in DCM as eluent. Yield: 715 mg (85%); beige solid. HPLC: $R_T$=2.08 min, 92%, 254 nm (1040×3). $^1$H NMR (400 MHz, CDCl$_3$): δ 3.75 (s, 3H), 3.83 (s, 2H), 7.10 (d, J 5.2 Hz, 1H), 7.24 (d, J 4.0 Hz, 1H), 7.35 (d, J 5.2 Hz, 1H), 7.86 (d, J 3.6 Hz, 1H).

Methyl iodide (232 μl, 3.74 mmol) was added to a mixture of the carboxylic acid from above (705 mg, 2.50 mmol) and sodium carbonate (529 mg, 4.99 mmol) in DMF (10 ml). The mixture was stirred at ambient temperature overnight. Water and diethyl ether were added. The aqueous layer was extracted with diethyl ether, The combined organic layers were concentrated and residue purified by flash chromatography using 5-20% EtOAc in iso-hexane. Yield: 364 mg (49%); white solid. HPLC: $R_T$=2.73 min, 99%, 254 nm (1090×3) $^1$H NMR (400 MHz, CDCl$_3$): δ 3.74 (s, 3H), 3.81 (s, 2H), 3.92 (s, 3H), 7.09 (d, J 5.6 Hz, 1H), 7.19 (d, J 4.0 Hz, 1H), 7.32 (d, J 5.2 Hz, 1H), 7.77 (d, J 4.0 Hz, 1H).

NBS (216 mg, 1.21 mmol) was added portionwise to a solution of the ester from above (360 mg, 1.21 mmol) in CHCl$_3$ (5 ml) and AcOH (5 ml). The mixture was stirred at ambient overnight. DCM and water was added. The organic layer was washed with sat. NaHCO$_3$ and concentrated. The residue was purified by flash chromatography using 15-20% EtOAc in iso-hexane as eluent. Yield: 349 mg (77%); white solid. HPLC: $R_T$=2.21 min, 98%, (254 nm, 4090A3) and $R_T$=3.04 min, 99%, 254 nm (1090A3). $^1$H NMR (400 MHz, CDCl$_3$): δ 3.74 (s, 2H), 3.76 (s, 3H), 3.92 (s, 3H), 7.07 (s, 1H), 7.14 (d, J 3.6 Hz, 1H), 7.76 (d, J 4.0 Hz, 1H).

Argon was bubbled through a mixture of the bromide from above (342 mg, 0.911 mmol), 2,5-thiophenediboronic acid (78 mg, 0.455 mmol) and K$_2$CO$_3$ (314 mg, 2.27 mmol) in toluene (8 ml) and MeOH (8 ml). PEPPSI-iPr™ (15 mg, 0.0228 mmol) was added and the mixture heated at 60° C. for 45 min under argon. Orange material precipitated during the reaction. Water and CHCl$_3$ were added. The organic layer was separated and silica was added to the mixture and the solvents were evaporated. The dry silica was applied on a flash column and eluted with 0-3% MeOH in DCM. Yield: 230 mg (75%); orange solid.

The ester from above (180 mg, 0.268 mmol) was suspended in dioxane (5 ml) and 1 M NaOH (10 ml). The mixture was stirred at rt overnight. 1 M NaOH (5 ml) was added and the mixture heated at 80° C. for 4 h. The solution was transferred to Falcon tubes, and 1 M HCl (20 ml) was added. The precipitate was isolated by centrifugation, and washed three times with water. The solid was dried under high vacuum overnight. Yield: 143 mg (87%); red solid. $^1$H NMR (400 MHz. DMSO-d$_6$): δ 3.79 (s, 4H), 7.31 (d, J 3.8 Hz, 2H), 7.38 (s, 2H), 7.39 (s, 2H), 7.74 (d, J 3.8 Hz, 2H). HPLC: $R_T$=2.36 min, 91% (254 nm, 0520×3). LC-MS: m/z=615 (M−1).

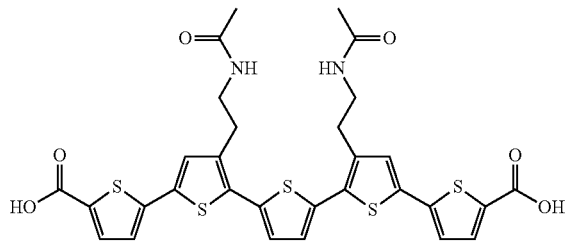 [SMILES: CC(=O)NCCc1cc(-c2ccc(C(=O)O)s2)sc1-c1ccc(-c2sc(-c3ccc(C(=O)O)s3)cc2CCNC(C)=O)s1]

Example 7

5-(5-{5-[5-(5-Carboxythiophen-2-yl)-3-(2-acetamidoethyl)thiophen-2-yl]thiophen-2-yl}-4-(2-acetamidoethyl)thiophene-2-carboxylic acid (P9707_010)

Intermediate M (165 mg, 0.185 mmol) was dissolved in DCM (2 ml) and TFA (2 ml) was added. The mixture was stirred at rt for 3 h. Solvents were evaporated. The crude mixture was suspended in DCM (10 ml). Et$_3$N (201 μl, 1.45 mmol) and acetyl chloride (52 μl, 0.726 mmol) was added. The mixture was stirred at rt for 2 h, solvent evaporated and residual purified by flash chromatography using 0-5% MeOH in DCM as eluent. Yield: 73 mg (68%); yellow solid. $^1$H NMR (400 MHz, CDCl$_3$): δ 1.96 (s, 6H), 2.98 (m, 4H), 3.47 (m, 4H), 6.68 (br s, 2H), 6.95 (s, 2H), 7.02 (s, 2H).

The dibromide (73 mg, 0.126 mmol) from above was dissolved in toluene (2 ml) and MeOH (2 ml). 5-Carboxythiophene-2-boronic acid (54.4 mg, 0.317 mmol) and K$_2$CO$_3$ (110 mg, 0.792 mmol) were added. The suspension was degassed by bubbling argon through the mixture. PEPPSI-iPr™ (ca. 2 mg) was added and the mixture heated at 60° C. for 1 h. MeOH (20 ml) and 1 M HCl (4 ml) was added. Solid material was isolated by centrifugation, washed with water and dried. Yield: 78 mg (92%); orange solid. HPLC: $R_T$=2.07 min, 96% (254 nm, 10-40% MeCN in 10 mM buffer, 3 min, XBridge) and $R_T$=2.09 min, 97% (400 nm, 10-40% MeCN in 10 mM buffer, 3 min, XBridge)

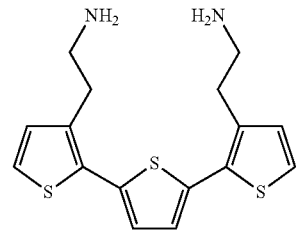 [SMILES: NCCc1ccsc1-c1ccc(-c2sccc2CCN)s1]

Example 8

2-(2-{5-[3-(2-Aminoethyl)thiophen-2-yl]thiophen-2-yl}thiophen-3-yl)ethan-1-amine (P9707_011)

Intermediate L (208 mg, 0.283 mmol) was dissolved DCM (2 ml) and TFA (2 ml) was added. The mixture was stirred at rt for 1 h. Solvents evaporated and residue dissolved in water. The solution was added 1 M NaOH (2 ml) and the aqueous layer extracted with CHCl$_3$. The combined organic layers were dried (MgSO$_4$) and 1.2 M HCl in EtOH (2 ml) was added. Solvents were evaporated to give the HCl-salt of the title compound. Yield: 105 mg (99%); yellow-orange solid. HPLC: $R_T$=2.68 min, 95% (254 nm, 10-40% MeCN in 0.1% TFA, 3 min, ACE) and $R_T$=2.68 min, 94% (350 nm, 10-40% MeCN in 0.1% TFA, 3 min, ACE). $^1$H NMR (400 MHz, DMSO-d$_6$): δ 3.06 (br s, 12H), 7.14 (d, J 5.2 Hz, 2H), 7.27 (s, 2H), 7.58 (d, J 5.2 Hz, 2H). LC-MS: m/z=335 (M+1).

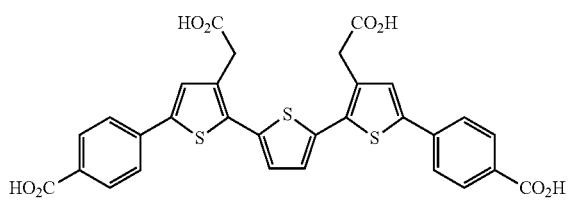 [SMILES: O=C(O)Cc1cc(-c2ccc(C(=O)O)cc2)sc1-c1ccc(-c2sc(-c3ccc(C(=O)O)cc3)cc2CC(=O)O)s1]

Example 9

4-[4-(Carboxymethyl)-5-{5-[3-(carboxymethyl)-5-(4-carboxyphenyl)thiophen-2-yl]thiophen-2-yl}thiophen-2-yl]benzoic acid (P9707_012)

Argon was bubbled through a mixture of intermediate D (100 mg, 0.188 mmol), 4-methoxycarbonylphenylboronic acid (82 mg, 0.454 mmol) and $K_2CO_3$ (100 mg, 0.728 mmol) in toluene (2 ml) and MeOH (2 ml). PEPPSI-iPr™ (ca 2 mg) was added and the tube sealed and heated in a microwave reactor at 100° C. for 15 min. $CHCl_3$ was added and the mixture filtered and concentrated. The residue was purified by flash chromatography using 0-1% MeOH in DCM. Yield: 96.1 mg (80%); orange solid. $^1$H NMR (400 MHz, DMSO-$d_6$): δ 3.69 (s, 6H), 3.88 (s, 6H), 3.91 (s, 4H), 7.36 (s, 2H), 7.69 (s, 2H), 7.82 (d, J 8.4 Hz, 4H), 8.01 (d, J 8.4 Hz, 4H). HPLC: $R_T$=2.77 min, 92% (350 nm, 60-90% MeCN in 10 mM buffer, 3 min, XBridge).

The ester from above (94 mg, 0.142 mmol) was dissolved in dioxane (2 ml) and 2 M NaOH (2 ml) was added. The mixture was heated at 140° C. for 10 min in a microwave reactor. Aqueous phase was acidified using 6 M HCl, precipitate isolated by centrifugation and washed twice with water. The material was dried under high vacuum for 2 d. Yield: 44 mg (51%); yellow-orange solid. $^1$H NMR (DMSO-$d_6$): δ 3.81 (s, 4H), 7.37 (s, 2H), 7.67 (s, 2H), 7.80 (d, J 8 Hz, 4H), 8.00 (d, J 8 Hz, 4H). HPLC: HPLC: $R_T$=1.88 min, 93% (254 nm, 5-20% MeCN in 10 mM buffer, 3 min, XBridge) and $R_T$=1.93 min, 94% (400 nm, 5-20% MeCN in 10 mM buffer, 3 min, XBridge). LC-MS: m/z=603 (M−1)

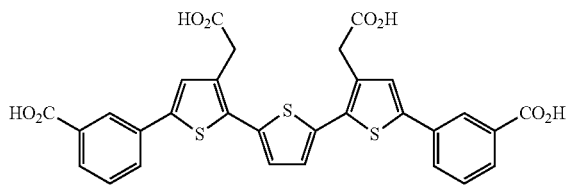 [SMILES: O=C(O)Cc1cc(-c2cccc(C(=O)O)c2)sc1-c1ccc(-c2sc(-c3cccc(C(=O)O)c3)cc2CC(=O)O)s1]

Example 10

3-[4-(Carboxymethyl)-5-{5-[3-(carboxymethyl)-5-(3-carboxyphenyl)thiophen-2-yl]thiophen-2-yl}thiophen-2-yl]benzoic acid (P9707_013)

Argon was bubbled through a mixture of intermediate D (168 mg, 0.305 mmol), 3-carboxybenzeneboronic acid (127 mg, 0.763 mmol) and $K_2CO_3$ in toluene (2.5 ml) and MeOH (2.5 ml). PEPPSI-iPr™ (ca 2 mg) was added to the degassed mixture and the mixture heated at 100° C. for 10 min in a microwave reactor. Solvents were evaporated and the crude material dissolved in dioxane (2.5 ml) and 2 M NaOH (2.5 ml). The mixture was stirred at rt overnight. Organic layer was removed and aqueous layer acidified by addition of 6 M HCl. Solid material was isolated by centrifugation and dissolved in 1 M $Na_2CO_3$ and purified by preparative HPLC (Xterra 19×50 mm, 5-20% MeCN in 50 mM $NH_4HCO_3$ buffer). Pure fractions were collected and amount of solvents reduced. The wanted product was precipitated by addition of 1 M HCl, isolated by centrifugation and washed with water. The material was dried at high vacuum for 3 d. Yield: 69 mg (38%, two steps); yellow solid. $^1$H NMR (400 MHz, MeOD-$d_4$): δ 3.84 (s, 4H), 7.31 (s, 2H), 7.47 (s, 2H), 7.53 (d, J 7.8 Hz, 2H)$_m$ 7.89 (d, J 8.3 Hz, 2H), 7.94-7.98 (m, 2H), 8.26-8.29 (m, 2H). LC-MS: m/z=622 (M+$NH_4^+$).

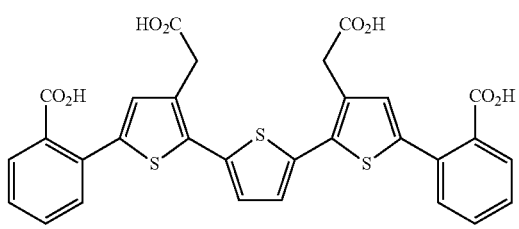 [SMILES: O=C(O)Cc1cc(-c2ccccc2C(=O)O)sc1-c1ccc(-c2sc(-c3ccccc3C(=O)O)cc2CC(=O)O)s1]

Example 11

2-[4-(Carboxymethyl)-5-{5-[3-(carboxymethyl)-5-(2-carboxyphenyl)thiophen-2-yl]thiophen-2-yl}thiophen-2-yl]benzoic acid (P9707_014)

Argon was bubbled through a mixture of intermediate D (152 mg, 0.276 mmol), 2-methoxycarboxyphenylboronic acid (138 mg, 0.690 mmol) and $K_2CO_3$ (190 mg, 1.38 mmol) in toluene (4 ml) and MeOH (4 ml). PEPPSI-iPr™ (15 mg) was added and the mixture was heated in a microwave reactor at 70° C. for 15 min. Solvent evaporated and residue purified by flash chromatography using 10-15% EtOAc in toluene as eluent. Yield: 124 mg (68%); orange-yellow solid. $^1$H NMR (400 MHz, $CDCl_3$): δ 3.75-3.81 (m, 16H), 6.99 (s, 2H)), 7.19 (s, 2H), 7.40-7.43 (m, 2H), 7.50-7.52 (m, 4H), 7.73 (d, J 7.3 Hz, 2H). The ester (124 mg, 0.187 mmol) was dissolved in dioxane (5 ml) and 2 M NaOH (5 ml) was added. The mixture was stirred at rt for 3 h and at 80° C. for 1 h. EtOAc was added and organic layer removed. The aqueous layer was acidified using 6 M HCl. Solid material was isolated by centrifugation, washed with 0.1 M HCl (three times) and dried at high vacuum for 2 d. Yield: 105 mg (93%); yellow solid. $^1$H NMR (400 MHz, methanol-$d_6$): δ 3.79 (s, 4H), 7.10 (s, 2H), 7.27 (s, 2H), 7.44-7.47 (m, 2H), 7.50-7.59 (m, 4H), 7.72 (d, J 7.5 Hz, 2H). HPLC: Rt=2.67 min, 97% at 254 nm (5-20% MeCN in buffer, XBridge) and Rt=2.59 min. 97% at 400 nm (5-20% MeCN in buffer, XBridge). LC-MS: m/z=622 (M+$NH_4^+$)

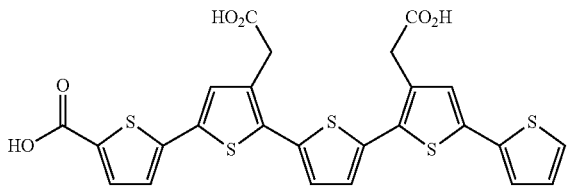 [SMILES: O=C(O)Cc1cc(-c2cccs2)sc1-c1ccc(-c2sc(-c3ccc(C(=O)O)s3)cc2CC(=O)O)s1]

Example 12

5-[4-(Carboxymethyl)-5-{5-[3-(carboxymethyl)-5-(thiophen-2-yl)thiophen-2-yl]thiophen-2-yl}thiophen-2-yl]thiophene-2-carboxylic acid (P9707_015)

Argon was bubbled through a mixture of intermediate N (162 mg, 0.26 mmol), 2-thiopheneboronic acid (51 mg, 0.397 mmol) and $K_2CO_3$ (91 mg, 0.660 mmol) in toluene (4 ml) and MeOH (4 ml). PEPPSI-iPr™ (5 mg) was added and the mixture stirred at 60⁺C for 45 min. Silica was added and solvents evaporated. The dry silica was applied on a flash column and product eluted using 10% EtOAc in toluene. Yield: 154 mg (95%); orange solid. The material from above was dissolved in dioxane (5 ml) and 2 M NaOH (5 ml) was added. The mixture was heated at 100° C. for 45 min. EtOAc was added and organic layer removed. The aqueous layer was acidified by addition of 6 M HCl and precipitated material isolated by centrifugation. The material was dissolved in 1 M $Na_2CO_3$ and purified by preparative hplc (10-40% MeCN in 50 mM buffer, big XBridge). Pure fractions were combined and amount of solvents was reduced. The product was precipitated by addition of 6 M HCl and isolated by centrifugation. The material was washed with water and dried at high vacuum for 2 d. Yield: 72 mg (50%); orange solid. $^1$H NMR (400 MHz, DMSO-$d_6$): δ 3.76 (s, 2H), 3.78 (s, 2H), 7.12 (dd, J 5.1 Hz, 3.6 Hz), 7.29 (s, 1H), 7.32 (d, J 3.8 Hz, 1H), 7.34 (d, J 3.8 Hz, 1H), 7.36 (dd, J 3.6 Hz, 1.1 Hz), 7.40 (d, J 3.8 Hz, 1H), 7.47 (s, 1H), 7.57 (dd, J 5.1 Hz, 1.1 Hz, 1H), 7.68 (d, J 4.0 Hz, 1H), 12.43-12.99 (m, 3H). HPLC: Rt=2.18 min, 98% at 254 nm (10-40% MeCN in buffer, XBridge). Rt=2.16 min. 98% at 400 nm (10-40% MeCN in buffer, XBridge). LC-MS: m/z=590 (M+$NH_4^+$)

was isolated by preparative hplc (10-35% MeCN in 50 mM buffer, big XBridge). Pure fractions were combined and amount of solvents reduced and solid material precipitated by addition of 6 M HCl. Solid material was isolated by centrifugation, washed with water and dried under high vacuum for 2 d. Yield: 65 mg (36%); red shiny solid. $^1$H NMR (400 MHz, DMSO-$d_6$): δ 3.80 (s, 2H), 3.81 (s, 2H), 7.37 (s, 2H), 7.42 (d, J 3.8 Hz, 1H), 7.49 (s, 1H), 7.62 (dd, J 7.8, 5.0 Hz, 1H), 7.69 (d, J 3.8 Hz, 1H), 7.71 (s, 1H), 8.24 (d, J 8.0 Hz, 1H), 8.60 (dd, J 4.9 Hz, 1.4 Hz, 1H), 9.00 (J 2.3 Hz, 1H). HPLC: Rt=1.67 min, 98% at 254 nm (10-40% MeCN in buffer, XBridge) Rt=1.68 min. 97% at 400 nm (10-40% MeCN in buffer, XBridge). LC-MS: m/z=568 (M+1).

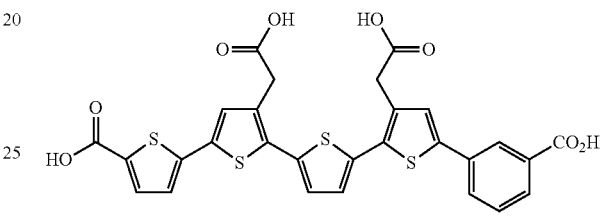

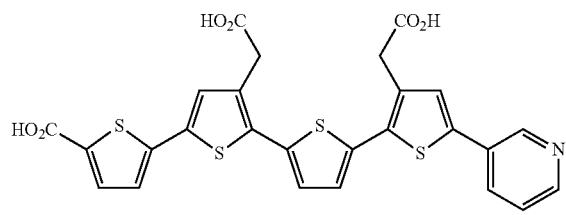 [SMILES: O=C(O)Cc1cc(-c2cccnc2)sc1-c1ccc(-c2sc(-c3ccc(C(=O)O)s3)cc2CC(=O)O)s1]

Example 13

5-[4-(Carboxymethyl)-5-{5-[3-(carboxymethyl)-5-(pyridin-3-yl)thiophen-2-yl]thiophen-2-yl}thiophen-2-yl]thiophene-2-carboxylic acid (P9707_016)

Intermediate N (700 mg, 1.14 mmol) was dissolved in dioxane (5 ml) and 2 M NaOH (5 ml) was added. The mixture was heated at 100° C. for 30 min. EtOAc was added and organic layer removed. Aqueous phase was acidified using 6 M HCl and precipitated material isolated by centrifugation and washed with water, the dried at high vacuum for 2 d.

The crude material from above (170 mg, 0.298 mmol) was dissolved in MeOH (6 ml) and toluene (4 ml). Pyridine-3-boronic acid (74 mg, 0.597 mmol) and $K_2CO_3$ (206 mg, 1.49 mmol) were added. The mixture was degassed by bubbling argon through the mixture. PEPPSI-iPr™ (22 mg, 0.0323 mmol) was added, and the mixture heated in a microwave reactor at 100° C. for 30 min. Solvents were evaporated and residue dissolved in 1 M $Na_2CO_3$ and filtered. The product

Example 14

5-[4-(Carboxymethyl)-5-{5-[3-(carboxymethyl)-5-(3-carboxyphenyl)thiophen-2-yl]thiophen-2-yl}thiophen-2-yl]thiophene-2-carboxylic acid (P9707_017)

Intermediate N (700 mg, 1.14 mmol) was dissolved in dioxane (5 ml) and 2 M NaOH (5 ml) was added. The mixture was heated at 100° C. for 30 min. EtOAc was added and organic layer removed. Aqueous phase was acidified using 6 M HCl and precipitated material isolated by centrifugation and washed with water, then dried at high vacuum for 2 d.

The crude material from above (166 mg, 0.291 mmol) was dissolved in MeOH (6 ml) and toluene (4 ml). 3-Carboxybenzeneboronic acid (97 mg, 0.583 mmol) and $K_2CO_3$(201 mg, 1.46 mmol) was added and the mixture was degassed by bubbling argon through the mixture. PEPPSI-iPr™ (15 mg, 0.022 mmol) was added and mixture heated at 100° C. for 30 min in a microwave reactor. Solvents were evaporated and residue dissolved in 1 M $Na_2CO_3$, filtered and purified by preparative hplc (5-25% MeCN in 50 mM buffer, XBridge). Pure fractions were combined and amount of solvents reduced. The wanted product precipitated by addition of 6 M HCl, separated by centrifugation, washed with water and dried at high vacuum for 2 d. Yield: 54.6 mg (31%); deep red solid with metallic shine. $^1$H NMR (400 MHz, DMSO-$d_6$): δ 3.80 (s, 2H), 3.80 (s, 2H), 7.36 (s, 2H), 7.41 (d, J 3.8 Hz, 1H), 7.48 (s, 1H), 7.59 (t, J 7.8 z, 1H), 7.63 (s, 1H), 7.69 (s, J 3.8 Hz, 1H), 7.86-7.99 (m, 2H), 8.14-8.18 (m, 1H). HPLC: $R_t$=2.36 min, 98% at 254 nm (5-20% MeCN in buffer, XBridge) and $R_t$=2.36 min. 98% at 400 nm (5-20% MeCN in buffer, XBridge). LC-MS: m/z=628 (M+$NH_4$

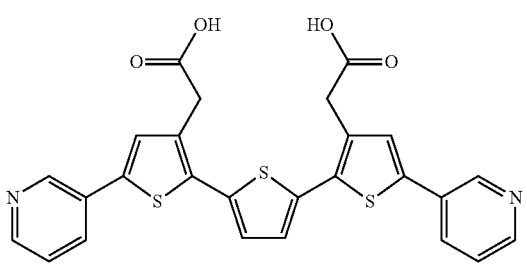 [SMILES: O=C(O)Cc1cc(-c2cccnc2)sc1-c1ccc(-c2sc(-c3cccnc3)cc2CC(=O)O)s1]

Example 15

2-(2-{5-[3-(Carboxymethyl)-5-(pyridin-3-yl) thiophen-2-yl]thiophen-2-yl}-5-(pyridin-3-yl) thiophen-3-yl)acetic acid (P9707_018)

Argon was bubbled through a mixture of intermediate D (156 mg, 0.283 mmol), pyridine-3-boronic acid (87 mg, 0.708 mmol) and potassium carbonate (196 mg, 1.417 mmol) in toluene (2.5 ml) and MeOH (2.5 ml). PEPPSI-iPr™ (10 mg, 0.283 mmol) was added and the mixture heated at 100° C. for 10 min in a microwave reactor. TLC indicated not full conversion. Silica was added and solvents evaporated. The material was purified twice by flash chromatography using 5% and 3% MeOH in DCM as eluents. Yield: 39.3 mg (25%); yellow solid. $^1$H NMR (400 MHz, CDCl$_3$): δ 3.77 (s, 6H), 3.84 (s, 4H), 7.24 (s, 2H), 7.33-7.34 (m, 2H), 7.34 (s, 2H), 7.87 (dt, J 8.0 Hz, 1.9 Hz, 2H), 8.54 (dd, J 4.8, 1.2 Hz, 1H), 8.88 (d, J 1.8 Hz, 1H).

The material from above (39 mg, 0.071 mmol) was dissolved in dioxane (3 ml) and 2 M NaOH (3 ml) was added. The mixture was stirred at rt for 4 h and heated at 60° C. for 1 h. EtOAc was added and organic layer removed. The aqueous layer was adjusted to pH 3 by addition of 1 M HCl. The solid material was isolated by centrifugation, washed with water and dried at high vacuum for 5 d. Yield: 38 mg; orange/yellow solid. HPLC: Rt=2.38 min, 95% at 254 nm (10-40% MeCN in buffer, XBridge) and Rt=2.35 min. 95% at 400 nm (10-40% MeCN in buffer, XBridge). MS: m/z=519 (M+1).

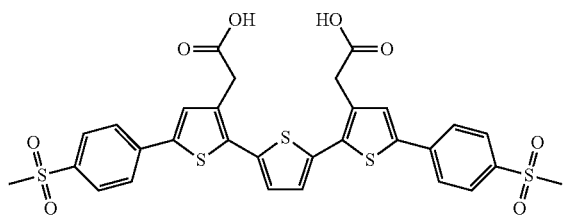

Example 16

2-(2-{5-[3-(Carboxymethyl)-5-(4-methanesulfonylphenyl)thiophen-2-yl]thiophen-2-yl}-5-(4-methanesulfonylphenyl)thiophen-3-yl)acetic acid (P9707_019)

Argon was bubbled through a mixture of intermediate D (165 mg, 0.300 mmol), 4-methylsulfonylphenylboronic acid (150 mg, 0.750 mmol) and K$_2$CO$_3$ (207 mg, 1.50 mmol) in toluene (5 ml) and MeOH (5 ml). PEPPSI-iPr™ (10 mg, 0.0147 mmol) was added and the mixture heated at 80° C. for 30 min in a microwave reactor. Silica gel was added and solvents evaporated. The dry silica was applied on a flash column and product eluted using toluene/EtOAc 2:1 and 1:1. Yield: 191 mg (91%); orange solid.

The material from above (188 mg, 0.268 mmol) was dissolved in dioxane (3 ml) and 2 M NaOH (3 ml) was added. The mixture was heated at 50° C. for 2 h before 6 M HCl was added (0.5 ml). The precipitate was washed several times with water and MeOH and dried at high vacuum for 3 d. Yield: 100 mg (55%); orange solid. $^1$H NMR (400 MHz, CDCl$_3$): δ 3.26 (s, 6H), 3.82 (s, 4H), 7.24 (s, 2H), 7.40 (s, 2H), 7.74 (s, 2H), 7.91-8.00 (m, 8H). HPLC: Rt=2.75 min, 91% at 254 nm (10-40% MeCN in buffer, XBridge) and Rt=2.74 min. 92% at 400 nm (10-40% MeCN in buffer, XBridge). LC-MS: m/z=690 (M+NH$_4^+$)

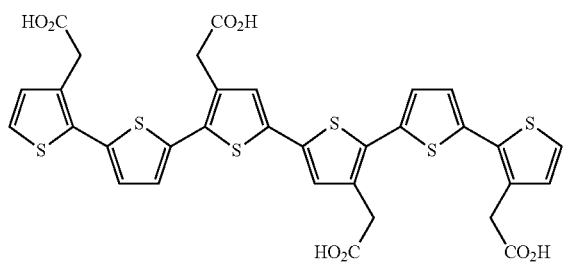 [SMILES: O=C(O)Cc1ccsc1-c1ccc(-c2sc(-c3cc(CC(=O)O)c(-c4ccc(-c5sccc5CC(=O)O)s4)s3)cc2CC(=O)O)s1]

Example 17

2-(2-{5-[3-(Carboxymethyl)-5-[4-(carboxymethyl)-5-{5-[3-(carboxymethyl)thiophen-2-yl]thiophen-2-yl}thiophen-2-yl]thiophen-2-yl]thiophen-2-yl}thiophen-3-yl)acetic acid (P9707_020)

Kosher's reagent (35 mg, 0.089 mmol) was added to a solution of intermediate C (350 mg, 0.892 mmol) and N-iodosuccinimide (180 mg, 0.803 mmol) in MeOH (20 ml). The mixture was stirred at rt for 1.5 h before DCM and water was added. The organic phase was washed with 5% Na$_2$S$_2$O$_3$ and concentrated. The residue was purified by flash chromatography using 1-2% EtOAc in toluene and a second time using DCM/CHCl$_3$ 2:1 as eluent. Yield: 138 mg (30%); colourless oil. $^1$H NMR (400 MHz, CDCl$_3$): δ 3.73 (s, 3H), 3.73 (s, 3H), 3.74 (s, 2H), 3.78 (s, 2H), 7.06 (d, J 5 Hz, 1H), 7.10 (d, J 4 Hz, 1H), 7.13 (d, J 4 Hz, 1H), 7.21 (s, 1H), 7.26 (d, J 5 Hz, 1H).

The iodide from above (137 mg, 0.264 mmol) in toluene (5 ml) was added palladium acetate (3 mg, 0.0133 mmol), tetrabutylammonium bromide (43 mg, 0.132 mmol) and diisopropylethylamine (46 µl, 0.264 mmol). The mixture was heated at 105° C. for 4 h. The material was applied on a flash column which was eluted with 5-15% EtOAc in toluene. Yield: 48.6 mg (47%); orange oil. $^1$H NMR (400 MHz, CDCl$_3$): δ 3.74 (s, 6H), 3.75 (s, 6H), 3.78 (s, 4H), 3.80 (s, 4H), 7.06 (d, J 5 Hz, 2H), 7.13 (s, 2H), 7.16-7.19 (m 4H), 7.25-7.28 (m, 2H). The ester from above (48 mg, 0.061 mmol) was dissolved in dioxane (2 ml) and 2 M NaOH (2 ml) was added. The mixture was heated at 80° C. for 1 h. Water and 6 M HCl was added. The precipitated was isolated by centrifugation, washed with water and dried at high vacuum for 2 d. Yield: 35.8 mg (81%); orange solid. $^1$H NMR (400 MHz, DMSO-d$_6$): δ 3.74 (s, 4H), 3.77 (s, 4H), 7.10 (d, J 5.3 Hz, 2H), 7.27 (d, J 4.0 Hz, 2H), 7.32 (d, J 4.0 Hz, 2H), 7.33 (s, 2H), 7.54 (d, J 5.0 Hz, 2H). HPLC: Rt=2.01 min, 85% at 254 nm (10-40%

MeCN in buffer, XBridge) and Rt=2.01 min. 93% at 400 nm (10-40% MeCN in buffer, XBridge). LC-MS: m/z=744 (M+NH$_4^+$)

gation, washed with water and dried at high vacuum for 3 d. Yield: 59.2 mg (46%); red solid. $^1$H NMR (400 MHz, DMSO-d$_6$): δ 3.79 (s, 4H), 7.34 (s, 2H), 7.39 (s, 2H), 7.45 (d, J 3.8 Hz,

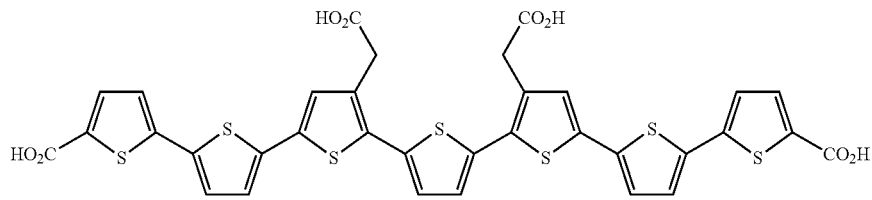 [SMILES: O=C(O)Cc1cc(-c2ccc(-c3ccc(C(=O)O)s3)s2)sc1-c1ccc(-c2sc(-c3ccc(-c4ccc(C(=O)O)s4)s3)cc2CC(=O)O)s1]

Example 18

5-{5-[4-(Carboxymethyl)-5-{5-[3-(carboxymethyl)-5-[5-(5-carboxythiophen-2-yl)thiophen-2-yl]thiophen-2-yl]thiophen-2-yl}thiophen-2-yl]thiophen-2-yl}thiophene-2-carboxylic acid (P9707_021)

Argon was bubbled through a mixture of intermediate P (102 mg, 0.149 mmol), 2-carboxythiophene-5-boronic acid (64 mg, 0.371 mmol) and K$_2$CO$_3$ (103 mg, 0.75 mmol) in MeOH (8 ml) and toluene (6 ml). PEPPSI-iPr™ (5 mg, 0.0073 mg) was added and mixture heated at 100° C. for 30 min in microwave reactor. Solvents were evaporated, residue dissolved in 1 M Na$_2$CO$_3$ and purified by preparative hplc (10-40% MeCN in 50 mM buffer, Xterra). Pure fractions were combined. Some solvents evaporated and 6 M HCl added. The solid material was separated by centrifugation, washed with water and dried at high vacuum for 2 d. Yield: 25.2 mg (22%); red solid. $^1$H NMR (400 MHz, DMSO-d$_6$): δ 3.78 (s, 4H), 7.33 (s, 2H), 7.38-7.43 (m, 6H), 7.49 (d, J 3.8 Hz, 2H), 7.67 (d, J 3.8 Hz, 2H). HPLC: Rt=2.06 min, 99% at 254 nm (10-40% MeCN in buffer, XBridge) and Rt=2.04 min, 98% at 400 nm (10-40% MeCN in buffer, XBridge). LC-MS: m/z=798 (M+NH$_4^+$)

2H), 7.70 (d, J 4.0 Hz, 2H), 7.82 (d, J 8.5 Hz, 4H), 7.98 (d, J 8.5 Hz, 4H. HPLC: Rt=2.08 min, 96% at 254 nm (10-40% MeCN in buffer, XBridge) and Rt=2.07 min. 98% at 400 nm (10-40% MeCN in buffer, XBridge). LC-MS: m/z=786 (M+NH$_4^+$).

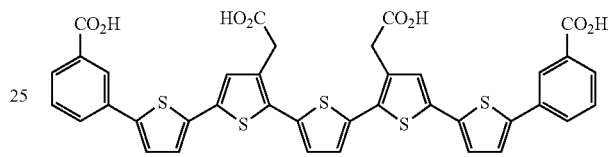

Example 20

3-{5-[4-(Carboxymethyl)-5-{5-[3-(carboxymethyl)-5-[5-(3-carboxyphenyl)thiophen-2-yl]thiophen-2-yl]thiophen-2-yl}thiophen-2-yl]thiophen-2-yl}benzoic acid (P9707_023)

Argon was bubbled through a mixture of intermediate P (128 mg, 0.186 mmol), 3-carboxybenzeneboronic acid (77

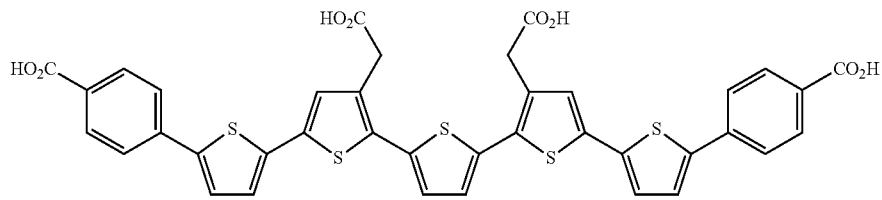 [SMILES: O=C(O)Cc1cc(-c2ccc(-c3ccc(C(=O)O)cc3)s2)sc1-c1ccc(-c2sc(-c3ccc(-c4ccc(C(=O)O)cc4)s3)cc2CC(=O)O)s1]

Example 19

4-{5-[4-(Carboxymethyl)-5-{5-[3-(carboxymethyl)-5-[5-(4-carboxyphenyl)thiophen-2-yl]thiothiophen-2-yl]thiophen-2-yl}thiophen-2-yl]thiophen-2-yl}benzoic acid (P9707_022)

Argon was bubbled through a mixture of intermediate P (125 mg, 0.168 mmol), 4-carboxyphenylboronic acid (69 mg, 0.419 mmol) and K$_2$CO$_3$ (196 mg, 1.18 mmol) in MeOH (8 ml) and toluene (6 ml), PEPPSI-iPr™ (5 mg, 0.0073 mg) was added and mixture heated at 100° C. for 30 min in microwave reactor. Solvents were evaporated. residue dissolved in 1 M Na$_2$CO$_3$ and purified by preparative hplc (10-40% MeCN in 50 mM buffer, XBridge). Pure fractions were combined and some solvents evaporated. Solid material precipitated by addition of 6 M HCl. The material was isolated by centrifumg, 0.466 mmol), K$_2$CO$_3$ (180 mg, 1.30 mmol) in MeOH (8 ml) and toluene (6 ml). PEPPSI-iPr™ (5 mg, 0.0073 mg) was added and mixture heated at 100° C. for 30 min in a microwave reactor. Solvents were evaporated, residue dissolved in 1 M Na$_2$CO$_3$ and purified by preparative hplc (10-40% MeCN in 50 mM buffer, XBridge). Yield: 62 mg (43%); red solid. $^1$H NMR (400 MHz, DMSO-d$_6$): δ 3.79 (s, 4H), 7.33 (s, 2H), 7.38 (s, 2H), 7.42 (d, J 3.8 Hz, 2H), 7.58 (t, J 7.9 Hz, 2H), 7.64 (d, J 4.0 Hz, 2H), 7.85-7.91 (m, 2H), 7.94-8.00 (m 2H), 8.17 (t, J 1.6 Hz, 2H). HPLC: Rt=2.35 min, 99% at 254 nm (10-40% MeCN in buffer, XBridge) and Rt=2.36 min. 97% at 400 nm (10-40% MeCN in buffer, XBridge). LC-MS: m/z=786 (M+NH$_4^+$)

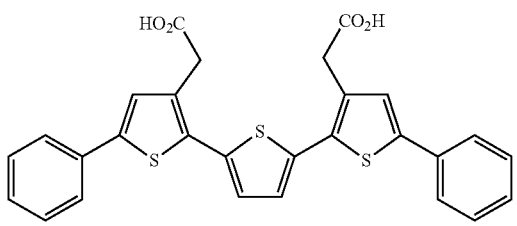 [SMILES: O=C(O)Cc1cc(-c2ccccc2)sc1-c1ccc(-c2sc(-c3ccccc3)cc2CC(=O)O)s1]

Example 21

2-(2-{5-[3-(Carboxymethyl)-5-phenylthiophen-2-yl]thiophen-2-yl}-5-phenylthiophen-3-yl)acetic acid
(P9707_024)

Argon was bubbled through a mixture of intermediate Q (123 mg, 0.236 mmol), benzeneboronic acid (72 mg, 0.589 mmol) and $K_2CO_3$ (195 mg, 1.41 mmol) in MeOH (2 ml) and toluene (2 ml). PEPPSI-iPr™ (15 mg, 0.022 mmol) was added and the mixture was heated at 90° C. for 30 min in a microwave reactor. Solvents were evaporated and residue dissolved in 0.5 M $Na_2CO_3$/MeOH and purified by preparative hplc (20-50% MeCN in 50 mM buffer, XBridge). Pure fractions were combined and some solvents were evaporated. 6 M HCl was added and precipitated material collected by centrifugation, washed with water and dried at high vacuum Yield: 22.7 mg (19%); yellow solid. $^1$H NMR (400 MHz, DMSO-$d_6$): δ 3.79 (s, 4H), 7.33 (s, 2H), 7.33-7.38 (m, 2H), 7.41-7.48 (m, 4H), 7.51 (s, 2H), 7.65-7.71 (m, 4H). HPLC: Rt=2.64 min, 99% at 254 nm (20-50% MeCN in buffer, XBridge) and Rt=2.64 min. 99% at 400 nm (20-50% MeCN in buffer, XBridge). LC-MS: m/z=534 (M+NH$_4^+$).

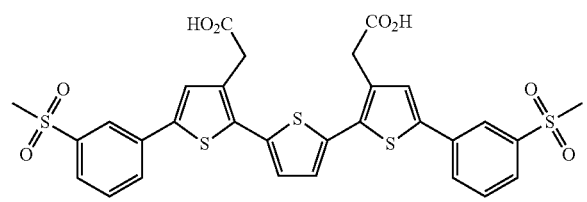

Example 22

2-(2-{5-[3-(Carboxymethyl)-5-(3-methanesulfonylphenyl)thiophen-2-yl]thiophen-2-yl}-5-(3-methanesulfonylphenyl)thiophen-3-yl)acetic acid
(P9707_025)

Argon was bubbled through a mixture of intermediate Q (123 mg, 0.236 mmol), 3-(methylsulfonyl)phenylboronic acid (118 mg, 0.589 mmol) and $K_2CO_3$ (196 mg, 1.41 mmol) in MeOH (2 ml) and toluene (2 ml). PEPPSI™ (15 mg, 0.0221 mmol) was added and the mixture heated at 90° C. for 30 min in a microwave reactor. Solvents were evaporated, residue dissolved in 0.5 M $Na_2CO_3$/water/MeOH and purified by preparative hplc (15-45% MeCN in 50 mM buffer). Pure fractions were combined and solid material precipitated using 6 M HCl. The precipitate was isolated by centrifugation, washed with water and dried at high vacuum for 2 d. Yield: 68.5 mg (43%); red solid. $^1$H NMR (400 MHz, DMSO-$d_6$): δ 3.33 (s, 6H), 3.82 (s, 4H), 7.39 (s, 2H), 7.68-7.77 (m, 4H), 7.88 (d, J=8.3 Hz, 2H), 7.99-8.04 (m, 2H), 8.16 (t, J=1.76H, 2H). HPLC: Rt=2.83 min, 96% at 254 nm (10-40% MeCN in buffer, XBridge) and Rt=2.83 min. 95% at 400 nm (10-40% MeCN in buffer, XBridge). LC-MS: m/z=690 (M+NH$_4^+$)

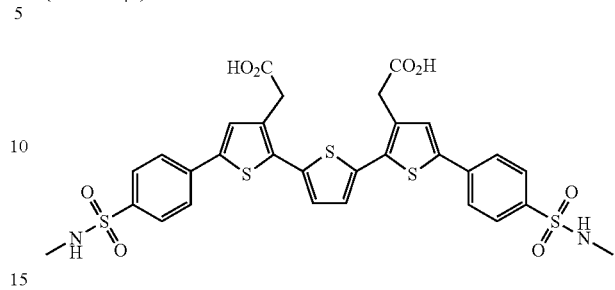

Example 23

2-(2-{5-[3-(Carboxymethyl)-5-[4-(methylsulfamoyl)phenyl]thiophen-2-yl]thiophen-2-yl}-5-[4-(methylsulfamoyl)phenyl]thiophen-3-yl)acetic acid
(P9707_026)

Argon was bubbled through a mixture of intermediate Q (123 mg, 0.236 mmol), methyl 4-boronobenzene sulfonamide (127 mg, 0.589 mmol) and $K_2CO_3$ (195 mg, 1.41 mmol) in MeOH (2 ml) and toluene (2 ml). PEPPSI-iPr™ (15 mg, 0.0221 mmol) was added and the mixture heated at 90° C. for 30 min in a microwave reactor. Solvents were evaporated, residue dissolved in 0.2 M $Na_2CO_3$ and purified by preparative hplc (15-45% MeCN in 50 mM buffer, XBridge). Pure fractions were combined, some solvents evaporated and 6 M HCl added. Precipitate was isolated by centrifugation, washed with water and dried at high vacuum for 2 d. Yield: 45.3 mg (27%); yellow solid. HPLC: Rt=2.83 min, 97% at 254 nm (10-40% MeCN in buffer, XBridge) and Rt=2.83 min. 98% at 400 nm (10-40% MeCN in buffer, XBridge). LC-MS: m/z=720 (M+NH$_4^+$).

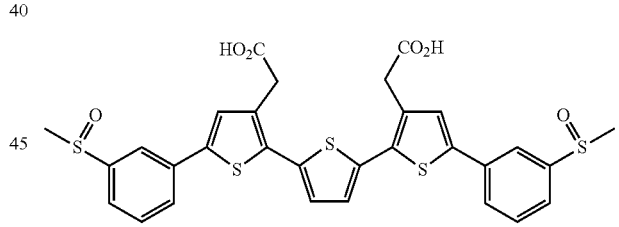

Example 24

2-(2-{5-[3-(Carboxymethyl)-5-(3-methanesulfinylphenyl)thiophen-2-yl]thiophen-2-yl}-5-(3-methanesulfinylphenyl)thiophen-3-yl)acetic acid
(P9707_027)

Argon was bubbled through a mixture of intermediate Q (123 mg, 0.236 mmol), 3-methylsulfinylphenylboronic acid (109 mg, 0.589 mmol) and $K_2CO_3$ (195 mg, 1.41 mmol) in MeOH (2 ml) and toluene (2 ml) PEPPSI-iPr™ (15 mg, 0.0221 mmol) was added and the mixture heated at 90° C. for 30 min in a microwave reactor. Solvents were evaporated, residue dissolved in 0.5 M $Na_2CO_3$/water and purified by preparative hplc (10-40% MeCN in 50 mM buffer, XBridge). Yield: 48.1 mg (32%); yellow solid. $^1$H NMR (400 MHz, DMSO-$d_6$): δ 2.82 (s, 6H), 3.80 (s, 4H), 7.37 (s, 2H), 7.62-

7.65 (m, 6H), 7.81 (m, 2H), 7.95 (d, J 1.0 Hz, 2H). HPLC: Rt=2.44 min, 99% at 254 nm (10-40% MeCN in buffer, XBridge) and Rt=2.44 min. 99% at 400 nm (10-40% MeCN in buffer, XBridge). LC-MS: m/z=641 (M+1).

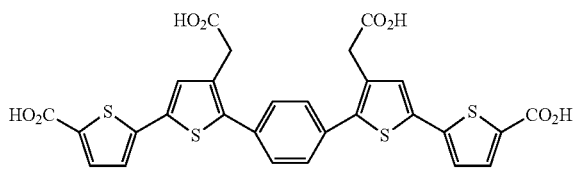 [SMILES: O=C(O)Cc1cc(-c2ccc(C(=O)O)s2)sc1-c1ccc(-c2sc(-c3ccc(C(=O)O)s3)cc2CC(=O)O)cc1]

Example 25

5-[4-(Carboxymethyl)-5-{4-[3-(carboxymethyl)-5-(5-carboxythiophen-2-yl)thiophen-2-yl]phenyl}thiophen-2-yl]thiophene-2-carboxylic acid (P9707_028)

Argon was bubbled through a mixture of intermediate S (202 mg, 0.37 mmol), 2-carboxythiophene-5-boronic acid (160 mg, 0.93 mmol) and K$_2$CO$_3$ (184 mg, 1.33 mmol) in toluene/MeOH (1:1, 5 ml). After 15 min, PEPPSI-iPr™ (10 mg, 0.014 mmol) was added and the mixture heated to 70° C. After 30 min, the reaction mixture was cooled to RT and evaporated to dryness. The residue was purified by flash chromatography using CHCl$_3$/MeOH (containing 1% Et$_3$N) 9:1→6:1) as eluent. Yield: 90 mg (38%); green solid. $^1$H NMR (400 MHz, DMSO-d$_6$, Et$_3$N-salt): δ 3.68 (s, 4H), 3.75 (s, 6H), 7.12 (d, J 4 Hz, 2H), 7.19 (s, 2H), 7.49 (d, J 4 Hz, 2H), 7.55 (s, 4H).

The ester from above (84 mg, 0.13 mmol) was dissolved in dioxane (4 ml) and 2 M NaOH (4 ml) was added. After 18 hrs at RT, the reaction mixture was diluted with water (15 ml) and acidified using 1 M HCl (approx. 12 ml). The formed precipitate was isolated by centrifugation and washed three times with water. The material was dried under high vacuum for 2 d. Yield: 47 mg (59%); yellow-green solid. $^1$H NMR (DMSO-d$_6$): δ 3.69 (s, 4H), 7.40 (d, J 4 Hz, 2H), 7.49 (s, 2H), 7.63 (s, 4H), 7.70 (d, J 4 Hz, 2H). HPLC: R$_T$=2.11 min, 98% (254 nm, 5-20% MeCN in 10 mM buffer, 3 min, XBridge) and R$_T$=2.08 min, 98% (400 nm, 5-20% MeCN in 10 mM buffer, 3 min, XBridge). LC-MS: m/z=609 (M−1).

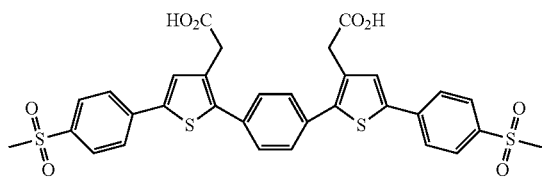

Example 26

2-(2-{4-[3-(Carboxymethyl)-5-(4-methanesulfonylphenyl)thiophen-2-yl]phenyl}-5-(4-methanesulfonylphenyl)thiophen-3-yl)acetic acid (P9707_029)

Argon was bubbled through a mixture of intermediate S (172 mg, 0.32 mmol), 4-methylsulfonylphenylboronic acid (170 mg, 0.85 mmol) and K$_2$CO$_3$ (162 mg, 1.17 mmol) in toluene/MeOH/DMF (2:1:1, 6 ml). After 15 min, PEPPSI-iPr™ (9 mg, 0.013 mmol) was added and the mixture heated to 65° C. After 45 min, the reaction mixture was cooled to RT and evaporated to dryness, the residue was dissolved in CH$_2$Cl$_2$ (40 ml), washed with water (40 ml) and evaporated to dryness. The residue was purified by flash chromatography using CHCl$_3$/MeOH 9:1→6:1) as eluent. Yield: 99 mg (45%); green solid. $^1$H NMR (400 MHz, DMSO-d$_6$): δ 3.26 (s, 6H), 3.66 (s, 6H), 3.83 (s, 4H), 7.65 (s, 4H), 7.73 (s, 2H), 7.94 (d, J 12 Hz, 4H), 7.98 (d, J 12 Hz, 4H).

The ester from above (87 mg, 0.13 mmol) was dissolved in dioxane (4 ml) and 2 M NaOH (4 ml) was added. After 18 hrs at RT, the reaction mixture was diluted with water (15 ml) and acidified using 1 M HCl (approx. 12 ml). The formed precipitate was isolated by centrifugation and washed three times with water. The material was dried under high vacuum for 2 d. Yield: 52 mg (62%); off-white solid. $^1$H NMR (DMSO-d$_6$): 3.26 (s, 6H), 3.73 (s, 4H), 7.68 (s, 4H), 7.74 (s, 2H), 7.95 (d, J 8 Hz, 4H), 7.98 (d, J 8 Hz, 4H). HPLC: R$_T$=2.81 min, 97% (254 nm, 10-40% MeCN in 10 mM buffer, 3 min, XBridge) and R$_T$=2.81 min, 100% (400 nm, 10-40% MeCN in 10 mM buffer, 3 min, XBridge). LC-MS: m/z=665 (M−1).

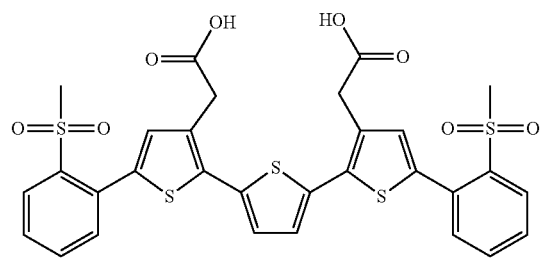 [SMILES: CS(=O)(=O)c1ccccc1-c1cc(CC(=O)O)c(-c2ccc(-c3sc(-c4ccccc4S(C)(=O)=O)cc3CC(=O)O)s2)s1]

Example 27

2-(2-{5-[3-(Carboxymethyl)-5-(2-methanesulfonylphenyl)thiophen-2-yl]thiophen-2-yl}-5-(2-methanesulfonylphenyl)thiophen-3-yl)acetic acid (P9707_030)

Argon was bubbled through a mixture of intermediate D (115 mg, 0.209 mmol), 2-(methylsulfonylphenyl)boronic acid (105 mg, 0.523 mmol) and K$_2$CO$_3$ (115 mg, 0.836 mmol) in MeOH (4 ml) and toluene (4 ml). PEPPSI-iPr™ (10 mg, 0.0147 mmol) was added and the mixture heated at 60° C. for 3 h under argon. Solvents were evaporated and residue purified by flash chromatography using 10-20% EtOAc as eluent. Yield: 108 mg (74%); slightly yellow oil. $^1$H NMR (400 MHz, CDCl$_3$): 2.89 (s, 6H), 3.76 (s, 6H), 3.85 (s, 4H), 7.22 (s, 2H), 7.47 (s, 2H), 7.54-7.67 (m, 6H), 8.23-8.31 (m, 2H).

The material from above (108 mg, 0.154 mmol) was dissolved in dioxane (3 ml) and 2 M NaOH (3 ml) was added. The mixture was heated at 80° C. for 3 h before 6 M HCl was added and yellow precipitate isolated by centrifugation, washed and dried at high vacuum for 3 d. Yield: 100.3 mg (97%); pale yellow solid. $^1$H NMR (400 MHz, DMSO-d$_6$): δ 3.05 (s, 6H), 3.81 (s, 4H), 7.36 (s, 2H), 7.37 (s, 2H), 7.66 (dd, J 7.6 Hz, 1.1 Hz, 2H), 7.69-7.76 (m, 2H), 7.79 (dd, J 7.5 Hz, 1.5 Hz, 2H), 8.14 (dd, J 7.9 Hz, 1.4 Hz, 2H). HPLC: Rt=2.91 min, 97% at 254 nm (10-40% MeCN in buffer, XBridge) and Rt=2.90 min. 95% at 400 nm (10-40% MeCN in buffer, XBridge). LC-MS: m/z=690 (M+NH$_4^+$).

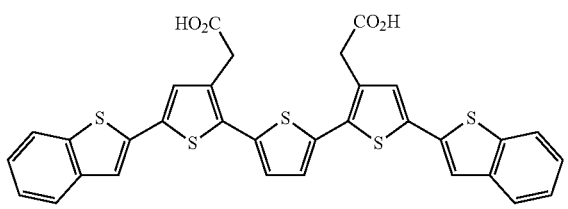 [SMILES: O=C(O)Cc1cc(-c2cc3ccccc3s2)sc1-c1ccc(-c2sc(-c3cc4ccccc4s3)cc2CC(=O)O)s1]

Example 28

2-[5-(1-benzothiophen-2-yl)-2-{5-[5-(1-benzothiophen-2-yl)-3-(carboxymethyl)thiophen-2-yl]thiophen-2-yl}thiophen-3-yl]acetic acid (P9707_031)

Argon was bubbled though a mixture of intermediate D (115 mg, 0.209 mmol), benzo[b]thiophene-2-boronic acid (93 mg, 0.522 mmol) and $K_2CO_3$ (115 mg, 0.832 mmol) in toluene (4 ml) and MeOH (4 ml). PEPPSI-iPr™ (10 mg, 0.0147 mmol) was added and the mixture heated at 60° C. for 20 min. Solvents were evaporated and residue purified by flash chromatography using 2% EtOAc in toluene as eluent. Yield: 105 mg (76%); yellow solid. $^1$H NMR (400 MHz, CDCl$_3$): δ 3.78 (s, 6H), 3.81 (s, 4H), 7.23 (s, 2H), 7.25 (s, 2H), 7.31-7.35 (m, 4H), 7.41 (s, 2H), 7.33-7.80 (m, 4H).

The ester from above (105 mg, 0.160 mmol) was dissolved in dioxane (3 ml) and 2 M NaOH (3 ml) was added. The mixture was heated at 80° C. for 3 h. 6 M HCl (ca 2 ml) was added and the precipitate isolated by centrifugation, washed several times with water and dried at high vacuum. Yield: 81 mg (81%). $^1$H NMR (400 MHz, DMSO-d$_6$): δ 3.75 (s, 4H), 7.37-7.41 (m, 6H), 7.42 (s, 2H), 7.69 (s, 2H), 7.80-7.85 (m, 2H), 7.96-7.98 (m, 2H).

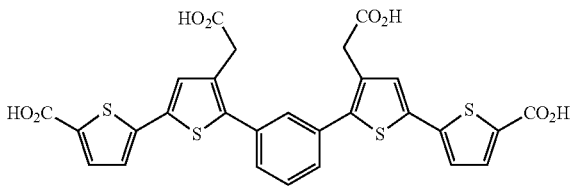 [SMILES: O=C(O)Cc1cc(-c2ccc(C(=O)O)s2)sc1-c1cccc(-c2sc(-c3ccc(C(=O)O)s3)cc2CC(=O)O)c1]

Example 29

5-[4-(Carboxymethyl)-5-{3-[3-(carboxymethyl)-5-(5-carboxythiophen-2-yl)thiophen-2-yl]phenyl}thiophen-2-yl]thiophene-2-carboxylic acid (P9707_032)

Argon was bubbled through a mixture of intermediate U (162 mg, 0.30 mmol), 2-carboxythiophene-5-boronic acid (133 mg, 0.77 mmol) and $K_2CO_3$ (144 mg, 1.04 mmol) in toluene/MeOH (1:1, 4 ml). After 15 min, PEPPSI-iPr™ (10 mg, 0.015 mmol) was added and the mixture heated to 45° C. After 2.5 hrs, the reaction mixture was cooled to RT and evaporated to dryness. The residue was purified by flash chromatography using CHCl$_3$/MeOH (containing 0.5% Et$_3$N) 9:1→5:1) as eluent. Yield: 138 mg (72%); yellow solid. $^1$H NMR (400 MHz, MeOH-d$_4$, Et$_3$N-salt): δ 3.73 (s, 6H), 3.75 (s, 4H), 7.24 (d, J 4 Hz, 2H), 7.31 (s, 2H), 7.54-7.57 (m, 5H), 7.63 (m, 1H).

The ester from above (98 mg, 0.15 mmol) was dissolved in dioxane (2.5 ml) and 2 M NaOH (2.5 ml) was added. After 18 hrs at RT, the reaction mixture was diluted with water (15 ml) and acidified using 1 M HCl (approx. 13 ml). The formed precipitate was isolated by centrifugation and washed three times with water. The material was dried under high vacuum for 2 d. Yield: 68 mg (72%); yellow solid. $^1$H NMR (DMSO-d$_6$): δ 3.67 (s, 4H), 7.39 (d, J 4 Hz, 2H), 7.48 (s, 2H), 7.54-7.57 (m, 2H), 7.61-7.65 (m, 2H), 7.69 (d, J 4 Hz, 2H), 12.96 (bs, 4H). HPLC: $R_T$=2.26 min, 100% (254 nm, 5-20% MeCN in 10 mM buffer, 3 min, XBridge) and $R_T$=2.27 min, 100% (400 nm, 5-20% MeCN in 10 mM buffer, 3 min, XBridge). LC-MS: m/z=628 (M+NH$_4^+$).

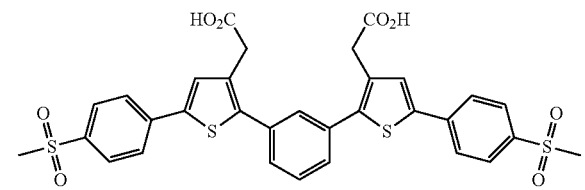

Example 30

2-(2-{3-[3-(Carboxymethyl)-5-(4-methanesulfonylphenyl)thiophen-2-yl]phenyl}-5-(4-methanesulfonylphenyl)thiophen-3-yl)acetic acid (P9707_033)

Argon was bubbled through a mixture of intermediate U (185 mg, 0.34 mmol), 4-methylsulfonylphenylboronic acid (176 mg, 0.88 mmol) and $K_2CO_3$ (162 mg, 1.17 mmol) in toluene/MeOH (1:1, 4 ml). After 15 min, PEPPSI-iPr™ (10 mg, 0.014 mmol) was added and the mixture heated to 50° C. After 1.5 hrs, the reaction mixture was cooled to RT, diluted with CH$_2$Cl$_2$ (20 ml), washed with water (40 ml) and evaporated to dryness. The residue was purified by flash chromatography using toluene/EtOAc 3:1→2:1→1:1) as eluent. Yield: 202 mg (86%); off-white solid. $^1$H NMR (400 MHz, CDCl$_3$): δ 3.09 (s, 6H), 3.75 (s, 10H), 7.47 (s, 2H), 7.55-7.56 (m, 3H), 7.67 (m, 1H), 7.79 (d, J 8 Hz, 4H), 7.96 (d, J 8 Hz, 4H).

The ester from above (200 mg, 0.29 mmol) was dissolved in dioxane (2.5 ml) and 2 M NaOH (2.5 ml) was added. After 18 hrs at RT, the reaction mixture was diluted with water (15 ml) and acidified using 1 M HCl (approx. 13 ml). The formed precipitate was isolated by centrifugation and washed three times with water. The material was dried under high vacuum for 2 d. Yield: 133 mg (69%); off-white solid. $^1$H NMR (DMSO-d$_6$): δ 3.26 (s, 6H), 3.71 (s, 4H), 7.58-7.69 (m, 4H), 7.74 (s, 2H), 7.95 (d, J 8 Hz, 4H), 7.98 (d, J 8 Hz, 4H), 12.63 (bs, 2H). HPLC: $R_T$=2.66 min, 99% (254 nm, 10-40% MeCN in 10 mM buffer, 3 min, XBridge) and $R_T$=2.65 min, 70% (400 nm, 10-40% MeCN in 10 mM buffer, 3 min, XBridge). LC-MS: m/z=684 (M+NH$_4^+$).

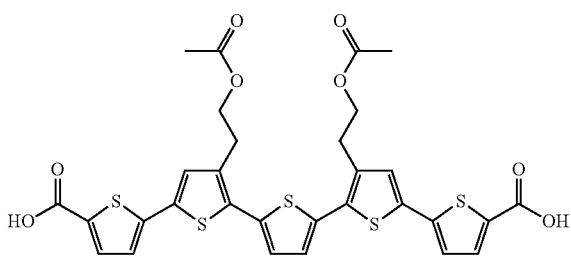 [SMILES: CC(=O)OCCc1cc(-c2ccc(C(=O)O)s2)sc1-c1ccc(-c2sc(-c3ccc(C(=O)O)s3)cc2CCOC(C)=O)s1]

Example 31

5-{4-[2-(Acetyloxy)ethyl]-5-(5-{3-[2-(acetyloxy)ethyl]-5-(5-carboxythiophen-2-yl)thiophen-2-yl}thiophen-2-yl)thiophen-2-yl}thiophene-2-carboxylic acid (P9707_034)

Nitrogen was bubbled through a mixture of intermediate H (250 mg, 0.506 mmol), 5-carboxythiopheneboronic acid (217 mg, 1.26 mmol) and $K_2CO_3$ (349 mg, 2.52 mmol) in toluene (10 ml) and MeOH (10 ml). PEPPSI-iPr™ (17 mg, 0.025 mmol) was added and the mixture stirred at 60° C. for 1 h. MeOH (70 ml) was added. The suspension was acidified 1 M HCl and a red solid precipitated, which was isolated by centrifugation. The solid material was washed with MeOH and water several times. Yield: 277 mg (93%); red solid. LC-MS: m/z=587 (M−1). HPLC: $R_T$=1.47 min, 99% (254 nm, 10-90% MeCN in 10 mM buffer, 3 min, XBridge) and $R_T$=2.13 min, 97% (400 nm, 10-40% MeCN in 10 mM buffer, 3 min, XBridge).

The diol above (60 mg, 0.10 mmol) was dissolved in pyridine (2 ml), cooled to 0° C. followed by addition of $Ac_2O$ (2 ml). After 16 hrs, the reaction mixture was evaporated to dryness, dissolved in $H_2O$/$NaHCO_3$ (sat.) (9:1, 10 ml) and acidified using 1 M HCl (approx. 15 ml). The formed precipitate was isolated by centrifugation and washed three times with water. Yield: 39 mg (57%); dark red solid. $^1$H NMR (DMSO-$d_6$): δ 1.98 (s, 6H), 3.09 (t, J 8 Hz, 4H), 4.32 (t, J 8 Hz, 4H), 7.36 (s, 2H), 7.38 (d, J 4 Hz, 2H), 7.51 (s, 2H), 7.66 (d, J 4 Hz, 2H). HPLC: $R_T$=2.87 min, 100% (254 nm, 10-40% MeCN in 10 mM buffer, 3 min, XBridge) and $R_T$=2.89 min, 100% (400 nm, 10-40% MeCN in 10 mM buffer, 3 min, XBridge). LC-MS: m/z=690 (M+$NH_4^+$).

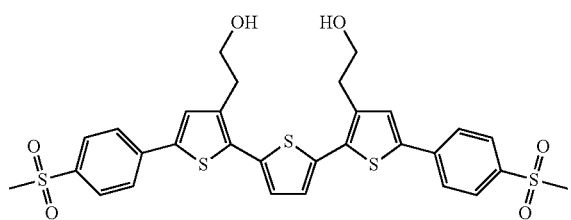

Example 32

2-(2-{5-[3-(2-hydroxyethyl)-5-(4-methanesulfonylphenyl)thiophen-2-yl]thiophen-2-yl}-5-(4-methanesulfonylphenyl)thiophen-3-yl)ethan-1-ol (P9707_035)

Argon was bubbled through a mixture of intermediate H (120 mg, 0.24 mmol), 4-methylsulfonylphenylboronic acid (126 mg, 0.63 mmol) and $K_2CO_3$ (116 mg, 0.84 mmol) in toluene/MeOH (3:2, 5 ml). After 15 min, PEPPSI-iPr™ (7 mg, 0.009 mmol) was added and the mixture heated to 55° C. After 45 min, the reaction mixture was cooled to RT, diluted with $CHCl_3$ (50 ml), washed with water/brine (1:1, 60 ml) and evaporated to dryness. The crude product was dissolved in dioxane/$H_2O$ (2:1, 30 ml) under reflux followed by dropwise addition of iPrOH (30 ml) and stirred at 4° C. for 4 days. The obtained solid was filtered, washed with cold MeOH (6 ml), EtOAc (6 ml), iso-hexane (2×6 ml) and dried under vacuum. Yield: 108 mg (69%); orange solid. $^1$H NMR (400 MHz, DMSO-d6): δ 2.96 (t, J 8 Hz, 4H), 3.25 (s, 6H), 3.75 (dt, J 8 Hz, 12 Hz, 4H), 4.93 (t, J 8 Hz, 2H), 7.40 (s, 2H), 7.75 (s, 2H), 7.93 (d, J 8 Hz, 4H), 7.96 (d, J 8 Hz, 4H). HPLC: $R_T$=2.64 min, 100% (254 nm, 30-60% MeCN in 10 mM buffer, 3 min, XBridge) and $R_T$=2.64 min, 100% (400 nm, 30-60% MeCN in 10 mM buffer, 3 min, XBridge). LC-MS: m/z=662 (M+$NH_4^+$).

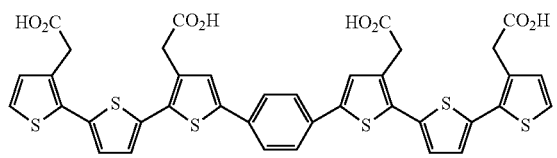 [SMILES: O=C(O)Cc1ccsc1-c1ccc(-c2sc(-c3ccc(-c4cc(CC(=O)O)c(-c5ccc(-c6sccc6CC(=O)O)s5)s4)cc3)cc2CC(=O)O)s1]

Example 33

2-(2-{5-[3-(Carboxymethyl)-5-{4-[4-(carboxymethyl)-5-{5-[3-(carboxymethyl)thiophen-2-yl]thiophen-2-yl}thiophen-2-yl]phenyl}thiophen-2-yl]thiophen-2-yl}thiophen-3-yl)acetic acid (P9707_036)

Argon was bubbled through a mixture of 1,4-benzenediboronic acid (24 mg, 0.15 mmol), intermediate E (150 mg, 0.32 mmol) and $K_2CO_3$ (64 mg, 0.46 mmol) in toluene/MeOH (1:1, 5 ml). After 15 min PEPPSI-iPr™ (4 mg, 0.006 mmol) was added and the mixture heated to 60° C. for 60 min. The reaction mixture was cooled to RT, diluted with $CH_2Cl_2$ (25 ml) and washed with water (30 ml). The aqueous layer was washed with $CH_2Cl_2$ (2×15 ml), the combined organic layers were evaporated to dryness to obtain the crude product. The residue was purified by flash chromatography using toluene/EtOAc 25:1→20:1→15:1) as eluent. Yield: 34 mg (28%); Orange solid. $^1$H NMR (400 MHz, $CDCl_3$): δ 3.74 (s, 6H), 3.76 (s, 6H), 3.81 (s, 4H), 3.82 (s, 4H), 7.07 (d, J 4 Hz, 2H), 7.17 (d, J 4 Hz, 2H), 7.20 (d, J 4 Hz, 2H), 7.27 (d, J 4 Hz, 2H), 7.31 (s, 2H), 7.60 (s, 4H).

The ester from above (43 mg, 0.04 mmol) was dissolved in dioxane (2.5 ml) and 2 M NaOH (2.5 ml) was added. After 18 hrs at RT, the reaction mixture was diluted with water (15 ml) and acidified using 1 M HCl (approx. 13 ml). The formed precipitate was isolated by centrifugation and washed three times with water. The material was dried under high vacuum for 2 d. Yield: 27 mg (86%); dark red solid. $^1$H NMR (DMSO-$d_6$): 3.74 (s, 4H), 3.78 (s, 4H), 7.10 (d, J 4 Hz, 2H), 7.27 (d, J 4 Hz, 2H), 7.32 (d, J 4 Hz, 2H), 7.55 (d, J 4 Hz, 2H), 7.57 (s, 2H), 7.73 (s, 4H), 12.60 (bs, 4H). HPLC: $R_T$=2.43 min, 96% (254 nm, 10-40% MeCN in 10 mM buffer, 3 min, XBridge) and $R_T$=2.44 min, 96% (400 nm, 10-40% MeCN in 10 mM buffer, 3 min, XBridge). LC-MS: m/z=820 (M+$NH_4^+$).

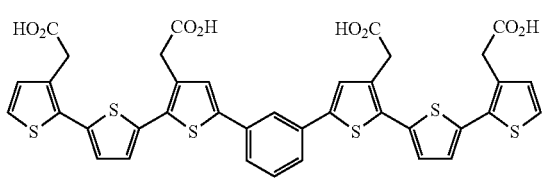 [SMILES: O=C(O)Cc1ccsc1-c1ccc(-c2sc(-c3cccc(-c4cc(CC(=O)O)c(-c5ccc(-c6sccc6CC(=O)O)s5)s4)c3)cc2CC(=O)O)s1]

Example 34

2-(2-{5-[3-(Carboxymethyl)-5-{3-[4-(carboxymethyl)-5-{5-[3-(carboxymethyl)thiophen-2-yl]thiophen-2-yl}thiophen-2-yl]phenyl}thiophen-2-yl]thiophen-2-yl}thiophen-3-yl)acetic acid (P9707_037)

Argon was bubbled through a mixture of 1,3-benzenediboronic acid (26 mg, 0.15 mmol), intermediate E (157 mg, 0.33 mmol) and $K_2CO_3$ (67 mg, 0.48 mmol) in toluene/MeOH (1:1, 5 ml). After 15 min PEPPSI-iPr™ (5 mg, 0.008 mmol) was added and the mixture heated to 55° C. for 2 hrs. The reaction mixture was cooled to RT, diluted with $CH_2Cl_2$ (30 ml) and washed with water (30 ml). The aqueous layer was washed with $CH_2Cl_2$ (2×15 ml), the combined organic layers was evaporated to dryness to obtain the crude product. The residue was purified by flash chromatography using toluene/EtOAc 25:1→20:1→15:1) as eluent. Yield: 95 mg (73%); dark green solid. $^1$H NMR (400 MHz, $CDCl_3$): δ 3.74 (s, 6H), 3.77 (s, 6H), 3.81 (s, 4H), 3.83 (s, 4H), 7.06 (d, J 4 Hz, 2H), 7.18 (d, J 4 Hz, 2H), 7.22 (d, J 4 Hz, 2H), 7.27 (d, J 4 Hz, 2H), 7.33 (s, 2H), 7.40 (m, 1H), 7.51-7.53 (m, 2H), 7.79 (m, 1H).

The ester from above (95 mg, 0.11 mmol) was dissolved in dioxane (2.5 ml) and 2 M NaOH (2.5 ml) was added. After 18 hrs at RT, the reaction mixture was diluted with water (20 ml) and acidified using 1 M HCl (approx. 13 ml). The formed precipitate was isolated by centrifugation and washed three times with water. The material was dried under high vacuum for 2 d. Yield: 43 mg (49%); green-yellow solid. $^1$H NMR (DMSO-$d_6$): 3.75 (s, 4H), 3.79 (s, 4H), 7.10 (d, J 4 Hz, 2H), 7.28 (d, J 4 Hz, 2H), 7.33 (d, J 4 Hz, 2H), 7.45-7.62 (m, 5H), 7.67 (s, 2H), 7.92 (m, 1H), 12.59 (bs, 4H). HPLC: $R_T$=2.60 min, 96% (254 nm, 10-40% MeCN in 10 mM buffer, 3 min, XBridge) and $R_T$=2.60 min, 97% (400 nm, 10-40% MeCN in 10 mM buffer, 3 min, XBridge). LC-MS: m/z=820 ($M+NH_4^+$).

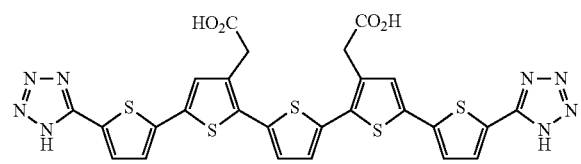 [SMILES: O=C(O)Cc1cc(-c2ccc(-c3nnn[nH]3)s2)sc1-c1ccc(-c2sc(-c3ccc(-c4nnn[nH]4)s3)cc2CC(=O)O)s1]

Example 35

2-(2-{5-[3-(Carboxymethyl)-5-[5-(1H-1,2,3,4-tetrazol-5-yl)thiophen-2-yl]thiophen-2-yl]thiophen-2-yl}-5-[5-(1H-1,2,3,4-tetrazol-5-yl)thiophen-2-yl]thiophen-3-yl)acetic acid (P9707_038)

Sodium azide (37 mg, 0.563 mmol) and $Et_3N$—HCl (71 mg, 0.563 mmol) was added to a solution of intermediate V (114 mg, 0.188 mmol) in DMF (5 ml). The mixture was heated at 50° C. for 30 min and at 100° C. overnight. Solvent was evaporated and residue dissolved in dioxane (3 ml). 2 M NaOH (3 ml) was added and the mixture heated at 80° C. for 1 h. 6 M HCl was added and solid material isolated by centrifugation. The product was purified by preparative hplc (10-30% MeCN in 50 mM buffer, XBridge). Pure fractions were combined and some solvents evaporated. 1 M HCl was added, precipitate collected by centrifugation, washed with water and dried at high vacuum. Yield: 88 mg (71%); deep orange solid, metallic shine. $^1$H NMR (400 MHz, DMSO-$d_6$): δ 3.80 (s, 4H), 7.36 (s, 2H), 7.48 (s, 4H), 7.52 (d, J 3.8 Hz, 2H), 7.75 (d, J 4.0 Hz, 2H). HPLC: $R_t$=1.78 min, 98% (400 nm, 10-30% MeCN in 10 mM buffer, 3 min, XBridge) and $R_t$=1.52 min, 97% (254 nm, 10-40% MeCN in 10 mM buffer, 3 min, XBridge). LC-MS: m/z=665 (M+1).

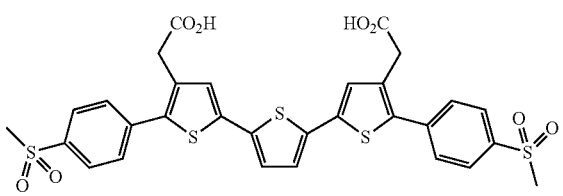 [SMILES: CS(=O)(=O)c1ccc(-c2sc(-c3ccc(-c4cc(CC(=O)O)c(-c5ccc(S(C)(=O)=O)cc5)s4)s3)cc2CC(=O)O)cc1]

Example 36

2-(5-{5-[4-(Carboxymethyl)-5-(4-methanesulfonylphenyl)thiophen-2-yl]thiophen-2-yl}-2-(4-methanesulfonylphenyl)thiophen-3-yl)acetic acid (P9707_039)

Argon was bubbled through a solution of intermediate Z (206 mg, 0.53 mmol) and 2,5-thiophenediylbisboronic acid (45 mg, 0.26 mmol) in MeOH (3 ml) and toluene (3 ml) for 5 min. PEPPSI-iPr™ (10 mg, 0.014 mmol) and $K_2CO_3$ (220, 1.06 mmol) were added and the mixture heated to 60° C. for 2 hours. The mixture was then concentrated under vacuum and the crude material was dissolved in DCM with some MeOH. The solution was purified by flash chromatography using 40% and 100% EtOAc in iso-hexane as eluent. Yield: 80 mg (42%); yellow solid. $^1$H NMR (400 MHz, $CDCl_3$): δ 3.12 (s, 6H), 3.67 (s, 4H), 3.78 (s, 6H), 7.15 (s, 2H), 7.22 (s, 2H), 7.69-7.76 (m, 4H), 8.00-8.06 (m, 4H).

The ester from above (70 mg, 0.10 mmol) was added dioxane (3 ml) and 2 M NaOH (3 ml) and the mixture was heated at 80° C. for 90 min. The solution was cooled to r.t. and added 6 M HCl (1.5 ml). The formed precipitate was isolated by centrifugation and washed three times with water. The material was added some MeOH and the solvent was removed in vacuo. The yellow solid was then dried under high vacuum for 2 days. Yield: 55 mg (82%); yellow solid. $^1$H NMR (400 MHz, DMSO-$d_6$): δ 3.28 (s, 6H), 3.68 (s, 4H), 7.39 (s, 2H), 7.40 (s, 2H), 7.75-7.80 (m, 4H), 8.01-8.05 (m, 4H). $R_t$=2.83 min, 98% (254 nm, 10-40% MeCN in 10 mM buffer, XBridge) $R_t$=2.83 min, 98% (400 nm, 10-40% MeCN in 10 mM buffer, XBridge). LC-MS: m/z=690 ($M+NH_4^+$).

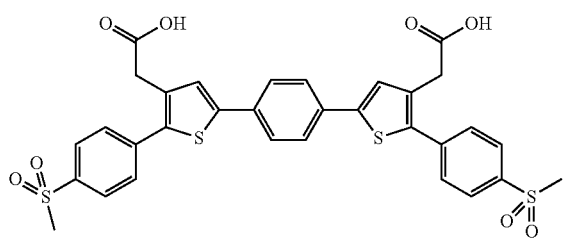 [SMILES: CS(=O)(=O)c1ccc(-c2sc(-c3ccc(-c4cc(CC(=O)O)c(-c5ccc(S(C)(=O)=O)cc5)s4)cc3)cc2CC(=O)O)cc1]

Example 37

2-(5-{4-[4-(Carboxymethyl)-5-(4-methanesulfonylphenyl)thiophen-2-yl]phenyl}-2-(4-methanesulfonylphenyl)thiophen-3-yl)acetic acid (P9707_040)

Argon was bubbled through a solution of intermediate Z (205 mg, 0.53 mmol) and 2,5-T thiophenediylbisboronic acid (44 mg, 0.26 mmol) in MeOH (3 ml) and toluene (3 ml) for 5 min. PEPPSI-iPr™ (10 mg, 0.014 mmol) and $K_2CO_3$ (220, 1.6 mmol) were added and the mixture heated to 60° C. for 2 hours. The mixture was then concentrated under vacuum and the crude material was dissolved in DCM with some MeOH. The solution was purified by flash chromatography using 40% and 100% EtOAc in iso-hexane as eluent. Yield: 104 mg (54%); pale yellow solid.

The ester from above (100 mg, 0.15 mmol) was added dioxane (4 ml) and 2 M NaOH (4 ml) and the mixture was heated at 80° C. for 90 min. The solution was cooled to r.t. and added 6 M HCl (2 ml). The formed precipitate was isolated by centrifugation and washed three times with water. The material was added some MeOH and the solvent was removed in vacuo. The yellow solid was then dried under high vacuum for 2 days. Yield: 59 mg (61%); yellow solid. $^1$H NMR (400 MHz, DMSO-$d_6$): δ 3.28 (s, 6H), 3.70 (s, 4H), 7.62 (s, 2H), 7.77 (s, 4H), 7.78-7.81 (m, 4H), 8.02-8.06 (m, 4H). $R_t$=2.76 min, 95% (254 nm, 10-40% MeCN in 10 mM buffer, XBridge) $R_t$=2.76 min, 95% (400 nm, 10-40% MeCN in 10 mM buffer, XBridge). LC-MS: m/z=684 (M+$NH_4^+$).

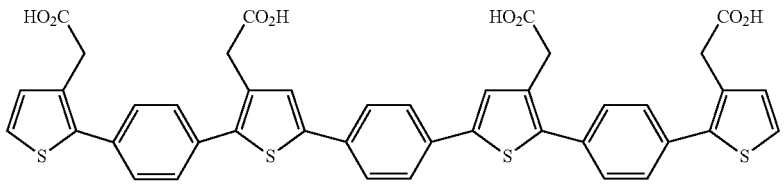 [SMILES: O=C(O)Cc1ccsc1-c1ccc(-c2sc(-c3ccc(-c4cc(CC(=O)O)c(-c5ccc(-c6sccc6CC(=O)O)cc5)s4)cc3)cc2CC(=O)O)cc1]

Example 38

2-(2-{4-[3-(Carboxymethyl)-5-{4-[4-(carboxymethyl)-5-{4-[3-(carboxymethyl)thiophen-2-yl]phenyl}thiophen-2-yl]phenyl}thiophen-2-yl]phenyl}thiophen-3-yl)acetic acid (P9707_041)

Argon was bubbled through a mixture of 1,4-benzenediboronic acid (24 mg, 0.15 mmol), intermediate X (151 mg, 0.32 mmol) and $K_2CO_3$ (65 mg, 0.47 mmol) in toluene/MeOH (1:1, 4 ml). After 15 min PEPPSI-iPr™ (5 mg, 0.007 mmol) was added and the mixture heated to 55° C. for 60 min. The reaction mixture was cooled to RT, diluted with $CH_2Cl_2$ (30 ml) and washed with water (30 ml). The aqueous layer was washed with $CH_2Cl_2$ (2×15 ml), the combined organic layers was evaporated to dryness to obtain the crude product. The residue was purified by flash chromatography using toluene/EtOAc (20:1→14:1→9:1) as eluent. Yield: 64 mg (51%); Off-white solid. $^1$H NMR (400 MHz, CDCl$_3$): δ 3.73 (s, 4H), 3.74 (s, 4H), 3.76 (s, 6H), 3.78 (s, 6H), 7.12 (d, J 5.0 Hz, 2H), 7.33 (d, J 5.0 Hz, 2H), 7.37 (s, 2H), 7.55-7.61 (m, 8H), 7.65 (s, 4H). The ester from above (64 mg, 0.08 mmol) was dissolved in dioxane (2 ml) and 2 M NaOH (2 ml) was added. After 2 hrs at 80° C. followed by 18 hrs at RT, the reaction mixture was diluted with water (20 ml) and acidified using 2 M HCl (approx. 5 ml). The formed precipitate was isolated by centrifugation and washed three times with water. The material was dried under high vacuum for 2 d. Yield: 50 mg (79%); Yellow solid. $^1$H NMR (DMSO-$d_6$): 3.65 (s, 4H), 3.69 (s, 4H), 7.12 (d, J 5.3 Hz, 2H), 7.55-7.64 (m, 12H), 7.74 (s, 4H). HPLC: $R_T$=2.55 min, 92% (254 nm, 10-40% MeCN in 10 mM buffer, 3 min, XBridge) and $R_T$=2.54 min, 94% (400 nm, 10-40% MeCN in 10 mM buffer, 3 min, XBridge). LC-MS: m/z=808 (M+$NH_4^+$).

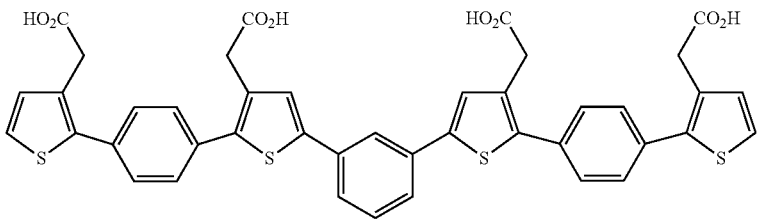 [SMILES: O=C(O)Cc1ccsc1-c1ccc(-c2sc(-c3cccc(-c4cc(CC(=O)O)c(-c5ccc(-c6sccc6CC(=O)O)cc5)s4)c3)cc2CC(=O)O)cc1]

Example 39

2-(5-{3-[4-(Carboxymethyl)-5-{4-[3-(carboxymethyl)thiophen-2-yl]phenyl}thiophen-2-yl]phenyl}-2-{4-[3-(carboxymethyl)thiophen-2-yl]phenyl}thiophen-3-yl)acetic acid (P9707_042)

Argon was bubbled through a mixture of 1,3-benzenediboronic acid (25 mg, 0.15 mmol), intermediate X (154 mg, 0.33 mmol) and $K_2CO_3$ (75 mg, 0.54 mmol) in toluene/MeOH (1:1, 4 ml). After 15 min PEPPSI-iPr™ (5 mg, 0.008 mmol) was added and the mixture heated to 55° C. for 90 min. The reaction mixture was cooled to RT, diluted with $CH_2Cl_2$ (30 ml) and washed with water/brine (3:2-50 ml). The organic layer was evaporated to dryness to obtain the crude product. The residue was purified by flash chromatography using toluene/EtOAc 14:1 as eluent. Yield: 68 mg (52%); Yellowish solid. $^1$H NMR (400 MHz, CDCl$_3$): δ 3.73 (s, 4H), 3.75 (s, 10H), 3.79 (s, 6H), 7.12 (d, J 5.3 Hz, 2H), 7.32 (d, J 5.3 Hz, 2H), 7.39 (s, 2H), 7.42 (m, 1H), 7.55-7.62 (m, 10H), 7.86 (m, 1H).

The ester from above (68 mg, 0.08 mmol) was dissolved in dioxane (2 ml) and 2 M NaOH (2 ml) was added. After 18 hrs at RT, the reaction mixture was diluted with water (20 ml) and acidified using 2 M HCl (approx. 5 ml). The formed precipitate was isolated by centrifugation and washed three times with water. The material was dried under high vacuum for 2 d. Yield: 57 mg (90%); Yellow solid. $^1$H NMR (DMSO-d$_6$): 3.65 (s, 4H), 3.71 (s, 4H), 7.13 (d, J 4 Hz, 2H), 7.50-7.67 (m, 15H), 7.95 (m, 1H). HPLC: $R_T$=2.68 min, 95% (254 nm, 10-40% MeCN in 10 mM buffer, 3 min, XBridge) and $R_T$=2.67 min, 50% (400 nm, 10-40% MeCN in 10 mM buffer, 3 min, XBridge). LC-MS: m/z=808 (M+NH$_4^+$).

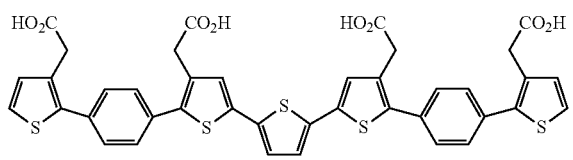 [SMILES: O=C(O)Cc1ccsc1-c1ccc(-c2sc(-c3ccc(-c4cc(CC(=O)O)c(-c5ccc(-c6sccc6CC(=O)O)cc5)s4)s3)cc2CC(=O)O)cc1]

Example 40

2-(5-{5-[4-(Carboxymethyl)-5-{4-[3-(carboxymethyl)thiophen-2-yl]phenyl}thiophen-2-yl]thiophen-2-yl}-2-{4-[3-(carboxymethyl)thiophen-2-yl]phenyl}thiophen-3-yl)acetic acid (P9707_043)

Argon was bubbled through a mixture of 2,5-thiophenediboronic acid (25 mg, 0.15 mmol), intermediate X (151 mg, 0.32 mmol) and $K_2CO_3$ (65 mg, 0.47 mmol) in toluene/MeOH (1:1, 6 ml). After 15 min PEPPSI-iPr™ (5 mg, 0.008 mmol) was added and the mixture heated to 50° C. for 90 min. The reaction mixture was cooled to RT, diluted with $CH_2Cl_2$ (30 ml) and washed with water/brine (10:1-55 ml). The organic layer was evaporated to dryness to obtain the crude product. The residue was purified by flash chromatography using toluene/EtOAc (25:1→20:1→18:1→12:1) as eluent. Yield: 46 mg (37%); Green oil. $^1$H NMR (400 MHz, CDCl$_3$): δ 3.71 (s, 4H), 3.73 (s, 4H), 3.75 (s, 6H), 3.78 (s, 6H), 7.12 (d, J 5.0 Hz, 2H), 7.12 (s, 2H), 7.20 (s, 2H), 7.32 (d, J 5.0 Hz, 2H), 7.56 (s, 8H).

The ester from above (42 mg, 0.05 mmol) was dissolved in dioxane (2 ml) and 2 M NaOH (2 ml) was added. After 18 hrs at RT, the reaction mixture was diluted with water (20 ml) and acidified using 2 M HCl (approx. 5 ml). The formed precipitate was isolated by centrifugation and washed three times with water. The material was dried under high vacuum for 2 d. Yield: 23 mg (59%); Green-yellow solid. $^1$H NMR (DMSO-d$_6$): 3.65 (s, 4H), 3.68 (s, 4H), 7.12 (d, J 4 Hz, 2H), 7.35 (s, 2H), 7.36 (s, 2H), 7.57 (d, J 4 Hz, 2H), 7.57-7.63 (m, 8H). HPLC: $R_T$=2.61 min, 91% (254 nm, 10-40% MeCN in 10 mM buffer, 3 min, XBridge) and $R_T$=2.61 min, 93% (400 nm, 10-40% MeCN in 10 mM buffer, 3 min, XBridge). LC-MS: m/z=797 (M+H$^+$).

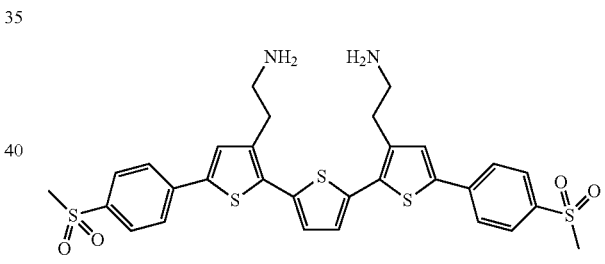

Example 41

2-(2-{5-[3-(2-Aminoethyl)-5-(4-methanesulfonylphenyl)thiophen-2-yl]thiophen-2-yl}-5-(4-methanesulfonylphenyl)thiophen-3-yl)ethan-1-amine (P9707_044)

Argon was flushed through a stirred solution of intermediate M (190 mg, 0.213 mmol) and 4-methylsulfonylphenylboronic acid (110 mg, 0.550 mmol) in a mixture of toluene (3 ml) and MeOH (3 ml). $K_2CO_3$ (250 mg, 1.81 mmol) and PEPPSI-iPr™ (7.8 mg, 0.011 mmol) were added and the reaction heated in a sealed flask at 60° C. for 1 hour. The solvents were removed in vacuo and the crude material was added water (~10 ml) and extracted with DCM (~5 ml). The organic phase was purified by flash chromatography (30% EtOAc in toluene, 200 ml silica). Yield: 185 mg, (83%) as a orange solid. $^1$H NMR (400 MHz, DMSO-d$_6$): δ 1.36 (s, 36H), 3.06 (t, J 6.90 Hz, 4H), 3.26 (s, 6H), 3.85 (t, J 6.90 Hz, 4H), 7.33 (s, 2H), 7.61 (s, 2H), 7.88-7.93 (m, 4H), 7.95-8.00 (m, 4H)

TFA (1 ml) was added to a stirred solution of the material from above (185 mg, 0.177 mmol) in DCM (3 ml). The reaction was stirred at r.t. for 2 hours and the solvents were removed in vacuo. 1 M NaOH (15 ml) was added and the mixture was extracted with DCM (250 ml). The organic phase was dried over $MgSO_4$ and removed in vacuo. The material was dissolved in AcOH (~5 ml) and conc HCl (~0.2 ml) was added. The solvents were removed in vacuo and the compound was placed under high vacuum over the weekend. Yield: 65 mg (51%) as a red solid, HCl-salt of title compound. $^1H$ NMR (400 MHz, DMSO-$d_6$): δ 3.08-3.25 (m, 8H), 3.27 (s, 6H), 7.44 (s, 2H), 7.83 (s, 2H), 7.92-8.03 (m, 8H). HPLC: $R_t$=1.98 min, 100% (254 nm, 10-90% MeCN in 0.1% TFA) and $R_t$=2.65 min, 100% (254 nm, 05-60% MeCN in 0.1% TFA). LC-MS: m/z=643 (M+1).

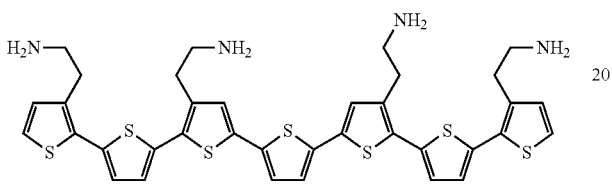

Example 42

2-(2-{5-[3-(2-Aminoethyl)-5-{5-[4-(2-aminoethyl)-5-{5-[3-(2-aminoethyl)thiophen-2-yl]thiophen-2-yl}thiophen-2-yl]thiophen-2-yl}thiophen-2-yl]thiophen-2-yl}thiophen-3-yl)ethan-1-amine (P9707_045)

NBS (39 mg, 0.22 mmol) was added to a stirred solution of intermediate L (160 mg, 0.22 mmol) in a mixture of $CHCl_3$ (2 ml) and AcOH (2 ml) at r.t. The reaction was stirred for 1 hour and poured on a stirred mixture of 5 M NaOH (15 ml) and ice. DCM (5 ml) was added and the organic phase was dried over $MgSO_4$ and removed in vacuo. The crude material was dissolved in MeCN (2 ml) and purified by prep-HPLC (90-100% MeCN, in 50 mM $NH_3/NH_4HCO_3$ buffer). The pure fractions were combined and concentrated to dryness. Yield: 81 mg (46%) as a yellow gum. $^1H$ NMR (400 MHz, $CDCl_3$): δ 1.46 (s, 18H), 1.46 (s, 18H), 2.97-3.09 (m, 4H), 3.79-3.88 (m, 4H), 6.93 (s, 1H), 6.97 (d, J 5.3 Hz, 1H), 7.07-7.10 (m, 1H), 7.11-7.13 (m, 1H), 7.22 (d, J 5.3 Hz, 1H)

Argon was flushed through a solution of the material from above (150 mg, 0.18 mmol) and 2,5-thiopenediboronic acid (15 mg, 0.092 mmol) in a mixture of toluene (2 ml) and MeOH (2 ml). $K_2CO_3$ (150 mg, 1.1 mmol) and PEPPSI-iPr™ (10 mg, 0.015 mmol) were added and the reaction heated at 55° C. for 90 min. The solvents were removed in vacuo and the crude material was added water (~10 ml) and extracted with DCM (~5 ml). The organic phase was dried over $MgSO_4$ and added TFA (2 ml). The reaction was stirred at r.t. for 2 hours and concentrated. The crude material was dissolved in MeOH (8 ml), filtered and purified by prep-HPLC (30-70% MeCN in 0.1% TFA aq). The pure fractions were combined and freeze dried. Not pure fractions containing product were combined and concentrated to dryness. The red solid was dissolved in MeOH (2 ml) and purified on prep-HPLC (30-70% MeCN in 0.1% TFA aq). The pure fractions were combined and freeze dried. The 2 batches were combined. $^1H$ NMR (400 MHz, DMSO-$d_6$): δ 3.00-3.22 (m, 16H), 7.17 (d, J 5.3 Hz, 2H), 7.30 (d J 4.0 Hz, 2H), 7.34 (d, J 4.0 Hz, 2H), 7.38 (s, 2H), 7.42 (s, 2H), 7.64 (d, J 5.3 Hz, 2H), 7.84-8.02 (m, 12H). HPLC: $R_t$=1.95 min, 100% (254 nm, 10-90% MeCN in 0.1% TFA) $R_t$=1.25 min, 100% (305 nm, 10-90% MeCN in 0.1% TFA) LC-MS: m/z=749 (M+1).

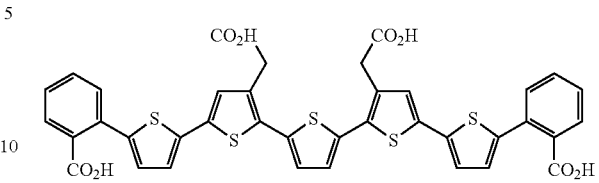

Example 43

2-{5-[4-(Carboxymethyl)-5-{5-[3-(carboxymethyl)-5-[5-(2-carboxyphenyl)thiophen-2-yl]thiophen-2-yl]thiophen-2-yl}thiophen-2-yl]thiophen-2-yl}benzoic acid (P9707_046)

Argon was bubbled through a mixture of intermediate O (174 mg, 0.244 mmol), 2-methoxycarbonylphenylboronic acid (131 mg, 0.731 mmol) and $K_2CO_3$ (168 mg, 1.22 mmol) in toluene (10 ml) and methanol (10 ml). PEPPSI-iPr™ (3 mg, 0.005 mmol) was added and the mixture was heated at 70° C. for 30 min. Solvents were evaporated and residue dissolved in dioxane (5 ml) and 2 M NaOH (5 ml) was added and the mixture heated at 80° C. for 1 h. The mixture was acidified by addition of 2 M HCl and solid material was isolated by centrifugation, dissolved in 1 M $Na_2CO_3$ and purified by prep. hplc. Pure fractions were combined and solid material precipitated by addition of 1 M HCl. Solid material was isolated by centrifugation and washed three times with water. Freeze-dried under high vacuum for 3 d. Yield: 54.4 mg (29%); orange solid. Rt=2.17 min, 96% at 254 nm (10-40% MeCN in buffer, XBridge) and Rt=2.18 min. 98% at 400 nm (10-40% MeCN in buffer, XBridge). MS: m/z=767 (M−1) (neg. ionization)

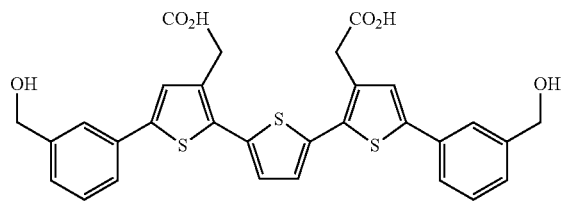 [SMILES: O=C(O)Cc1cc(-c2cccc(CO)c2)sc1-c1ccc(-c2sc(-c3cccc(CO)c3)cc2CC(=O)O)s1]

Example 44

2-(2-{5-[3-(Carboxymethyl)-5-[3-(hydroxymethyl)phenyl]thiophen-2-yl]thiophen-2-yl}-5-[3-(hydroxymethyl)phenyl]thiophen-3-yl)acetic acid (P9707_047)

Argon was bubbled through a mixture of intermediate D (150 mg, 0.273 mmol), 3-(hydroxymethyl)phenylboronic acid (104 mg, 0.681 mmol) and $K_2CO_3$ (150 mg, 1.09 mmol) in toluene (2 ml) and methanol (2 ml). PEPPSI-iPr™ (4 mg, 0.005 mmol) was added and the mixture heated in a microwave reactor at 80° C. for 15 min. Solvents were evaporated and residue dissolved dioxane (2 ml) and 2 M NaOH (2 ml) and the mixture was heated at 80° C. for 1 h. 2 M HCl (ca 5 ml) was added and the precipitated material isolated by centrifugation and dissolved in 1 M $Na_2CO_3$/water, and purified by prep. hplc using 10-40% MeCN in 50 mM buffer (XBridge). Yield: 7.6 mg (5%); yellow solid. Rt=2.73 min, 99% at 254 nm (10-40% MeCN in buffer, XBridge) and $R_t$=2.73 min. 98% at 400 nm (10-40% MeCN in buffer, XBridge). MS: m/z=575 (M−1) (neg. ionization)

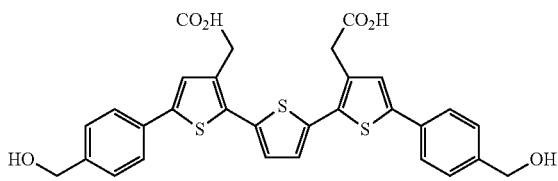 [SMILES: O=C(O)Cc1cc(-c2ccc(CO)cc2)sc1-c1ccc(-c2sc(-c3ccc(CO)cc3)cc2CC(=O)O)s1]

Example 45

2-(2-{5-[3-(Carboxymethyl)-5-[4-(hydroxymethyl)phenyl]thiophen-2-yl]thiophen-2-yl}-5-[4-(hydroxymethyl)phenyl]thiophen-3-yl)acetic acid (P9707_048)

Argon was bubbled through a mixture of intermediate D (162 mg, 0.294 mmol), 4-(hydroxymethyl)phenylboronic acid (111 mg, 0.736 mmol) and $K_2CO_3$ (162 mg, 1.78 mmol) in toluene (2 ml) and methanol (2 ml). PEPPSI-iPr™ (4 mg, 0.005 mmol) was added and the mixture heated in a microwave reactor at 80° C. for 15 min. Solvents were evaporated and the residue added dioxane (2 ml) and 2 M NaOH (2 ml). The mixture was heated at 80° C. for 1 h. 2 M HCl (ca 5 ml) was added and the precipitated material isolated by centrifugation and purified by prep. hplc using 10-40% MeCN in 50 mM buffer. Pure fractions were collected and some solvents were evaporated. 1 M HCl was added and solid precipitate extracted with EtOAc, dried with $MgSO_4$ filtered and concentrated. Yield: 61.1 mg (36%); yellow solid. Rt=2.46 min, 99% at 254 nm (10-40% MeCN in buffer, XBridge) and Rt=2.47 min. 98% at 400 nm (10-40% MeCN in buffer, XBridge). $^1$H NMR (400 MHz, $CDCl_3$): δ 3.77 (s, 4H), 4.52 (s, 4H), 7.31 (s, 2H), 7.38 (d, J 8 Hz, 4H), 7.47 (s, 2H), 7.62 (d, J 8 Hz, 4H). MS: m/z=575 (M−1) (neg. ionization)

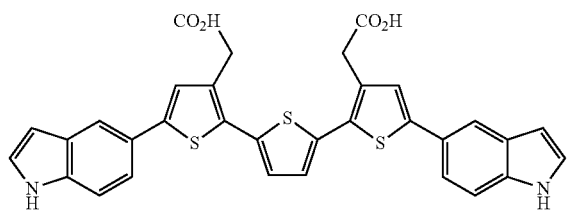 [SMILES: O=C(O)Cc1cc(-c2ccc3[nH]ccc3c2)sc1-c1ccc(-c2sc(-c3ccc4[nH]ccc4c3)cc2CC(=O)O)s1]

Example 46

2-(2-{5-[3-(Carboxymethyl)-5-(1H-indol-5-yl)thiophen-2-yl]thiophen-2-yl}-5-(1H-indol-5-yl)thiophen-3-yl)acetic acid (P9707_049)

Argon was bubbled through a mixture of intermediate D (193 mg, 0.351 mmol), 1H-Indole-5-boronic acid (141 mg, 0.0.877 mmol) and $K_2CO_3$ (150 mg, 1.09 mmol) in toluene (2 ml) and methanol (2 ml). PEPPSI-iPr™ (5 mg, 0.007 mmol) was added and the mixture heated in a microwave reactor at 90° C. for 10 min. Solvents were evaporated, the residue added dioxane (2 ml) and 2 M NaOH (2 ml), and the mixture heated at 80° C. for 1 h. 2 M HCl (ca 5 ml) was added and the precipitated material isolated by centrifugation and purified by prep. hplc using 20-45% MeCN in 50 mM buffer as eluent. Pure fractions were collected and some solvents were evaporated. 1 M HCl was added and mixture was extracted with EtOAc. Combined organic layers were dried ($MgSO_4$) and concentrated. Yield: 50.6 mg (24%); yellow-brown solid. Rt=2.27 min, 90% at 254 nm (20-50% MeCN in buffer, XBridge) and Rt=2.27 min. 90% at 400 nm (20-50% MeCN in buffer, XBridge). MS: m/z=593 (M−1) (neg. ionization).

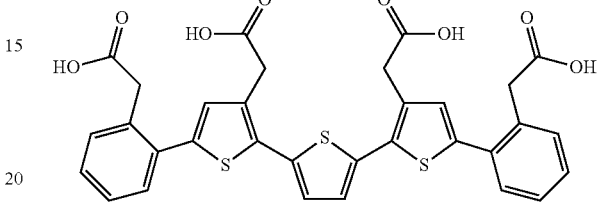

Example 47

2-(2-{5-[3-(Carboxymethyl)-5-[2-(carboxymethyl)phenyl]thiophen-2-yl]thiophen-2-yl}-5-[2-(carboxymethyl)phenyl]thiophen-3-yl)acetic acid (P9707_050)

Argon was flushed through a stirred solution of intermediate D (80.2 mg, 0.146 mmol) and 2-(methoxycarbonylmethyl)phenylboronic acid pinacol ester (115 mg, 0.416 mmol) in a mixture of toluene (3 ml) and MeOH (3 ml). $K_2CO_3$ (489 mg, 3.54 mmol) and PEPPSI-iPr™ (15.2 mg, 0.0210 mmol) were added and the reaction heated at 65° C. for 1 hour. The solvents were removed in vacuo and the crude material was added water (1 ml) and 2 M NaOH (1 ml). The reaction was stirred at 80° C. for 1 hour. The mixture was cooled to r.t. and filtered. Some (~0.5 ml) water was added and the mixture was purified by prep-HPLC (5-40% MeCN, in 50 mM $NH_3$/$NH_4HCO_3$ buffer). The combined pure fractions were concentrated to dryness. The compound was dissolved in water (20 ml) and some 1 M HCl was added. The solid was collected and washed several times with water and dried. Yield: 55 mg (60%) as a yellow solid. $^1$H NMR (400 MHz, DMSO-$d_6$): δ 3.7-3.8 (m, 8H), 7.07-7.13 (m, 2H), 7.22-7.47 (m, 9H), 7.51-7.56 (m, 1H), 12.5 (s, 4H). HPLC $R_t$=1.78 min, 100% (254 nm, 10-40% MeCN in 10 mM buffer, XBridge) and $R_t$=1.13 min, 100% (254 nm, 10-90% MeCN in 10 mM buffer, XBridge). LC-MS: m/z=650 (M+18).

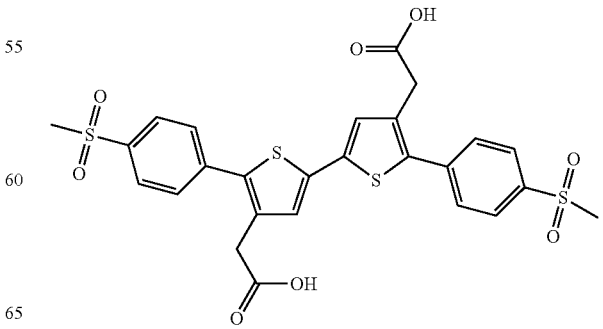

Example 48

2-{5-[4-(Carboxymethyl)-5-(4-methanesulfonylphenyl)thiophen-2-yl]-2-(4-methanesulfonylphenyl)thiophen-3-yl}acetic acid (P9707_051)

NIS (638 mg, 2.84 mmol) was added in portions to a stirred solution of intermediate Y (800 mg, 2.58 mmol) in a mixture of AcOH (5 ml) and CHCl$_3$ (5 ml) at 0° C. The reaction was stirred at this temperature for 5 min and then at r.t. for 3 days. The mixture was concentrated, added some DCM (~5 ml), washed with diluted NaOH and purified by flash chromatography (50% EtOAc in toluene). Yield: 1.06 g (94%). HPLC R$_t$=2.71 min, 92% (254 nm, 10-90% MeCN in 10 mM buffer, XBridge).

Argon was bubbled through a mixture of material from above (109 mg, 0.250 mmol), K$_2$CO$_3$ (104 mg, 0,750 mmol) and DMSO (2 ml) for 5 min. Bis(pinacolato)diboron (254 mg, 0.125 mmol) and 1,1'-bis(diphenylphosphino)ferrocene-palladium(II)dichloride (9.1 mg, 0,013 mmol) were added and the reaction was stirred at 80° C. in a sealed tube overnight. The reaction was added water (0.60 ml) and 5 M NaOH (0.60 ml) and stirred at 80° C. for 1 hour. The mixture was cooled and filtered. Some (~0.5 ml) water was added and the mixture was purified by prep-HPLC (5-45% MeCN, in 50 mM NH$_3$/NH$_4$HCO$_3$ buffer). The combined pure fractions were concentrated to dryness. The compound was dissolved in water (20 ml) and some 1 M HCl was added. The solid was collected and washed several times with water and dried. Yield: 47 mg (32%) as a pale yellow solid. $^1$H NMR (400 MHz, DMSO-d$_6$): δ 3.28 (s, 6H), 3.70 (s, 4H), 7.41 (s, 2H), 7.76-7.81 (m, 2H), 8.00-8.05 (m, 2H), 12.62 (s br, 2H). HPLC: R$_t$=2.14 min, 90% (254 nm, 10-40% MeCN in 10 mM buffer, XBridge) and R$_t$=1.47 min, 90% (254 nm, 10-90% MeCN in 10 mM buffer, XBridge). LC-MS: m/z=608 (M+18).

Example 49

2-{2-[3-(Carboxymethyl)-1-benzothiophen-2-yl]-1-benzothiophen-3-yl}acetic acid (P9707_052)

Acetyl chloride (0.882 ml, 12.4 mmol) was added to a stirred solution of benzothiophene-3-acetic (950 mg, 4.94 mmol) in MeOH (10 ml) at 0° C. The reaction was then stirred at r.t. over night and the solvent was removed in vacuo. The crude material was dissolved in EtOAc (~50 ml) and washed with 0.5 M NaOH. The organic phase was dried over MgSO$_4$ and removed in vacuo. Yield: 0.865 g (85%). HPLC R$_t$=2.62 min, 100% (254 nm, 10-90% MeCN in 10 mM buffer, XBridge).

Br$_2$ (0.121 ml, 2.36 mmol) in DCM (1 ml) was slowly added to a stirred solution of the material from above (0.486 g, 2.36 mmol) in DCM (7 ml) at 0° C. The reaction was stirred at this temperature for 1 hour. The mixture was added sat. Na$_2$S$_2$O$_3$ (1 ml) and washed with (~20 ml) water. The organic phase was purified on a plug of silica using 15% EtOAc in toluene as eluent. Yield: 622 mg (93%) as a colourless oil. $^1$H NMR (400 MHz, CDCl$_3$): δ 3.71 (s, 3H), 3.90 (s, 2H), 7.32-7.41 (m, 2H), 7.66-7.70 (m, 1H), 7.72-7.76 (m, 1H)

Argon was bubbled through a stirred mixture of the material from above (113 mg, 0.396 mmol), K$_2$CO$_3$ (164 mg, 1.19 mmol) and DMSO (1 ml) for 5 min. Bis(pinacolato)diboron (50.3 mg, 0.198 mmol) and 1,1'-bis(diphenylphosphino)ferrocene-palladium(II)dichloride (14.5 mg, 0.0200 mmol) were added and the reaction was stirred at 80° C. in a sealed tube overnight. The reaction was added water (1.5 ml) and 5 M NaOH (0.5 ml) and heated at 80° C. for 30 min. The mixture was cooled and filtered. Water (~0.5 ml) was added and the mixture was purified by prep-HPLC (5-45% MeCN, in 50 mM NH$_3$/NH$_4$HCO$_3$ buffer). The combined pure fractions were concentrated to dryness. Water and some HCl were added and the mixture was extracted with EtOAc. The organic phase was dried over MgSO$_4$ and removed in vacuo. Yield: 37 mg, (24%) as a white solid. $^1$H NMR (400 MHz, DMSO-d$_6$): δ 3.80 (s, 4H), 7.42-7.51 (m, 4H), 7.78-7.84 (m, 2H), 8.01-8.07 (m, 2H), 12.51 (s, 2H), HPLC: R$_t$=1.86 min, 100% (254 nm, 10-40% MeCN in 10 mM buffer, XBridge) and R$_t$=1.36 min, 100% (254 nm, 10-90% MeCN in 10 mM buffer, XBridge). LC-MS: m/z=400 (M+18).

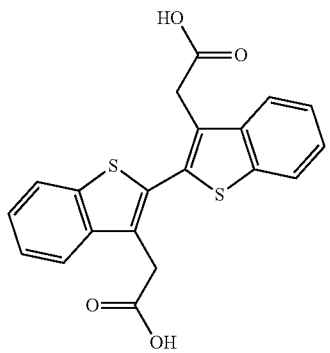 [SMILES: O=C(O)Cc1c(-c2sc3ccccc3c2CC(=O)O)sc2ccccc12]

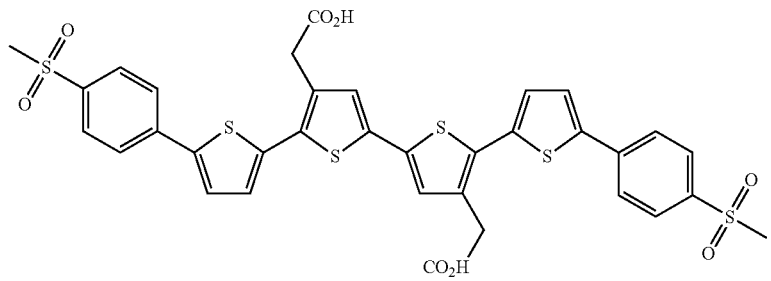

Example 50

2-{5-[4-(Carboxymethyl)-5-[5-(4-methanesulfonylphenyl)thiophen-2-yl]thiophen-2-yl]-2-[5-(4-methanesulfonylphenyl)thiophen-2-yl]thiophen-3-yl}acetic acid (P9707_053)

Argon was bubbled through a mixture of intermediate A2 (360 mg, 1.320 mmol), 4-methylsulfonylphenylboronic acid (328 mg, 1.64 mmol) and K$_2$CO$_3$ (454 mg, 3.29 mmol) in toluene (4 ml) and MeOH (4 ml). PEPPSI-iPr™ (17 mg, 0.025 mmol) was added and the mixture heated at 70° C. for 30 min in a sealed tube. Water and toluene were added. The aqueous layer was extracted with toluene. Combined organic layers were concentrated and residue purified by flash chromatography using 10% EtOAc in toluene as eluent. Yield: 507 mg (98%); yellow oil which solidifies when stored in the fridge. $^1$H NMR (400 MHz, CDCl$_3$): δ 3.10 (s, 3H), 3.76 (s, 3H), 3.84 (s, 2H), 7.10 (d, J 5.2 Hz, 1H), 7.23 (d, J 3.6 Hz, 1H), 7.31 (d, J 5.2 Hz, 1H), 7.44 (d, J 3.6 Hz, 1H), 7.79 (d, J 8.0 Hz, 2H), 7.97 (d, J 8.0 Hz, 2H).

The material from above (570 mg, 1.29 mmol) was dissolved in CHCl$_3$ (10 ml) and AcOH (10 ml). NBS (253 mg, 1.42 mmol) was added portion-wise at 0° C. The mixture was stirred at ambient temperature for 3 h. Solvents were evaporated and residue purified by flash chromatography using 10-15% EtOAc in toluene as eluent. Yield: 509 mg (83%); yellow solid. $^1$H NMR (400 MHz, CDCl$_3$): δ 3.10 (s, 3H), 3.77 (s, 5H), 7.08 (s, 1H), 7.19 (d, J 4 Hz, 1H), 7.43 (d, J 4.0 Hz, 1H), 7.78 (d, J 8 Hz, 2H), 7.97 (d, J 8 Hz, 2H).

The material from above (209 mg, 0.443 mmol) and bispinacolatodiboron (56 mg, 0.222 mmol) was dissolved in DMSO (5 ml). Potassium carbonate (245 mg, 1.77 mmol) was added and the mixture was degassed by bubbling argon through the mixture. 1,1'-bis(diphenylphosphino)ferrocene dichloropalladium (II) (16 mg, 0.022 mmol) was added and the mixture heated at 80° C. for 22 h in a sealed tube. 2 M NaOH (3 ml) was added and heating continued for 2 h. The mixture was filtered and purified by prep. hplc using 15-45% MeCN in 50 mM buffer as eluent. Pure fractions were combined, some solvent evaporated and 1 M HCl added. Precipitated material was isolated by centrifugation and washed with water three times. The material was freeze-dried for 2 days. Yield: 42.5 mg (25%); orange solid. Rt=3.09 min, 99% at 254 nm (10-40% MeCN in buffer, XBridge) and Rt=3.10 min. 99% at 400 nm (10-40% MeCN in buffer, XBridge) $^1$H NMR (400 MHz, DMSO-d$_6$): δ 3.24 (s, 6H, 7.35 (s, 2H), 7.37 (d, J 4 Hz, 2H), 7.79 (d, J 4 Hz, 2H), 7.93-7.98 (m, 8H). MS: m/z=753 (M−1) (neg. ionization).

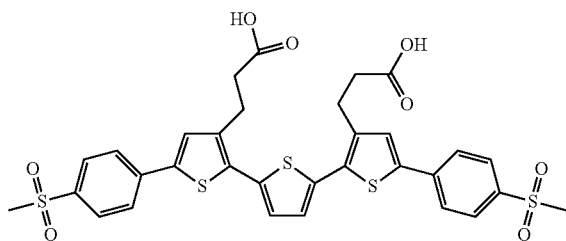

Example 51

3-(2-{5-[3-(2-Carboxyethyl)-5-(4-methanesulfonylphenyl)thiophen-2-yl]thiophen-2-yl}-5-(4-methanesulfonylphenyl)thiophen-3-yl)propanoic acid (P9707_054)

The intermediate C2 (201.9 mg, 0.35 mmol) and 4-(methylsulfonyl)phenylboronic acid (177.6 mg, 0.89 mmol) were dissolved in methanol (5 ml) and toluene (5 ml). Potassium carbonate (242 mg, 2 mmol) was added and argon (g) was bubbled through the reaction mixture before the PEPPSI-iPr™ (12.2 mg, 0.018 mmol) was added. The reaction mixture was heated at 60° C. for 30 minutes. Silica gel was added and the mixture was concentrated under reduced pressure. The silica-adsorbed compound was purified using column chromatography, eluent: toluene-ethyl acetate (2:1).

The formed diester was hydrolyzed in 2 M NaOH (3.5 ml) and 1,4-dioxane (3 ml) at 60° C. for 1.5 h. Ethyl acetate (2 ml) was added and the phases were separated. The desired compound precipitated upon addition of 6 M HCl. The obtained crystals were collected by centrifugation and washed with water two times. Further purification using preparative HPLC was necessary. Yield: 26.5 mg, (4%); orange solid. $^1$H NMR (400 MHz, CDCl$_3$): δ 2.70 (t, J 7.2 Hz, 4H), 3.04 (t, J 7.2 Hz, 4H), 3.25 (s, 6H), 7.39 (s, 2H), 7.57 (s, 2H), 7.95 (q, J 8.4 Hz, 8H).

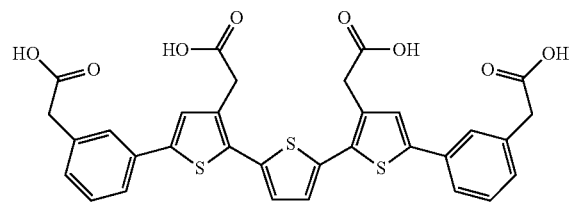 [SMILES: O=C(O)Cc1cccc(-c2cc(CC(=O)O)c(-c3ccc(-c4sc(-c5cccc(CC(=O)O)c5)cc4CC(=O)O)s3)s2)c1]

Example 52

2-(2-{5-[3-(Carboxymethyl)-5-[3-(carboxymethyl)phenyl]thiophen-2-yl]thiophen-2-yl}-5-[3-(carboxymethyl)phenyl]thiophen-3-yl)acetic acid (P9707_055)

Argon was flushed through a solution of intermediate D (91.7 mg, 0.167 mmol) and 3-(2-methoxy-2-oxoethyl)phenylboronic acid, pinacol ester (115 mg, 0.416 mmol) in a stirred mixture of toluene (3 ml) and MeOH (3 ml). K$_2$CO$_3$ (345 mg, 2.50 mmol) and PEPPSI-iPr™ (15.2 mg, 0.0210 mmol) were added and the reaction heated at 60° C. for 2 hours. The solvents were removed in vacuo and the crude material was added dioxane (2 ml), water (2 ml) and 5 M NaOH (1 ml). The reaction was stirred at 80° C. for 1 hour, then cooled and concentrated to dryness. Some water and 1 M NH$_4$HCO$_3$ were added and the mixture was purified by prep-HPLC (5-45% MeCN, in 50 mM NH$_3$/NH$_4$HCO$_3$ buffer). The combined pure fractions were concentrated to dryness. The compound was dissolved in water (20 ml) and some 1 M HCl was added. The solid was collected and washed several times with water and dried. Yield: 31 mg (29%) as a yellow solid. $^1$H NMR (400 MHz, DMSO-d$_6$): δ 3.65 (s, 4H), 3.79 (s, 4H), 7.24 (d, 2H), 7.33 (s, 2H), 7.39 (t, 2H), 7.50 (s, 2H), 7.55 (d, 2H), 7.58 (s, 2H). HPLC: R$_t$=1.56 min, 100% (254 nm, 10-40% MeCN in 10 mM buffer, XBridge) and $R_t$=1.13 min, 100% (214 nm, 10-90% MeCN in 10 mM buffer, XBridge). LC-MS: m/z=650 (M+18).

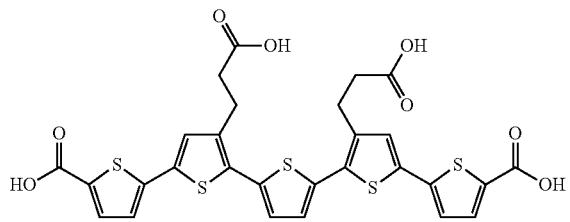 [SMILES: O=C(O)CCc1cc(-c2ccc(C(=O)O)s2)sc1-c1ccc(-c2sc(-c3ccc(C(=O)O)s3)cc2CCC(=O)O)s1]

Example 53

5-[4-(2-Carboxethyl)-5-{5-[3-(2-carboxyethyl)-5-(5-carboxythiophen-2-yl)thiophen-2-yl]thiophen-2-yl}thiophen-2-yl]thiophene-2-carboxylic acid (P9707_056)

The intermediate C2 (199 mg, 0.34 mmol) and (5-methoxycarbonyl-2-thiophenyl) boronic acid (166 mg, 0.89 mmol) were dissolved in methanol (5 ml) and toluene (5 ml). Potassium carbonate (241 mg, 1.74 mmol) was added and argon (g) was bubbled through the reaction mixture before the PEPPSI-iPr™ (12 mg, 0.017 mmol) was added. The reaction mixture was heated for 30 minutes at 60° C. and temperature was then elevated to 80° C. for another 30 minutes. Solution went from bright yellow to brown. The solvents were removed under reduced pressure. The diester was hydrolyzed using 1,4-dioxane (7 ml) and 2 M NaOH (7 ml) and the mixture was left to stir over night. The temperature was raised to 80° C. and stirred for 30 minutes and the solution was dark and transparent. $H_2O$ and EtOAc were added to the reaction and the phases were separated and the acid was precipitated using 6 M HCl. The crystals were collected by centrifugation and washed twice with water and purified by preparative HPLC. The desired compound was obtained as a red solid in 23% yield (51 mg). $^1$H NMR (400 MHz, DMSO-$d_6$): δ 2.67 (t, J 7.6 Hz, 4H), 3.00 (t, J 7.6 Hz, 4H), 7.36-7.38 (m, 4H), 7.48 (br s, 2H), 7.67 (d, J 3.6 Hz, 2H)

Example 54

4-{5-[3-(Carboxymethyl)-5-{5-[4-(carboxymethyl)-5-[5-(4-carboxyphenyl)thiophen-2-yl]thiophen-2-yl]thiophen-2-yl}thiophen-2-yl]thiophen-2-yl}benzoic acid (P9707_057)

Argon was bubbled through a mixture of intermediate A2 (331 mg, 1.21 mmol), 4-methoxycarboxyphenylboronic acid (327 mg, 1.82 mmol) and $K_2CO_3$ (503 mg, 3.64 mmol) in toluene (4 ml) and MeOH (4 ml). PEPPSI-iPr™ (16 mg, 0.024 mmol) was added and the mixture heated at 60° C. for 1 h under argon. EtOAc and water were added. Organic layer was separated and evaporated. The residue was purified by flash chromatography using 0-1% EtOAc in toluene as eluent, Yield: 424 mg (93%); yellow oil which solidifies. $^1$H NMR (400 MHz, CDCl$_3$): δ 3.75 (s, 3H), 3.81 (s, 2H), 3.93 (s, 3H), 7.07 (d, J 5.2 Hz, 1H), 7.18 (d, J 3.6 Hz, 1H), 7.27 (d, J 5.6 Hz, 1H), 7.39 (d, J 4.0 Hz, 1H), 7.65 (d, J 8.4 Hz, 2H), 8.04 (d, J 8.4 Hz, 2H).

NBS (260 mg, 1.46 mmol) was added portion-wise to a solution of the material from above (546 mg, 1.46 mmol) in chloroform (5 ml) and AcOH (5 ml) at 0° C. and the mixture was stirred at 4° C. overnight. Solvents were evaporated and residue purified by flash chromatography using 2% EtOAc in toluene as eluent. Yield: 512 mg (78%); pale yellow solid. $^1$H NMR (400 MHz, CDCl$_3$): δ 3.74 (s, 5H), 3.93 (s, 3H), 7.04 (s, 1H), 7.14 (d, J 3.6 Hz, 1H), 7.37 (d, J 3.6 Hz, 1H), 7.65 (d, J 8.4 Hz, 2H), 8.05 (d, J 8.4 Hz, 2H).

Argon was bubbled through a mixture of the material from above (204 mg, 0.452 mmol), 2,5-thiophenediboronic acid (38 mg, 0.226 mol) and $K_2CO_3$ (78 mg, 0.565 mmol) in toluene (8 ml) and MeOH (8 ml). PEPPSI-iPr™ (6 mg, 0.009 mmol) was added and mixture heated at 60° C. under argon for 45 min. Solvents were evaporated and residue added dioxane (5 ml) and 2 M NaOH (5 ml). The mixture was heated and 80° C. for 1 h. Material was precipitated by addition of 2 M HCl and purified by prep. hplc using 10-30% MeCN in 50 mM buffer as eluent. Pure fractions were combined and some solvents evaporated. Solid material was precipitated by addition of 2 M HCl, isolated by centrifugation, washed three times with water and dried at high vacuum for 3 d. Yield: 24.7 mg (14%); deep red solid. Rt=2.07 min, 95% at 254 nm (10-40% MeCN in buffer, XBridge) and Rt=2.09 min. 95% at 400 nm (10-40% MeCN in buffer, XBridge). $^1$H NMR (400 MHz, DMSO-$d_6$): δ 3.81 (s, 4H), 7.34 (d, J 4.0 Hz, 2H), 7.37 (s, 2H), 7.74 (d, J 3.8 Hz, 2H), 7.82 (d, J 8.5 Hz, 4H), 7.99 (d, J 8.5 Hz, 4H). MS: m/z=767 (M−1) (neg. ionization).

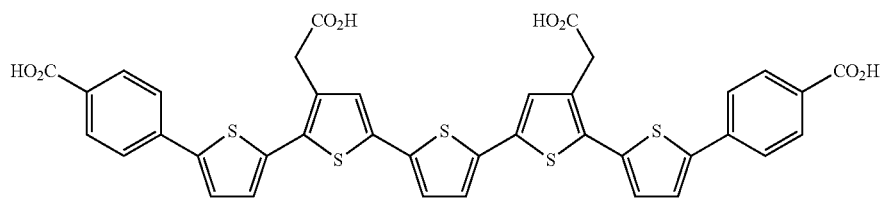 [SMILES: O=C(O)Cc1cc(-c2ccc(-c3cc(CC(=O)O)c(-c4ccc(-c5ccc(C(=O)O)cc5)s4)s3)s2)sc1-c1ccc(-c2ccc(C(=O)O)cc2)s1]

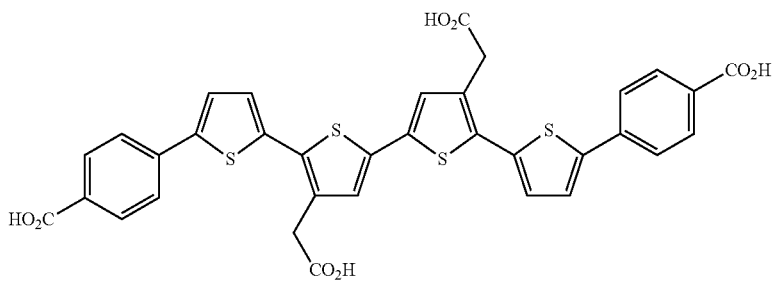 [SMILES: O=C(O)Cc1cc(-c2cc(CC(=O)O)c(-c3ccc(-c4ccc(C(=O)O)cc4)s3)s2)sc1-c1ccc(-c2ccc(C(=O)O)cc2)s1]

Example 55

4-{5-[3-(Carboxymethyl)-5-[4-(carboxymethyl)-5-[5-(4-carboxyphenyl)thiophen-2-yl]thiophen-2-yl]thiophen-2-yl]thiophen-2-yl}benzoic acid (P9707_058)

Argon was bubbled through a mixture of intermediate A2 (331 mg, 1.21 mmol), 4-methoxycarboxyphenylboronic acid (327 mg, 1.82 mmol) and $K_2CO_3$ (503 mg, 3.64 mmol) in toluene (4 ml) and MeOH (4 ml). PEPPSI-iPr™ (16 mg, 0.024 mmol) was added and the mixture heated at 60° C. for 1 h under argon. EtOAc and water was added. Organic layer was separated and evaporated. The residue was purified by flash chromatography using 0-1% EtOAc in toluene as eleuent. Yield: 424 mg (93%); yellow oil which solidifies. $^1$H NMR (400 MHz, $CDCl_3$): δ 3.75 (s, 3H), 3.81 (s, 2H), 3.93 (s, 3H), 7.07 (d, J 5.2 Hz, 1H), 7.18 (d, J 3.6 Hz, 1H), 7.27 (d, J 5.6 Hz, 1H), 7.39 (d, J 4.0 Hz, 1H), 7.65 (d, J 8.4 Hz, 2H), 8.04 (d, J 8.4 Hz, 2H).

NBS (260 mg, 1.46 mmol) was added portion-wise to a solution of the material from above (546 mg, 1.46 mmol) in chloroform (5 ml) and AcOH (5 ml) at 0° C. and the mixture was stirred at 4° C. overnight. Solvent was evaporated and residue purified by flash chromatography using 2% EtOAc in toluene as eluent. Yield: 512 mg (78%); pale yellow solid. $^1$H NMR (400 MHz, $CDCl_3$): δ 3.74 (s, 5H), 3.93 (s, 3H), 7.04 (s, 1H), 7.14 (d, J 3.6 Hz, 1H), 7.37 (d, J 3.6 Hz, 1H), 7.65 (d, J 8.4 Hz, 2H), 8.05 (d, J 8.4 Hz, 2H).

Argon was bubbled through a mixture of the material from above (174 mg, 0.386 mmol), bispinacolatodiboron (49 mg, 0.193 mg) and $K_2CO_3$ (266 mg, 1.93 mmol) in DMSO (2 ml). 1,1'-Bis(diphenylphosphino)ferrocene dichloropalladium (II) (49 mg, 0.193 mmol) was added and the mixture was heated at 80° C. in a sealed tube overnight. 2 M NaOH (2 ml) was added and heating was continued at 80° C. for 1 h. Solid material was precipitated by addition of 2 M HCl and isolated by centrifugation. The solid was purified by prep. hplc using 5-25% MeCN in buffer as eluent. Pure fractions were combined and some solvents evaporated. Solid material precipitated upon addition of 2 M HCl and this was isolated by centrifugation, washed three times with water and dried at high vacuum for 3 d. Yield: 45.5 mg (34%); red solid. Rt=2.96 min, 96% at 400 nm (5-20% MeCN in buffer, XBridge) and Rt=1.74 min. 97% at 400 nm (10-30% MeCN in buffer, XBridge). $^1$H NMR (400 MHz, DMSO-$d_6$): δ 3.82 (s, 4H), 7.35 (s, 2H), 7.37 (s, 2H), 7.75 (d, J 4.0 Hz, 2H), 7.82 (d, J 8.5 Hz, 4H), 8.00 (d, J 8.5 Hz, 4H). MS: m/z=685 (M−1) (neg. ionization).

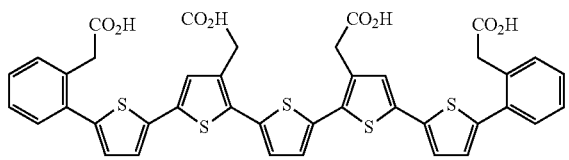 [SMILES: O=C(O)Cc1ccccc1-c1ccc(-c2cc(CC(=O)O)c(-c3ccc(-c4sc(-c5ccc(-c6ccccc6CC(=O)O)s5)cc4CC(=O)O)s3)s2)s1]

Example 56

2-(2-{5-[3-(Carboxymethyl)-5-{5-[2-(carboxymethyl)phenyl]thiophen-2-yl}thiophen-2-yl]thiophen-2-yl}-5-{5-[2-(carboxymethyl)phenyl]thiophen-2-yl}thiophen-3-yl)acetic acid (P9707_059)

Argon was bubbled through the mixture of intermediate P (144 mg, 0.210 mmol), 2-(methoxycarbonylmethyl)phenylboronic acid pinacol ester (144 mg, 0.524 mmol) in dioxane (3 ml) and 1 M $K_2CO_3$ (3 ml). PEPPSI-iPr™ (5 mg, 0.007 mmol) was added and the mixture heated at 100° C. for 2.5 h. 2 M NaOH (3 ml) was added and the mixture was heated at 80° C. for 1 h. Mixture was added water and 2 M HCl (ca 10 ml) the precipitate was filtered and washed with water. Solid material was purified by prep. hplc using 10-40% MeCN in buffer, Pure fractions were combined and some solvents were evaporated. 2 M HCl was added and the precipitate isolated by centrifugation and washed three times with water. The material was dried under high vacuum for 2 d. Yield: 35.7 mg (22%); red solid. Rt=2.43 min, 95% at 254 nm (10-40% MeCN in buffer, XBridge) and Rt=2.43 min, 95% at 400 nm (10-40% MeCN in buffer, XBridge). $^1$H NMR (400 MHz, DMSO-$d_6$): δ 3.75 (s, 4H), 3.78 (s, 4H), 7.12 (d, J 3.8 Hz, 2H), 7.31 (s, 2H), 7.33 (s, 2H), 7.34-7.47 (m, 10H). MS: m/z=795 (M−1) (neg. ionization).

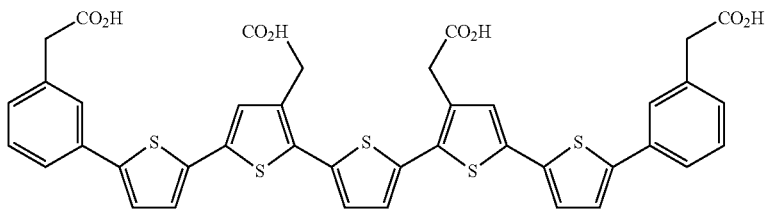 [SMILES: O=C(O)Cc1cccc(-c2ccc(-c3cc(CC(=O)O)c(-c4ccc(-c5sc(-c6ccc(-c7cccc(CC(=O)O)c7)s6)cc5CC(=O)O)s4)s3)s2)c1]

Example 57

2-(2-{5-[3-(Carboxymethyl)-5-{5-[3-(carboxymethyl)phenyl]thiophen-2-yl}thiophen-2-yl]thiophen-2-yl}-5-{5-[3-(carboxymethyl)phenyl]thiophen-2-yl}thiophen-3-yl)acetic acid (P9707_060)

Argon was bubbled through a mixture of intermediate O (118 mg, 0.165 mmol), 3-(2-methoxy-2-oxoethyl)phenylboronic acid, pinacol ester (114 mg, 0.413 mmol) and $K_2CO_3$ (114 mg, 0.826 mmol) in toluene (8 ml) and MeOH (8 ml). PEPPSI-iPr™ (5 mg, 0.0074 mmol) was added and the mixture heated at 70° C. in a sealed tube for 45 min. Solvents were evaporated and residue added dioxane (5 ml) and 2 M NaOH (5 ml). The mixture was heated at 80° C. for 1 h. 2 M HCl was added and precipitated material isolated by centrifugation, and purified by prep. hplc. Pure fractions were combined and some solvents evaporated. 2 M HCl was added and precipitate isolated by centrifugation and washed with water (three times). The material was dried at high vacuum for 2 d. Yield: 37.4 mg (26%); dark red almost black solid. Rt=2.40 min, 97% at 400 nm (10-40% MeCN in buffer, XBridge) and Rt=2.40 min. 96% at 254 nm (10-40% MeCN in buffer, XBridge). $^1$H NMR (400 MHz, DMSO-$d_6$): δ 3.65 (s, 4H), 3.79 (s, 4H), 7.24 (d, J 7.5 Hz, 2H), 7.33 (s, 2H), 7.35 (s, 2H), 7.37-7.41 (m, 4H), 7.52 (d, J 4.0 Hz, 2H), 7.58-7.60 (m, 4H). MS: m/z=795 (M−1) (neg. ionization).

NMR (400 MHz, CDCl$_3$): δ 3.69 (s, 2H), 3.71 (s, 2H), 3.74 (s, 6H), 6.90 (s, 1H), 7.03 (s, 1H), 7.09 (s, 2H).

Argon was bubbled through a mixture of the material from above (205 mg, 0.407 mmol), 2,5-thiophenediboronic acid and $K_2CO_3$ (224 mg, 1.63 mmol) in toluene (4 ml) and MeOH (4 ml). PEPPSI-iPr™ was added and the mixture heated at 60° C. for 30 min under argon. Solvents were evaporated and dioxane (5 ml) and 2 M NaOH (5 ml) was added. The mixture was heated at 80° C. for 2 h. Solid material was precipitated by addition of 2 M HCl and separated by centrifugation. The solid material was purified by prep. hplc. Pure fractions were combined, some solvents evaporated and material precipitated by addition of 2 M HCl. The solid was isolated by centrifugation, washed three times with water and dried at high vacuum for 2 d. Yield: 19.0 mg (10%); black solid. Rt=2.98 min, 96% at 254 nm (10-40% MeCN in buffer, XBridge) and Rt=2.98 min. 96% at 400 nm (10-40% MeCN in buffer, XBridge). $^1$H NMR (400 MHz, DMSO-$d_6$): δ 3.71 (s, 4H), 3.76 (s, 4H), 7.15 (s, 2H), 7.27 (d, J 4 Hz, 2H), 7.31 (d, J 4 Hz, 2H), 7.35 (s, 4H). MS: m/z=877 (M−1) (neg. ionization).

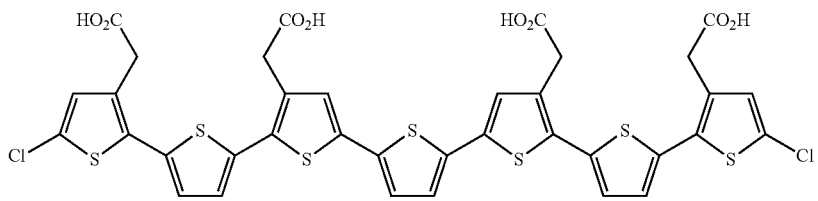 [SMILES: O=C(O)Cc1cc(Cl)sc1-c1ccc(-c2sc(-c3ccc(-c4cc(CC(=O)O)c(-c5ccc(-c6sc(Cl)cc6CC(=O)O)s5)s4)s3)cc2CC(=O)O)s1]

Example 58

2-(2-{5-[3-(Carboxymethyl)-5-{5-[4-(carboxymethyl)-5-{5-[3-(carboxymethyl)-5-chlorothiophen-2-yl]thiophen-2-yl}thiophen-2-yl]thiophen-2-yl}thiophen-2-yl]thiophen-2-yl}-5-chlorothiophen-3-yl)acetic acid (P9707_061)

NCS (73 mg, 0.547 mmol) was added to a solution of intermediate E (258 mg, 0.547 mmol) in AcOH (5 ml). The mixture was stirred at rt for 3 days. Solvent was evaporated and residue purified by flash chromatography using 2% EtOAc in toluene. Yield: 205.8 mg (74%); yellow oil. $^1$H

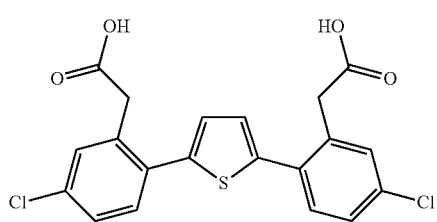 [SMILES: O=C(O)Cc1cc(Cl)ccc1-c1ccc(-c2ccc(Cl)cc2CC(=O)O)s1]

Example 59

2-(2-{5-[2-(Carboxymethyl)-4-chlorophenyl]thiophen-2-yl}-5-chlorophenyl)acetic acid (P9707_062)

Acetyl chloride (1.43 ml, 20.0 mmol) was added to a stirred solution of 2-bromo-5-chlorophenylacetic acid (2.00 g, 8.00 mmol) in MeOH (50 ml) at 0° C. The reaction was then stirred at r.t. overnight and the solvent was removed in vacuo. The crude material was dissolved in $EtO_2$ (~100 ml) and washed with diluted $Na_2CO_3$. The organic phase was dried over $MgSO_4$ and removed in vacuo. Yield: 1.93 g (91%). LC-MS: m/z=263, 265 (M+17, 19)

The material from above (866 mg, 3.29 mmol) in dry 1,4 dioxane (15 ml) was added to bis(pinacolato)diboron (918 mg, 3.62 mmol) and AcOK (1.19 g, 12.2 mmol). The stirred mixture was flushed with argon and 1,1'-bis(diphenylphosphino)ferrocene-palladium(II)dichloride (120 mg, 0.164 mmol) was added. The reaction was heated in a sealed tube at 100° C. for 3 hours. Cooled and diluted with $Et_2O$. The organic phase was washed with water and brine, dried over $MgSO_4$ and removed in vacuo. The crude material was dissolved in toluene and purified by flash chromatography (5% EtOAc in toluene, 200 ml silica). Yield: 511 mg (50%) as a colourless oil. LC-MS: m/z=311 (M+1).

Argon was flushed through a stirred solution of the material from above (140 mg, 0.451 mmol) and 2,5-dibromothiophene (32.7 mg, 0.135 mmol) in a mixture of toluene (3 ml) and MeOH (3 ml). $K_2CO_3$ (374 mg, 2.71 mmol) and PEPPSI-iPr™ (16.5 mg, 0.0230 mmol) were added and the reaction heated at 60° C. for 3 hours. The solvents were removed in vacuo. The crude material was dissolved in a mixture of water, MeOH and some 1 M $NH_4HCO_3$ and purified by prep-HPLC (5-40% MeCN, in 50 mM $NH_3/NH_4HCO_3$ buffer). The combined pure fractions were concentrated to dryness. The compound was dissolved in water and some 1 M HCl was added. The mixture was extracted with EtOAc. The organic phase was dried over $MgSO_4$ and concentrated in vacuo. Yield: 15 mg (8%) as a white solid. $^1$H NMR (400 MHz, DMSO-$d_6$): δ 3.77 (s, 4H), 7.15 (s, 2H), 7.42 (d, J 2.0 Hz, 0.4H), 7.44 (d, J 2.0 Hz, 1.6H), 7.45 (s, 1.6H), 7.47 (s, 0.4H), 7.51 (d, J 2.3 Hz, 2H). HPLC: Rt=2.59 min, 95% (254 nm, 10-40% MeCN in 10 mM buffer, XBridge) and Rt=1.65 min, 97% (214 nm, 10-90% MeCN in 10 mM buffer, XBridge). LC-MS: m/z=438 (M+18).

mmol) in MeOH (50 ml) at 0° C. The reaction was then stirred at r.t. over night. More acetyl chloride (1 ml, 14.0 mmol) was added and the reaction was stirred for 24 hours. The solvent was removed in vacuo and the crude material was dissolved in $EtO_2$ (~100 ml) and washed with 0.5 M NaOH. The organic phase was dried over $MgSO_4$ and removed in vacuo. Yield: 1.97 g (92%). $^1$H NMR (400 MHz, DMSO-$d_6$): δ 2.33 (s, 3H), 3.94 (s, 3H), 7.13 (d, 1H), 7.52 (d, 1H), 7.60 (s, 1H)

The ester from above (800 mg, 3.49 mmol) in dry 1,4 dioxane (15 ml) was added to bis(pinacolato)diboron (976 mg, 3.84 mmol) and AcOK (1.27 g, 12.9 mmol). The stirred mixture was flushed with argon and 1,1'-bis(diphenylphosphino)ferrocene-palladium(II)dichloride (25.6 mg, 0.035 mmol) was added. The reaction was heated in a sealed flask at 100° C. for 3 hours then cooled and diluted with $Et_2O$. The organic phase was washed with water and brine, dried over $MgSO_4$ and removed in vacuo. The crude material was diluted with iso-hexane and purified by flash chromatography (20% EtOAc in iso-hexane, 200 ml silica). Yield: 697 mg (72%) as a colourless oil. $^1$H NMR (400 MHz, DMSO-$d_6$): δ 1.42 (s, 12H), 2.38 (s, 3H), 3.91 (s, 3H), 7.31-7.35 (m, 1H), 7.38-7.43 (m, 1H), 7.76 (s, 1H).

Argon was flushed through a stirred solution of intermediate D (120 mg, 0.217 mmol) and the pinacolester from above (150 mg, 0.543 mmol) in a mixture of toluene (3 ml) and MeOH (3 ml). $K_2CO_3$ (150 mg, 0.543 mmol) and PEPPSI-iPr™ (19.8 mg, 0.027 mmol) were added and the reaction heated at 60° C. for 2 hours in a sealed flask. The solvents were removed in vacuo and the crude material was added dioxane (2 ml), water (2 ml) and 5 M NaOH (1 ml). The reaction was stirred at 80° C. for 30 min. The mixture was cooled and concentrated. Some water and 1 M $NH_4HCO_3$ (until pH~10) were added and the mixture was purified by prep-HPLC (5-40% MeCN, in 50 mM $NH_3/NH_4HCO_3$ buffer). The combined pure fractions were concentrated to dryness. The compound was dissolved in water (20 ml) and some 2 M HCl was added. The solid was collected and washed several times with water and dried. Yield: 25 mg (18%); yellow solid. $^1$H NMR (400 MHz, DMSO-$d_6$): δ 2.37 (s, 6H), 3.74 (s, 4H), 7.10 (s, 2H), 7.29 (s, 2H), 7.36-7.44 (m, 4 H), 7.47-7.49 (m, 2 H). HPLC: Rt=1.82 min, 100% (254 nm, 10-40% MeCN in 10 mM buffer, XBridge) and Rt=1.35 min, 97% (400 nm, 10-90% MeCN in 10 mM buffer, XBridge). LC-MS: m/z=650 (M+18).

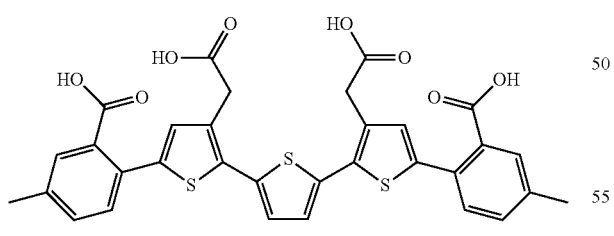

Example 60

2-(5-{5-[5-(2-Carboxy-4-methylphenyl)-3-(carboxymethyl)thiophen-2-yl]thiophen-2-yl}-4-(carboxymethyl)thiophen-2-yl)-5-methylbenzoic acid (P9707_063)

Acetyl chloride (1.66 ml, 23.3 mmol) was added to a stirred solution of 2-bromo-5-methylbenzoic acid (2.00 g, 9.30

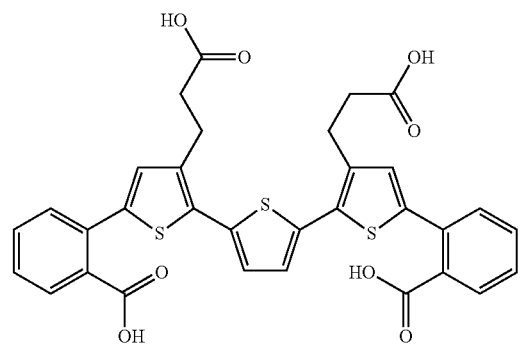 [SMILES: O=C(O)CCc1cc(-c2ccccc2C(=O)O)sc1-c1ccc(-c2sc(-c3ccccc3C(=O)O)cc2CCC(=O)O)s1]

Example 61

2-[4-(2-Carboxethyl)-5-{5-[3-(2-carboxyethyl)-5-(2-carboxyphenyl)thiophen-2-yl]thiophen-2-yl}thiophen-2-yl]benzoic acid (P9707_064)

Intermediate B2 (198.5 mg, 0.34 mmol) and (2-methoxycarbonylbenzene)boronic acid (149.9 mg, 0.83 mmol) were dissolved in methanol (5 ml) and toluene (5 ml). Potassium carbonate (239.4 mg, 1.73 mmol) was added and argon was bubbled through the solution before PEPPSI-iPr™ was added. The reaction was stirred at 60° C. for 2 h. The solvents were removed under reduced pressure. Column chromatography using toluene/ethyl acetate (3:1→2:1) as eluent was performed. 132 mg of the desired material was afforded (not completely pure) and 45 mg of the starting material was retrieved.

The coupled product was dissolved in 1,4-dioxane (3 ml) and NaOH 2 M (3 ml) and heated at 60° C. for 30 minutes. The acid was precipitated by adding HCl 6 M (0.5 ml) and solid material purified by preparative HPLC (Xbridge 5%-50% MeCN) was necessary. The compound was precipitated using 6 M HCl and collected 38.2 mg (18%) pure compound. $^1$H NMR (400 MHz, DMSO-$d_6$): δ 2.62 (t, J 7.8 Hz, 4H), 3.00 (t, J 7.6 Hz, 4H), 7.13 (s, 2H), 7.29 (s, 2H), 7.42-7.49 (m, 2H), 7.50-7.59 (m, 4H), 7.64 (d, J 7.5 Hz, 2H).

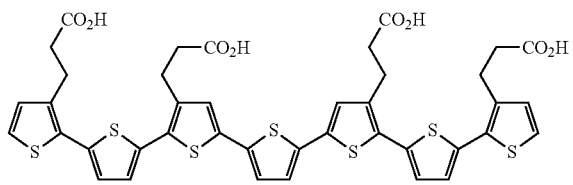 [SMILES: O=C(O)CCc1ccsc1-c1ccc(-c2sc(-c3ccc(-c4cc(CCC(=O)O)c(-c5ccc(-c6sccc6CCC(=O)O)s5)s4)s3)cc2CCC(=O)O)s1]

$K_2CO_3$ (52.4 mg, 0.38 mmol) was suspended in toluene (3 ml) and methanol (3 ml). Argon was bubbled through the mixture before PEPPSI-iPr™ (4.9 mg, 0.007 mmol) was added. The reaction was stirred at 70° C. for 45 minutes; temperature was lowered to 55° C. and stirred for another hour. More $K_2CO_3$ (51.5 mg, 0.37 mmol) was added and reaction continued for 45 minutes. The solvents were removed under reduced pressure.

The red solid was dissolved in 1,4-dioxane (3.5 ml) and 2 M NaOH (3 ml) and heated at 60° C. for 50 minutes. Precipitated with 6 M HCl and collected the solid by centrifugation. Purification: prep HPLC (5-40% MeCN in $NH_4COO_3$) →80% pure; Prep HPLC (15-45% MeCN in $NH_4COO_3$) →99% pure. The pure fractions were combined and the product was precipitated using 6 M HCl and washed twice with $H_2O$. Compound dried on freeze-drier for 3 d. The dark red compound was afforded in 21 mg (19%) yield.

$^1$H NMR (400 MHz, DMSO-$d_6$): δ 2.55-2.69 (m, 8H), 2.99 (t, J 7.6 Hz, 8H), 7.09 (d, J 5.3 Hz, 2H), 7.26 (d, J 3.8 Hz, 2H), 7.30 (d, J 3.8 Hz, 2H), 7.34 (d, J 7.8 Hz, 4H), 7.52 (d, J 5.0 Hz, 2H).

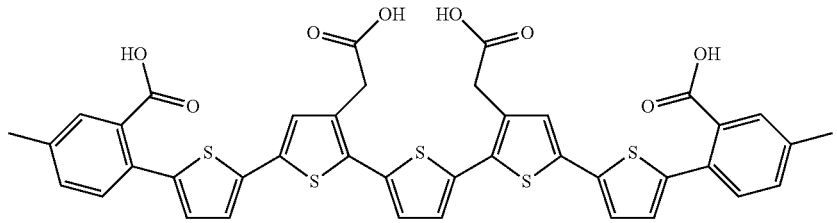

Example 62

3-(2-{5-[3-(2-Carboxyethyl)-5-{5-[4-(2-carboxyethyl)-5-{5-[3-(2-carboxyethyl)thiophen-2-yl]thiophen-2-yl}thiophen-2-yl]thiophen-2-yl}thiophen-2-yl]thiophen-2-yl}thiophen-3-yl)propanoic acid (P9707_065)

The intermediate B2 (373.6 mg, 0.89 mmol) was dissolved chloroform (4 ml) and acetic acid (4 ml). The solution was cooled to 0° C. and N-iodosuccinimide (199.8 mg, 0.89 mmol) was added. The reaction was slowly warmed to room temperature overnight. The reaction mixture was poured onto $Na_2S_2O_3$ and extracted with DCM (×2). The organic phases were combined and washed with water and brine and dried with $MgSO_4$. Concentration under reduced pressure gave a 519 mg red residue. The residue was purified by column chromatography, 2% ethyl acetate in toluene: 191.5 mg (38%) of a yellow oil. $^1$H NMR (400 MHz, CDCl$_3$): δ 2.64 (dt, J 11.5, 7.8 Hz, 4H), 3.10 (dt, J 15.9, 7.8 Hz, 4H), 3.69 (d, J 1.5 Hz, 6H), 6.96 (d, J 5.3 Hz, 1H), 7.02-7.06 (m, 1H), 7.07-7.12 (m, 2H), 7.22 (d, J 5.3 Hz, 1H).

The monoido-product (138.9 mg, 0.25 mmol) from above, 2,5-thiophenediboronic acid (21.6 mg, 0.13 mmol) and Example 63

2-{5-[5-(5-{5-[5-(2-Carboxy-4-methylphenyl)thiophen-2-yl]-3-(carboxymethyl)thiophen-2-yl}thiophen-2-yl)-4-(carboxymethy)thiophen-2-yl]thiophen-2-yl}-5-methylbenzoic acid (P9707_066)

Acetyl chloride (1.66 ml, 23.3 mmol) was added to a stirred solution of 2-bromo-5-methylbenzoic acid (2.00 g, 9.30 mmol) in MeOH (50 ml) at 0° C. The reaction was then stirred at r.t. overnight. More acetyl chloride (1 ml, 14.0 mmol) was added and the reaction was stirred for 24 hours. The solvent was removed in vacuo and the crude material was dissolved in $EtO_2$ (~100 ml) and washed with 0.5 M NaOH. The organic phase was dried over $MgSO_4$ and removed in vacuo. Yield: 1.97 g (92%). $^1$H NMR (400 MHz, DMSO-$d_6$): δ 2.33 (s, 3H), 3.94 (s, 3H), 7.13 (d, 1H), 7.52 (d, 1H), 7.60 (s, 1H).

The ester from above (800 mg, 3.49 mmol) in dry 1,4 dioxane (15 ml) was added to bis(pinacolato)diboron (976 mg, 3.84 mmol) and AcOK (1.27 g, 12.9 mmol). The stirred mixture was flushed with argon and 1,1'-bis(diphenylphosphino)ferrocene-palladium(II)dichloride (25.6 mg, 0.035 mmol) was added. The reaction was heated in a sealed flask at 100° C. for 3 hours then cooled and diluted with $Et_2O$. The organic phase was washed with water and brine, dried over $MgSO_4$ and concentrated in vacuo. The crude material was diluted with iso-hexane and purified by flash chromatography (20% EtOAc in iso-hexane, 200 ml silica). Yield: 697 mg (72%) as a colourless oil. $^1$H NMR (400 MHz, DMSO-d$_6$): δ 1.42 (s, 12H), 2.38 (s, 3H), 3.91 (s, 3H), 7.31-7.35 (m, 1H), 7.38-7.43 (m, 1H), 7.76 (s, 1H).

Argon was flushed through a solution of intermediate O (155 mg, 0.217 mmol) and the boronic ester from above (150 mg, 0.543 mmol) in a mixture of toluene (5 ml) and MeOH (5 ml). K$_2$CO$_3$ (450 mg, 3.26 mmol) and PEPPSI-iPr™ (19.8 mg, 0.027 mmol) were added and the reaction heated at 60° C. for 3 hours. The solvents were removed in vacuo and the crude material was added dioxane (1 ml) and 5 M NaOH (1 ml). The reaction was stirred at 80° C. for 30 min. The mixture was cooled and water and 1 M NH$_4$HCO$_3$ were added. The mixture was purified by prep-HPLC (20-50% MeCN, in 50 mM NH$_3$/NH$_4$HCO$_3$ buffer). The combined pure fractions were concentrated to dryness. The compound was dissolved in water (20 ml) and some 2 M HCl was added. The solid was collected and washed several times with water and dried. Yield: 25 mg (18%) as a orange solid. $^1$H NMR (400 MHz, DMSO-d$_6$): δ 2.38 (s, 6H), 3.78 (s, 4H), 7.08 (d, J 3.8 Hz, 2H), 7.31 (s, 2H), 7.32 (s, 2H), 7.34 (d, J 3.5 Hz, 2H), 7.36-7.41 (m, 2H), 7.43-7.47 (m, 2H), 7.47-7.50 (m, 2H). HPLC: Rt=2.42 min, 97% (254 nm, 10-40% MeCN in 10 mM buffer, XBridge) and Rt=1.55 min, 100% (400 nm, 10-90% MeCN in 10 mM buffer, XBridge). LC-MS: m/z=797 (M+1).

was dissolved in water (~8 ml). Solid NH$_4$HCO$_3$ was added. The mixture was stirred, filtered and purified by prep-HPLC (10-40% MeCN, in 50 mM NH$_3$/NH$_4$HCO$_3$ buffer). The combined pure fractions were concentrated to dryness. The compound was dissolved in water (20 ml) and some 2 M HCl was added. The solid was collected and washed several times with water and dried. Yield: 85 mg, (76%) as a orange solid. $^1$H NMR (400 MHz, DMSO-d$_6$): δ 3.78 (s, 4H), 6.17 (d, J 15.8 Hz, 2H), 7.34 (s, 2H), 7.38-7.42 (m, 4H), 7.51 (d, J 3.8 Hz, 2H), 7.73 (d, J 15.6 Hz, 2H). HPLC: Rt=1.50 min, 95% (254 nm, 10-40% MeCN in 10 mM buffer, XBridge) and Rt=1.49 min, 95% (400 nm, 10-40% MeCN in 10 mM buffer, XBridge). LC-MS: m/z=669 (M+1).

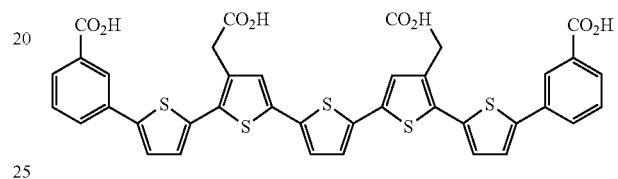

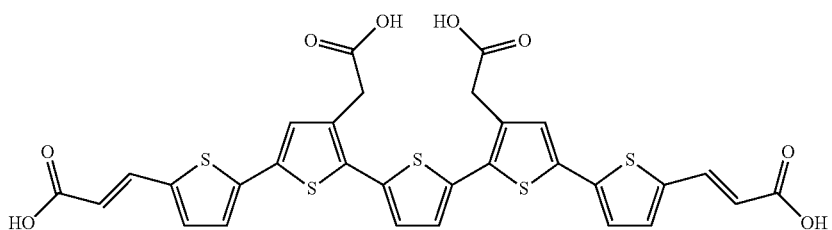 [SMILES: O=C(O)/C=C/c1ccc(-c2cc(CC(=O)O)c(-c3ccc(-c4sc(-c5ccc(/C=C/C(=O)O)s5)cc4CC(=O)O)s3)s2)s1]

Example 64

(2E)-3-(5-{5-[5-(5-{5-[(1E)-2-Carboxyeth-1-en-1-yl]thiophen-2-yl}-3-carboxymethyl)thiophen-2-yl)thiophen-2-yl]-4-(carboxymethyl)thiophen-2-yl}thiophen-2-yl)prop-2-enoic acid (P9707_067)

Argon was bubbled though a mixture of intermediate D (480 mg, 0.873 mmol), 5-formylthiophene-2-boronic acid (409 mg, 2.62 mmol) and K$_2$CO$_3$ (724 mg, 5.24 mmol) in MeOH (10 ml) and toluene (10 ml). PEPPSI-iPr™ (30 mg, 0.0437 mmol) was added and the mixture heated under argon at 80° C. for 30 min. Chloroform was added and mixture filtered. Silica was added to the filtrate and solvents evaporated. The silica was applied on a flash column which was eluted with 1% MeOH in DCM. Yield: 430 mg (80%). $^1$H NMR (400 MHz, CDCl$_3$): δ 3.77 (s, 6H), 3.81 (s, 4H), 7.24 (s, 2H), 7.27 (d, J 4.0 Hz, 2H), 7.32 (s, 2H), 7.68 (d, J 4.0 Hz, 2H), 9.88 (s, 2H).

The material from above (103 mg, 0.168 mmol), methyl triphenylphosphoranylidene)acetate (115 mg, 0.345 mmol) and toluene (15 ml) were stirred at 90° C. for 3 hours. More methyl (triphenylphosphoranylidene)acetate (130 mg, 0.389 mmol) was added and the reaction stirred for 3 hours. The solvent was removed in vacuo and the crude material was dissolved in dioxane (2 ml) and water (2 ml). 5 M NaOH (2 ml) was added the reaction was stirred at 70° C. for 30 min. The solvents were removed in vacuo and the crude material

Example 65

3-{5-[3-(Carboxymethyl)-5-{5-[4-(carboxymethyl)-5-[5-(3-carboxyphenyl)thiophen-2-yl]thiophen-2-yl]thiophen-2-yl}thiophen-2-yl]thiophen-2-yl}thiophen-2-benzoic acid (P9707_068)

Argon was bubbled through a mixture of intermediate A2 (607 mg, 2.23 mmol) and 3-methoxycarboxyphenylboronic acid (480 mg, 2.67 mmol) and K$_2$CO$_3$ (738 mg, 5.34 mmol) in toluene (8 ml) and MeOH (8 ml). PEPPSI-iPr™ (30 mg, 0.045 mmol) was added and mixture was heated in a sealed tube for 45 min. Chloroform was added and mixture filtered and concentrated. The residue was purified by flash chromatography using 2% EtOAc in toluene as eluent. Yield: 749 mg (90%); pale yellow oil. $^1$H NMR (400 MHz, CDCl$_3$) δ 3.74 (s, 3H), 3.82 (s, 2H), 3.96 (s, 3H), 7.06 (d, J 5.2 Hz, 1H), 7.17 (d, J 4.0 Hz, 1H), 7.26 (d, J 5.2 Hz, 1H), 7.35 (d, J 4.0 Hz, 1H), 7.46 (t, J 8 Hz, 1H), 7.78 (d, J 8 Hz, 1H), 7.95 (d, J 8 Hz, 1H), 8.27 (s, 1H). NBS (358 mg, 2.01 mmol) was added portionwise to the material from above (749 mg, 2.01 mmol) in CHCl$_3$ (8 ml) and AcOH (8 ml) and the mixture was stirred at ambient temperature overnight. Solvents were evaporated and residue purified by flash chromatography using 2% EtOAc in toluene. Yield: 702 mg, pure on tlc, pale yellow solid. $^1$H NMR (400 MHz, CDCl$_3$): δ 3.74 (s, 5H), 3.96 (s, 3H), 7.04 (s, 1H), 7.12 (d, J 4 Hz, 1H), 7.34 (d, J 4 Hz, 1H), 7.47 (t, J 8 Hz, 1H), 7.77 (d, J 8 Hz, 1H), 7.96 (d, J 8 Hz, 1H), 8.23 (s, 1H).

Argon was bubbled through a mixture of material from above (204 mg, 0.452 mmol), 2,5-thiophenediboronic acid (35 mg, 0.204 mmol) and K$_2$CO$_3$ (140 mg, 1.02 mmol) in toluene (8 ml) and MeOH (8 ml). PEPPSI-iPr™ was added and mixture heated at 60° C. under argon for 2 h. Solvents were evaporated and residue added dioxane (5 m,l) and 2 M NaOH (5 ml) the mixture was heated at 80° C. for 1 h. Material was purified by prep. hplc. Pure fractions were combined and some solvents evaporated. 2 M HCl was added and solid material isolated by centrifugation, washed with water and freeze-dried for 2 d. Yield: 36.8 mg (24%); deep red solid. Rt=2.32 min, 91% at 400 nm (10-40% MeCN in buffer, XBridge) and Rt=2.32 min. 91% at 254 nm (10-40% MeCN in buffer, XBridge). $^1$H NMR (400 MHz, DMSO-d$_6$): δ 3.81 (s, 4H), 7.33/d, J 3.8 Hz, 2H), 7.36 (s, 4H), 7.59 (t, J 7.7 Hz, 2H), 7.69 (d, J 3.8 Hz, 2H), 7.91 (d, J 7.8 Hz, 2H), 7.97 (d, J 7.8 Hz, 2H), 8.17 (s, 2H). MS: m/z=767 (M−1) (neg. ionization).

the mixture was stirred at 80° C. for 1 h. 2 M HCl and water was added. Solid material was isolated by centrifugation and purified by prep. hplc using 10-30% MeCN in buffer.

Pure fractions were collected and some solvents evaporated. 2 M HCl was added and solid material was isolated by centrifugation. The solid material was washed with water (three times) and freeze-dried for 3 d. Yield: 15.9 mg (6%); deep red solid. Rt=1.78 min, 95% at 254 nm (10-40% MeCN in buffer, XBridge) and Rt=2.14 min. 95% at 400 nm (10-30% MeCN in buffer, XBridge). $^1$H NMR (400 MHz, DMSO-d$_6$): δ 3.81 (s, 4H), 7.33 (d, J 4 Hz, 2H), 7.34 (s, 2H), 7.59 (t, J 8 Hz, 2H), 7.69 (d, J 3.2 Hz, 2H), 7.90 (d, J 8 Hz, 2H), 7.97 (d, J 8 Hz, 2H), 8.17 (s, 2H). MS: m/z=685 (M−1) (neg. ionization)

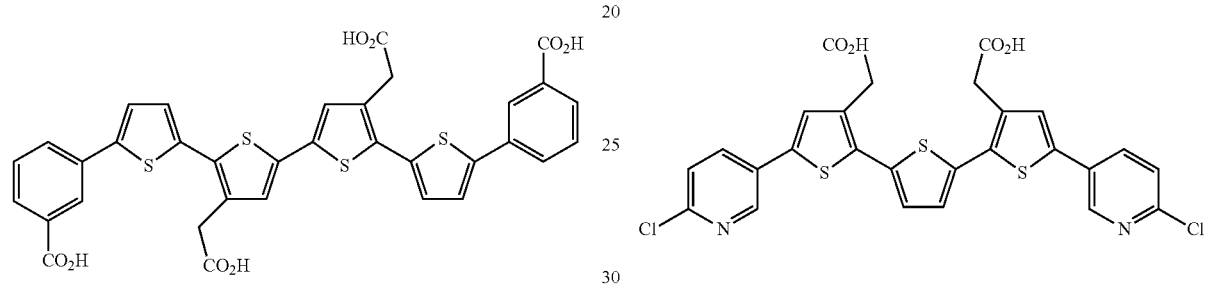

Example 66

3-{5-[3-(Carboxymethyl)-5-[4-(carboxymethyl)-5-[5-(3-carboxyphenyl)thiophen-2-yl]thiophen-2-yl]thiophen-2-yl]thiophen-2-yl}benzoic acid (P9707_069)

Argon was bubbled through a mixture of intermediate A2 (607 mg, 2.23 mmol) and 3-methoxycarboxyphenylboronic acid (480 mg, 2.67 mmol) and K$_2$CO$_3$ (738 mg, 5.34 mmol) in toluene (8 ml) and MeOH (8 ml). PEPPSI-iPr™ (30 mg, 0.045 mmol) was added and mixture was heated in a sealed tube for 45 min. Chloroform was added and mixture filtered and concentrated. The residue was purified by flash chromatography using 2% EtOAc in toluene as eluent. Yield: 749 mg (90%); pale yellow oil. $^1$H NMR (400 MHz, CDCl$_3$): δ 3.74 (s, 3H), 3.82 (s, 2H), 3.96 (s, 3H), 7.06 (d, J 5.2 Hz, 1H), 7.17 (d, J 4.0 Hz, 1H), 7.26 (d, J 5.2 Hz, 1H), 7.35 (d, J 4.0 Hz, 1H), 7.46 (t, J 8 Hz, 1H), 7.78 (d, J 8 Hz, 1H), 7.95 (d, J 8 Hz, 1H), 8.27 (s, 1H). NBS (358 mg, 2.01 mmol) was added portionwise to the material from above (749 mg, 2.01 mmol) in CDCl$_3$ (8 ml) and AcOH (8 ml) and the mixture was stirred at ambient temperature overnight. Solvents were evaporated and residue purified by flash chromatography using 2% EtOAc in toluene. Yield: 702 mg, pure on tlc, pale yellow solid. $^1$H NMR (400 MHz, CDCl$_3$): δ 3.74 (s, 5H), 3.96 (s, 3H), 7.04 (s, 1H), 7.12 (d, J 4 Hz, 1H), 7.34 (d, J 4 Hz, 1H), 7.47 (t, J 8 Hz, 1H), 7.77 (d, J 8 Hz, 1H), 7.96 (d, J 8 Hz, 1H), 8.23 (s, 1H).

Argon was flushed though the mixture of the material from above (174 mg, 0.386 mmol), bispinacolatodiboron (49 mg, 0.193 mmol) and K$_2$CO$_3$ in DMSO (3 ml). 1,1'-bis(diphenylphosphino)ferrocene dichloropalladium (II) (14 mg, 0.019 mmol) was added and the mixture heated at 80° C. overnight in a sealed tube. 2 M NaOH (2 ml) was added and Example 67

2-(2-{5-[3-(Carboxymethyl)-5-(6-chloropyridin-3-yl)thiophen-2-yl]thiophen-2-yl}-5-(6-chloropyridin-3-yl)thiophen-3-yl)acetic acid (P9707_070)

Argon was bubbled through a mixture of intermediate G2 (134 mg, 0.208 mmol), 2-chloropyridine-5-boronic acid (72 mg, 0.458 mmol) and K$_2$CO$_3$ (144 mg, 1.04 mmol) in toluene (3 ml) and MeOH (3 ml). PEPPSI-iPr™ (1.4 mg, 0.002 mmol) was added and the mixture heated in a sealed tube at 80° C. for 45 min. Chloroform was added and mixture filtered and evaporated. The residue was purified by flash chromatography using 10-20% EtOAc in toluene. Yield: 91.2 mg (71%); bright yellow solid. $^1$H NMR (400 MHz, CDCl$_3$): δ 3.77 (s, 6H), 3.83 (s, 4H), 7.23 (s, 2H, 7.32 (s, 2H), 7.36 (d, J 8.4 Hz, 2H), 7.82 (dd, J 8 Hz, 2 Hz, 2H), 8.63 (d, J 2 Hz, 2H). The material from above (91.2 mg, 0.148 mmol) was dissolved in dioxane (3 ml) and 2 M NaOH (3 ml) was added. The mixture was heated at 80° C. for 1 h. EtOAc was added and aqueous layer separated. The organic layer was filtered, colourless solution, yellow solid on filter which was suspended in 2 M HCl and solid material washed with water (three times). The material was dried at high vacuum for 3 d. Yield: 72.6 mg (83%); yellow solid. Rt=2.18 min, 98% at 254 nm (20-50% MeCN in buffer, XBridge) and Rt=2.20 min. 99% at 400 nm (20-50% MeCN in buffer, XBridge). $^1$H NMR (400 MHz, DMSO-d$_6$): δ 3.72 (s, 4H), 7.36 (s, 2H), 7.57 (d, J 8 Hz, 2H), 7.65 (s, 2H), 8.11 (d, J 9 Hz, 2H), 8.72 (s, 2H). MS: m/z=589 (M+1)

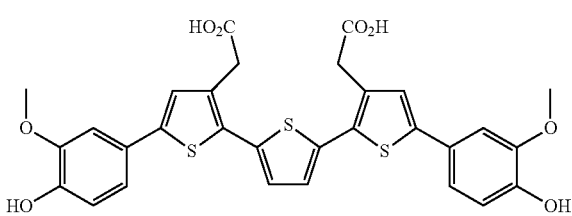 [SMILES: COc1cc(-c2cc(CC(=O)O)c(-c3ccc(-c4sc(-c5ccc(O)c(OC)c5)cc4CC(=O)O)s3)s2)ccc1O]

Example 68

2-(2-{5-[3-(Carboxymethyl)-5-(4-hydroxy-3-methoxyphenyl)thiophen-2-yl]thiophen-2-yl}-5-(4-hydroxy-3-methoxyphenyl)thiophen-3-yl)acetic acid (P9707_071)

Argon was flushed through a solution of intermediate D (130 mg, 0.236 mmol) and 4-hydroxy-3-methoxyphenylboronic acid (120 mg, 0.714 mmol) in a mixture of toluene (3 ml) and MeOH (3 ml). PEPPSI-iPr™ (26.1 mg, 0.036 mmol) and KF (125 mg, 2.14 mmol) were added and the reaction heated at 55° C. for 120 min. The solvents were removed in vacuo and the crude was added water (3 ml), 5 M NaOH (1 ml) and dioxane (2 ml). The reaction was heated to 70° C. for 30 min then cooled, filtered and washed with water. 1 M NH$_4$HCO$_3$ was added and the product was collected as a solid by filtration. Water and 2 M HCl were added. The solid was once more collected by filtration and washed with water. Yield: 110 mg (77%) as a off white solid. $^1$H NMR (400 MHz, DMSO-d$_6$): δ 3.74 (s, 4H), 3.85 (s, 6H), 6.82 (d, J 8.3 Hz, 2H), 7.05 (dd, J 8.28, 2.01 Hz, 2H), 7.17 (d, J 2.0 Hz, 2H), 7.26 (s, 2H), 7.34 (s, 2H), 9.32 (s, 2H), 12.54 (br. s., 2H). HPLC: Rt=2.61 min, 99% (254 nm, 10-40% MeCN in 10 mM buffer, XBridge) and Rt=2.60 min, 98% (400 nm, 10-40% MeCN in 10 mM buffer, XBridge). LC-MS: m/z=626 (M+18).

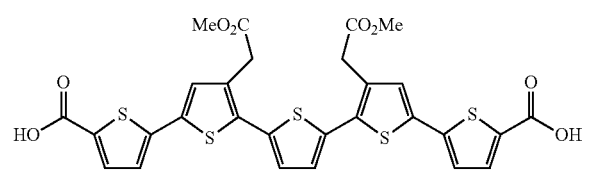 [SMILES: COC(=O)Cc1cc(-c2ccc(C(=O)O)s2)sc1-c1ccc(-c2sc(-c3ccc(C(=O)O)s3)cc2CC(=O)OC)s1]

Example 69

5-(5-{5-[5-(5-Carboxythiophen-2-yl)-3-(2-methoxy-2-oxoethyl)thiophen-2-yl]thiophen-2-yl}-4-(2-methoxy-2-oxoethyl)thiophen-2-yl)thiophene-2-carboxylic acid (P9707_072)

Argon was bubbled through a mixture of intermediate D (208 mg, 0.378 mmol) and 5-carboxythiophene-2-boronic acid (162 mg, 0.945 mmol) and KF (109 mg, 1.89 mmol) in toluene (5 ml) and MeOH (5 ml). PEPPSI-iPr™ (5.2 mg, 0.008 mmol) and the mixture heated at 60° C. for 1 h. Solvents were removed and residue dissolved in 1 M NH$_4$HCO$_3$/water/dioxane and purified by prep. hplc using 15-45% MeCN in 50 mM buffer as eluent. Pure fractions were combined and some solvent evaporated. 1 M HCl was added and the precipitate isolated by centrifugation and washed twice with water. The material was freeze-dried for 3 d. Yield: 51.3 mg (21%); dark red solid. Rt=2.70 min, 98% at 400 nm (10-40% MeCN in buffer, XBridge) and Rt=2.70 min. 98% at 254 nm (10-40% MeCN in buffer, XBridge). $^1$H NMR (400 MHz, DMSO-d$_6$): δ 3.68 (s, 6H), 3.90 (s, 4H), 7.34 (s, 2H), 7.41 (d, J 4 Hz, 2H), 7.48 (s, 2H), 7.68 (d, J 4 Hz, 2H). MS: m/z=662 (M+NH4).

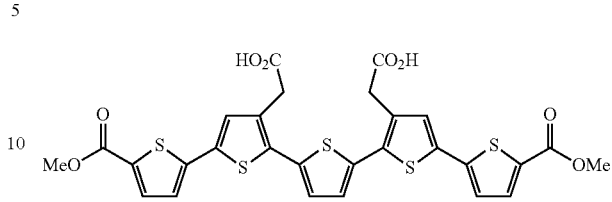

Example 70

2-(2-{5-[3-(Carboxymethyl)-5-[5-(methoxycarbonyl)thiophen-2-yl]thiophen-2-yl]thiophen-2-yl}-5-[5-(methoxycarbonyl)thiophen-2-yl]thiophen-3-yl) acetic acid (P9707_073)

Argon was bubbled through a mixture of intermediate Q (90 mg, 0.172 mmol), 5-methoxycarbonyl)thiophen-2-ylboronic acid (80 mg, 0.431 mmol) and KF (50 mg, 0.862 mmol) in toluene (5 ml) and MeOH (10 ml). PEPPSI-iPr™ was added and the mixture heated at 60° C. for 30 min. Solvents were evaporated and the residue purified by prep. hplc. Pure fractions were combined, some solvents evaporated and 1 M HCl added. The precipitate was filtered and washed several times with water. The material was dried at high vacuum for 1 d. Yield: 6.2 mg (6%); red solid. Rt=2.57 min, 99% at 400 nm (20-50% MeCN in buffer, XBridge) and Rt=2.57 min. 98% at 254 nm (20-50% MeCN in buffer, XBridge). $^1$H NMR (400 MHz, DMSO-d$_6$): δ 3.78 (s, 4H), 3.84 (s, 6H), 7.36 (s, 2H), 7.44 (d, J 4 Hz, 2H), 7.51 (s, 2H), 7.77 (d, J 4 Hz, 2H). MS: m/z=643 (M−1).

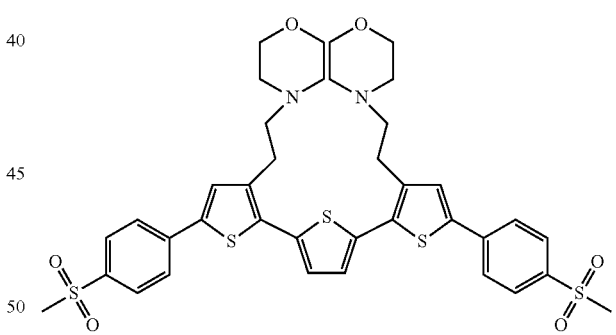

Example 71

4-{2-[5-(4-Methanesulfonylphenyl)-2-{5-[5-(4-methanesulfonylphenyl)-3-[2-(morpholin-4-yl)ethyl]thiophen-2-yl]thiophen-2-yl}thiophen-3-yl]ethyl}morpholine (P9707_074)

Argon was bubbled through a stirred mixture of intermediate J (660 mg, 2.31 mmol), 2,5-thiophenediboronic acid (240 mg, 1.40 mmol), KF (530 mg, 9.12 mmol), MeOH (7 ml) and toluene (7 ml) for 10 min. PEPPSI-iPr™ (40 mg, 0.055 mmol) was added and the reaction was heated at 55° C. in a sealed flask for 90 min. The solvents were removed in vacuo and DCM (~7 ml) was added. The mixture was washed with water and the organic phase was purified by flash chromatography (12.5% EtOAc in toluene, 100 ml silica). Yield: 390 mg (68%) as a yellow solid. $^1$H NMR (400 MHz, CDCl$_3$): δ 2.92 (s, 6H), 3.27 (t, J 6.8 Hz, 4H), 4.45 (t, J 6.9 Hz, 4H), 7.02 (d, J 5.3 Hz, 2H), 7.12 (s, 2H), 7.28 (d, J 5.3 Hz, 2H).

Br$_2$ (0.082 ml, 1.58 mmol) in DCM (1 ml) was added to a stirred solution of the material from above (390 mg, 0.792 mmol) in DCM (10 ml) at 0° C. The reaction was stirred at this temperature for 15 min. DCM (~10 ml) was added and the mixture was washed with saturated Na$_2$S$_2$O$_3$ and diluted NaHCO$_3$. The organic phase was dried over MgSO$_4$ and removed in vacuo. Yield: 486 mg LC-MS: m/z=668 (M+18).

Argon was bubbled through a stirred mixture of the material from above (258 mg, 0.396 mmol), 4-methylsulfonylphenylboronic acid (240, 1.20 mmol), KF (209 mg, 3.60 mmol) in MeOH (10 ml) and toluene (10 ml) for 10 min. PEPPSI-iPr™ (26.3 mg, 0.036 mmol) was added and the reaction was heated at 55° C. in a sealed flask for 3 hours. The mixture was added MeCN (~40 ml) and heated until most material had dissolved and then filtered. The solvents were removed in vacuo and the solid was dissolved in boiling MeCN (~15-20 ml). MeOH (~10 ml) were added and the mixture left at r.t. over the weekend. The product was collected, washed with some MeOH and dried. Yield: 137 mg (43%) as a red solid. $^1$H NMR (400 MHz, DMSO-d$_6$): δ 3.18 (s, 4H), 3.22-3.28 (m, 4H), 3.26 (s, 6H), 4.58 (t, J 6.8 Hz, 4H), 7.42 (s, 2H), 7.85 (s, 2H), 7.92-8.00 (m, 8H).

The material from above (100 mg, 0.125 mmol) and morpholine (0.406 ml, 4.71 mmol) were stirred neat in a small tube at 55° C. for 1 hour and at 70° C. for 1 hour in a sealed tube. The mixture was cooled and water (~20 ml) was added. A solid was collected by filtration, washed with water and dried at reduced pressure. The compound was added water (~20 ml) and 6 M HCl (0.5 ml). The mixture was heated to 70° C., added MeOH (~10 ml) and filtered. The solution was left at r.t. for 5 days and the product was collected as a red solid. The solid was dried in the rotavapor and under high vacuum for 2 days. Yield: 71 mg (66%). $^1$H NMR (400 MHz, DMSO-d$_6$): δ 3.27 (s, 6H), 3.30-3.42 (m, 8H), 3.56 (s, 8H), 3.84 (t, J 11.8 Hz, 4H), 4.02 (d, J 11.0 Hz, 4H), 7.49 (s, 2H), 7.81 (s, 2H), 7.91-7.96 (m, 4H), 7.98-8.03 (m, 4H), 11.37 (br. s., 2H). HPLC: Rt=2.82 min, 99% (254 nm, 10-90% MeCN in 10 mM buffer, Ace) and Rt=2.82 min, 98% (400 nm, 10-90% MeCN in 10 mM buffer, Ace). LC-MS: m/z=783 (M+1).

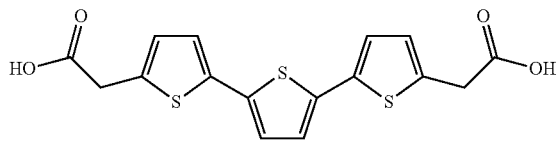 [SMILES: O=C(O)Cc1ccc(-c2ccc(-c3ccc(CC(=O)O)s3)s2)s1]

Example 72

2-(5-{5-[5-(Carboxymethyl)thiophen-2-yl]thiophen-2-yl}thiophen-2-yl)acetic acid (P9707_075)

Acetyl chloride (2.43 ml, 34.1 mmol) was added to a solution of the 2-thiopheneacetic acid (1.94 g, 13.7 mmol) in MeOH (100 ml) at 0° C. The reaction was then stirred at r.t. over night and the solvent was removed in vacuo. The crude material was dissolved in Et$_2$O (~50 ml) and washed with diluted K$_2$CO$_3$. The organic phase was dried over MgSO$_4$ and removed in vacuo. Yield: 1.81 g (85%). LC-MS: m/z=174 (M+1).

Br$_2$ (0.333 ml, 6.47 mmol) in DCM (3 ml) was added to a solution of the ester from above (1.01 g, 6.47 mmol) in DCM (20 ml) at 0° C. The reaction was stirred at this temp for 30 min. DCM (~10 ml) was added and the mixture was washed with saturated Na$_2$S$_2$O$_3$ and diluted Na$_2$CO$_3$. The organic phase was dried over MgSO$_4$ and removed in vacuo. The crude product was dissolved in DCM and run though a plug of silica with 5% EtOAc in iso-hexane as eluent. Yield: 1.21 g (80%) as a pale yellow oil. $^1$H NMR (400 MHz, CDCl$_3$): δ 3.74 (s, 3H), 3.78 (s, 2H), 6.70 (d, J 3.8 Hz, 1H), 6.91 (d, J 3.8 Hz, 1H).

Argon was bubbled through a stirred mixture of bromide from above (274 mg, 1.16 mmol), 2,5-thiopenediboronic acid (80 mg, 0.466 mmol), KF (162 mg, 2.79 mmol), MeOH (3 ml) and toluene (3 ml) for 10 min. PEPPSI-iPr™ (13.6 mg, 0.019 mmol) was added and the reaction was heated at 55° C. for 3 hours. The mixture was concentrated and added water and DCM (~4 ml). The DCM mixture was purified by flash chromatography (2.5% EtOAc in toluene, 12 g Redisep silica). The solid was dissolved in dioxane (2 ml) and water (1 ml) and 1 M NaOH (0.600 ml) were added. The reaction was heated at 75° C. for 30 min. The solvents were removed in vacuo and the crude was dissolved in water with some NH$_4$HCO$_3$. The mixture was filtered and purified by prep-HPLC (5-40% MeCN, in 50 mM NH$_3$/NH$_4$HCO$_3$ buffer). The combined pure fractions were concentrated to dryness. Water and HCl were added and the mixture extracted with EtOAc. The organic phase was dried over MgSO$_4$ and removed in vacuo. Yield: 30 mg (52%) as a pale yellow solid. $^1$H NMR (400 MHz, DMSO-d$_6$): δ 3.84 (s, 4H), 6.91 (d, J 3.5 Hz, 2H), 7.16 (d, J 3.5 Hz, 2H), 7.20 (s, 2H), 12.63 (br. s., 2H). HPLC: Rt=1.48 min, 100% (254 nm, 10-40% MeCN in 10 mM buffer, XBridge) and Rt=1.45 min, 100% (400 nm, 10-40% MeCN in 10 mM buffer, XBridge). LC-MS: m/z=365 (M+1).

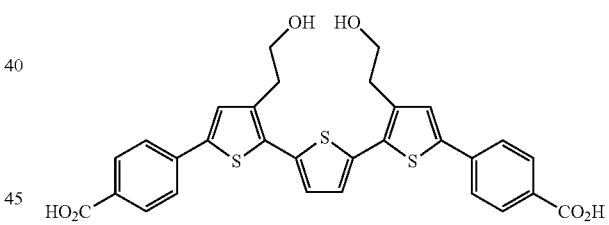

Example 73

4-(5-{5-[5-(4-Carboxyphenyl)-3-(2-hydroxyethyl)thiophen-2-yl]thiophen-2-yl}-4-(2-hydroxyethyl)thiophen-2-yl)benzoic acid (P9707_076)

Argon was bubbled through a mixture of intermediate H (150 mg, 0.303 mmol), 4-carboxyphenylboronic acid (126 mg, 0.759 mmol) and KF (88 mg, 1.52 mmol) in toluene (5 ml), MeOH (5 ml) and dioxane (1 ml). PEPPSI-iPr™ (4.1 mg, 0.006 mmol) was added and the mixture heated in a sealed tube at 80° C. for 30 min. Solvents were evaporated and residue purified by prep. hplc, Pure fractions were combined. Some solvents were evaporated and 2 M HCl was added. Precipitate was isolated by centrifugation, washed with water (twice) and freeze-dried for 3 d. Yield: 9.6 mg (5%); yellow solid. Rt=2.10 min, 98% at 254 nm (10-40% MeCN in buffer, XBridge) and Rt=2.07 min. 98% at 400 nm (10-40% MeCN in buffer, XBridge). $^1$H NMR (400 MHz, DMSO-d$_6$): δ 2.96

(t, J 7 Hz, 4H), 3.73-3.76 (m, 4H), 4.89 (t, J 5 Hz, 2H), 7.38 (s, 2H), 7.67 (s, 2H), 7.79 (d, J 8 Hz, 4H), 7.97 (d, J 8 Hz, 4H). MS: m/z=575 (M−1).

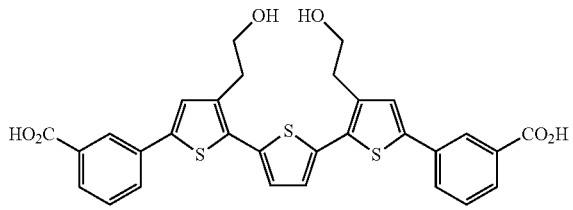 [SMILES: O=C(O)c1cccc(-c2cc(CCO)c(-c3ccc(-c4sc(-c5cccc(C(=O)O)c5)cc4CCO)s3)s2)c1]

Example 74

3-(5-{5-[5-(3-Carboxyphenyl)-3-(2-hydroxyethyl)thiophen-2-yl]thiophen-2-yl}-4-(2-hydroxyethyl)thiophen-2-yl)benzoic acid (P9707_077)

Argon was bubbled through a mixture of intermediate H (150 mg, 0.303 mmol), 3-carboxyphenylboronic acid (126 mg, 0.759 mmol) and KF (88 mg, 1.52 mmol) in toluene (5 ml), MeOH (5 ml) and dioxane (1 ml). PEPPSI-iPr™ (4.1 mg, 0.006 mmol) was added and the mixture heated in a sealed tube at 80° C. for 90 min. Solvents were evaporated and residue purified by prep. hplc. Pure fractions were combined. Some solvents were evaporated and 2 M HCl was added. Precipitate was isolated by centrifugation, washed with water (twice) and freeze-dried for 3 d. Yield: 37.6 mg (22%); yellow solid. Rt=2.44 min, 98% at 254 nm (10-40% MeCN in buffer, XBridge) and Rt=2.44 min. 99% at 400 nm (10-40% MeCN in buffer, XBridge). $^1$H NMR (400 MHz, DMSO-$d_6$): δ 2.96 (t, J 7 Hz, 4H), 3.72-3.80 (m, 4H), 7.37 (s, 2H), 7.58 (t, J 8 Hz, 2H), 7.63 (s, 2H), 7.87-7.91 (m, 2H), 7.91-7.93 (m, 2H), 8.17 (t, J 2 Hz, 2H). MS: m/z=575 (M−1).

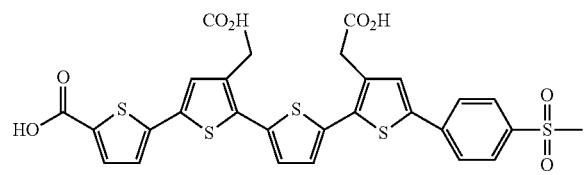 [SMILES: CS(=O)(=O)c1ccc(-c2cc(CC(=O)O)c(-c3ccc(-c4sc(-c5ccc(C(=O)O)s5)cc4CC(=O)O)s3)s2)cc1]

Example 75

5-[4-(Carboxymethyl)-5-{5-[3-(carboxymethyl)-5-(4-methanesulfonylphenyl)thiophen-2-yl]thiophen-2-yl}thiophen-2-yl]thiophene-2-carboxylic acid (P9707_078)

Argon was bubbled through a mixture of intermediate N (104 mg, 0.170 mmol), 4-methylsolfonylboronic acid (51 mg, 0.255 mmol) and KF (30 mg, 0.510 mmol) in toluene (2 ml) and MeOH (2 ml). PEPPSI-iPr™ (2.3 mg, 0.003 mmol) was added and the mixture heated in a sealed tube at 80° C. for 30 min. Solvents were evaporated and residue dissolved in dioxane (4 ml), 2 M NaOH (2 ml) was added and the mixture was heated at 80° C. for 2 h. Solvents were evaporated 6 M HCl (0.2 ml) and water (3 ml) was added the mixture was filtered and solid purified by prep. hplc Pure fractions were combined, some solvent removed and 1 M HCl added. The precipitate was isolated by centrifugation, washed with water three times and freeze dried for 2 d. Yield: 39.7 mg (36%); deep red powder. Rt=1.76 min, 99% at 254 nm (10-40% MeCN in buffer, XBridge) and Rt=1.77 min. 99% at 400 nm (10-40% MeCN in buffer, XBridge). $^1$H NMR (400 MHz, DMSO-$d_6$): δ 3.28 (s, 3H), 3.80 (br s, 4H), 7.32-7.52 (m, 4H), 7.64-7.96 (m, 6H). MS: LC-MS: m/z=643 (M−1).

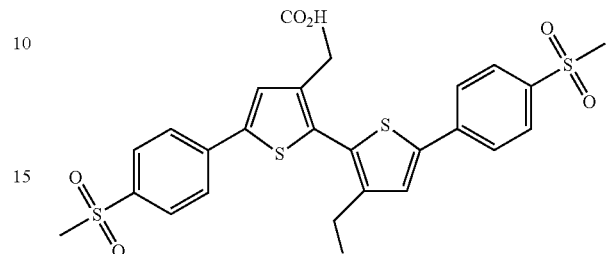

Example 76

2-{2-[3-(Carboxymethyl)-5-(4-methanesulfonylphenyl)thiophen-2-yl]-5-(4-methanesulfonylphenyl)thiophen-3-yl}acetic acid (P9707_079)

Argon was bubbled through a mixture of intermediate E2 (80 mg, 0171 mmol), 4-methylsulfonylphenylboronic acid (85 mg, 0.427 mmol) and KF (49 mg, 0.854 mmol) in toluene (2 ml) and MeOH (2 ml). PEPPSI-iPr™ (2.3 mg, 0.003 mmol) was added and the mixture heated at 60° C. for 30 min under argon. Solvents were evaporated and dioxane (2 ml) and 2 M NaOH (2 ml) was added. The mixture was heated at 80° C. for 1 h. EtOAc and 6 M HCl (0.5 ml) was added. The aqueous phase was diluted with some 1 M NH$_4$HCO$_3$ filtered and purified by prep. hplc. Pure fractions were combined, some solvents were removed, the compound was precipitated by addition of 1 M HCl, isolated by centrifugation, washed three times with water and freeze-dried for 2 d. Yield: 45.3 mg (45%); bright yellow powder. Rt=1.98 min, 99% at 254 nm (10-40% MeCN in buffer, XBridge) and Rt=1.98 min. 99% at 400 nm (10-40% MeCN in buffer, XBridge). $^1$H NMR (400 MHz, DMSO-$d_6$): δ 3.25 (s, 6H), 3.57 (s, 4H), 7.75 (s, 2H), 7.91-8.00 (m, 8H). MS: m/z=608 (M+NH$_4^+$).

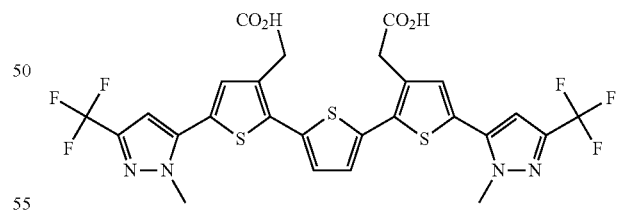

Example 77

2-(2-{5-[3-(Carboxymethyl)-5-[1-methyl-3-(trifluoromethyl)-1H-pyrazol-5-yl]thiophen-2-yl]thiophen-2-yl}-5-[1-methyl-3-(trifluoromethyl)-1H-pyrazol-5-yl]thiophen-3-yl)acetic acid (P9707_080)

Argon was bubbled through a mixture of intermediate D (55 mg, 0.100 mmol), 1-methyl-3-trifluoromethylpyrazole-5-boronic acid (48.4 mg, 0.250 mmol) and KF (29 mg, 0.500 mmol) in toluene (1 ml) and MeOH (1 ml). PEPPSI-iPr™ (2 mg, 0.003 mmol) was added and the mixture heated at 80° C. for 30 min in a sealed tube. Solvents were evaporated and dioxane (1 ml) and 2 M NaOH (1 ml) was added. The mixture was heated at 80° C. for 2 h. The product was isolated by prep. hplc using 25-55% MeCN in 50 mM buffer as eluent. Pure fractions were combined, product precipitated by addition of 6 M HCl and isolated by centrifugation. The precipitate was washed several times with water and freeze dried for 2 d. Yield: 27.0 mg (41%); bright yellow solid. Rt=2.72 min, 99% at 254 nm, (20-50% MeCN in buffer, XBridge) and Rt=2.72 min, 98% at 400 nm (20-50% MeCN in buffer, XBridge). $^1$H NMR (400 MHz, DMSO-$d_6$): δ 3.82 (s, 4H), 4.07 (s, 6H), 7.09 (d, J 0.5 Hz, 2H), 7.38 (s, 2H), 7.54 (s, 2H). LC-MS: m/z=661 (M+1)

8H), 3.25-3.50 (m, 8H), 3.79 (s, 4H), 7.36 (s, 2H), 7.45-7.51 (m, 2H), 7.53-7.58 (m, 2H), 7.74 (dd, J=10.9 Hz, J=1.6 Hz, 2H), 7.66 (s, 2H).

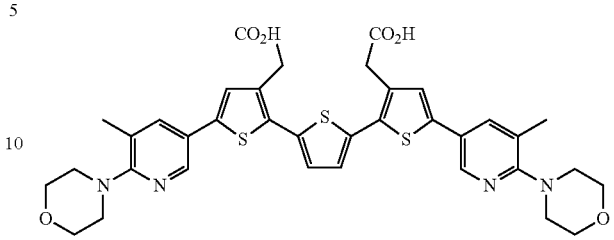

Example 78

2-(2-{5-[3-(Carboxymethyl)-5-[3-fluoro-4-(pyrrolidine-1-carbonyl)phenyl]thiophen-2-yl]thiophen-2-yl}-5-[3-fluoro-4-(pyrrolidine-1-carbonyl)phenyl]thiophen-3-yl)acetic acid (P9707_081)

Argon was bubbled through a mixture of intermediate D (55 mg, 0.100 mmol), 3-fluoro-4-(pyrrolidine-1-carbonyl)phenylboronic acid (59 mg, 0.250 mmol) and KF (29 mg, 0.500 mmol) in toluene (1 ml) and MeOH (1 ml). PEPPSI-iPr™ (2 mg, 0.003 mmol) was added and the mixture heated at 80° C. for 30 min in a sealed tube. Solvents were evaporated and dioxane (1.5 ml) and 2 M NaOH (1.5 ml) was added. The mixture was heated at 80° C. for 1 h. The product was isolated by prep. hplc using 20-50% MeCN in 50 mM buffer as eluent. Pure fractions were combined, product precipitated by addition of 6 M HCl and isolated by centrifugation. The precipitate was washed several times with water and freeze dried for 2 d. Yield: 24.7 mg (33%); bright yellow solid. Rt=2.16 min, 99% at 254 nm, (20-50% MeCN in buffer, XBridge) and Rt=2.16 min, 98% at 400 nm (20-50% MeCN in buffer, XBridge). $^1$H NMR (400 MHz, DMSO-$d_6$): δ 1.80-1.93 (m,

Example 79

2-(2-{5-[3-(Carboxymethyl)-5-[5-methyl-6-(morpholin-4-yl)pyridin-3-yl]thiophen-2-yl]thiophen-2-yl}-5-[5-methyl-6-(morpholin-4-yl)pyridin-3-yl]thiophen-3-yl)acetic acid (P9707_082)

Argon was bubbled through a mixture of intermediate D (55 mg, 0.100 mmol), 5-methyl-6-morpholin-4-yl)pyridine-3-boronic acid (64 mg, 0.250 mmol) and KF (29 mg, 0.500 mmol) in toluene (1 ml) and MeOH (1 ml). PEPPSI-iPr™ (2 mg, 0.003 mmol) was added and the mixture heated at 80° C. for 30 min in a sealed tube. Solvents were evaporated and dioxane (1.5 ml) and 2 M NaOH (1.5 ml) was added. The mixture was heated at 80° C. for 1 h. The material was dissolved in HCl/water and filtered. 2 M NaOH was carefully added and precipitate filtered, washed with water and dried at high vacuum for 3 d. Yield: 41.9 mg (58%); yellow solid. Rt=2.27 min, 90% at 254 nm (20-50% MeCN in buffer, XBridge) and Rt=2.27 min. 93% at 400 nm (20-50% MeCN in buffer, XBridge). $^1$H NMR (400 MHz, DMSO-$d_6$): δ 2.31 (s, 6H), 3.05-3.18 (m, 8H), 3.66-3.82 (m, 12H), 7.30 (s, 2H), 7.46 (s, 2H), 7.77-7.89 (m, 2H), 8.41 (d, J 2.3 Hz, 2H). MS: m/z=717 (M+1)

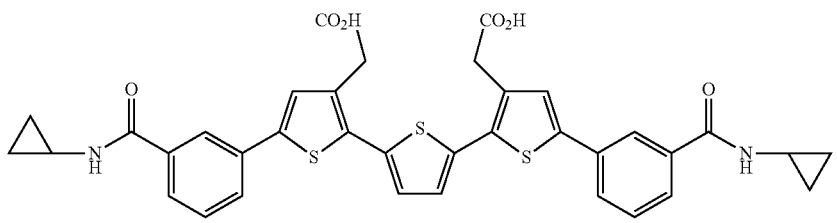 [SMILES: O=C(O)Cc1cc(-c2cccc(C(=O)NC3CC3)c2)sc1-c1ccc(-c2sc(-c3cccc(C(=O)NC4CC4)c3)cc2CC(=O)O)s1]

Example 80

2-(2-{5-[3-(Carboxymethyl)-5-[3-(cyclopropylcarbamoyl)phenyl]thiophen-2-yl]thiophen-2-yl}-5-[3-(cyclopropylcarbamoyl)phenyl]thiophen-3-yl)acetic acid (P9707_083)

Argon was bubbled through a mixture of intermediate D (55 mg, 0.100 mmol), 3-(cyclopropylaminocarbonyl)benzeneboronic acid (51 mg, 0.250 mmol) and KF (29 mg, 0.500 mmol) in toluene (1 ml) and MeOH (1 ml). PEPPSI-iPr™ (2 mg, 0.003 mmol) was added and the mixture heated at 80° C. for 30 min in a sealed tube. Solvents were evaporated and dioxane (1.5 ml) and 2 M NaOH (1.5 ml) were added. The mixture was heated at 80° C. for 1 h. Mixture was acidified and mixture extracted with EtOAc. The organic phase was evaporated and residue purified by prep. hplc. Pure fractions were combined and material precipitated by addition of 6 M HCl. The solid material was isolated by centrifugation and washed three times with water. The material was freeze-dried for 2 d. Yield: 7.9 mg (12%); yellow solid. Rt=1.82 min, 97% at 254 nm (20-50% MeCN in buffer, XBridge) and Rt=2.27 min. 97% at 400 nm (20-50% MeCN in buffer, XBridge). $^1$H NMR (400 MHz, DMSO-$d_6$): δ 0.57-0.78 (m, 8H), 2.87-2.88 (m, 2H), 3.80 (s, 4H), 7.36 (s, 2H), 7.52 (t, J 7.8 Hz, 2H), 7.59 (s, 2H), 7.74-7.85 (m, 4H), 8.07 (t, J 1.5 Hz, 2H), 8.60 (d, J 4.0 Hz, 2H). MS: m/z=681 (M−1).

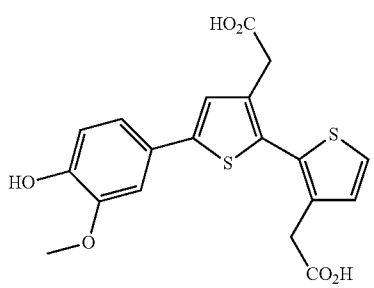 [SMILES: COc1cc(-c2cc(CC(=O)O)c(-c3sccc3CC(=O)O)s2)ccc1O]

Example 81

2-{2-[3-(Carboxymethyl)thiophen-2-yl]-5-(4-hydroxy-3-methoxyphenyl)thiophen-3-yl}acetic acid (P9707_084)

Argon was bubbled through a mixture of 4-hydroxy-3-methoxyphenylboronic acid (0.186 g, 1.11 mmol), KF (0.172 g, 2.95 mmol) and intermediate F2 in MeOH/toluene (1:1, 8 ml). After 15 min PEPPSI-iPr™ (15 mg, 0.022 mmol) was added and the mixture heated to 55° C. After 60 min, the reaction mixture was evaporated to dryness, dissolved in CH$_2$Cl$_2$ (30 ml) and washed with water (30 ml). The organic layer was evaporated to dryness to obtain the crude product.

The residue was purified by flash chromatography using toluene/EtOAc (9:1→7:1) as eluent. Yield: 256 mg (80%); $^1$H NMR (400 MHz, CDCl$_3$): δ 3.55 (s, 2H), 3.62 (s, 2H), 3.69 (s, 3H), 3.69 (s, 3H), 3.96 (s, 3H), 6.93 (d, J 8.0 Hz, 1H), 7.06 (d, J 4 Hz, 1H), 7.10 (d, J 4.0 Hz, 1H), 7.12 (dd, J 4.0, 8.0 Hz, 1H), 7.17 (s, 1H), 7.39 (d, J 4.0 Hz, 1H).

The ester from above (54 mg, 0.13 mmol) was dissolved in dioxane (2 ml) and 2 M NaOH (2 ml) was added. After stirring 45 min at 70° C., the reaction was cooled to RT, diluted with water (6 ml) and acidified using 2 M HCl (approx. 3 ml). The formed precipitate was isolated by centrifugation and washed two times with water. The material was dried under high vacuum for 48 hrs. Yield: 26 mg (52%); White solid. $^1$H NMR (DMSO-$d_6$): δ 3.42 (s, 2H), 3.49 (s, 2H), 3.84 (s, 3H), 6.80 (d, J 8.2 Hz, 1H), 7.01 (dd, J 8.2, 2.0 Hz, 1H), 7.10 (d, J 5.3 Hz, 1H), 7.15 (d, J 2.0 Hz, 1H), 7.32 (s, 1H), 7.62 (d, J 5.2 Hz, 1H), 9.28 (s, 1H), 12.39 (bs, 2H). HPLC: $R_T$=1.20 min, 99% (254 nm, 10-40% MeCN in 10 mM buffer, 3 min, XBridge). LC-MS: m/z=422 (M+NH$_4$$^+$).

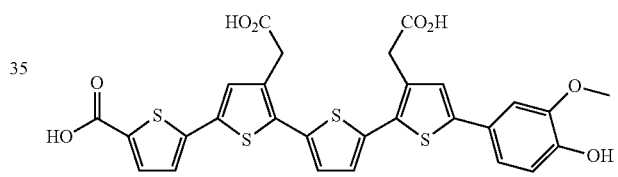

Example 82

5-[4-(Carboxymethyl)-5-{5-[3-(carboxymethyl)-5-(4-hydroxy-3-methoxyphenyl)thiophen-2-yl]thiophen-2-yl}thiophen-2-yl]thiophene-2-carboxylic acid (P9707_085)

Argon was bubbled through a mixture of intermediate N (60 mg, 0.10 mmol), 4-hydroxy-3-methoxyphenylboronic acid (25 mg, 0.15 mmol) and KF (19 mg, 0.32 mmol) in MeOH/toluene (1:1, 4 ml). After 10 min, PEPPSI-iPr™ (2 mg, 0.003 mmol) was added and the mixture stirred at 80° C. in a sealed tube. After 10 min, the reaction was cooled to RT, diluted with CH$_2$Cl$_2$ (30 ml), washed with water (30 ml) and the aqueous layer was subsequently extracted with DCM (15 ml×2). The organic layers were combined and evaporated to dryness to obtain the crude product. The residue was purified by flash chromatography using toluene/EtOAc (6:1) as eluent. Yield: 55 mg (85%)

The ester from above (55 mg, 0.08 mmol) was dissolved in dioxane (2 ml) and 2 M NaOH (2 ml) was added. After stirring 45 min at 70° C., the reaction was cooled to RT, diluted with water (11 ml) and acidified using 2 M HCl (approx. 3 ml). The formed precipitate was isolated by centrifugation and washed two times with water. The material was dried under high vacuum for 48 hrs. Yield: 44 mg (86%); Red solid; $^1$H NMR (DMSO-d$_6$): δ 3.74 (s, 2H), 3.78 (s, 2H), 3.85 (s, 3H), 6.82 (d, J 8.0 Hz, 1H), 7.06 (dd, J 8.0, 2.1 Hz, 1H), 7.17 (d, J 2.1 Hz, 1H), 7.27 (d, J 4.0 Hz, 1H), 7.33 (d, J 4.0 Hz, 1H), 7.35 (s, 1H), 7.40 (d, J 4.0 Hz, 1H), 7.47 (s, 1H), 7.68 (d, J 4.0 Hz, 1H), 9.33 (s, 1H), 12.74 (bs, 3H). HPLC: R$_T$=1.76 min, 97% (254 nm, 10-40% MeCN in 10 mM buffer, 3 min, XBridge) and R$_T$=1.77 min, 97% (400 nm, 10-40% MeCN in 10 mM buffer, 3 min, XBridge). LC-MS: m/z=630 (M+NH$_4^+$).

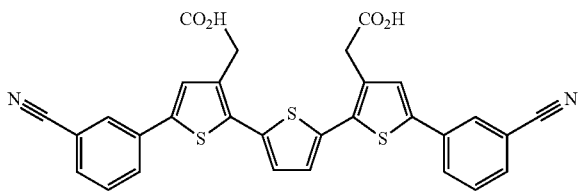 [SMILES: N#Cc1cccc(-c2cc(CC(=O)O)c(-c3ccc(-c4sc(-c5cccc(C#N)c5)cc4CC(=O)O)s3)s2)c1]

Example 83

2-(2-{5-[3-(Carboxymethyl)-5-(3-cyanophenyl)thiophen-2-yl]thiophen-2-yl}-5-(3-cyanophenyl)thiophen-3-yl)acetic acid (P9707_086)

Argon was bubbled through a mixture of intermediate Q (57 mg, 0.109 mmol) and 3-cyanophenylboronic acid (40.1 mg, 0.273 mmol) in dioxane (1.5 ml) and 1 M K$_2$CO$_3$ (1.5 ml). PEPPSI-iPr™ (3.7 mg, 0.005 mmol) was added and the mixture heated in a sealed tube at 100° C. for 30 min. Mixture was filtered and purified by prep. hplc using 25-50% MeCN in buffer. Pure fractions were combined and some solvents evaporated. 6 M HCl (ca 2 ml) was added and the aqueous layer extracted with EtOAc. The organic layer was washed with water (twice) and solvent concentrated. The material was dried under high vacuum for 6 d. Yield: 22.1 mg (36%.); light yellow solid. Rt=2.37 min, 100% at 254 nm (20-50% MeCN in buffer, XBridge) and Rt=2.37 min. 100% at 400 nm (20-50% MeCN in buffer, XBridge) $^1$H NMR (400 MHz, DMSO-d$_6$): □3.85 (s, 4H), 7.43 (s, 2H), 7.69-7.73 (m, 2H), 7.76 (s, 2H), 7.85 (d, J 7.5 Hz, 2H), 8.05 (d, J 8.0 Hz, 2H), 8.25 (s, 2H). MS: m/z=565 (M−1).

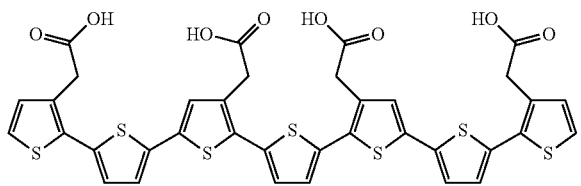 [SMILES: O=C(O)Cc1ccsc1-c1ccc(-c2cc(CC(=O)O)c(-c3ccc(-c4sc(-c5ccc(-c6sccc6CC(=O)O)s5)cc4CC(=O)O)s3)s2)s1]

Example 84

2-(2-{5-[3-(Carboxymethyl)-5-{5-[3-(carboxymethyl)thiophen-2-yl]thiophen-2-yl}thiophen-2-yl]thiophen-2-yl}-5-{5-[3-(carboxymethyl)thiophen-2-yl]thiophen-2-yl}thiophen-3-yl)acetic acid (P9707_087)

Intermediate B (500 mg, 2.13 mmol) in dry 1,4-dioxane (4 ml) was added to bis(pinacolato)diboron (594 mg, 2.34 mmol) and dry AcOK (772 mg, 7.87 mmol). The mixture was flushed with argon and 1,1'-bis(diphenylphosphino)ferrocene-palladium(II)dichloride (31.1 mg, 0.043 mmol) was added. The reaction was heated in a sealed tube at 95° C. for 3 hours. After cooling the mixture was filtered trough celite and new AcOK (600 mg, 6.11 mmol) was added. Argon was flushed trough the mixture for 10 min and 1,1'-bis(diphenylphosphino)ferrocene-palladium(II)dichloride (~50 mg, 0.068 mmol) was added. The reaction was heated in a sealed tube at 95° C. for 1 hour then cooled and diluted with Et$_2$O (~150 ml). The organic phase was washed with water and brine, dried over MgSO$_4$ and removed in vacuo. The crude was dissolved in toluene (~3 ml) and purified by flash chromatography (10% diisopropyl ether in iso-hexane, 24 gram silica redisep colon). Yield: 55 mg (9%). $^1$H NMR (400 MHz, CDCl$_3$) δ 1.33 (s, 12H), 3.70 (s, 3H), 4.00 (s, 2H), 7.12 (d, J 4.77 Hz, 1H), 7.55 (d, J 4.52 Hz, 1H).

Argon was flushed through a solution of the boronic ester from above (52.1 mg, 0.185 mmol), intermediate O (60 mg, 0.084 mmol) and KF (36.6 mg, 0.0630 mmol) in a mixture of toluene (5 ml) and MeOH (5 ml) for 10 min. PEPPSI-iPr™ (3.0 mg, 0.0042 mmol) was added and the reaction heated at 60° C. for 3 hours. The solvents were removed in vacuo. The crude material was added dioxane (1 ml), 5 M NaOH (1 ml) and water (2 ml) and the reaction was heated to 65° C. for 30 min. The solution was filtered and purified by prep-HPLC (5-45% MeCN, in 50 mM NH$_3$/NH$_4$HCO$_3$ buffer). The pure fractions were combined and concentrated to dryness. The solid was dissolved in water and 2 M HCl (6 ml) was added. A red solid was collected, washed several times with water and dried in the rotavapor and at high vacuum. Yield: 33 mg (49%) as a red solid. $^1$H NMR (400 MHz, DMSO-d$_6$) δ 3.75 (s, 4H), 3.78 (s, 4H), 7.10 (d, J 5.0 Hz, 2H), 7.20 (d, J 3.7 Hz, 2H), 7.33 (s, 2H), 7.33 (s, 2H), 7.39 (d, J 3.7 Hz, 2H), 7.54 (d, J 5.3 Hz, 2H). HPLC: Rt=2.45 min, 99% (254 nm, 10-40% MeCN in 10 mM buffer, XBridge) and Rt=2.44 min, 98% (400 nm, 10-40% MeCN in 10 mM buffer, XBridge). LC-MS: m/z=826 (M+18).

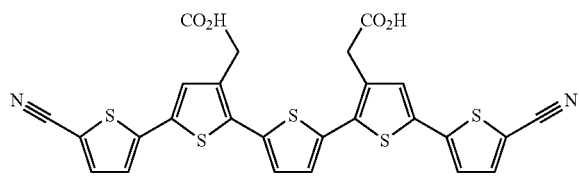 [SMILES: N#Cc1ccc(-c2cc(CC(=O)O)c(-c3ccc(-c4sc(-c5ccc(C#N)s5)cc4CC(=O)O)s3)s2)s1]

Example 85

2-(2-{5-[3-(Carboxymethyl)-5-(5-cyanothiophen-2-yl)thiophen-2-yl]thiophen-2-yl}-5-(5-cyanothiophen-2-yl)thiophen-3-yl)acetic acid (P9707_088)

Argon was bubbled through a mixture of intermediate Q (55 mg, 0.105 mmol), 5-cyanothiophene-2-boronic acid (64 mg, 0.421 mmol) and KF (37 mg, 0.032 mmol) in toluene (2 ml) and MeOH (2 ml). The mixture was heated at 60° C. for 2 h. Solvents were evaporated and residue purified by prep. hplc using 20-50% MeCN in 50 mM buffer as eluent. Pure fractions were combined and 2 M HCl was added. The aqueous phase was extracted with EtOAc and dried under high vacuum for 3 d. Yield: 22.5 mg (37%); orange solid. Rt=2.36 min, 99% at 254 nm (20-50% MeCN in buffer, XBridge) and Rt=2.38 min. 100% at 400 nm (20-50% MeCN in buffer, XBridge). $^1$H NMR (400 MHz, DMSO-d$_6$): δ 3.79 (s, 4H), 7.38 (s, 2H), 7.52 (d, J 3.8 Hz, 2H), 7.55 (s, 2H), 7.97 (d, J 4.0 Hz, 2H). MS: m/z=577 (M−1).

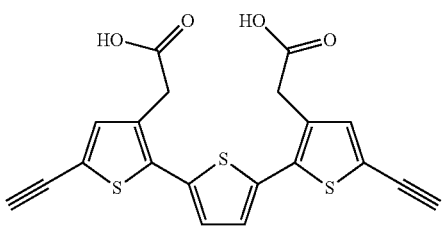 [SMILES: C#Cc1cc(CC(=O)O)c(-c2ccc(-c3sc(C#C)cc3CC(=O)O)s2)s1]

Example 86

2-(2-{5-[3-(Carboxymethyl)-5-ethynylthiophen-2-yl]thiophen-2-yl}-5-ethynylthiophen-3-yl)acetic acid (P9707_089)

Argon was bubbled through a stirred mixture of the intermediate G2 (50 mg, 0.078 mmol), CuI (3.0 mg, 0.016 mmol) water (0.056 ml, 3.1 mmol) and toluene (10 ml) for 10 min. PdCl$_2$(PPh$_3$)$_2$ (3.3 mg, 0.0047 mmol) and trimethylsilylacetylene (0.0215 ml, 0.155 mmol) were added and the mixture stirred in a sealed tube at r.t. over night. The solvent was removed in vacuo and the residue purified by flash chromatography (1% EtOAc in toluene, 24 g silica). The solid was dissolved in dioxane (2 ml) and 5 M NaOH (0.5 ml) and water (1 ml) were added. The mixture was stirred at r.t. overnight, filtered and purified by prep-HPLC (10-50% MeCN, in 50 mM NH$_3$/NH$_4$HCO$_3$ buffer). The combined pure fractions were concentrated, added water and HCl and extracted with EtOAc. The organic phase was dried over MgSO$_4$ and removed in vacuo. Yield: 21 mg (85%), as a yellow solid. $^1$H NMR (400 MHz, DMSO-d$_6$): δ 3.73 (s, 4H), 4.71 (s, 2H), 7.31 (s, 2H), 7.34 (s, 2H), 12.58 (br. s., 2H). HPLC: Rt=2.54 min, 95% (254 nm, 10-40% MeCN in 10 mM buffer, XBridge) and Rt=2.53 min, 95% (400 nm, 10-40% MeCN in 10 mM buffer, XBridge). LC-MS: m/z=430 (M+18).

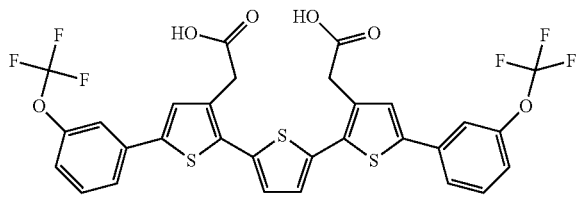 [SMILES: O=C(O)Cc1cc(-c2cccc(OC(F)(F)F)c2)sc1-c1ccc(-c2sc(-c3cccc(OC(F)(F)F)c3)cc2CC(=O)O)s1]

Example 87

2-(2-{5-[3-(Carboxymethyl)-5-[3-(trifluoromethoxy)phenyl]thiophen-2-yl]thiophen-2-yl}-5-[3-(trifluoromethoxy)phenyl]thiophen-3-yl)acetic acid (P9707_090)

Argon was flushed through a solution of intermediate D (60.0 mg, 0.109 mmol), 3-(trifluoromethoxy)phenylboronic acid (50.0 mg, 0.248 mmol) and KF (47.5 mg, 0.818 mmol) in a mixture of toluene (2 ml) and MeOH (2 ml) for 10 min. PEPPSI-iPr™ (4.0 mg, 0.0055 mmol) was added and the reaction heated at 60° C. for 3 hours. The solvents were removed in vacuo and the crude material was purified by flash chromatography (1% EtOAc in toluene, 24 g silica). The product was dissolved in dioxane (2 ml) and 5 M NaOH (0.5 ml) and water (1 ml) were added. The mixture was stirred at r.t. over night. The mixture was concentrated to dryness added water (~2 ml) and MeCN (~2 ml). The water phase was removed and new water was added (~2 ml). The homogen solution was filtered and purified by prep-HPLC (10-60% MeCN, in 50 mM NH$_3$/NH$_4$HCO$_3$ buffer). The combined pure fractions were concentrated and added water and 2 M HCl. The solid was collected washed several times with water and dried. Yield: 24 mg (37%) as a yellow solid. $^1$H NMR (400 MHz, DMSO-d$_6$): δ 3.73 (s, 4H), 4.71 (s, 2H), 7.31 (s, 2H), 7.34 (s, 2H), 12.58 (br. s., 2H). HPLC: Rt=2.45 min, 99% (254 nm, 10-90% MeCN in 10 mM buffer, XBridge) and Rt=2.45 min, 99% (400 nm, 10-90% MeCN in 10 mM buffer, XBridge). LC-MS: m/z=702 (M+18).

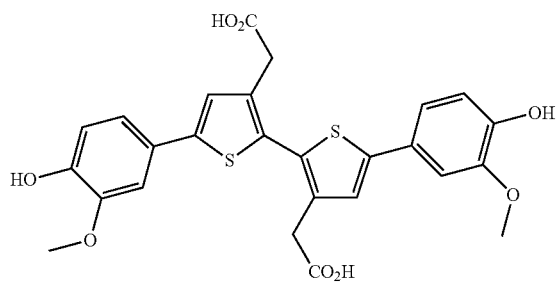 [SMILES: COc1cc(-c2cc(CC(=O)O)c(-c3sc(-c4ccc(O)c(OC)c4)cc3CC(=O)O)s2)ccc1O]

Example 88

2-{2-[3-(Carboxymethyl)-5-(4-hydroxy-3-methoxyphenyl)thiophen-2-yl]-5-(4-hydroxy-3-methoxyphenyl)thiophen-3-yl}acetic acid (P9707_091)

Argon was bubbled through a mixture of 4-hydroxy-3-methoxyphenylboronic acid (0.171 g, 1.02 mmol), KF (0.158 g, 3.00 mmol) and Intermediate E2 (0,159 g, 0.34 mmol) in MeOH/toluene (1:1, 5 ml). After 15 min PEPPSI-iPr™ (12 mg, 0.017 mmol) was added and the mixture heated to 55° C. After 90 min, the reaction mixture was evaporated to dryness. The residue was purified by flash chromatography using toluene/EtOAc (6:1→3:1-1:3→1:6) as eluent. Yield: 101 mg (54%); $^1$H NMR (400 MHz, CDCl$_3$): δ 3.61 (s, 4H), 3.71 (s, 6H), 3.96 (s, 6H), 5.70 (bs, 2H), 6.94 (d, J 8.4 Hz, 2H), 7.07 (d, J 2.0 Hz, 2H), 7.13 (dd, J 8.4, 2.0 Hz, 2H), 7.18 (s, 2H).

The ester from above (101 mg, 0.18 mmol) was dissolved in dioxane (3 ml), followed by addition of 2 M NaOH (3 ml) and water (1 ml). After stirring 45 min at 70° C., the reaction was cooled to RT, diluted with water (8 ml) and acidified using 1 M HCl (approx. 6 ml). The formed precipitate was isolated by centrifugation and washed two times with water. The material was dried under high vacuum for 48 hrs. Yield: 82 mg (86%); brown solid. $^1$H NMR (DMSO-d$_6$): δ 3.48 (s, 4H), 3.84 (s, 6H), 6.82 (d, J 8.3 Hz, 2H), 7.01 (dd, J 8.3, 2.0 Hz, 2H), 7.16 (d, J 2.0 Hz, 2H), 7.33 (s, 2H), 9.29 (s, 2H), 12.42 (bs, 2H). HPLC: R$_T$=1.91 min. 96% at 254 nm (10-40% MeCN in buffer, 3 min, XBridge) and R$_T$=1.91 min, 100% at 400 nm (10-40% MeCN in buffer, 3 min, XBridge).). LC-MS: m/z=544 (M+NH$_4^+$).

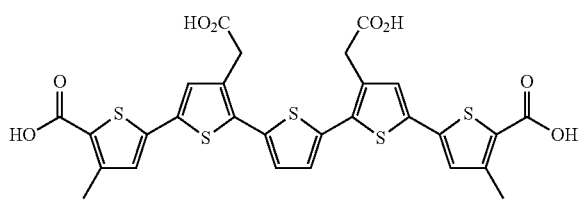 [SMILES: Cc1cc(-c2cc(CC(=O)O)c(-c3ccc(-c4sc(-c5cc(C)c(C(=O)O)s5)cc4CC(=O)O)s3)s2)sc1C(=O)O]

Example 89

5-(5-{5-[5-(5-Carboxy-4-methylthiophen-2-yl)-3-(carboxymethyl)thiophen-2-yl]thiophen-2-yl}-4-(carboxymethyl)thiophen-2-yl)-3-methylthiophene-2-carboxylic acid (P9707_092)

Argon was bubbled through a mixture of intermediate D (61 mg, 0.11 mmol), 2-carboxy-4-methylthiophene-5-boronic acid (60 mg, 0.30 mmol) and KF (42 mg, 0.72 mmol) in MeOH/toluene (1:1, 4 ml). After 10 min, PEPPSI-iPr™ (4 mg, 0.006 mmol) was added and the mixture stirred at 80° C. in a sealed tube. After 10 min, the reaction was cooled to RT, diluted with CH$_2$Cl$_2$ (30 ml), washed with water/brine (1:1, 30 ml) and the aqueous layer was subsequently washed with CH$_2$Cl$_2$ (15 ml×2). The organic layers were combined and evaporated to dryness to obtain the crude product. The residue was purified by flash chromatography using toluene/EtOAc (100:1→19:1→9:1) as eluent. Yield: 60 mg (77%); $^1$H NMR (400 MHz, CDCl$_3$): δ 2.55 (s, 6H), 3.77 (s, 6H), 3.79 (s, 4H), 3.88 (s, 6H), 7.01 (s, 2H), 7.21 (s, 2H), 7.22 (s, 2H). The ester from above (60 mg, 0.09 mmol) was dissolved in dioxane (2 ml), followed by addition of 2 M NaOH (2 ml) and water (1 ml). After stirring 35 min at 70° C., the reaction was cooled to RT, diluted with water (10 ml) and acidified using 1 M HCl (approx. 4 ml). The formed precipitate was isolated by centrifugation and washed two times with water. The material was dried under high vacuum for 48 hrs. The obtained solid was dissolved in 1 M Na$_2$CO$_3$ and purified by preparative hplc (5-40% MeCN in 50 mM buffer, XBridge). Pure fractions were combined and some solvents were evaporated. Solid material precipitated by addition of 6 M HCl, centrifuged, washed with two times with water. The material was dried under high vacuum for 4 d. Yield: 33 mg (57%); Dark red solid. $^1$H NMR (400 MHz, DMSO-d$_6$): δ 2.46 (s, 6H), 3.77 (s, 4H), 7.29 (s, 2H), 7.33 (s, 2H), 7.42 (s, 2H), 12.90 (bs, 4H). HPLC: R$_T$=1.41 min. 98% at 254 nm (10-40% MeCN in buffer, 3 min, XBridge) and R$_T$=1.41 min, 99% at 400 nm (10-40% MeCN in buffer, 3 min, XBridge). LC-MS: m/z=662 (M+NH$_4$$^+$).

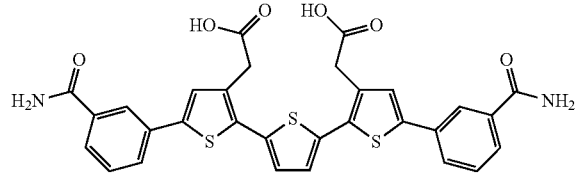 [SMILES: NC(=O)c1cccc(-c2cc(CC(=O)O)c(-c3ccc(-c4sc(-c5cccc(C(N)=O)c5)cc4CC(=O)O)s3)s2)c1]

Example 90

2-[5-(3-Carbamoylphenyl)-2-{5-[5-(3-carbamoylphenyl)-3-(carboxymethyl)thiophen-2-yl]thiophen-2-yl}thiophen-3-yl]acetic acid (P9707_093)

Argon was flushed through a solution of intermediate D (60.0 mg, 0.109 mmol), 3-aminocarbonylphenylboronic acid (41.0 mg, 0.249 mmol) and KF (47.5 mg, 0.818 mmol) in a mixture of toluene (2 ml) and MeOH (2 ml) for 10 min. PEPPSI-iPr™ (4.0 mg, 0.0054 mmol) was added and the reaction heated at 60° C. for 3 hours. The solvents were removed in vacuo and the crude was dissolved in dioxane (2 ml) and 5 M NaOH (0.5 ml) and water (1 ml) were added. The mixture was stirred at r.t. overnight, concentrated to dryness and dissolved in 0.1 M NaOH solution. 2 M HCl was added and the solid was collected by centrifugation. ~⅓ of the solid was dissolved in a mixture of water (~7 ml), MeCN (~1 ml) and a small amount of conc NH$_3$. The mixture were filtered and purified by prep-HPLC (5-50% MeCN, in 50 mM NH$_3$/NH$_4$HCO$_3$ buffer). The combined pure fractions were concentrated and added water and HCl. The solid was washed several times with water and collected by centrifugation. The solid was dried on the rotavapor and under high vacuum. Yield: 7 mg (11%) as a yellow solid. $^1$H NMR (400 MHz, DMSO-d$_6$) δ 3.80 (s, 4H), 7.35 (s, 2H), 7.49 (s, 2H), 7.53 (t, J 7.8 Hz, 2H), 7.60 (s, 2H), 7.78-7.86 (m, 4H), 8.14-8.18 (m, 4H). HPLC: Rt=1.52 min, 100% (254 nm, 10-90% MeCN in 10 mM buffer, XBridge) and Rt=1.52 min, 100% (400 nm, 10-90% MeCN in 10 mM buffer, XBridge). LC-MS: m/z=620 (M+18).

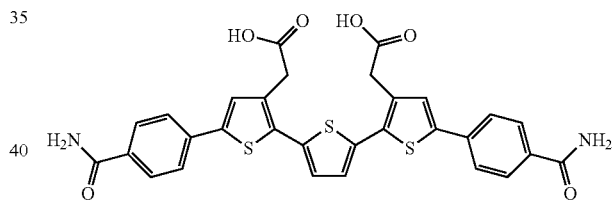

Example 91

2-[5-(4-Carbamoylphenyl)-2-{5-[5-(4-carbamoylphenyl)-3-(carboxymethyl)thiophen-2-yl]thiophen-2-yl}thiophen-3-yl]acetic acid (P9707_094)

Argon was flushed through a solution of intermediate D (60.0 mg, 0.109 mmol), 4-Aminocarbonylphenylboronic acid (41.0 mg, 0.249 mmol) and KF (47.5 mg, 0.818 mmol) in a mixture of toluene (2 ml) and MeOH (2 ml) for 10 min. PEPPSI-iPr™ (4.0 mg, 0.0054 mmol) was added and the reaction heated in a sealed tube at 60° C. for 3 hours. The solvents were removed in vacuo and the crude was dissolved in dioxane (2 ml) and 5 M NaOH (0.5 ml) and water (1 ml) were added. The mixture was stirred at r.t. over night, concentrated to dryness and dissolved in 0.1 M NaOH solution. 2 M HCl was added and the solid was collected by centrifugation. ~⅓ of the solid was dissolved in a mixture of water (~7 ml) MeCN (~1 ml) and some conc NH$_3$. The mixture were filtered and purified by prep-HPLC (5-45% MeCN, in 50 mM NH$_3$/NH$_4$HCO$_3$ buffer). The combined pure fractions were concentrated and added water and HCl. The solid was washed several times with water and collected by centrifugation. The solid was dried on the rotavapor and under high vacuum. Yield: 11 mg (16%) as a yellow solid. $^1$H NMR (400 MHz, DMSO-$d_6$) δ 3.80 (s, 4H), 7.35 (s, 2H), 7.40 (br. s., 2H), 7.63 (s, 2H), 7.71-7.78 (m, 4H), 7.76 (s, 3H), 7.91-7.97 (m, 4H), 8.03 (br. s., 1H). HPLC: Rt=1.39 min, 100% (254 nm, 10-90% MeCN in 10 mM buffer, XBridge) and Rt=1.38 min, 100% (400 nm, 10-90% MeCN in 10 mM buffer, XBridge). LC-MS: m/z=603 (M+1).

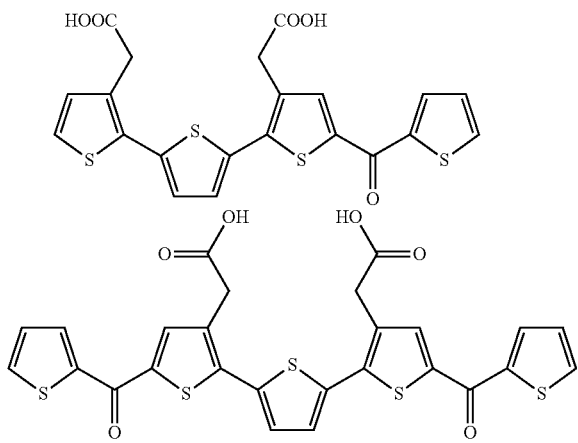

Example 92 and 93

2-(2-{5-[3-(Carboxymethyl)-5-(thiophene-2-carbonyl)thiophen-2-yl]thiophen-2-yl}thiophen-3-yl)acetic acid (P9707_095) and 2-(2-{5-[3-(carboxymethyl)-5-(thiophene-2-carbonyl)thiophen-2-yl]thiophen-2-yl}-5-(thiophene-2-carbonyl)thiophen-3-yl)acetic acid (P9707_096)

Intermediate C (146 mg, 0.372 mmol) was dissolved in dry CH$_2$Cl$_2$ (3 ml), 2-thiophenecarbonyl chloride (92 µL, 0.856 mmol) and AlCl$_3$ (114 mg, 0.856 mmol) were added and the mixture was sealed under Ar-atmosphere. After 26 hrs, the reaction was diluted with CH$_2$Cl$_2$ (10 ml), washed with water (20 ml) and the aqueous layer was subsequently washed with CH$_2$Cl$_2$ (10 ml×2). The organic layers were combined and evaporated to dryness to obtain the crude product. The residue was purified by flash chromatography using toluene/EtOAc (19:1→9:1→6:1) as eluent to first obtain the monoacylated product methyl 2-(2-{5-[3-(2-methoxy-2-oxoethyl)-5-(thiophene-2-carbonyl)thiophen-2-yl]thiophen-2-yl}thiophen-3-yl)acetate Yield: 63 mg (34%). $^1$H NMR (400 MHz, CDCl$_3$): δ 3.75 (s, 3H), 3.77 (s, 3H), 3.81 (s, 2H), 3.87 (s, 2H), 7.08 (d, J 4.0 Hz, 1H), 7.20-7.23 (m, 2H), 7.29-7.31 (m, 2H), 7.72 (dd, J 2.0, 4.0 Hz, 1H), 7.87 (s, 1H), 7.94 (dd, J 2.0, 4.0 Hz, 1H). Second eluted compound; the diacylated product methyl 2-(2-{5-[3-(2-methoxy-2-oxoethyl)-5-(thiophene-2-carbonyl)thiophen-2-yl]thiophen-2-yl}-5-(thiophene-2-carbonyl)thiophen-3-yl)acetate. Yield: 90 mg (39%) $^1$H NMR (400 MHz, CDCl$_3$): δ 3.79 (s, 6H), 3.87 (s, 4H), 7.23 (dd, J 4.0, 4.0 Hz, 2H), 7.36 (s, 2H), 7.73 (dd, J 2.0, 4.0 Hz, 2H), 7.88 (s, 2H), 7.94 (dd, J 2.0, 4.0, 2H).

Methyl 2-(2-{5-[3-(2-methoxy-2-oxoethyl)-5-(thiophene-2-carbonyl)thiophen-2-yl]thiophen-2-yl}thiophen-3-yl)acetate (63 mg, 0.125 mmol) was dissolved in dioxane (2 ml), followed by addition of 2 M NaOH (2 ml) and water (1 ml). After stirring 45 min at 70° C., the reaction was cooled to RT, diluted with water (10 ml) and acidified using 1 M HCl (approx. 4 ml). The reaction mixture was evaporated to dryness, dissolved in EtOAc (15 ml), washed with water (15 ml). The organic layer was dried with MgSO$_4$ (s), filtered and evaporated to dryness to obtain the product. Yield: 58 mg (98%); orange solid. $^1$H NMR (400 MHz, DMSO-$d_6$): δ 3.75 (s, 2H), 3.88 (s, 2H), 7.12 (d, J 5.3 Hz, 1H), 7.31 (d, J 3.8 Hz, 1H), 7.35 (d, J 4.9, 3.8 Hz, 1H), 7.47 (dd, J 3.8 Hz, 1H), 7.57 (d, J 5.3 Hz, 1H), 8.06-8.11 (m, 2H), 8.13 (dd, J 4.9, 1.1 Hz, 12.63 (bs, 2H). HPLC: R$_T$=2.35 min. 97% at 254 nm (10-40% MeCN in buffer, 3 min, XBridge) and R$_T$=2.33 min, 99% at 400 nm (10-40% MeCN in buffer, 3 min, XBridge). LC-MS: m/z=475 (M+H). Methyl 2-(2-{5-[3-(2-methoxy-2-oxoethyl)-5-(thiophene-2-carbonyl)thiophen-2-yl]thiophen-2-yl}-5-(thiophene-2-carbonyl)thiophen-3-yl)acetate. (90 mg, 0.146 mmol) was dissolved in dioxane (3 ml), followed by addition of 2 M NaOH (3 ml) and water (1 ml). After stirring 45 min at 70° C., the reaction was cooled to RT, diluted with water (8 ml) and acidified using 1 M HCl (approx. 6 ml). The formed precipitate was isolated by centrifugation and washed two times with water. The material was dried under high vacuum for 48 hrs. Yield: 71 mg (83%); orange solid. $^1$H NMR (400 MHz, DMSO-$d_6$): δ 3.91 (s, 4H), 7.35 (dd, J 4.9, 3.9 Hz, 2H), 7.54 (s, 2H), 8.08-8.11 (m, 4H), 8.14 (dd, J 4.9, 1.1 Hz, 2H), 1.72 (bs, 2H). HPLC: R$_T$=2.96 min. 97% at 254 nm (10-40% MeCN in buffer, 3 min, XBridge) and R$_T$=2.97 min, 96% at 400 nm (10-40% MeCN in buffer, 3 min, XBridge). LC-MS: m/z=585 (M+H).

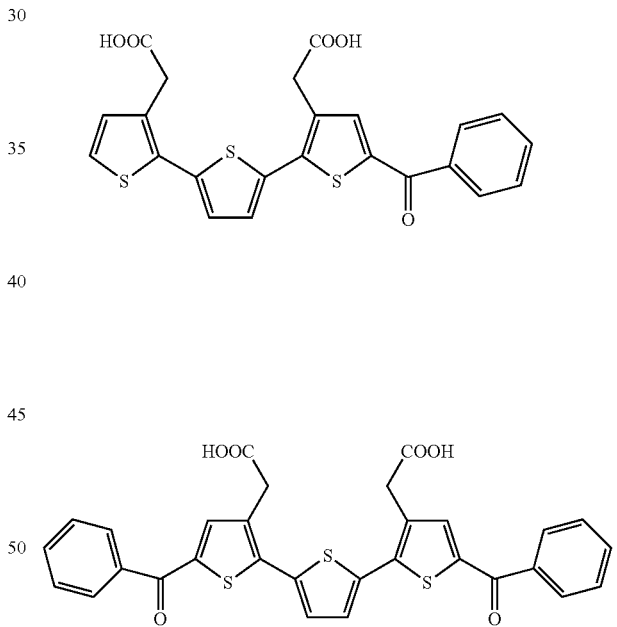

Example 94 and 95

2-(2-{5-[5-Benzoyl-3-(carboxymethyl)thiophen-2-yl]thiophen-2-yl}thiophen-3-yl)acetic acid (P9707_097) and 2-(5-benzoyl-2-{5-[5-benzoyl-3-(carboxymethyl)thiophen-2-yl]thiophen-2-yl}thiophen-3-yl)acetic acid (P9707_098)

Intermediate C (144 mg, 0.367 mmol) was dissolved in dry CH$_2$Cl$_2$ (3 ml), benzoyl chloride (98 µL, 0.844 mmol) and AlCl$_3$ (113 mg, 0.844 mmol) were added and the mixture was sealed under Ar-atmosphere. After 19 hrs, the reaction was diluted with $CH_2Cl_2$ (10 ml), washed with water (20 ml) and the aqueous layer was subsequently washed with $CH_2Cl_2$ (10 ml×2). The organic layers were combined and evaporated to dryness to obtain the crude product. The residue was purified by flash chromatography using toluene/EtOAc (19:1→14:1→9:1) as eluent to first obtain the monoacylated product; methyl 2-(2-{5-[5-benzoyl-3-(2-methoxy-2-oxoethyl)thiophen-2-yl]thiophen-2-yl}thiophen-3-yl)acetate Yield: 81 mg (45%), followed by the diacylated product methyl 2-(5-benzoyl-2-{5-[5-benzoyl-3-(2-methoxy-2-oxoethyl)thiophen-2-yl]thiophen-2-yl}thiophen-3-yl)acetate and 47 mg (21%)

Methyl 2-(2-{5-[5-benzoyl-3-(2-methoxy-2-oxoethyl)thiophen-2-yl]thiophen-2-yl}thiophen-3-yl)acetate (81 mg, 0.163 mmol) was dissolved in dioxane (3 ml), followed by addition of 2 M NaOH (3 ml) and water (1 ml). After stirring 45 min at 70° C., the reaction was cooled to RT, diluted with water (10 ml) and acidified using 1 M HCl (approx. 4 ml). The reaction mixture was evaporated to dryness, dissolved in EtOAc (15 ml), washed with water (15 ml). The organic layer was dried with $MgSO_4$ (s), filtered and evaporated to dryness to obtain the product. Yield: 51 mg (63%); orange solid. $^1$H NMR (400 MHz, DMSO-d6): δ 3.75 (s, 2H), 3.86 (s, 2H), 7.12 (d, J 5.3 Hz, 1H), 7.32 (d, J 3.9 Hz, 1H), 7.47 (d, J 3.9 Hz, 1H), 7.57 (d, J 5.3 Hz, 1H), 7.61 (m, 2H), 7.70 (m, 1H), 7.74 (s, 1H), 7.82-7.88 (m, 2H), 12.62 (bs, 2H). HPLC: $R_T$=2.50 min. 98% at 254 nm (10-40% MeCN in buffer, 3 min, XBridge) and $R_T$=2.49 min, 96% at 400 nm (10-40% MeCN in buffer, 3 min, XBridge). LC-MS: m/z=469 (M+H).

Methyl 2-(5-benzoyl-2-({5-[5-benzoyl-3-(2-methoxy-2-oxoethyl)thiophen-2-yl]thiophen-2-yl}thiophen-3-yl)acetate (47 mg, 0.078 mmol) was dissolved in dioxane (2 ml), followed by addition of 2 M NaOH (2 ml) and water (1 ml). After stirring 45 min at 70° C., the reaction was cooled to RT, diluted with water (10 ml) and acidified using 1 M HCl (approx. 4 ml). The reaction mixture was evaporated to dryness, dissolved in EtOAc (15 ml), washed with water (15 ml). The organic layer was dried with $MgSO_4$ (s), filtered and evaporated to dryness to obtain the product. Yield: 47 mg (94%); yellow oil. $^1$H NMR (400 MHz, DMSO-d$_6$): δ 3.88 (s, 4H), 7.55 (s, 2H), 7.57-7.64 (m, 4H), 7.71 (m, 2H), 7.76 (s, 2H), 7.84-7.88 (m, 4H), 12.72 (bs, 2H). HPLC: $R_T$=3.10 min. 95% at 254 nm (10-40% MeCN in buffer, 3 min, XBridge) and $R_T$=3.09 min, 96% at 400 nm (10-40% MeCN in buffer, 3 min, XBridge). LC-MS: m/z=573 (M+H).

Example 96

5-[5-(5-{5-[5-(5-Carboxythiophen-2-yl)-3-(2-hydroxyethyl)thiophen-2-yl]thiophen-2-yl}thiophen-2-yl)-4-(2-hydroxyethyl)thiophen-2-yl]thiophene-2-carboxylic acid (P9707_099)

Argon was bubbled through a mixture of intermediate F (633 mg, 3.06 mmol), 2,2'-bithiophene-5-5'-diboronic acid pinacol ester (575 mg, 1.38 mmol) and KF (532 mg, 9.17 mmol) in toluene (8 ml) and MeOH (8 ml). PEPPSI-iPr™ (41 mg, 0.061 mmol) was added and the mixture heated at 55° C. for 45 min. Silica was added to the mixture and solvents evaporated. The dry silica was applied on a column which was eluted with 30-50% ethyl acetate in toluene. Yield: 324 mg (56%); yellow solid. $^1$H NMR (400 MHz, CDCl$_3$): δ 3.09 (t, J 6.7 Hz, 4H), 3.92 (t, 6.5 Hz, 4H), 7.01 (d, J 5.3 Hz, 2H), 7.08 (d, J 3.8 Hz, 2H), 7.13 (d, 3.8 Hz, 2H), 7.24 (d, J 5.3 Hz, 2H). NBS (275 mg, 1.54 mmol) was added portion-wise to the solution of the material from above (324 mg, 0.774 mmol) in CHCl$_3$ (10 ml) and AcOH (10 ml). The mixture was stirred at ambient temperature overnight. 2 M NaOH and EtOAc were added. Organic phase was separated, washed with water and evaporated. Yield: 421 mg (94%).

Argon was bubbled through the solution of the crude material from above (50 mg, 0.0867 mmol) and 5-carboxythiophene-2-boronic acid (48 mg, 0.481 mmol) in dioxane (1 ml) and 1 M $K_2CO_3$ (1 ml). PEPPSI-iPr™ (2 mg, 0.003 mmol) was added and the mixture heated at 80° C. for 20 min. Mixture was filtered and product isolated by prep. hplc. Pure fractions were combined and some solvents were evaporated. Solid material was precipitated with 2 M HCl, collected by centrifugation and washed with water three times. Yield: 23.2 mg (40%); red solid. Rt=2.75 min, 100% at 254 nm (10-40% MeCN in buffer, XBridge) and Rt=2.74 min, 100% at 400 nm (10-40% MeCN in buffer, XBridge). $^1$H NMR (400 MHz, DMSO-d$_6$): δ 2.93 (t, J 6.8 Hz, 4H), 3.69.3.77 (m, 4H), 4.87 (t, J 5.0 Hz, 2H), 7.33 (d, J 3.8 Hz, 2H), 7.38 (d, J 4.0 Hz, 2H), 7.43 (d, J 4.0 Hz, 2H), 7.67 (d, J 3.8 Hz, 2H). LC-MS: m/z=669 (M−1).

Further Compounds

The following compounds may further be synthesized.

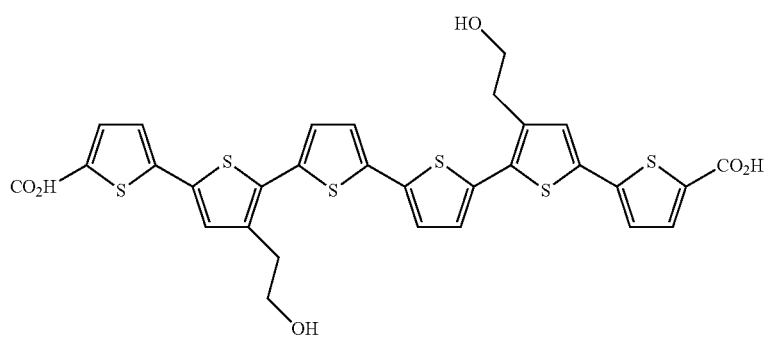 [SMILES: O=C(O)c1ccc(-c2cc(CCO)c(-c3ccc(-c4ccc(-c5sc(-c6ccc(C(=O)O)s6)cc5CCO)s4)s3)s2)s1]

103 104
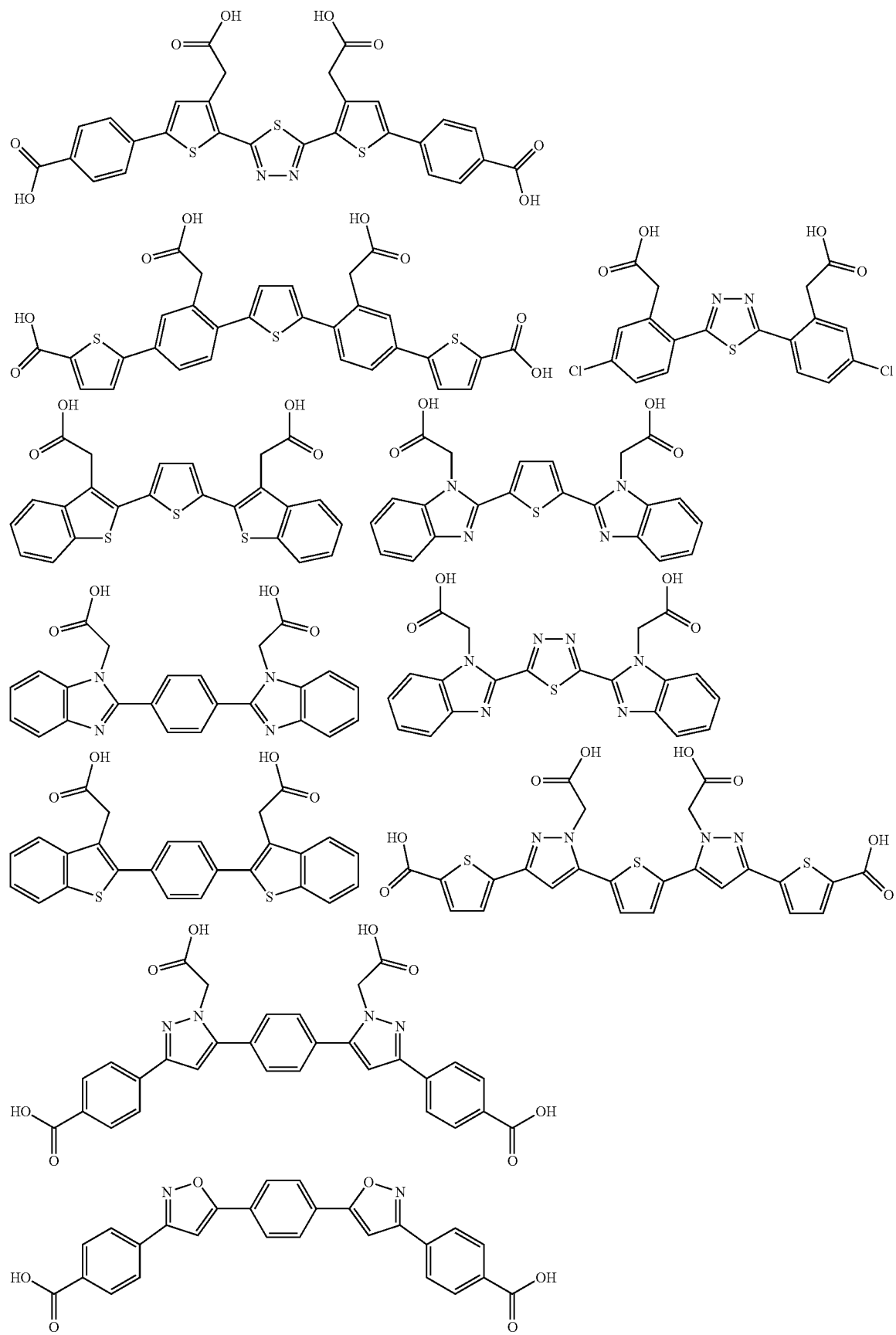

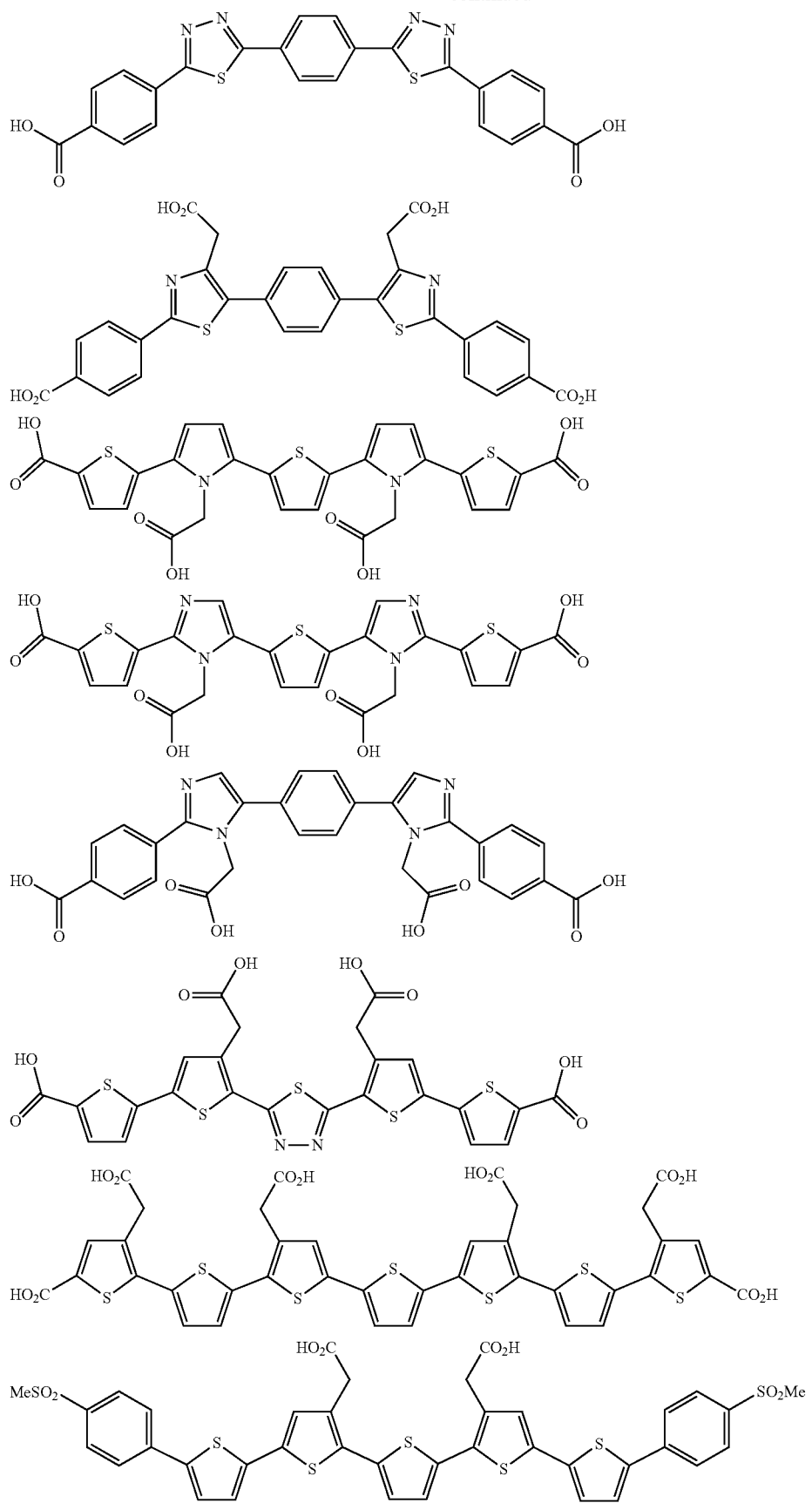

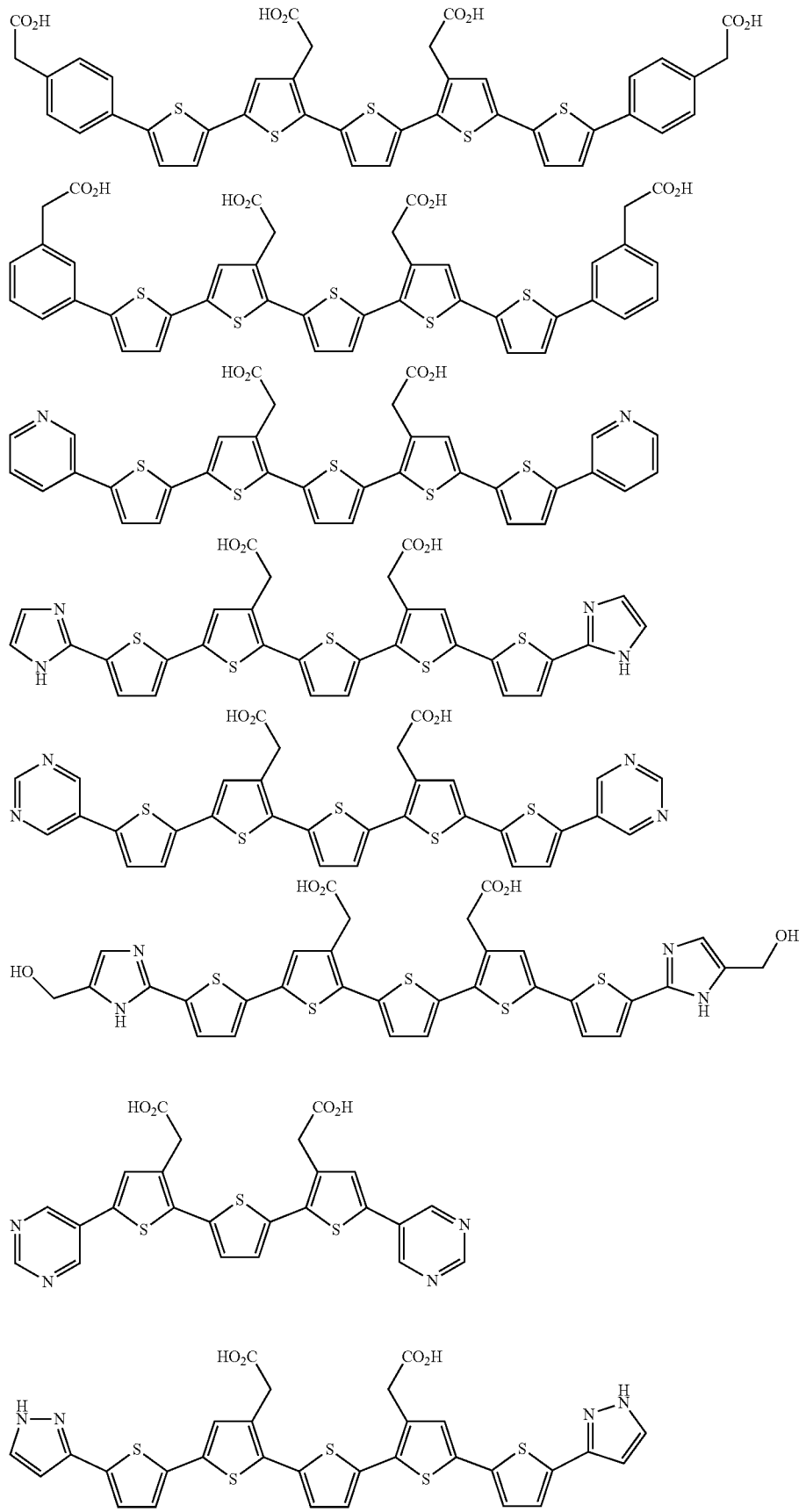

-continued
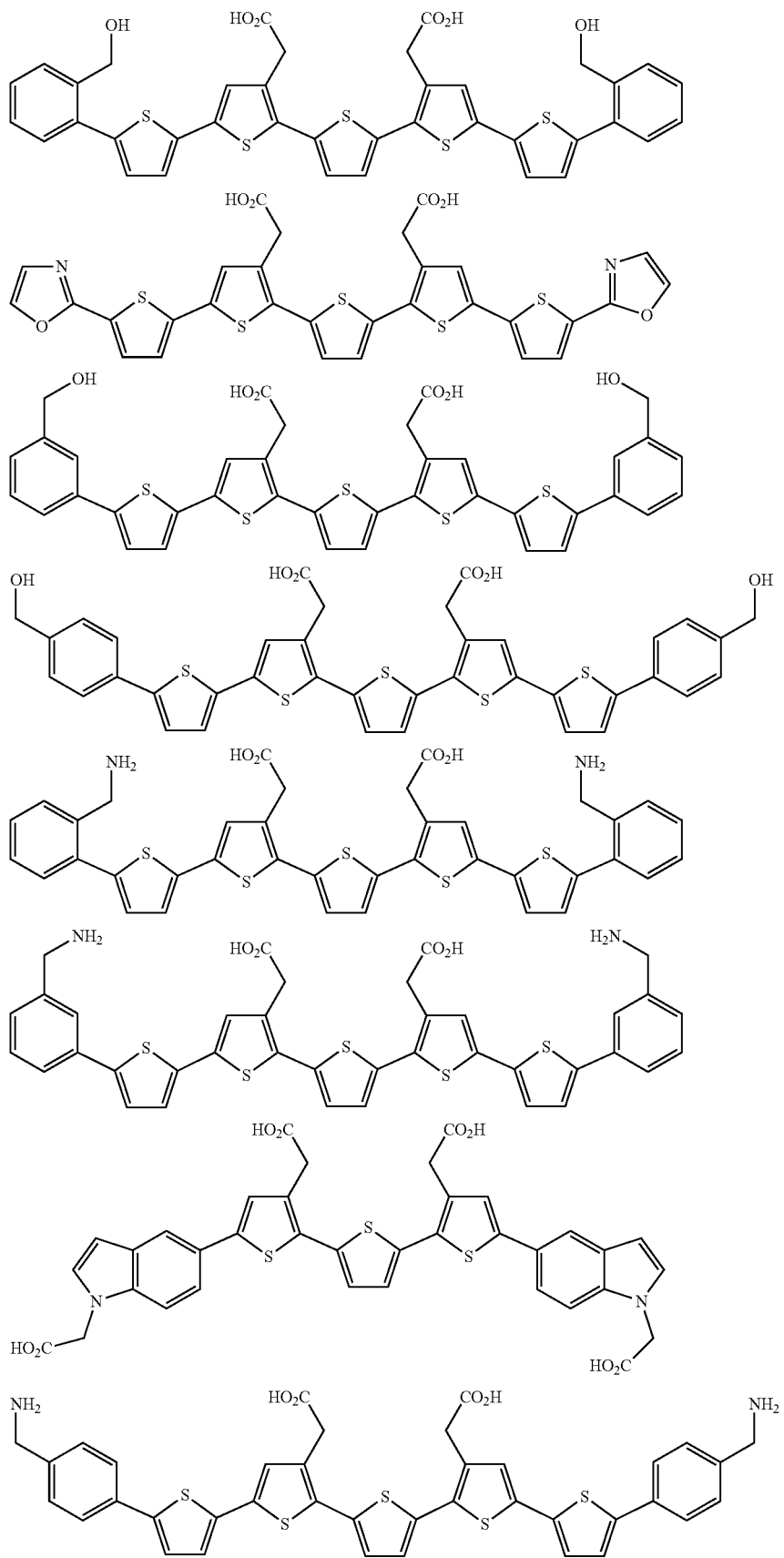

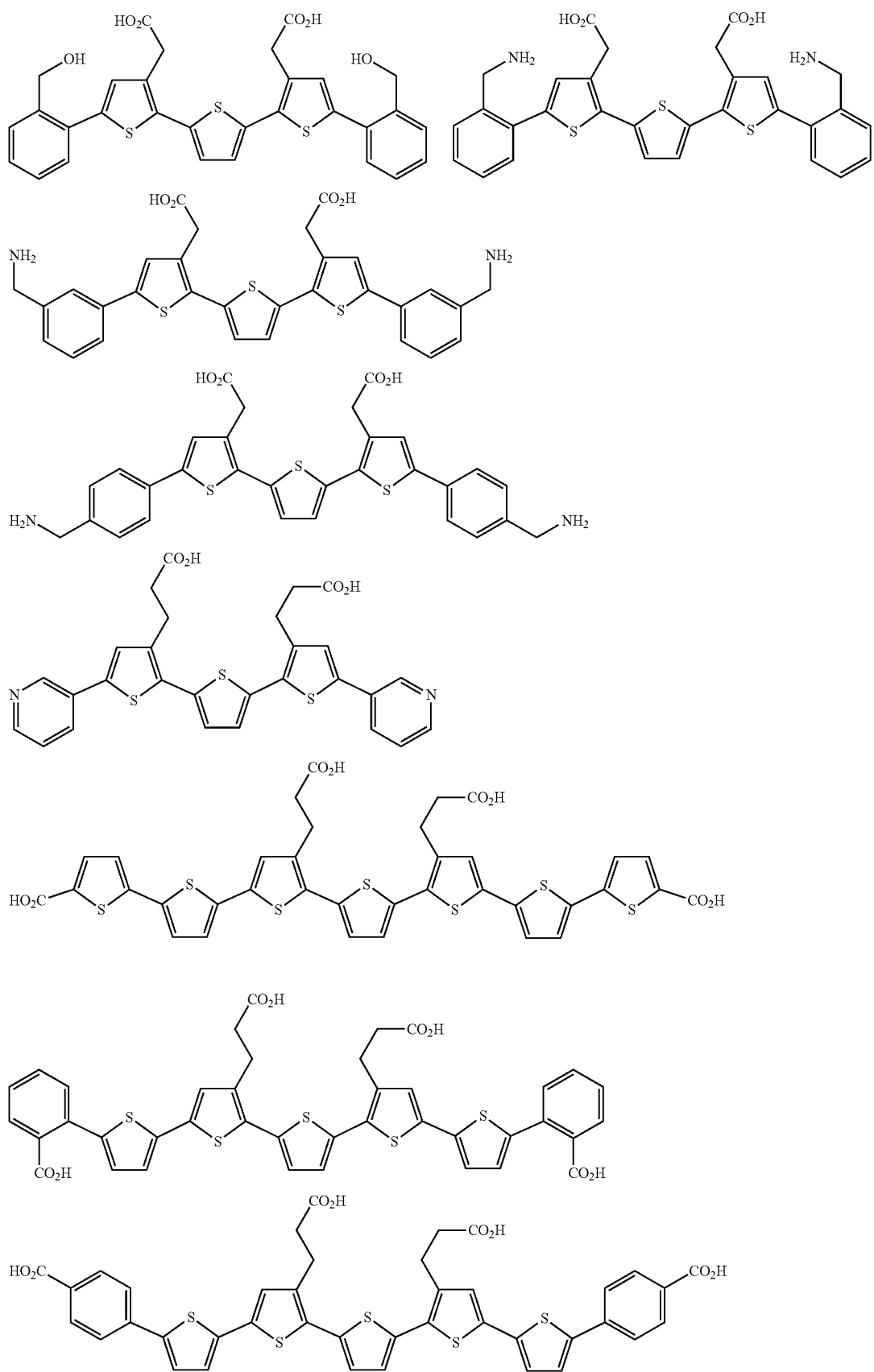

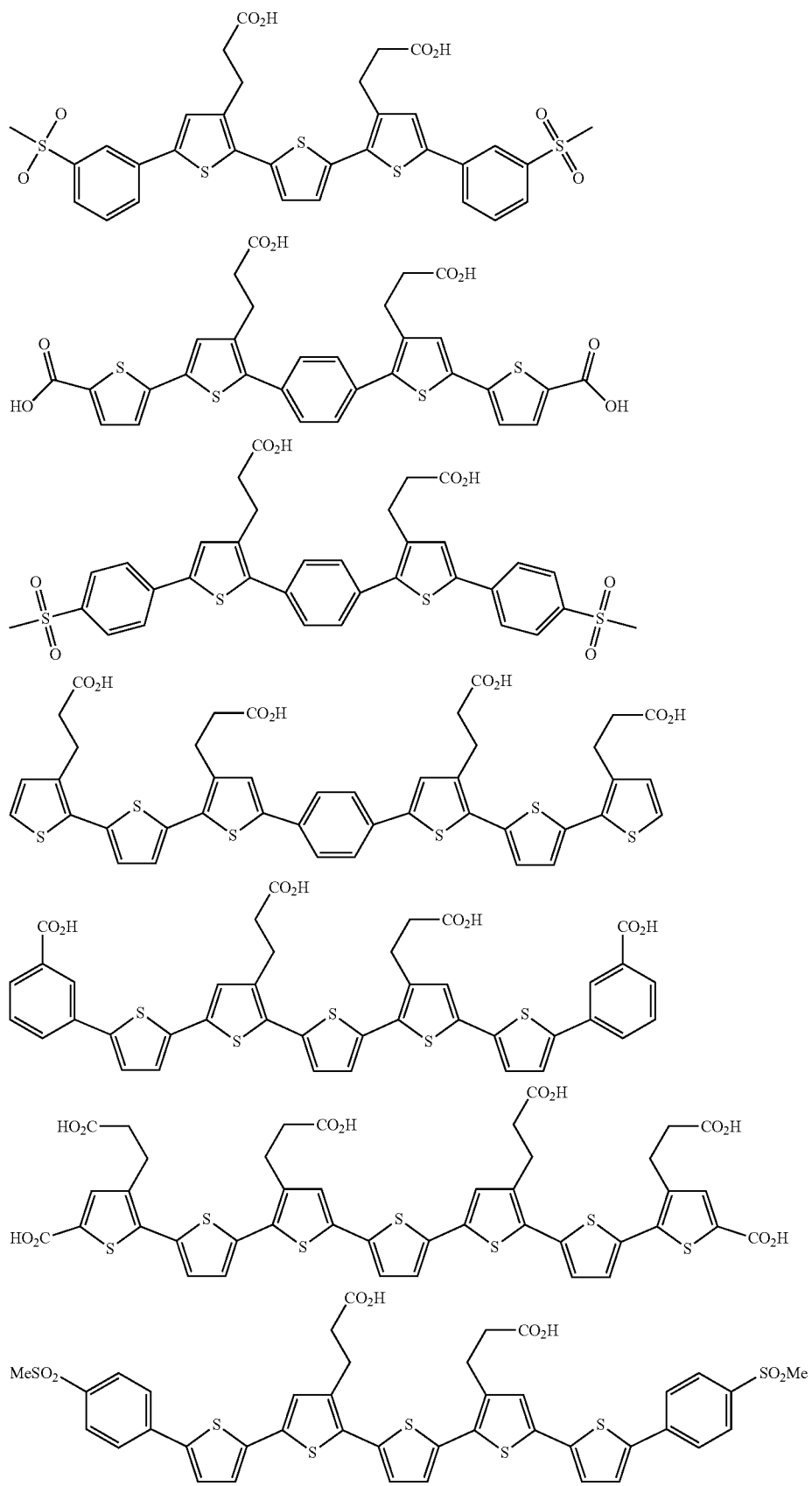

-continued
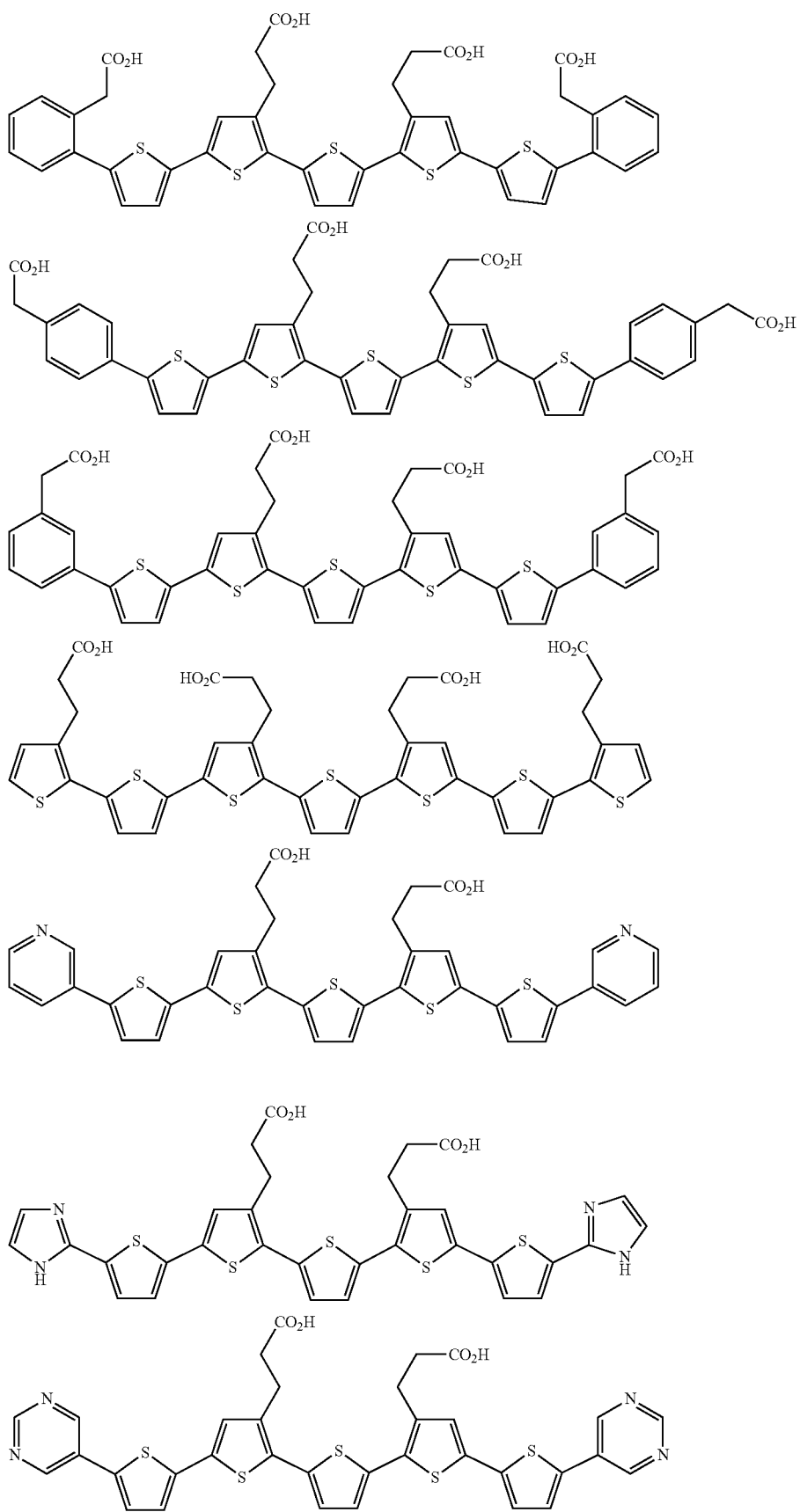

-continued
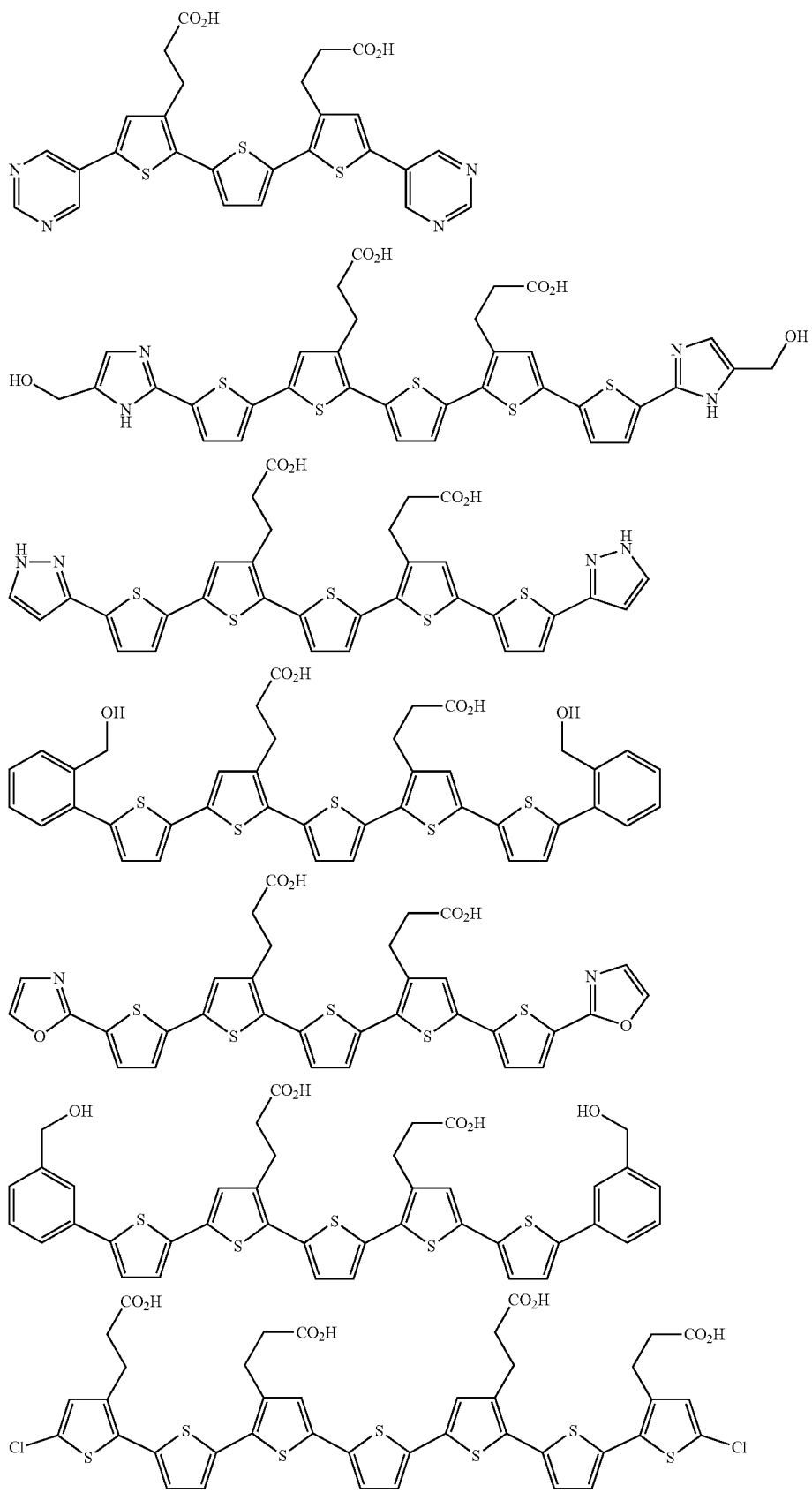

-continued
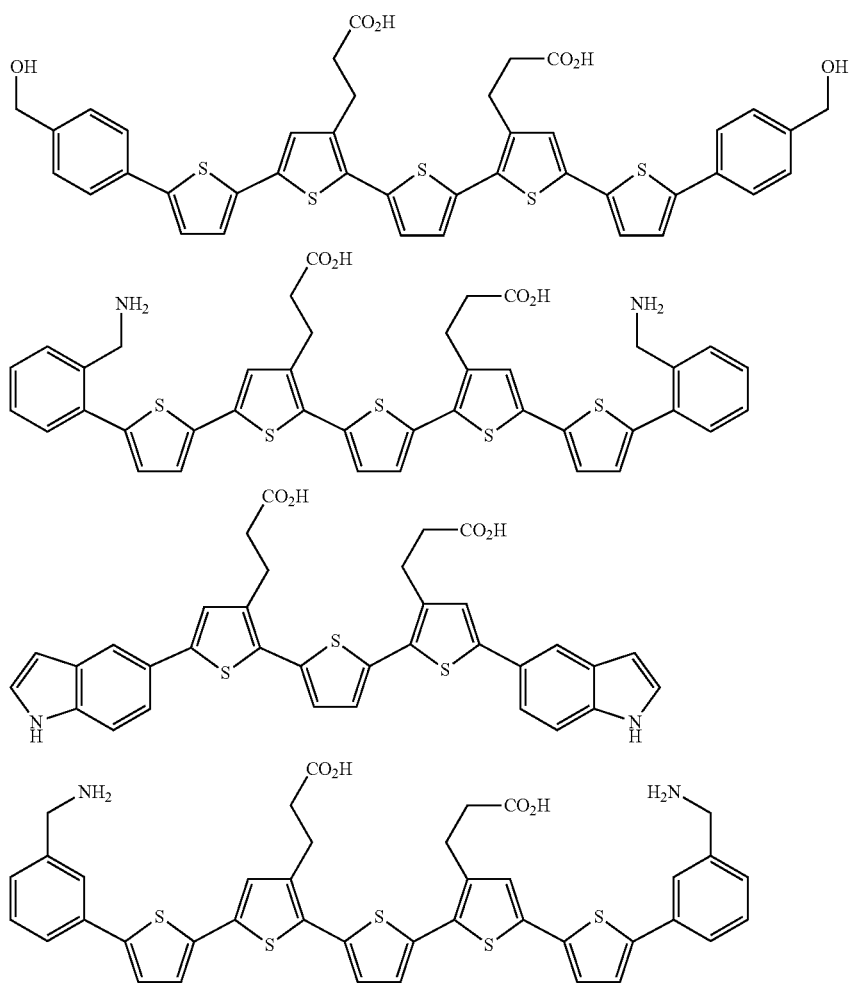
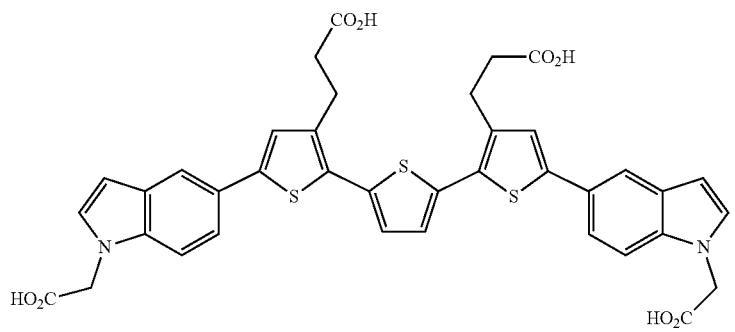
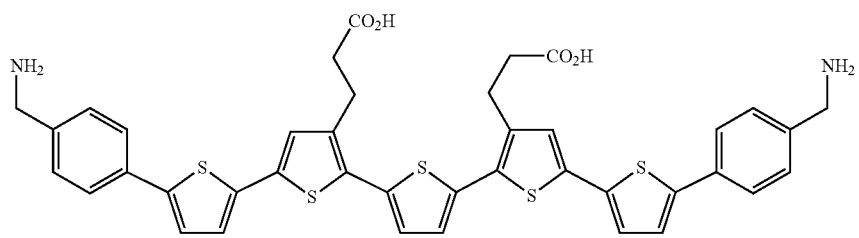

-continued
| 121 | 122 |
|---|---|
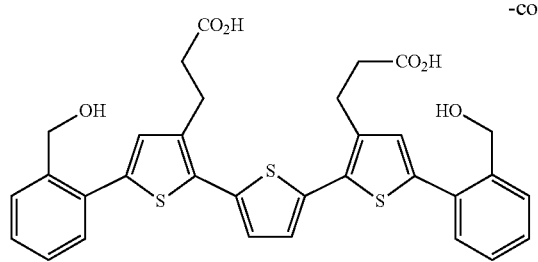
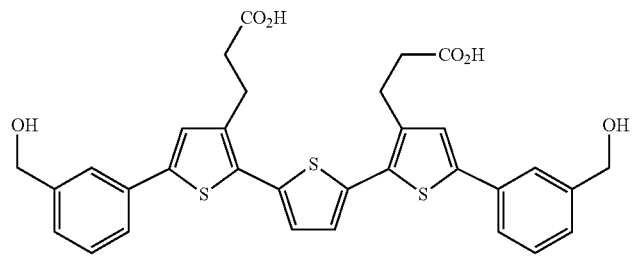
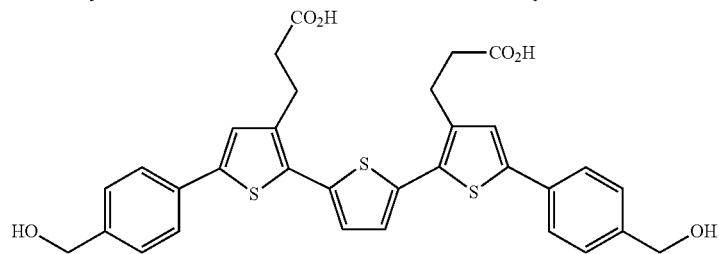
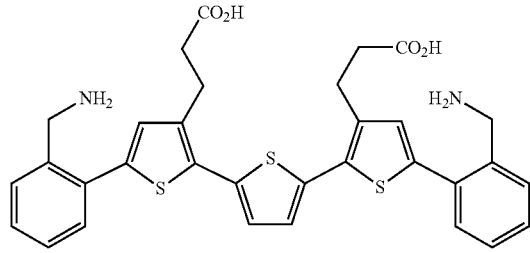
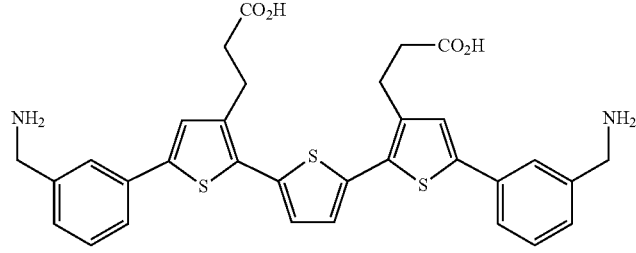
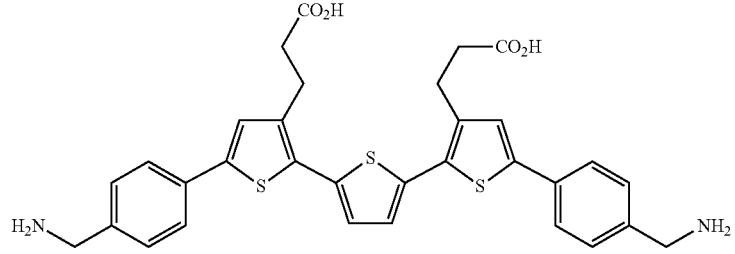
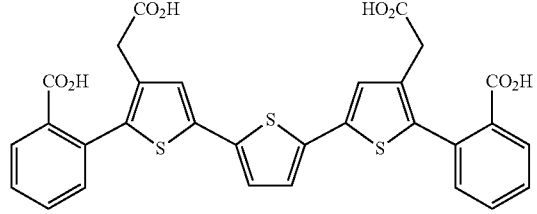
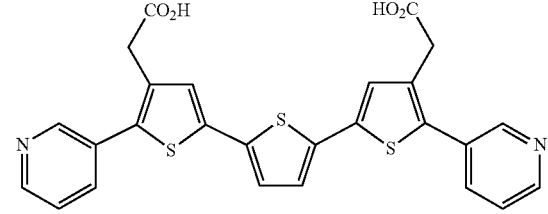

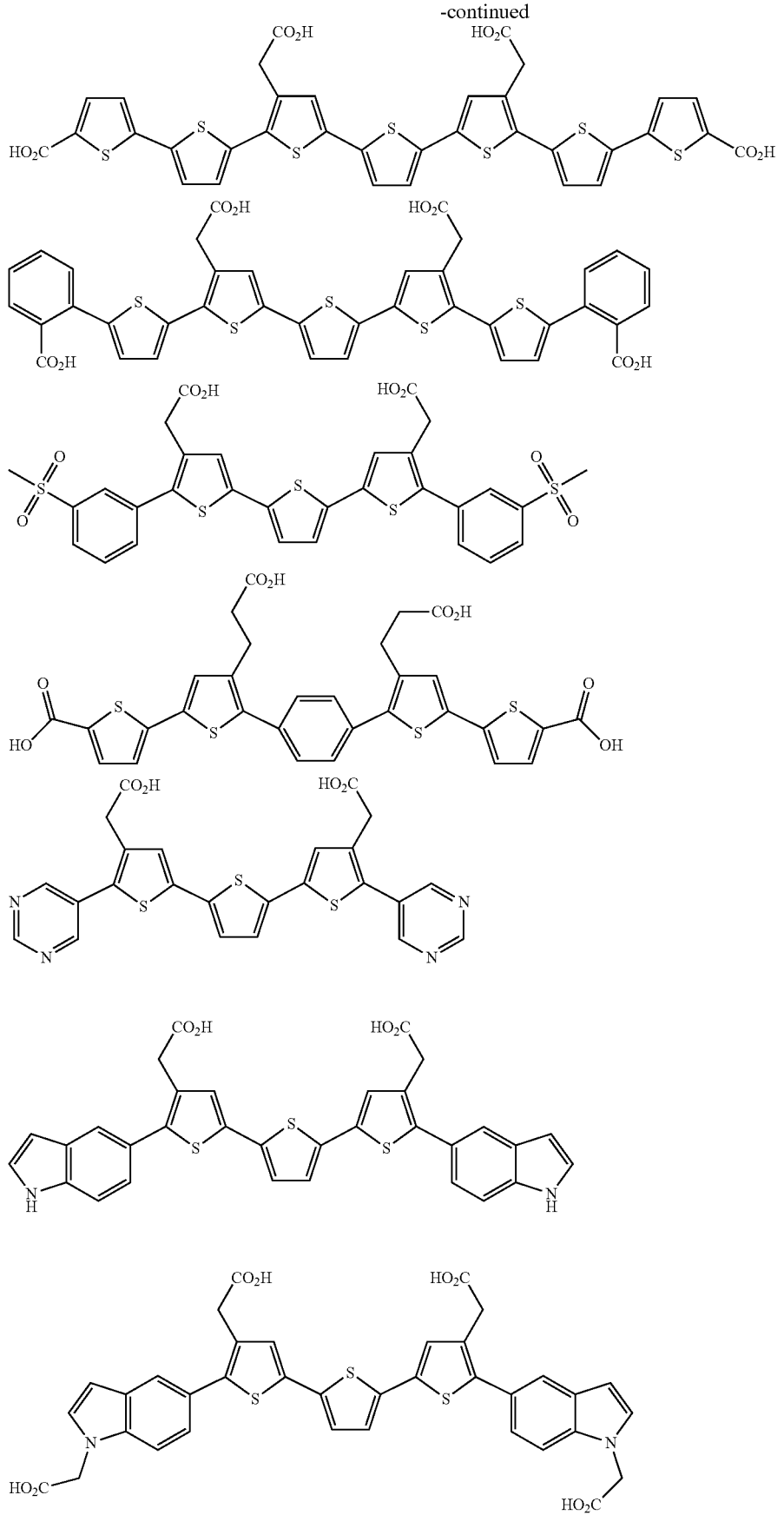

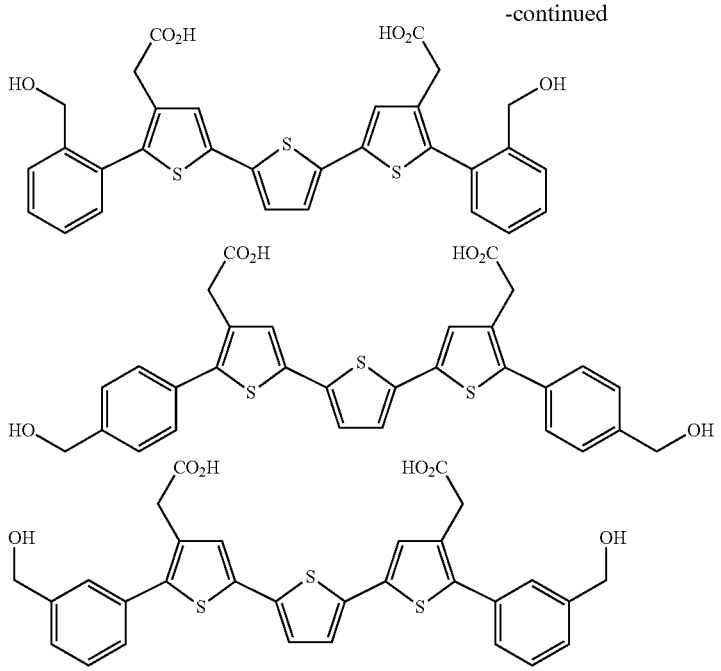
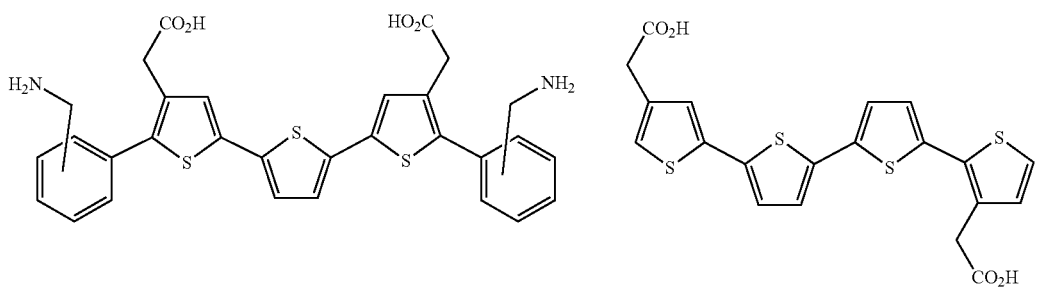
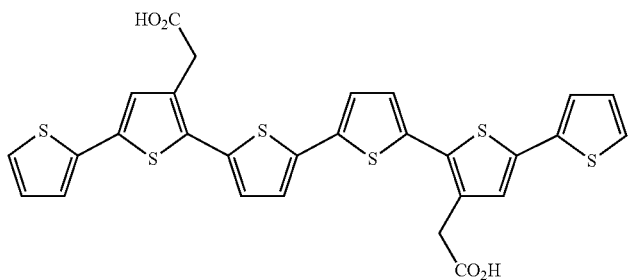
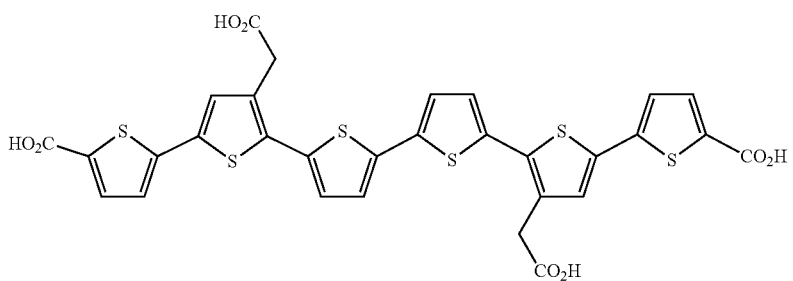

127
Other core scaffolds (aromat(s)=any aromatic group)
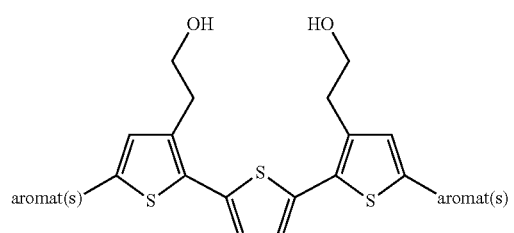
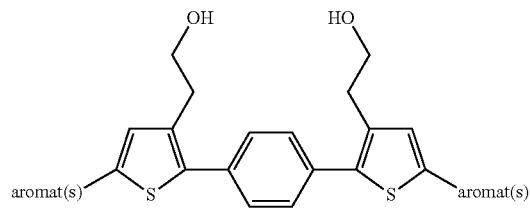
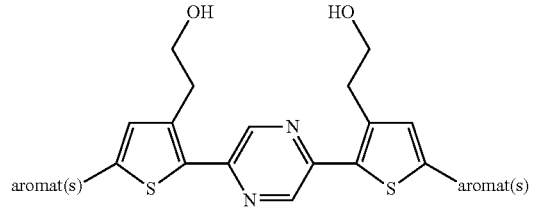
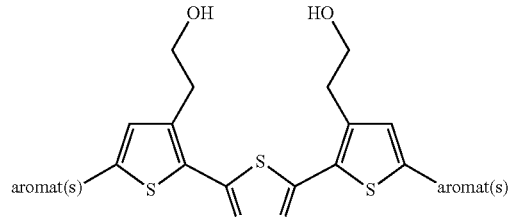
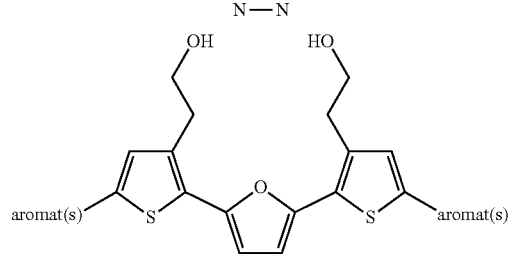
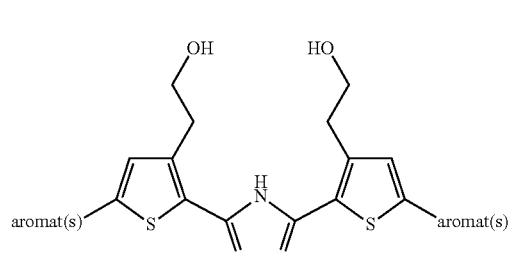
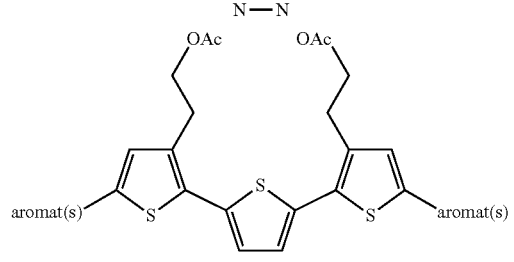
128
-continued
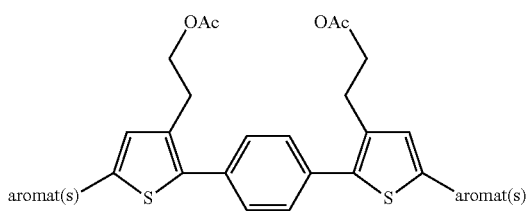
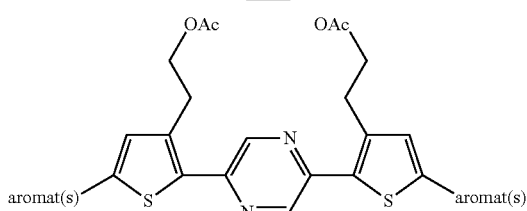
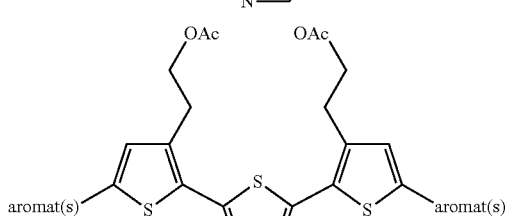
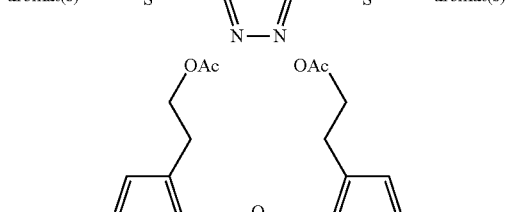
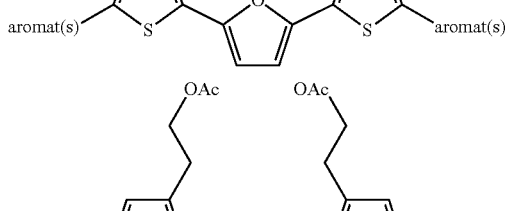
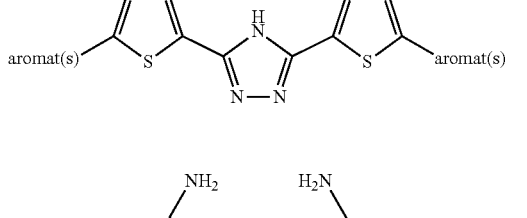
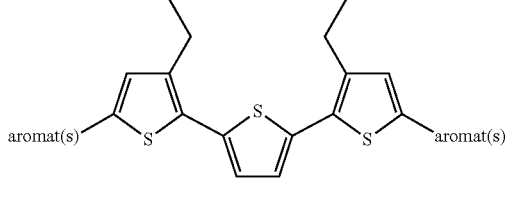

129
-continued
130
-continued
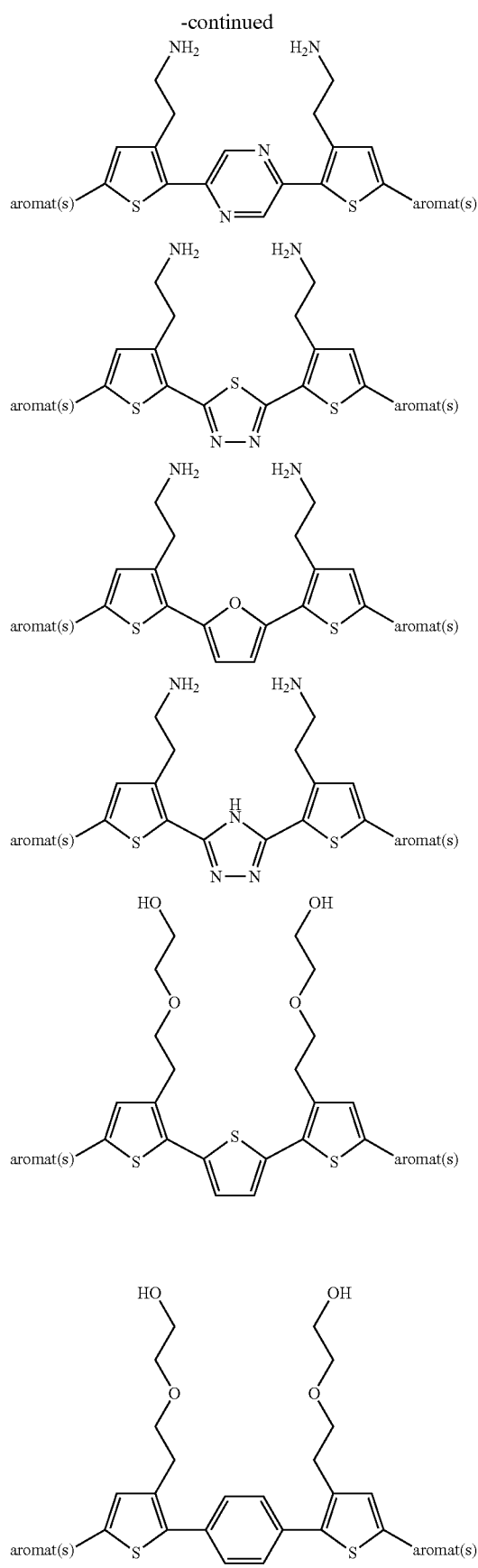
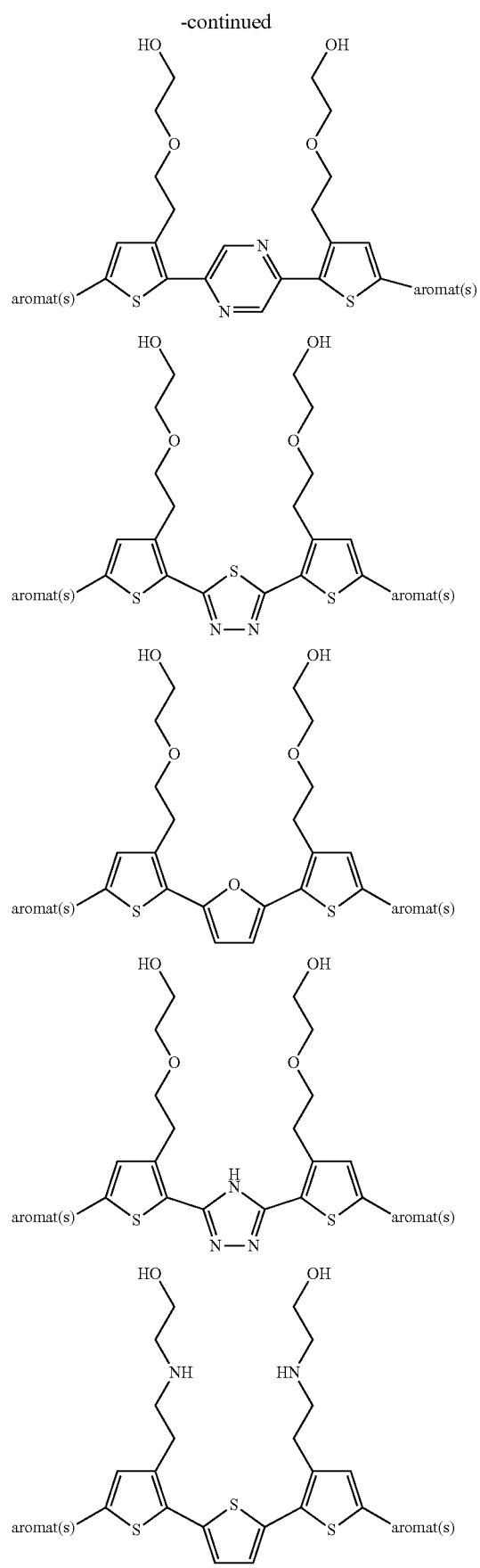

131
-continued
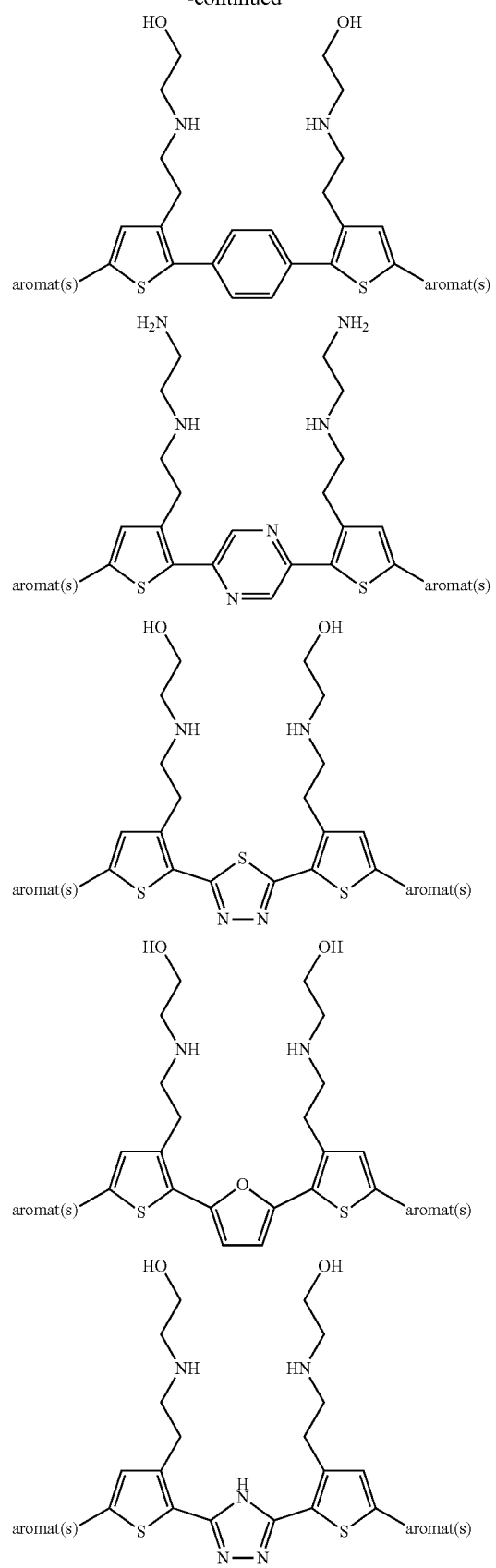
132
-continued
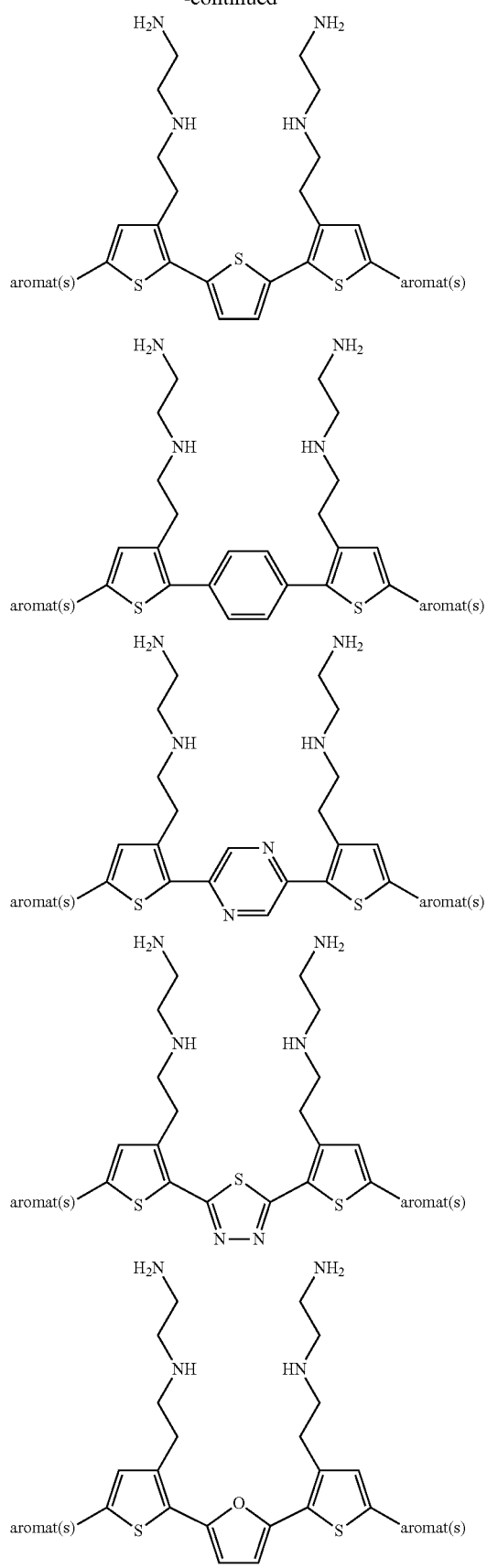

133
-continued
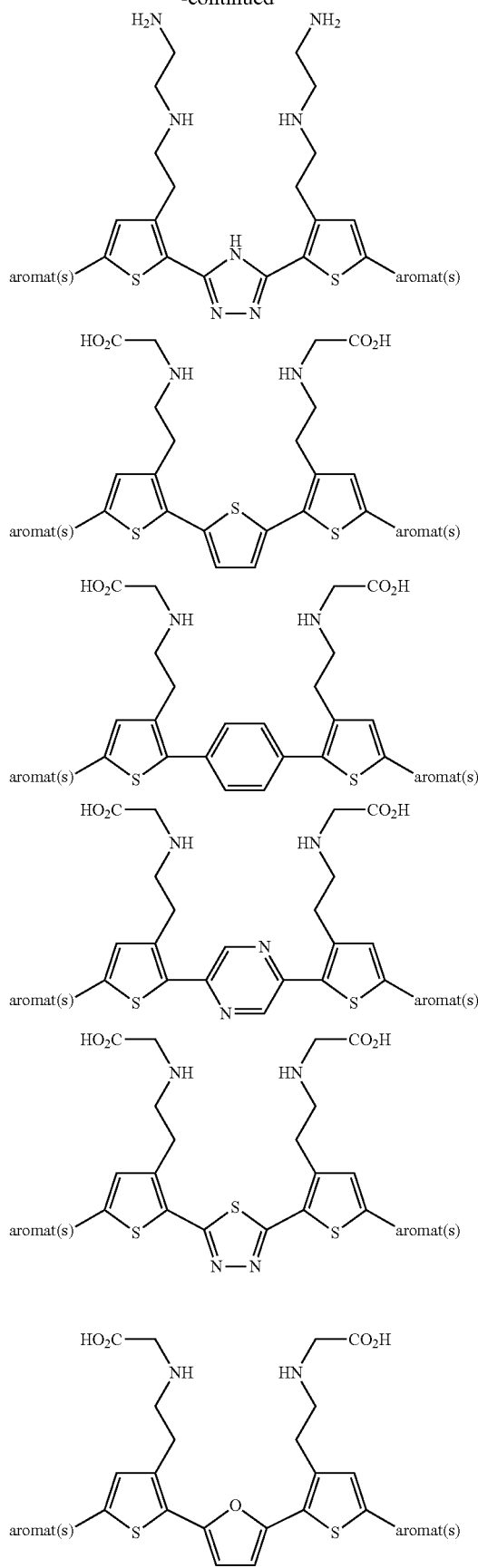
134
-continued
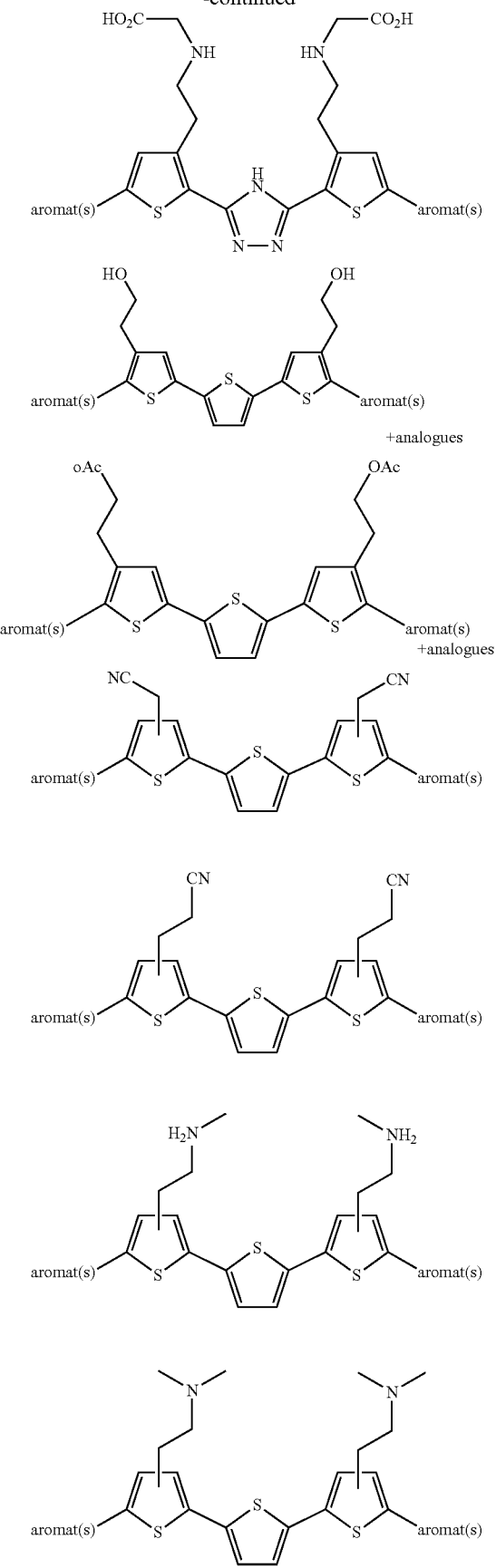

-continued

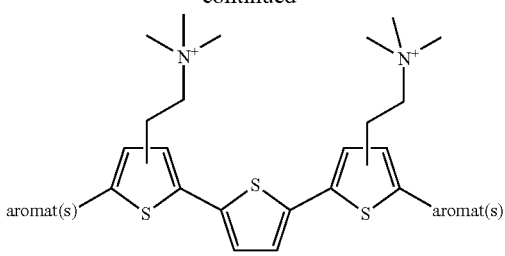

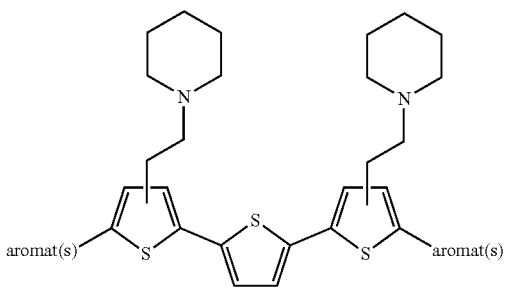

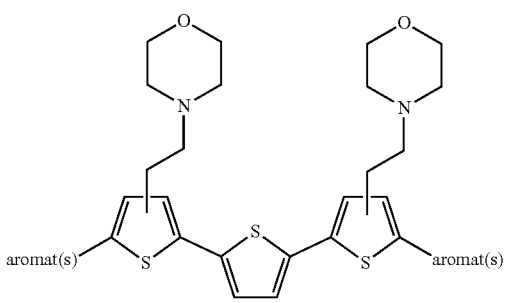

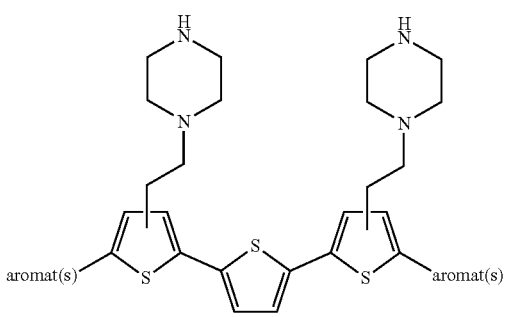

Examples 97-103 disclose the evaluation of potential therapeutic effect of compounds. Examples 1-96 disclose further compounds which may be evaluated for therapeutic effect in similar fashion.

Example 97

Effects of Compounds p-FTAA and P9707_003 (Example 1), 90 Days Treatment, in 6.5 Months Old Female hAPPSL Transgenic Mice: Results of Human Aβ Determinations in CSF and Brain Samples

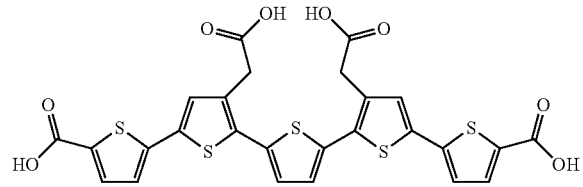

Compound p-FTAA (prior art)

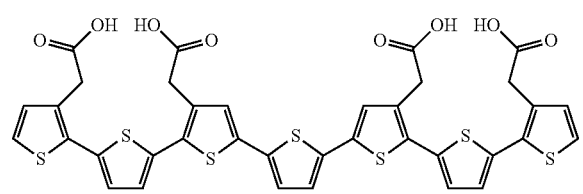

Compound P9707_003 (Example 1)

Vehicle: Phosphate Buffered Saline (PBS; 6.7 mM PO4, 155 mM NaCl, pH=7.3-7.5) (BioWhittaker PBS from Lonza).

Test item (T.I.): p-FTAA and P9707_003 diluted in vehicle from stock solution in deionized water (10 mg/ml).

Tg hAPPSL: Transgenic hAPPSL mice over-expressing hAPP(751) under the control of the murine Thy-1 promoter with a C57BL/6xDBA background.

Human Aβ38, Aβ40 and Aβ42 were determined in homogenates of the left brain hemispheres and in CSF samples of all Tg animals by an immunosorbent assay from Mesoscale Discovery Treatment 48 hAPP Tg mice plus 4 reserves allocated to 4 different treatment groups were treated with either vehicle only (control), p-FTAA or P9707_003. As an additional control, 12 nTg littermates of the hAPPSL mice (plus 1 reserve) were treated with vehicle only. Starting at 6.5 months of age, female hAPPSL mice were treated with vehicle only, p-FTAA (dosage: 1 or 10 mg/kg/day) or P9707_003 (dosage: 10 mg/kg/day) for 90 days. The Test Items (T.I.s) were administered in in Vehicle. Compound and vehicle were administered twice daily i.p. for 90 days. Tg hAPPSL mice with a C57BL/6xDBA background and corresponding nTg littermates at an age of 6.5 months (±2 weeks) were randomly assigned to the treatment groups.

Brain Protein Extraction

Left hemi-brain samples (without cerebellum) of Tg animals were homogenized and separated. SDS fraction was prepared, after thawing, hemispheres were homogenized with the Homogenizer "Ultra Turrax T8" at highest speed in TBS (20 mM Tris, 137 mM NaCl, pH=7.6; containing protease inhibitor cocktail; 100 mg brain wet weight per ml TBS). One aliquot (1 ml) was centrifuged (74,200×g for 1 h at 4° C.). The pellets were suspended in 1 ml SDS (2% SDS in Aqua bidest), centrifuged as above and the supernatants were kept at −20° C. (SDS fraction).

Determination of Aβ Species

In the brain homogenate SDS fraction and in CSF of each Tg mouse, human Aβ38, Aβ40 and Aβ42 levels were measured with a Aβ-kit from Mesoscale Discovery. Aβ levels were evaluated in comparison to a peptide standard as pg/mg brain (wet weight) or pg/ml CSF.

Statistics for Biochemical Parameters

Descriptive statistical analysis was performed on all evaluated parameters. All data were represented as mean±standard error of mean (SEM). Grubb's test was used to detect outliers. Normality distribution of the values was tested with Kolmogorov Smirnov normality distribution test. Group differences between all Tg groups were calculated by a parametric ANOVA followed by a Bonferroni post test.

Aβ Levels in CSF Samples

Human Aβ38, Aβ40 and Aβ42 levels were measured in CSF samples of each Tg mouse with an immunosorbent assay. In the APPSL mice, CSF levels of Aβ40 typically exceed those of Aβ42 and Aβ38. Mean Aβ38, Aβ40 and Aβ42 levels were highest in the vehicle treated group (PBS control) and lowest in the animals treated with 10 mg/kg/day P9707_003. Mean Aβ levels in the P9707_003 (Example 1) treated animals were decreased to about 60% of the vehicle control (PBS control) (FIG. 1).

Aβ Levels in Brain Samples

Figure 2:
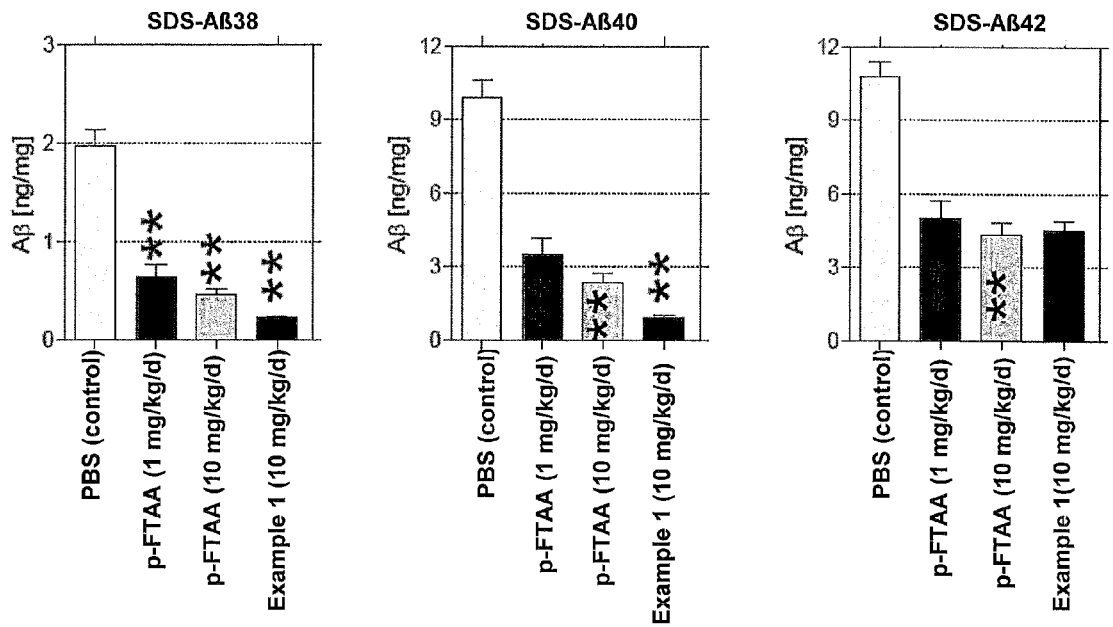
FIG. 2: Aβ38, Aβ40 and Aβ42 in brain homogenate. Graphs represent Aβ38 (left), Aβ40 (mid), and Aβ42 (right) in SDS brain homogenate fraction of APPSL Tg mice. Data are represented as group mean+SEM. Statistical significant group differences according to ANOVA with Dunnett's multiple comparison test vs PBS control group are indicated with asterisks: * p<0.05, ** p<0.01

Aβ was extracted sequentially from the brain with solvents of increasing power until SDS. Human Aβ38, Aβ40, and Aβ42 levels were measured in the SDS fraction of each Tg mouse with an immunosorbent assay. For the Aβ levels in the SDS fractions, highly significant group differences were observed: In accordance with the decreased CSF Aβ levels, P9707_003 led to a significant decrease of aggregated Aβ38, Aβ40 and Aβ42. A significant SDS soluble Aβ lowering effect was also observed for both dosages of p-FTAA. Beside the lower means, the intra group variability for the 10 mg/kg/day group was very low, which can be interpreted as another sign of T.I. affectivity (FIG. 2).

No impairment due to the treatment was observed in the animals. Eight out of the in total 91 Tg animals died prematurely during the treatment period of 90 days which is in the normal range for the animals.

Compound p-FTAA in both dosages reduced aggregated Aβ species dissolved in SDS and CSF Aβ levels.

Compound P9707_003 reduced aggregated Aβ species dissolved SDS and FA in brain homogenates. CSF Aβ was decreased.

Example 98

Effects of Compounds p-FTAA and P9707_003 (Example 1), 90 Days Treatment, in 6.5 Months Old Female hAPPSL Transgenic Mice: Histology of the Hippocampus, Plaque Number and Plaque Area Vehicle: Phosphate Buffered Saline (PBS; 6.7 mM PO4, 155 mM NaCl, pH=7.3-7.5) (BioWhittaker PBS from Lonza).

Test Item (T.I.): p-FTAA and P9707_003, diluted in vehicle from stock solution in deionized water (10 mg/ml).

Tg hAPPSL: Transgenic hAPPSL mice over-expressing hAPP(751) under the control of the murine Thy-1 promoter with a C57BL/6xDBA background.

Treatment 48 hAPP Tg mice plus 4 reserves allocated to 4 different treatment groups were treated with either vehicle only (control), p-FTAA or P9707_003. As an additional control, 12 nTg littermates of the hAPPSL mice (plus 1 reserve) were treated with vehicle only. Starting at 6.5 months of age, female hAPPSL mice were treated with vehicle only, p-FTAA (dosage: 1 or 10 mg/kg/day) or P9707_003 (dosage: 10 mg/kg/day) for 90 days. The Test Items (T.I.s) were administered in in Vehicle. Compound and vehicle were administered twice daily i.p. for 90 days. Tg hAPPSL mice with a C57BL/6xDBA background and corresponding nTg littermates at an age of 6.5 months (+2 weeks) were randomly assigned to the treatment groups.

Histology

Histological evaluations were performed with six randomly chosen cryo-frozen brain hemispheres of treatment groups PBS Control, p-FTAA 1 mg/kg/day, p-FTAA 10 mg/kg/day, and P9707_003 10 mg/kg/day.

Tissue Sectioning 15 cryo-sections per level (altogether 5 levels), each 10 μm thick (Leica CM 3050S) were sagittally cut. Brain levels were chosen according to the morphology atlas "The Mouse Brain" from Paxinos and Franklin (2nd edition). The cutting of the five levels started with a random slice, then sampling was continued uniformly and systematically, always retaining 15 slices per level in series and discarding 100 μm in between the levels.

ThioflavinS Staining

Plaque load was quantified by staining with ThioflavinS staining of beta-sheet structures in a double incubation.

Evaluation of Plaque Load

For determination of amyloid depositions 5 slices (1 from each level) per brain were stained and screened. Region areas (hippocampus and cortex) were measured and plaque surface area, number of plaques and mean size of objects within each region were quantified separately using automated image analysis software (Image Pro Plus, version 6.2).

Imaging

Mosaic images for plaque load quantification including the whole cortex and hippocampus were recorded on a Zeiss AxioImager.Z1 microscope using high aperture lenses and an AxioVision 4.8 software driven AxioCam MRm (10× lens, 1× optocoupler). Plaques for AT180 quantifcation were imaged with a 20× lens. Detail images for qualitative figures are 40× image stacks collapsed to 2D by the extended depth of field function of AxioVision software.

Statistics for Histological Analysis

Descriptive statistical analysis was performed on all evaluated parameters, Kolmogorov Smirnov test were performed to test normal distribution of data. Data in graphs are represented as mean±SEM.

Quantitative Results

Measured region areas of the hippocampus and the cortex were constant throughout all investigated brains, which excludes negative effects on tissue in staining steps (e.g. unequivocal shrinkage, different cutting circumstances), and is furthermore a sign that there was no treatment induced atrophy. Anyhow, measured data were related to the individual region size in the slice to be able to cope with artifacts, folding or missing pieces.

Results: ThioflavinS Staining

Figure 3:
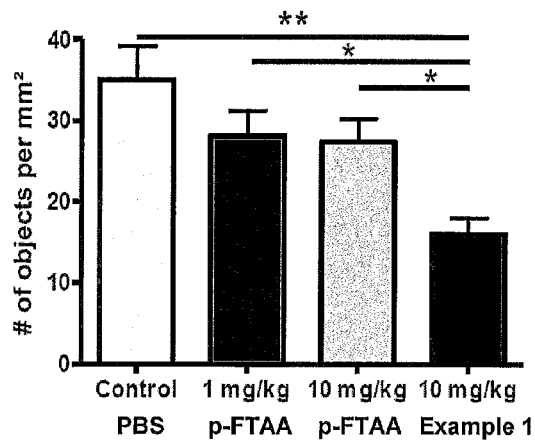
FIG. 3: Plaque number (visualized by ThioflavinS staining). Graphs represent the number of ThioflavinS stained objects in the hippocampus of Tg mice receiving PBS vehicle (N=6), 1 mg/kg/day p-FTAA (N=6), 10 mg/kg/day p-FTAA (N=6) or 10 mg/kg/day of compound of Example 1 (N=6). A reduced object number is visible in the hippocampus of 10 mg/kg P9707_003 treated mice, compared to the other groups. Data are represented as mean+SEM. Statistically significant effects (ANOVA) are marked by asterisks. * indicates p<0.05, ** indicates p<0.01.
Figure 3:
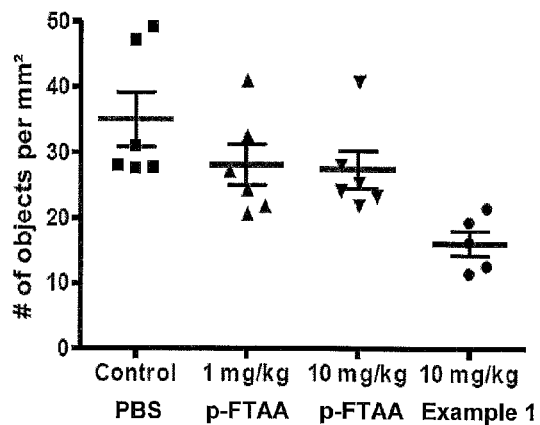

FIG. 3 indicates the major effect of P9707_003 (Example 1) treatment on the number of plaques in the hippocampus. This perfectly fits to the concept of an aggregation-inhibiting compound. The hippocampal plaque area percentage in the P9707_003 treated mice was reduced according to a t-test (t-test: p=0.036, FIG. 4) and the number of ThioflavinS positive objects is highly significant reduced compared to the vehicle control in Newman-Keuls post hoc test (ANOVA: p<0.01, FIG. 3). P9707_003 treatment led to a reduction of plaque number by 54% in the hippocampus.

Figure 4:
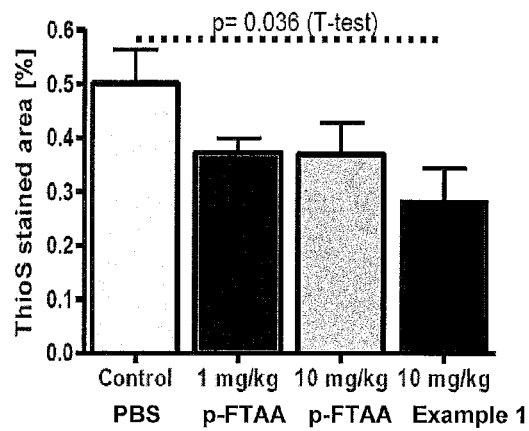
FIG. 4: Plaque area (visualized by ThioflavinS staining). Graphs represent the ThioflavinS stained area in the hippocampus of Tg mice receiving PBS vehicle (N=6), 1 mg/kg/day p-FTAA (N=5), 10 mg/kg/day p-FTAA (N=6) or 10 mg/kg/day of compound of Example 1 (N=6). Data are represented as mean+SEM. The scattered bar indicate a significant difference in an unpaired two-tailed t-test. 10 mg/kg P9707_003 treatment led to significantly lower plaque load in the hippocampus.
Figure 4:
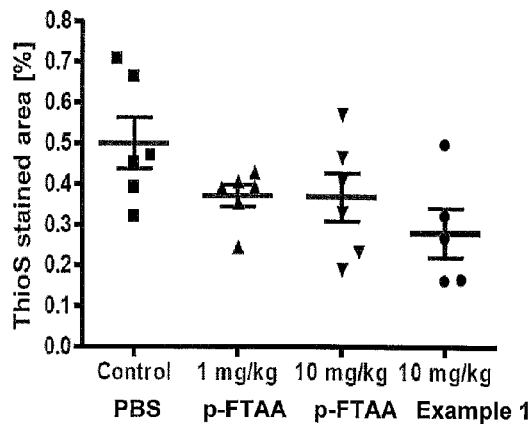

A similar trend on the reduction of plaque number and plaque area percentage was also observed for p-FTAA but with lacking statistical significance (FIGS. 3 and 4).

Example 99

Effects of Compounds p-FTAA and P9707_003 (Example 1), 90 Days Treatment, in 6.5 Months Old Female hAPPSL Transgenic Mice: Phosphorylation of Tau in Neuritis Crossing Mature Amyloid Plaques Vehicle: Phosphate Buffered Saline (PBS; 6.7 mM PO4, 155 mM NaCl, pH=7.3-7.5) (BioWhittaker PBS from Lonza).

Test Item (T.I.): p-FTAA and P9707_003, diluted in vehicle from stock solution in deionized water (10 mg/ml).

Tg hAPPSL: Transgenic hAPPSL mice over-expressing hAPP(751) under the control of the murine Thy-1 promoter with a C57BL/6xDBA background.

Treatment 48 hAPP Tg mice plus 4 reserves allocated to 4 different treatment groups were treated with either vehicle only (control), p-FTAA or P9707_003. As an additional control, 12 nTg littermates of the hAPPSL mice (plus 1 reserve) were treated with vehicle only. Starting at 6.5 months of age, female hAPPSL mice were treated with vehicle only, p-FTAA (dosage: 1 or 10 mg/kg/day) or P9707_003 (dosage: 10 mg/kg/day) for 90 days. The Test Items (T.I.s) were administered in Vehicle. Compound and vehicle were administered twice daily i.p. for 90 days. Tg hAPPSL mice with a C57BL/6xDBA background and corresponding nTg littermates at an age of 6.5 months (+2 weeks) were randomly assigned to the treatment groups.

Histology

Histological evaluations were performed with six randomly chosen cryo-frozen brain hemispheres of treatment groups PBS Control, p-FTAA 1 mg/kg/day, p-FTAA 10 mg/kg/day, and P9707_003 10 mg/kg/day.

Tissue Sectioning 15 cryo-sections per level (altogether 5 levels), each 10 µm thick (Leica CM 3050S) were sagittally cut. Brain levels were chosen according to the morphology atlas "The Mouse Brain" from Paxinos and Franklin (2nd edition). The cutting of the five levels started with a random slice, then sampling was continued uniformly and systematically, always retaining 15 slices per level in series and discarding 100 µm in between the levels.

AT180 IHC

TAU phosphorylation was visualized immunohistochemically using the AT180 antibody. Clone AT180 recognizes PHF-tau doubly-phosphorylated at Thr231 and Ser235.

Evaluation of AT180 load

For determination of amyloid depositions 5 slices (1 from each level) per brain were stained and screened. From each slice five images were captured from 5 defined areas in the brain. The order of these positions reflect the time course of plaque deposition in the APPsl model, which starts in the frontal cortex (P11) at the age of 3 months and then spreads to the medial (P12) and dorsal cortex over age. At six months of age, plaques can be found in the medial cortex (P13), from then plaque load spreads into the hippocampal formation with hot spots in the subiculum (P14) and the dentate gyrus (P15) at the age of nine months.

Imaging

Mosaic images for plaque load quantification including the whole cortex and hippocampus were recorded on a Zeiss AxioImager.Z1 microscope using high aperture lenses and an AxioVision 4.8 software driven AxioCam MRm (10× lens, 1× optocoupler). Plaques for AT180 quantifcation were imaged with a 20× lens. Detail images for qualitative figures are 40× image stacks collapsed to 2D by the extended depth of field function of AxioVision software.

Statistics for Histological Analysis

Descriptive statistical analysis was performed on all evaluated parameters, Kolmogorov Smirnov test were performed to test normal distribution of data. Data in graphs are represented as mean±SEM.

Quantitative Results

Measured region areas of the hippocampus and the cortex were constant throughout all investigated brains, which excludes negative effects on tissue in staining steps (e.g. unequivocal shrinkage, different cutting circumstances), and is furthermore a sign that there was no treatment induced atrophy. Anyhow, measured data were related to the individual region size in the slice to be able to cope with artifacts, folding or missing pieces.

Results: AT180 IHC

Figure 5:
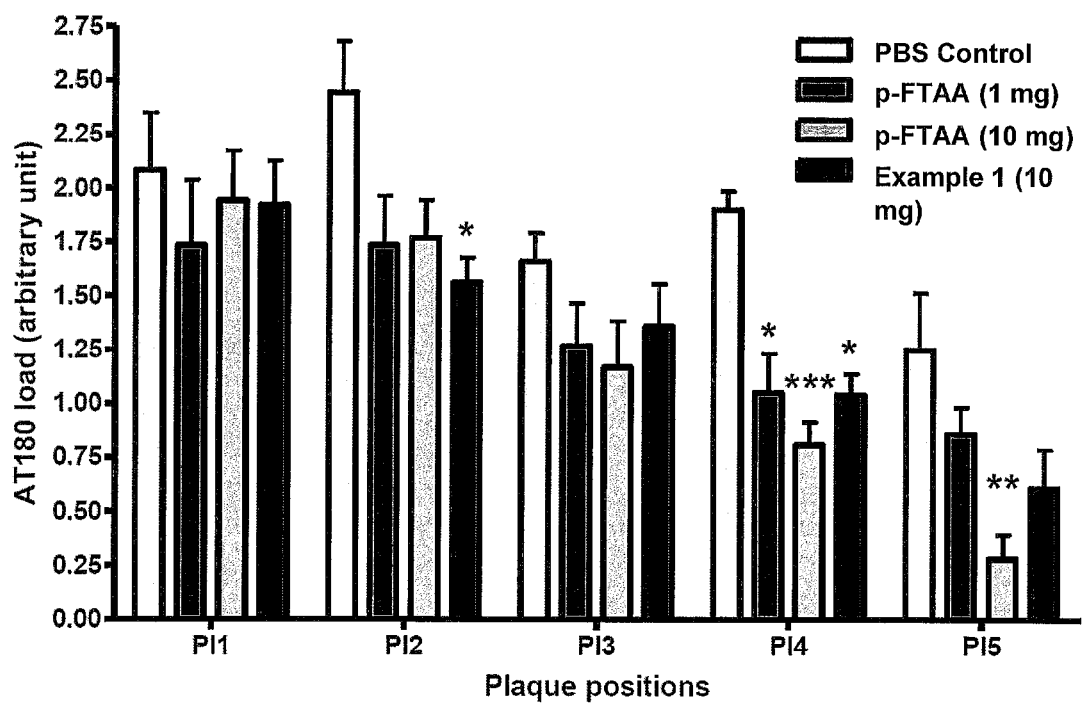
FIG. 5: pTAU (dystrophic neurites) visualized by AT180 IHC. Graphs represent the AT180 immunoreactive area of dystrophic neuritis in cortical (P11 to P13) and hippocampal (P14+P15) of Tg mice receiving PBS vehicle (N=6), 1 mg/kg/day p-FTAA (N=6), 10 mg/kg/day p-FTAA (N=6) or 10 mg/kg/day of compound of Example 1 (N=6 in the cortex, N=5 in the hippocampus). Data are represented as mean±SEM. Statistically significant effects (Two-way ANOVA) are marked by asterisks. * indicates p<0.05,  indicates p<0.01, * indicates <0.001.

Phosphorylation of Tau in neurites crossing mature amyloid plaques are a sign of dystrophy. Clone AT180 recognizes PHF-tau doubly-phosphorylated at Thr231 and Ser235. Both p-FTAA and P9707_003 (Example 1) drastically reduced AT180 IR in plaques of younger history of origin, especially those of the hippocampal formation, the subiculum and the dentate gyrus. In detail 1 mg p-FTAA treatment significantly reduced AT180 load at position 4, 10 mg p-FTAA treatment led to highly significant reduction in positions 4 and 5 (steadily increasing from position 2 onwards up to 77% on position 5). From plaque positions 3 to 5 the p-FTAA effect was increasingly dose-dependent. 10 mg P9707_003 (Example 1) treatment led to significant reduction of AT180 at plaque sides 2 and 4 with more than 40% reduction at positions 4 and 5 (FIG. 5).

Phosphorylated TAU detected by AT180 IR at plaques was reduced by all three tested treatments, p-FTAA (10 mg/kg/day), p-FTAA (1 mg/kg/day) and P9707_003 (10 mg/kg/day). p-FTAA dose-dependently decreased pTAU with a maximum of 77% reduction in plaques of youngest historical origin. Similarly P9707_003 treatment reduced AT180 load to approximately 45% at hippocampal plaques.

Example 100

In vitro Target Engagement: Staining

General Information

Staining of brain sections from an APPSL x TMHT double-transgenic mouse that features several hallmarks of familial Alzheimer's disease (AD) that contain pathological material such as Aβ deposits.

The human APP with London (717) and Swedish (670/671) mutations, hAPP751SweLon, is expressed in high levels, resulting in an age-dependent increase of β-amyloid 1-40 and β-amyloid 1-42, the pathologically relevant forms of amyloid protein. The mice develop plaques consisting of amyloid depositions in early age, starting at 3-6 months in the frontal cortex. Severity of the brain pathology correlates with increasing age and behavioral deficits.

Staining of brain sections brain sections from R6/2 mice that feature several hallmarks of Huntington's Disease (HD) that contain pathological material such as Htt deposits.

Staining of brain sections brain sections from a SOD1-G93A transgenic mouse that features several hallmarks of familial inherited Amyotrophic Lateral Sclerosis (ALS) that contain pathological material such as SOD deposits.

Staining of brain sections brain sections from TDP43+/+ transgenic mouse that features several hallmarks of familial inherited Amyotrophic Lateral Sclerosis (ALS).

The staining capacity of compounds on slices of Tg mouse models in different clinical indications (Alzheimer's Disease (AD), Amyotrophic Lateral Sclerosis (ALS) and Huntington Disease (HD)) was investigated. This study provides important information on in vitro target engagement that indicates therapeutic possibilities to use the compounds of the present invention for staining and treatment of pathological features in various neurodegenerative disorders.

Material

Material: Alzheimer's Disease (AD)—APPSL x TMHT

Brain slices from an APPSL x TMHT mouse at 6 months of age were obtained. They are crossbreds of APPSL mice (Rockenstein et al. 2001) and TMHT mice. Mice were bred and maintained in a certified animal facility until sacrification. At sacrifice, mice were transcardially perfused with 0.9% NaCl to wash out the majority of erythrocytes. After extraction, brains were post-fixed for one hour in 4% Paraformaldehyde in PBS at room temperature and then transferred to 15% sucrose over night for cryoprotection. Thereafter brains were shock-frozen in dry ice cooled liquid Isopentane. Mounted in OCT medium, brains were cut systematically on a Leica CM3050 S cryotome with 10 µm slice thickness.

Material: Alzheimer's Disease (AD)—hAPP751SweLon

Brain slices from hAPP751SweLon mouse at 9.5-12 months of age were obtained. Mice were bred and maintained in a certified animal facility until sacrification. At sacrifice, mice were transcardially perfused with 0.9% NaCl to wash out the majority of erythrocytes. After extraction, brains were post-fixed for one hour in 4% Paraformaldehyde in PBS at room temperature and then transferred to 15% sucrose over night for cryoprotection. Thereafter brains were shock-frozen in dry ice cooled liquid Isopentane. Mounted in OCT medium, brains were cut systematically on a Leica CM3050 S cryotome with 10 µm slice thickness.

Material: Huntington's Disease (HD)

Brain slices from a R6/2 mouse at 4.5 months of age were obtained. Mice were bred and maintained in the AAALAC certified animal facility of JSW Life Sciences until sacrification. At sacrifice, mice were transcardially perfused with 0.9% NaCl to wash out the majority of erythrocytes. After extraction, brains were post-fixed for 24 hours in 4% Paraformaldehyde in PBS at 4° C. and then paraffin embedded. Brains were cut systematically on a Leica SM2000 R slide microtome with 5 µm slice thickness.

Material: Amyotrophic Lateral Sclerosis (ALS)—SOD1

Brain slices from SOD1-G93A Tg mice, further referred to as SOD1 mice, at 17 weeks of age were obtained. SOD1 transgenic mice were first introduced by Gurney et al. in 1994. Animals express high levels of mutated human SOD1 that carries a G93→A substitution. The SOD1-G93A mice were purchased from the Jackson Laboratory (http://jaxmice.jax.org/strain/002726.html) and maintained in the AAALAC certified animal facility of JSW Life Sciences until sacrifice. At sacrifice, mice were transcardially perfused with 0.9% NaCl to wash out the majority of erythrocytes. After extraction, brains were post-fixed for one hour in 4% Paraformaldehyde in PBS at room temperature and then transferred to 15% sucrose over night for cryoprotection. Thereafter brains were shock-frozen in dry ice cooled liquid Isopentane. Mounted in OCT medium, brains were cut systematically on a Leica CM3050 S cryotome with 10 µm slice thickness.

Material: Amyotrophic Lateral Sclerosis (ALS)—TDP43

Brain sections from TDP43+/+ transgenic mouse that features several hallmarks of familial inherited Amyotrophic Lateral Sclerosis (ALS). Overexpressses hTAR DNA binding protein-43 hThy-1 promotor (constitutive neuronal expression). Ubiqutinated, phosphorylated TDP43 inclusions in nucleus and cytoplasm.

Histochemical Staining Protocol

1) Pre-treatment:
1a) Cryosections: Dry cryosections 60 min at room-temperature.
1b) Paraffin sections: Deparaffinize and rehydrate as following: 10 min with Tissue Clear, 05 min with Tissue Clear/100% Ethanol (1:1), 02 min with 100% Ethanol, 02 min with 96% Ethanol, 02 min with 70% Ethanol, 02 min with 50% Ethanol and finally 02 min with PBS.
2) Post-fixation in 4% Paraformaldehyde: Fixate air-dried cryosections for 10 min with 4% paraformaldehyde at room temperature.
3) Washing: 2 times for 5 min with PBS at room temperature.
4) Fixation: 10 min in ice-cold 100% Ethanol.
5) Fixation: 5 min in ice-cold 70% Ethanol.
6) Washing 1 min in ddH2O.
7) Washing: 10 min in 100 mM Sodium-Carbonate Puffer (pH=10).
8) Compound incubation: Incubate for 30 min at room temperature light-protected in a damp chamber.
9) Washing: 2 times for 5 min with 100 mM Sodium-Carbonate Puffer (pH=10) (light-protected).
10) Washing: 5 min in PBS (light-protected).
11) Labeling the cell nuclei: Incubate for 15 min with DAPI [(25 mg/ml in ddH2O) and 40 ml methanol] at room temperature (light-protected).

Imaging

A fully automated Zeiss Axio.Imager Z1 fluorescent microscope equipped with LED illumination (Colibri) and AxioCam MRm B&W camera served to record the images.

Results

Images of cortical plaques were systematically recorded.

Results: Alzheimer's Disease (AD)—APPSL x TMHT

The table summarizes the results of compound staining in brain slices of APPSL x TMHT mice.

| Compound | Plaque cores | Mature fibers | Immature fibers |
| --- | --- | --- | --- |
| p-FTAA | +++ | + | |
| Ex. 1 | +++ | ++ | |
| Ex. 5 | + | | + |
| Ex. 19 | + | +++ | ++ |
| Ex. 21 | ++ | ++ | + |
| Ex. 35 | ++ | ++ | |
| Ex. 56 | + | +++ | |
| Ex. 62 | +++ | +++ | +++ |
| Ex. 68 | ++ | | |

Results: Alzheimer's Disease (AD)—hAPPSweLon

The table summarizes the results of compound staining in brain slices of hAPPSweLon.

| Compound | Plaque cores | Mature fibers | Immature fibers |
|---|---|---|---|
| p-FTAA | ++ | + | |
| Ex. 1 | +++ | ++ | + |
| Ex. 21 | ++ | + | |

Results: Huntington's Disease (HD)

The table summarizes the results of compound staining in brain slices of HD/htt related pathology in R6/2 mice.

| Compound | Neuronal nuclear htt | Nuclear htt aggregates |
|---|---|---|
| Ex. 1 | + | + |
| Ex. 5 | + | + |
| Ex. 19 | +++ | +++ |
| Ex. 35 | ++ | +++ |
| Ex. 56 | ++ | +++ |
| Ex. 62 | +++ | +++ |

Results: Amyotrophic Lateral Sclerosis (ALS)—SOD1

The table summarizes the results of compound staining in brain slices of ALS/SOD related pathology in SOD1-G93A Tg mice.

| Compound | Neuronal somata | Fibers | Astrocytes | Amyloid | SOD1 aggregate |
|---|---|---|---|---|---|
| p-FTAA | + | + | + | + | + |
| Ex. 1 | +++ | +++ | +++ | +++ | ++ |
| Ex. 13 | + | + | + | + | + |
| Ex. 15 | + | | | + | + |
| Ex. 19 | +++ | +++ | +++ | +++ | ++ |
| Ex. 35 | + | ++ | ++ | + | + |
| Ex. 47 | | + | | | |
| Ex. 52 | ++ | ++ | ++ | ++ | + |
| Ex. 56 | +++ | +++ | +++ | +++ | ++ |
| Ex. 62 | +++ | +++ | +++ | +++ | +++ |

Results: Amyotrophic Lateral Sclerosis (ALS)—TDP43

The compounds of the present invention stain both human TARDBP (nuclear) and phospho TDP-43 (extra-nuclear aggregates). The table below summarizes the obtained results in various parts of the brain.

| Compound | Cortex | Hippocampus (DG) | Thalamus |
|---|---|---|---|
| Ex. 1 | + | + | + |
| Ex. 19 | + | + | + |
| Ex. 35 | ++ | ++ | ++ |
| Ex. 56 | + | + | + |

Example 101

Inhibition of Abeta Oligomerisation

Inhibition of Aβ1-42 aggregation was analyzed at an Aβ1-42 concentration of approximately 12 nM.

The method was set up according to LeVine, Analytical Biochemistry 356 (2006) 265-272. The assay use biotinylated Aβ1-42 and detects the amount of free biotin when attached to a neutravidin plate. Monomeric Aβ results in no free biotin as all biotin molecules are bound to the neutravidin at the bottom of the well. Aggregated Aβ on the other hand has a number of free biotin molecules that are detected by streptavidin-HRP. We can therefore investigate how well the compounds of the invention inhibit Aβ aggregation.

Method in Short:

To assure monomerisation of biotinylated Aβ1-42 (Anaspec #23523-0.5) the peptide was thoroughly monomerised by the following procedure. Lyophilized peptide was solubilized in 1,1,1,3,3,3-hexafluor-2-propanole, HFIP (SigmaAldrich #325244) to a concentration of 0.5 mg/ml (105 uM) and dispensed in 5 uL aliquots and stored at −80° C.

One aliquot was used for each day of analysis. The HFIP was evaporated using argon, dissolved again in TFA, incubation for 10 min at RT, evaporated using argon, dissolved in HFIP, 10 min at RT, evaporated with argon and finally dissolved in DMSO to an approximate concentration of 2.7 µg/ml.

Compounds were diluted in PBS (1×PBS buffer, 9.7 mM Pb+140 mM Salt, pH 7.4) ranging from 32 µM down to 0.1 µM.

2 µL of a biotinylated Aβ1-42 DMSO-solution was added to each well of a 96 well plate followed by 100 uL of cpd dilutions to initiate the aggregation. Several wells containing PBS+0.1% Tween20, which inhibit the aggregation (MIN values) plus wells containing only PBS (MAX-values) were also included on the plate. After a 30 min incubation at RT the reaction was stopped by adding a 0.3% or a 0.1% Tween20 solution to a final concentration of 0.1%.

The aggregated Aβ was analyzed on neutravidin coated plates using streptavidin-HRP for detection.

Table: pIC50 values from plotting percent inhibition ((result-averageMIN)/(averageMAX−averageMIN)* 100) as compared to Aβ1-42 aggregation in PBS, pH 7.4 containing 2% DMSO. The pIC50 values were calculated using non-linear regression 4-parameter variable slope.

| Cpd name | pIC50 | SD |
|---|---|---|
| Congo Red | 5.8 | 0.35 |
| p-FTAA | 5.3 | 0.21 |
| p-HTAA | 5.7 | 0.06 |
| Ex 1 | 6.1 | 0.22 |
| Ex 5 | 5.4 | 0.26 |
| Ex 6 | 5.1 | 0.07 |
| Ex 7 | 5.4 | 0.10 |
| Ex 8 | 4.8 | |
| Ex 9 | 4.8 | |
| Ex 10 | 5.1 | 0.12 |
| Ex 11 | 4.9 | |
| Ex 12 | 5.8 | 0.36 |
| Ex 13 | 5.1 | 0.49 |
| Ex 14 | 5.7 | 0.07 |
| Ex 15 | 4.3 | |
| Ex 16 | 5.3 | 0.14 |
| Ex 17 | 5.3 | 0.35 |
| Ex 18 | 5.9 | 0.4 |
| Ex 19 | 5.4 | 0.29 |
| Ex 20 | 6.0 | 0.07 |
| Ex 21 | 5.6 | 0.35 |
| Ex 22 | 5.6 | 0.17 |
| Ex 23 | 5.5 | 0.28 |
| Ex 24 | 5.0 | 0.21 |
| Ex 33 | 6.1 | 0.28 |
| Ex 34 | 6.1 | 0.15 |
| Ex 36 | 5.3 | 0.28 |
| Ex 37 | 5.3 | 0.14 |
| Ex 38 | 5.8 | 0.35 |
| Ex 39 | 6.1 | 0.07 |
| Ex 40 | 5.9 | 0.14 |
| Ex 41 | 6.1 | 0.07 |
| Ex 42 | 6.6 | |
| Ex 43 | 5.4 | |

| Cpd name | pIC50 | SD |
|---|---|---|
| Ex 50 | 5.6 | |
| Ex 51 | 5.8 | |
| Ex 51 | 5.1 | |
| Ex 53 | 5.4 | |
| Ex 54 | 5.9 | 0.35 |
| Ex 56 | 5.5 | 0.23 |
| Ex 57 | 6.4 | 0.49 |
| Ex 58 | 6.4 | 0.08 |
| Ex 62 | 6.4 | 0.07 |
| Ex 63 | 6.0 | 0.18 |
| Ex 64 | 5.6 | 0.63 |
| Ex 65 | 6.2 | 0.37 |
| Ex 66 | 5.3 | 0.15 |
| Ex 69 | 5.6 | |
| Ex 70 | 5.5 | |
| Ex 72 | 4.6 | |
| Ex 74 | 5.3 | 0.21 |
| Ex 75 | 4.5 | |
| Ex 77 | 5.3 | |
| Ex 78 | 5.3 | |
| Ex 80 | 5.1 | |
| Ex 83 | 4.9 | |
| Ex 84 | 5.8 | |
| Ex 85 | 5.4 | |
| Ex 86 | 4.7 | |
| Ex 87 | 6.0 | |

Example 102

Inhibition of Abeta 1-42 toxicity on primary chicken neurons

Method in Short:

One-day-old fertilized eggs are stored under appropriate conditions until start of breeding. On embryonic day 0 eggs are transferred to the breeding incubator and under turning, kept at 37.8° C. and 55% humidity until embryonic day eight. Neurons are prepared as follows: In short, embryos are transferred to a plastic dish, and decapitated. Both brain hemispheres are removed, collected and any loose tissue removed. Hemispheres are mechanically dissociated and $4.8 \times 10^4$ cells per well (96-well plates) are seeded in a volume of 160 µl.

Aβ1-42 (MW 4514.1) was obtained from American Peptide Company as a lyophilized powder. A stock solution of 340 µM Aβ1-42 was prepared in 50 mM Tris-Buffer, 150 mM NaCl, pH7.6 according to the manufacturer's instructions. After sonication, the stock solution is diluted 1:1 with the test compounds to obtain a concentration of 170, 17 and 1.7 µM. After aggregation at 4° C. for 48 h, the solutions are sonicated again prior to application to the cells. The final concentration of Aβ1-42 applied to the primary chicken neurons is 10 µM.

Aβ1-42 aggregated together with compound for 48 hrs was applied to chicken neurons at DIV4 (days in vitro) and analyzed at DIV10 (144 hrs) and all others were applied to chicken neurons at DIV6 and analysed at DIV10 (96 hrs).

Viability of cultures is determined by the MTT assay. The MTT assay allows for the measurement of the mitochondrial dehydrogenase activity which reduces yellow MTT to dark blue formazan crystals. Since this reaction is catalyzed in living cells only this assay is used for the determination of cell viability. MTT solution is added to each well in a final concentration of 0.5 mg/ml. After 2 hours the MTT containing medium is aspired. Cells are lysed in 3% SDS and the formazan crystals are dissolved in isopropanol/HCl. Optical density is measured with a plate-reader at wavelength 570 nm. Cell survival rate is expressed as a percentage of optical density (OD) relative to control cells not treated with Aβ or compound.

| Compound name | Conc. [µM] | Rescue of Abeta toxicity (MTT) |
|---|---|---|
| Ex 1 | 0.1 | no |
| | 1 | +++ |
| | 10 | +++ |
| Ex 5 | 0.1 | no |
| | 1 | ++ |
| | 10 | + |
| Ex 6 | 0.1 | ++ |
| | 1 | + |
| | 10 | +++ |
| Ex 9 | 1 | ++ |
| | 10 | +++ |
| Ex 16 | 1 | +++ |
| | 10 | +++ |
| Ex 17 | 0.1 | + |
| | 1 | no |
| | 10 | +++ |
| Ex 18 | 0.1 | ++ |
| | 1 | + |
| | 10 | no |
| Ex 21 | 0.1 | no |
| | 1 | ++ |
| | 10 | no |
| Ex 33 | 0.1 | no |
| | 1 | ++ |
| | 10 | no |
| Ex 39 | 0.1 | + |
| | 1 | + |
| | 10 | no |
| Ex 47 | 0.1 | +++ |
| | 1 | +++ |
| | 10 | +++ |
| Ex 50 | 0.1 | no |
| | 1 | +++ |
| | 10 | +++ |
| Ex 56 | 0.1 | + |
| | 1 | +++ |
| | 10 | +++ |
| Ex 62 | 0.1 | ++ |
| | 1 | +++ |
| Ex 93 | 0.1 | + |
| | 1 | ++ |
| | 10 | +++ |
| Ex 95 | 0.1 | no |
| | 1 | no |
| | 10 | +++ |
| CongoRed | 5 | ++ |

No: no effect
+: minor positive effect on cell viability in the presence of aggregated Aβ 1-42
++: medium positive effect on cell viability in the presence of aggregated Aβ 1-42
+++: strong positive effect on cell viability in the presence of aggregated Aβ 1-42

Example 103

Comparing Binding to Aβ 1-42 Monomer and Aβ 1-42 Aggregates Using SPR (Surface Plasmon Resonance)

To investigate how well the compounds bind to synthetic Aβ monomer and Aβ aggregates a Biacore T200 was used. The analysis was performed using PBS, pH 7.4, 0.05% Tween20 as running buffer, a flow rate of 20 uL/min and an interaction time of 180 sec.

Flow cell 1 (Fc1) was used as a blank surface i.e. a surface that is activated and then deactivated using amine coupling chemistry according to the manufacturer instructions (GE life science). Fc1 was used to make blank surface subtracted sensorgrams to remove bulk effects.

Aβ 1-42 monomer was prepared as in the anti-aggregation assay to ensure complete monomerization. The DMSO stock of Aβ 1-42 monomer (approximately 35 uM) was diluted one hundred times in 10 mM sodium acetate pH 3.5 immediately before immobilization. The monomer was covalently attached to a CM5 chip surface using amine coupling according to the manufacturer instructions (GE life science). The aggregated Aβ 1-42 was prepared at a 20 uM concentration in PBS, pH 7.4 and incubated for 5 hrs at 37° C. The aggregates were analyzed using the dye ThT to measure fibril content as well as cross-linking followed by western blot using 6E10 for Aβ detection. The aggregates were diluted one to ten in Acetate pH 3.5 before amine coupling.

Figure 6:
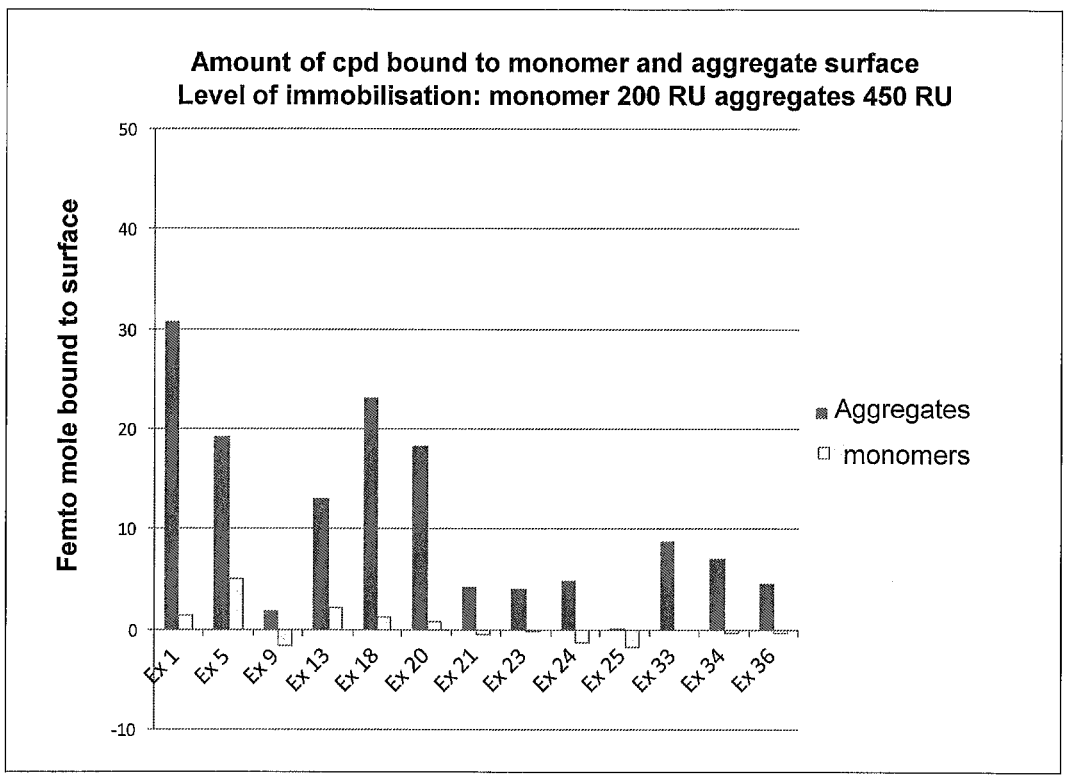
FIG. 6: A histogram showing the amount of compound bound to each surface at the end of a 10 μM injection. All numbers are from blank-subtracted sensorgrams.
Figure 7:
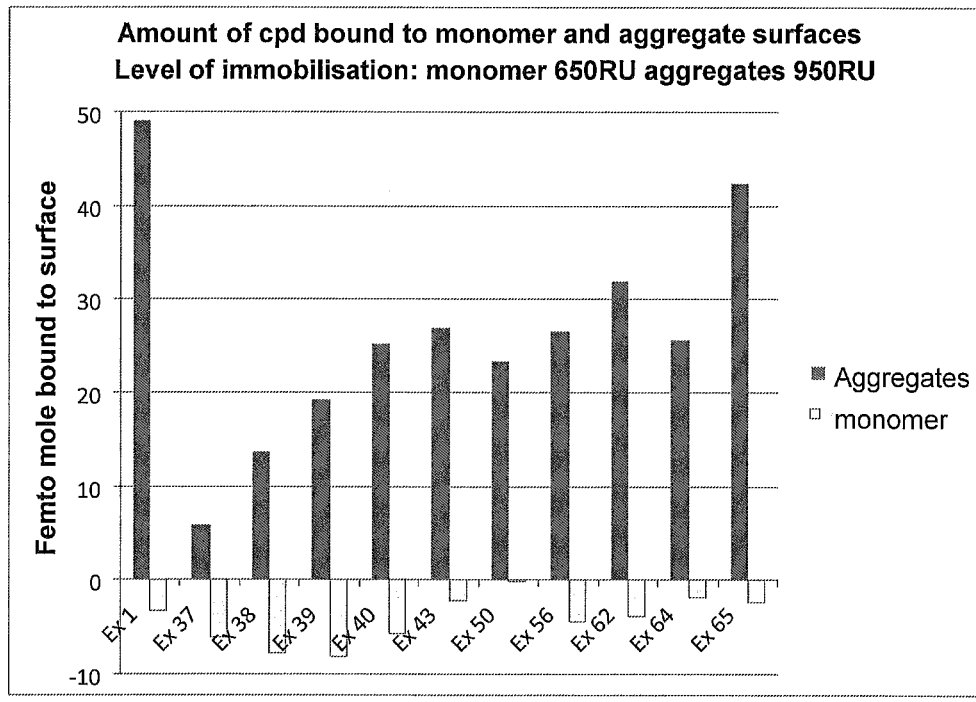
FIG. 7: A histogram showing the amount of compound bound to each surface at the end of a 10 μM injection. All numbers are from blank-subtracted sensorgrams.

The compounds were analyzed at a concentration of 10 uM in running buffer. The level of bound compound to each surface was determined at the end of the 180 sec injection using blank-subtracted sensorgrams. The results are shown in FIGS. 6 and 7.

The invention claimed is:
1. A compound of formula (II)

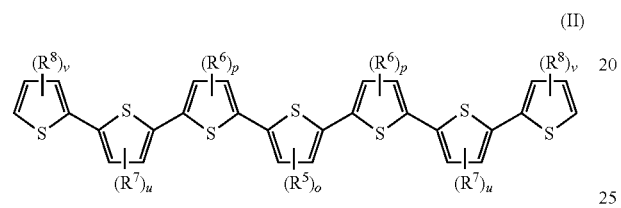

or a pharmaceutically acceptable salt thereof, wherein
  each o is independently 0, 1, or 2;
  each p is independently 0, 1, or 2;
  each u is independently 0, 1, or 2;
  each v is independently 0, 1, 2, or 3,
  with the proviso that the sum of o, p, u, and v is greater than 1;
  each $R^5$, $R^6$, and $R^7$ are independently selected from carboxyalkyl, aminoalkyl, acylaminoalkyl, acyloxyalkyl, hydroxyalkyl, alkylsulphonyl, alkylsulphinyl, alkylaminosulphonyl, alkoxycarbonylalkyl, morpholinoalkyl, carboxyalkenyl, hydroxy, alkoxycarbonyl, pyrrolidinecarbonyl, morpholino, cycloalkylcarbamoyl, cyano, trifluoromethoxy, carbamoyl, hydroxyalkoxyalkyl, carbamoylalkyl, hydroxyalkylaminoalkyl, cyanoalkyl, alkylaminoalkyl, aminoalkylaminoalkyl, carboxyalkylaminoalkyl, piperidinealkyl, and piperazinealkyl;
  each $R^8$ is independently selected from halo, alkyl, trifluoromethyl, carboxy, carboxyalkyl, aminoalkyl, acylaminoalkyl, acyloxyalkyl, hydroxyalkyl, alkylsulphonyl, alkylsulphinyl, alkylaminosulphonyl, alkoxycarbonylalkyl, morpholinoalkyl, carboxyalkenyl, hydroxy, alkoxycarbonyl, pyrrolidinecarbonyl, morpholino, cycloalkylcarbamoyl, cyano, trifluoromethoxy, carbamoyl, hydroxyalkoxyalkyl, carbamoylalkyl, hydroxyalkylaminoalkyl, cyanoalkyl, alkylaminoalkyl, aminoalkylaminoalkyl, carboxyalkylaminoalkyl, piperidinealkyl, and piperazinealkyl; and
  any alkyl moiety is $C_{1-6}$-alkyl and any alkenyl moiety is $C_{2-6}$-alkenyl, respectively.

2. A pharmaceutical composition comprising a compound according to claim 1, and optionally, pharmaceutically acceptable buffers, diluents, excipients and/or carriers.

3. A compound selected from the group consisting of

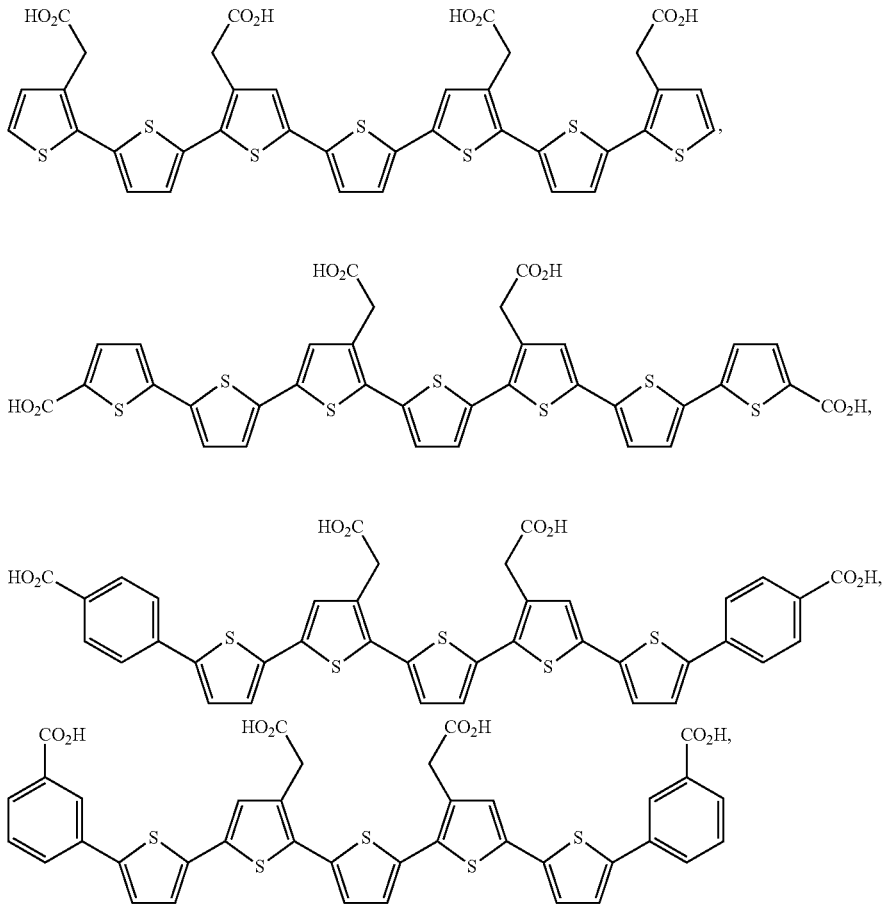

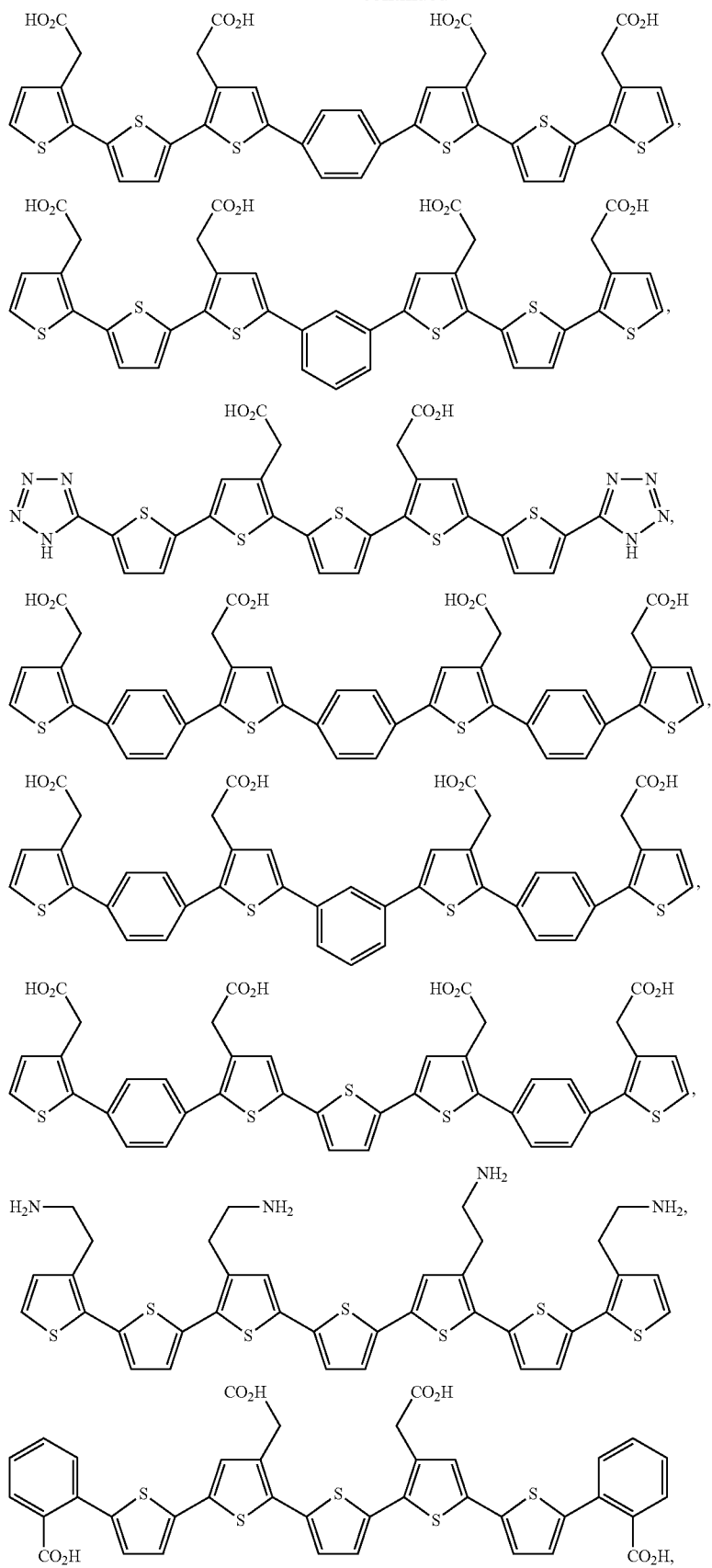

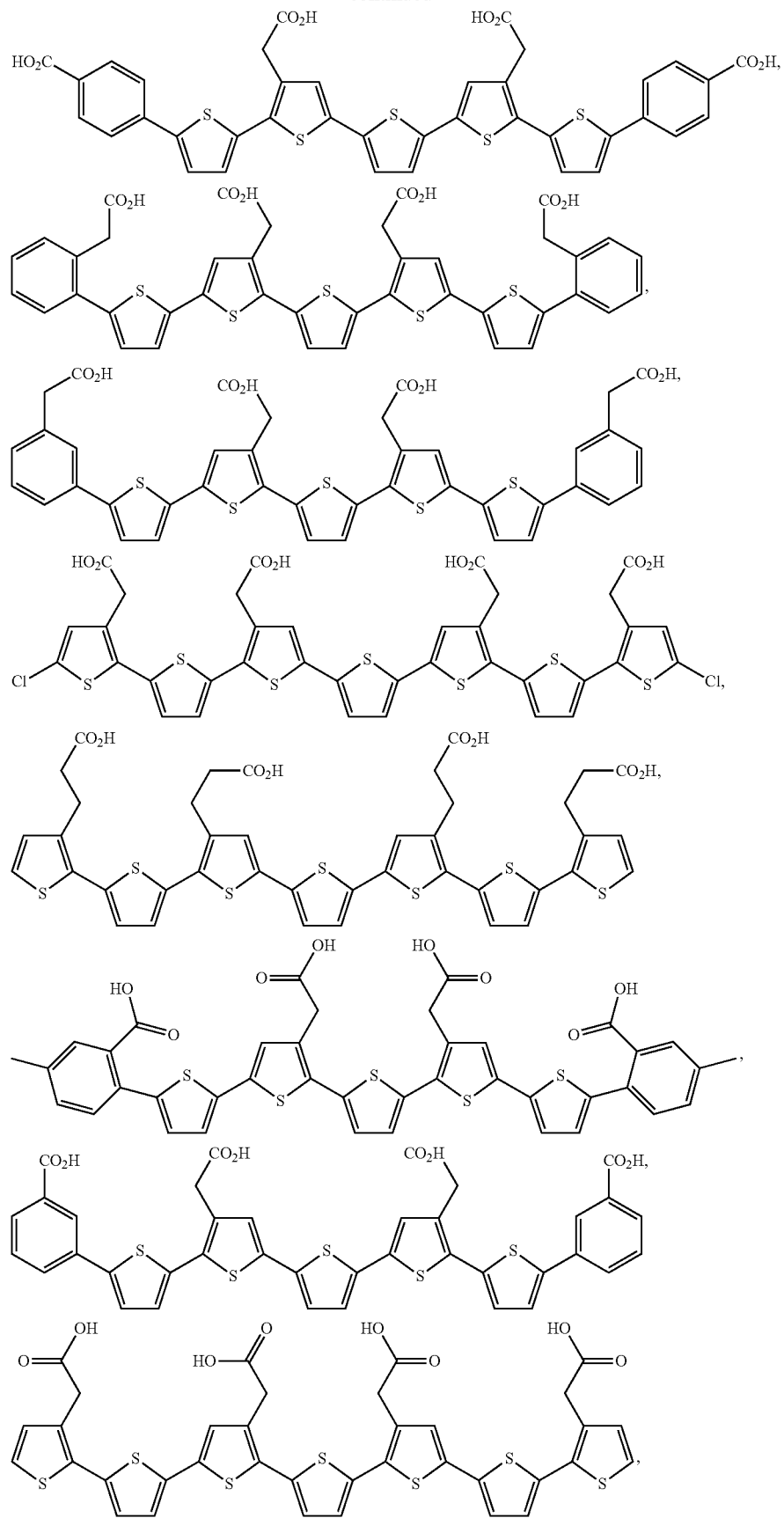

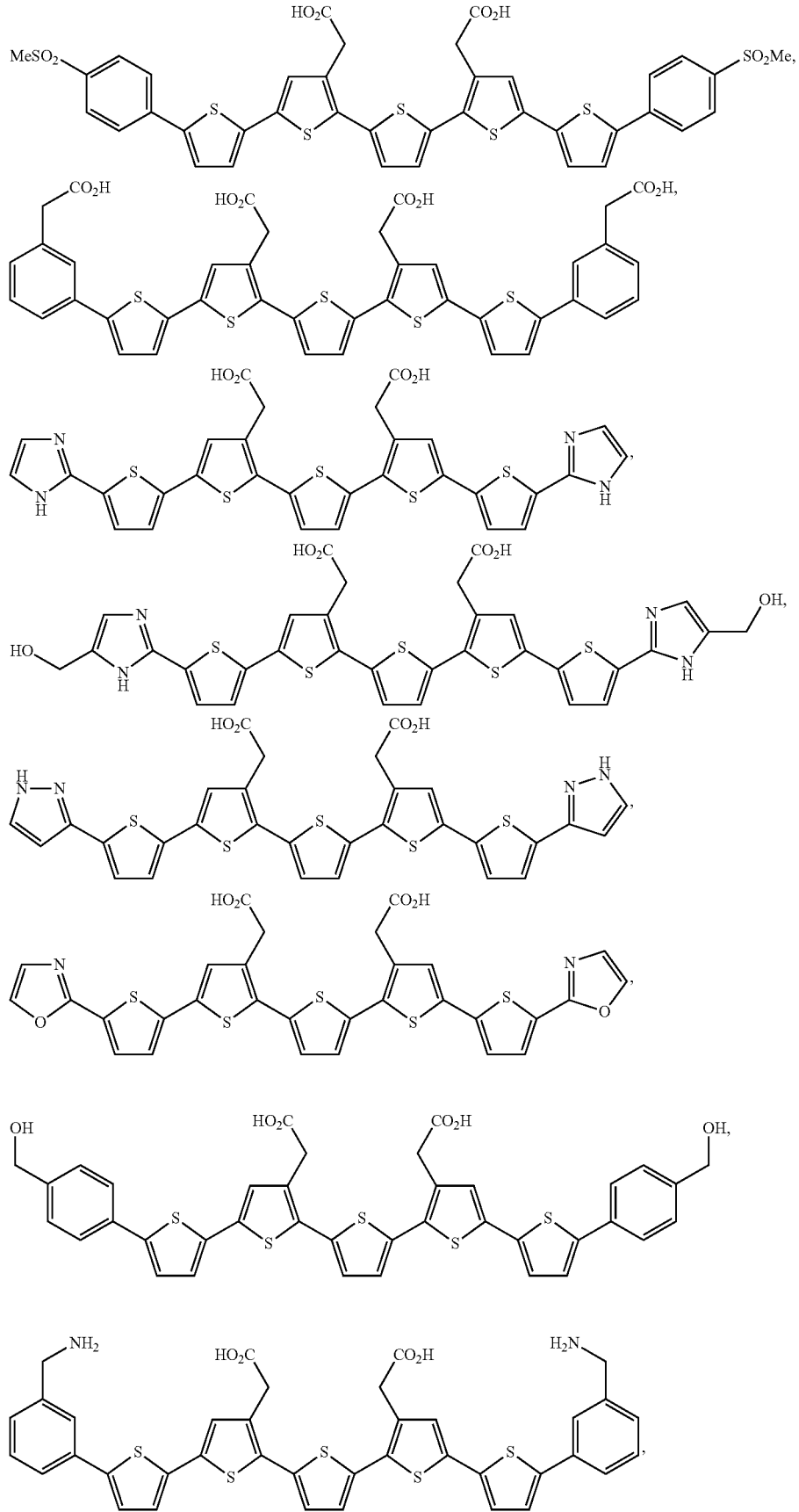

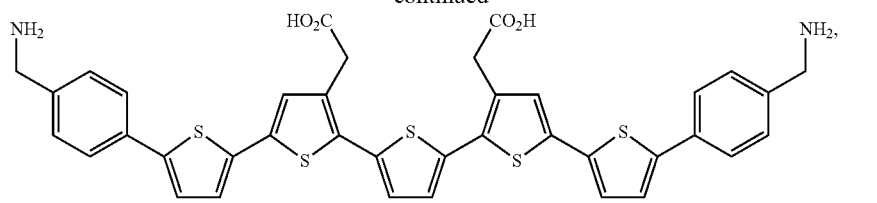
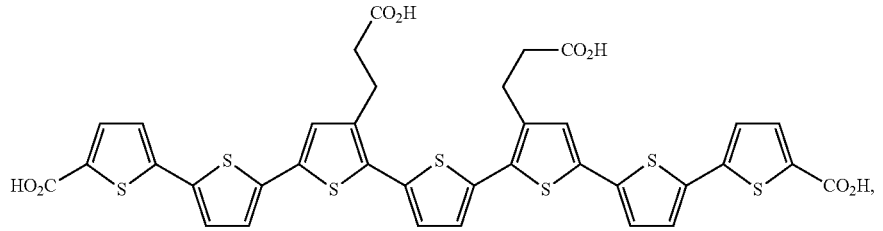
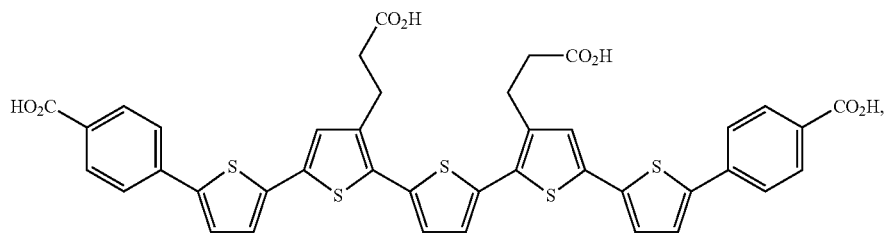
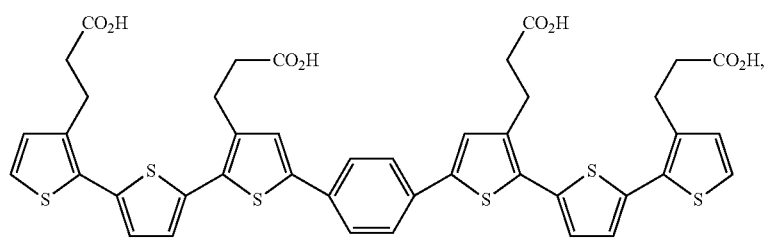
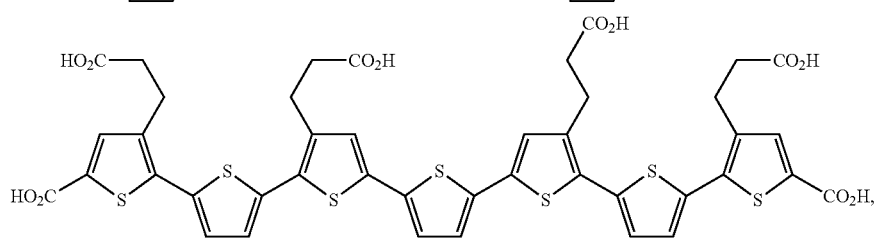
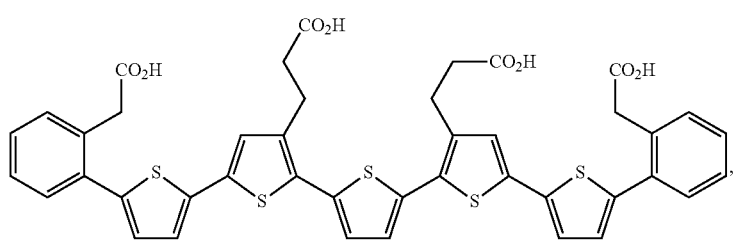
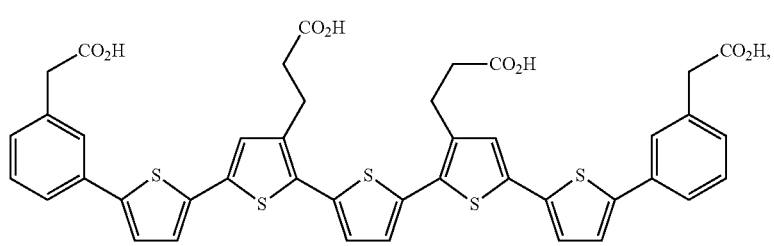

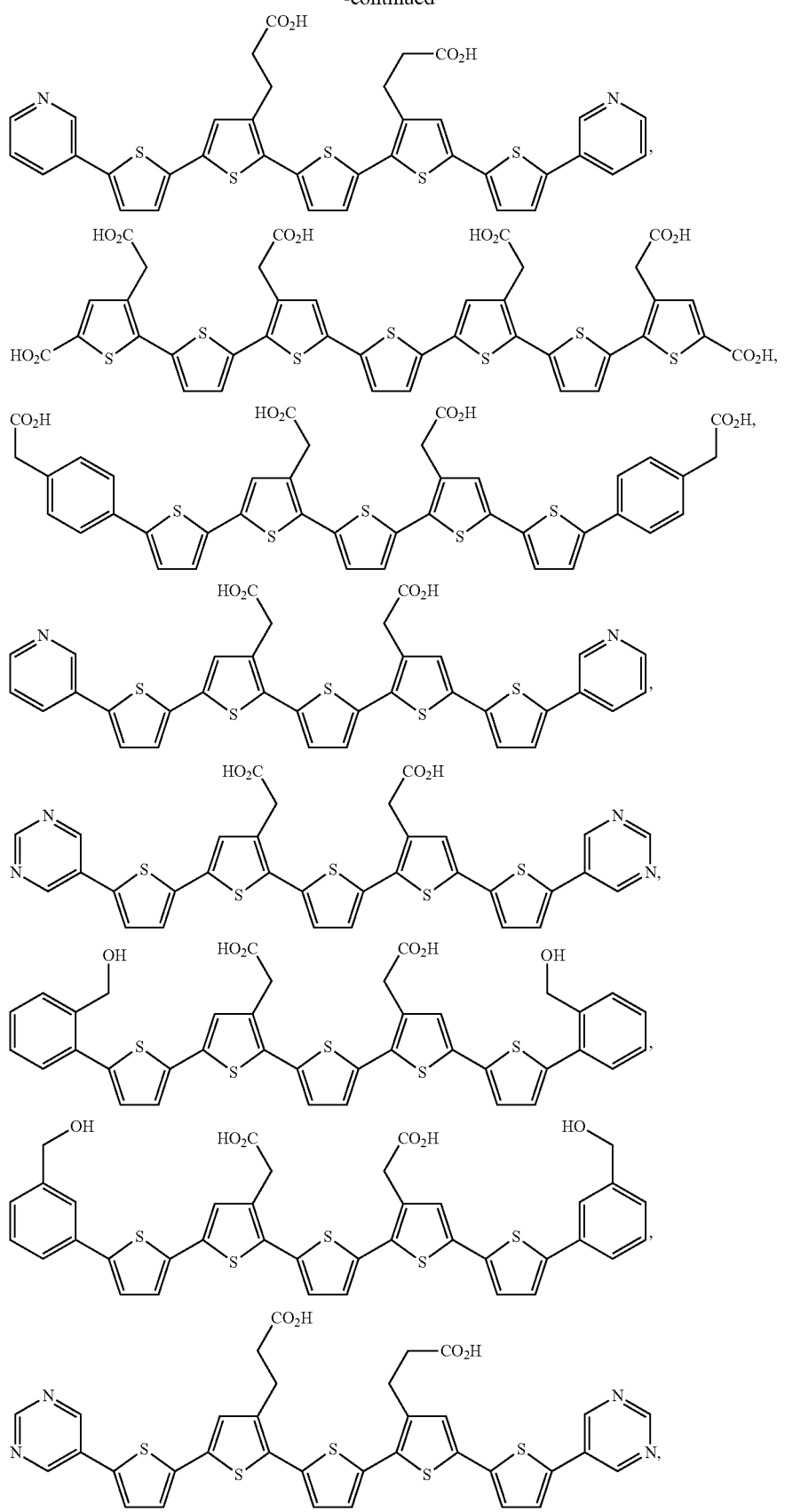

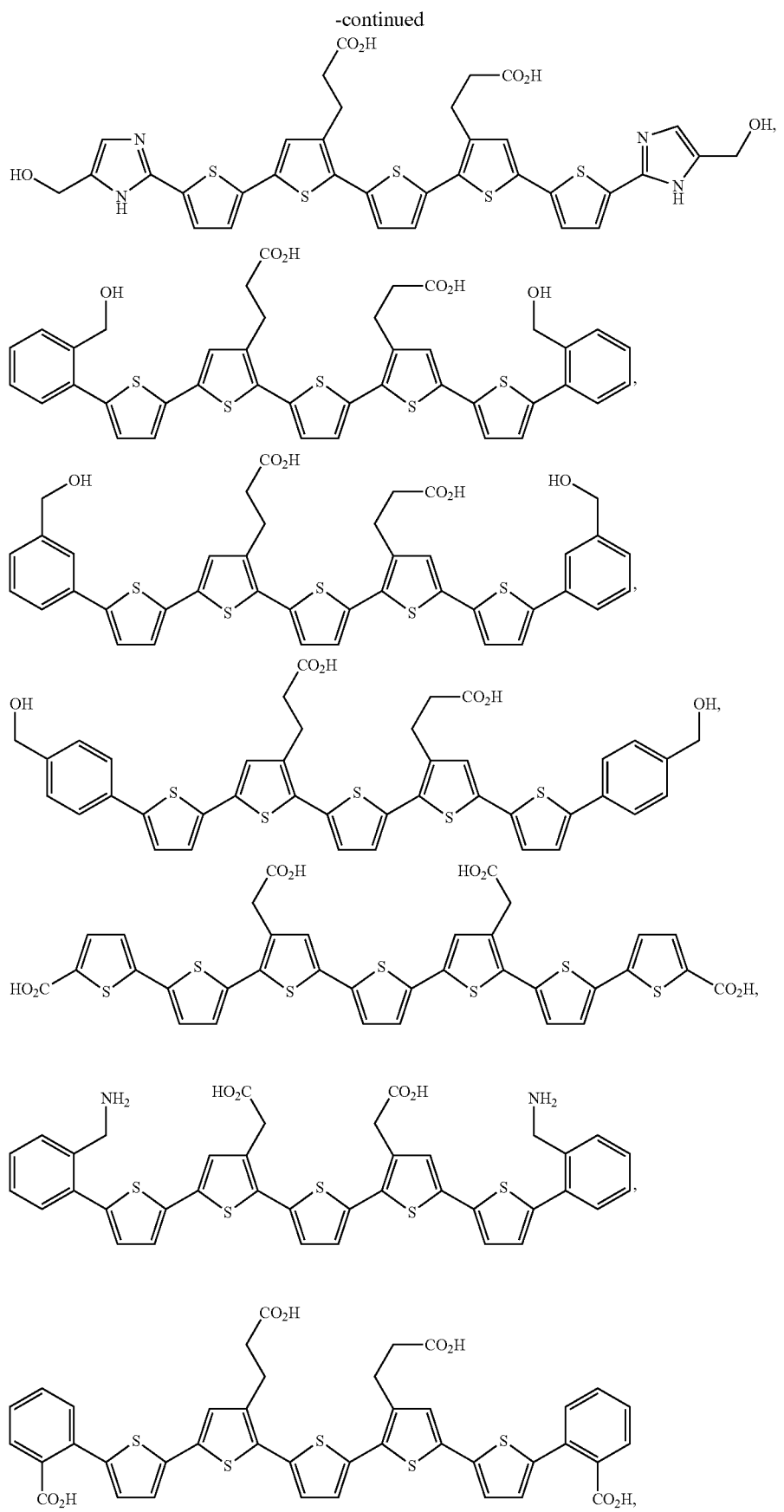

-continued
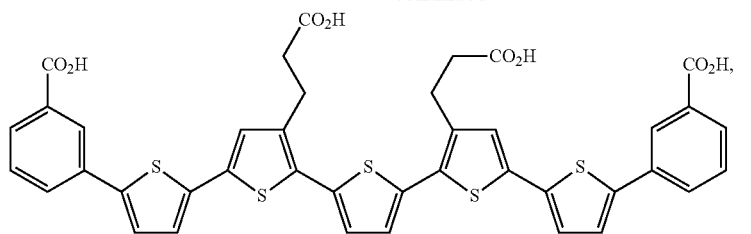
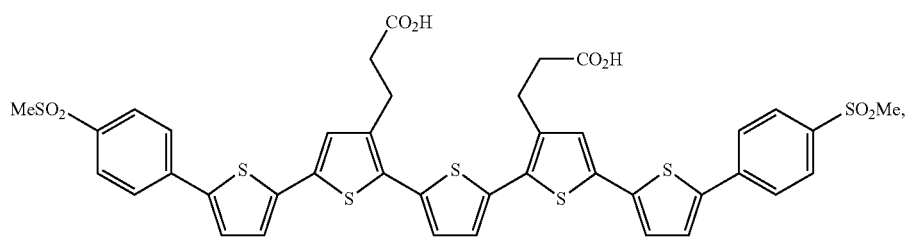
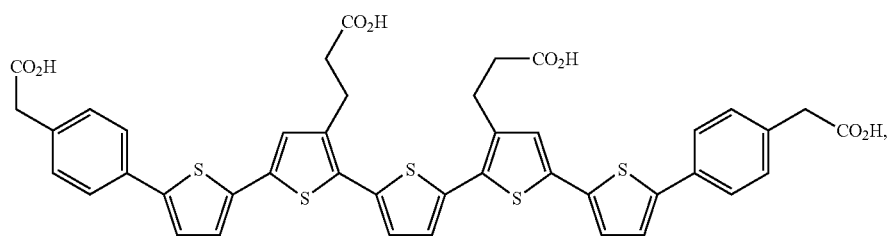
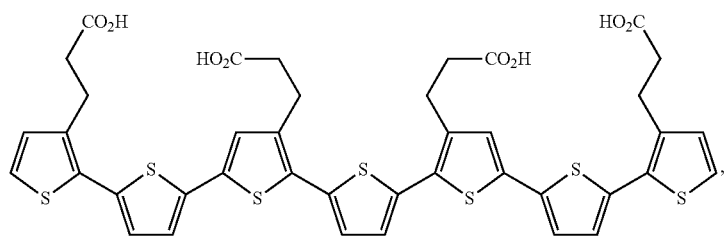
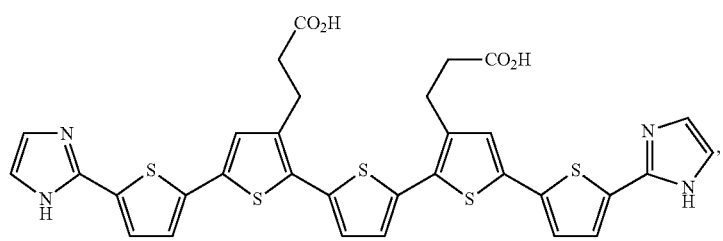
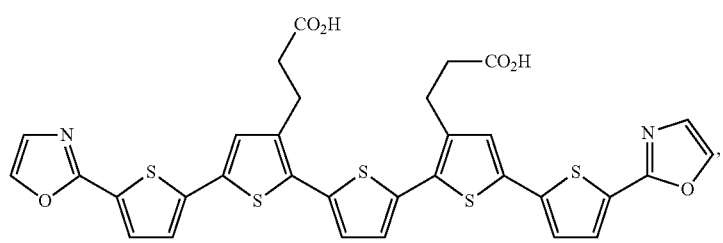
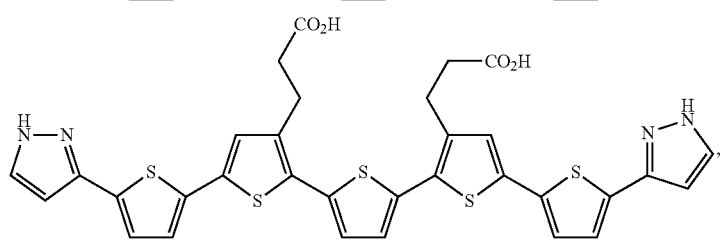

-continued
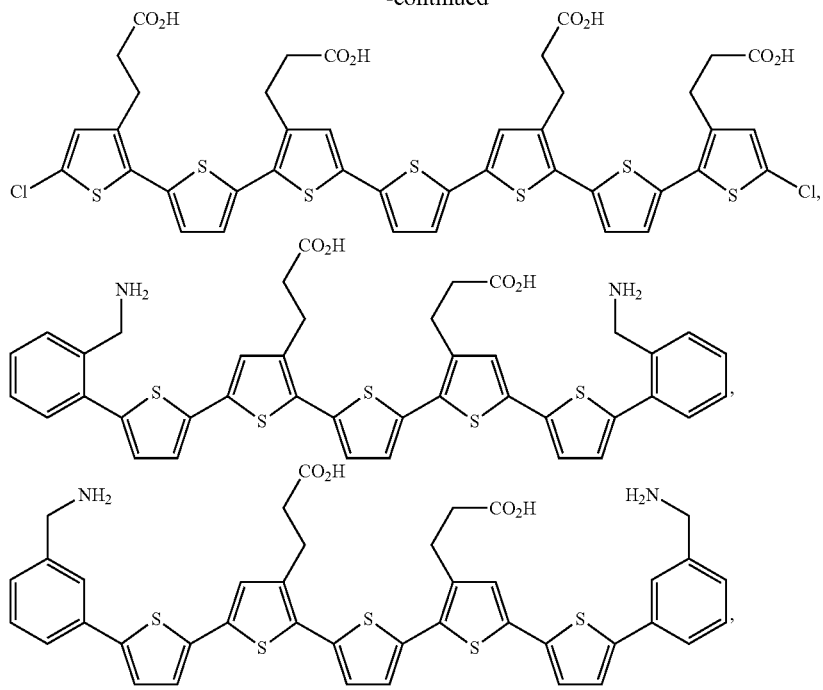
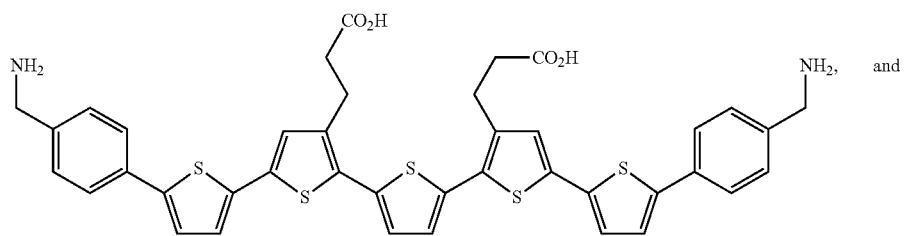
or a pharmaceutically acceptable salt thereof.
4. A pharmaceutical composition comprising a compound according to claim 3, and optionally, pharmaceutically acceptable buffers, diluents, excipients and/or carriers.
5. A compound selected from the group consisting of
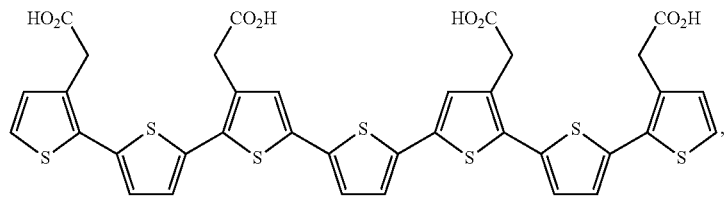

-continued
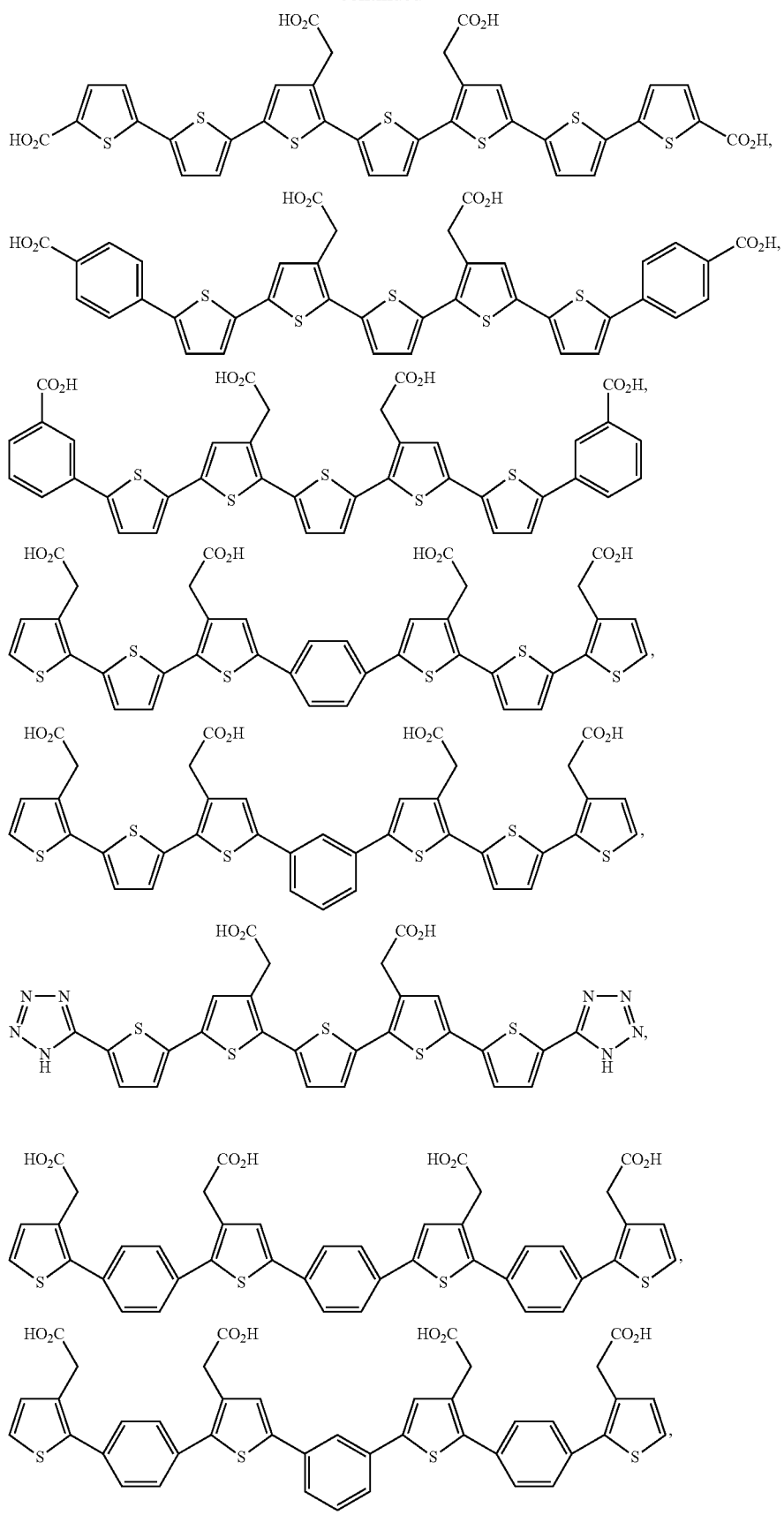

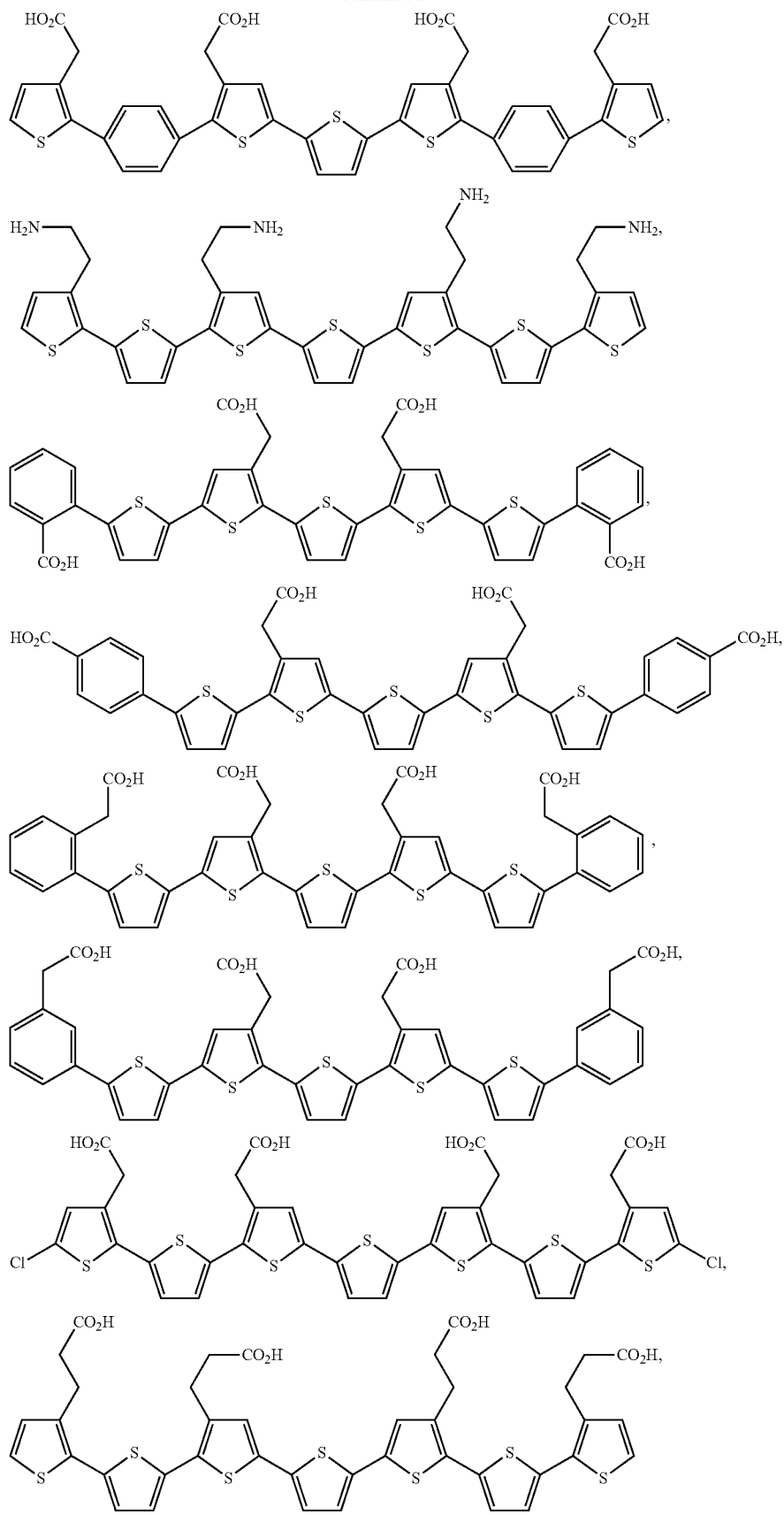

-continued
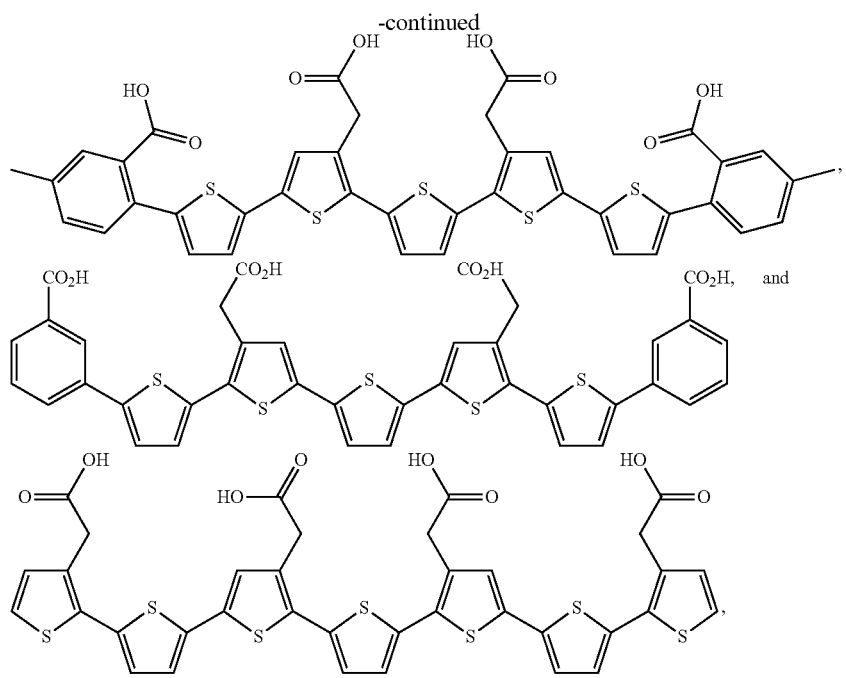
or a pharmaceutically acceptable salt thereof.
6. A pharmaceutical composition comprising a compound according to claim 5, and optionally, pharmaceutically acceptable buffers, diluents, excipients and/or carriers.
7. A compound selected from the group consisting of
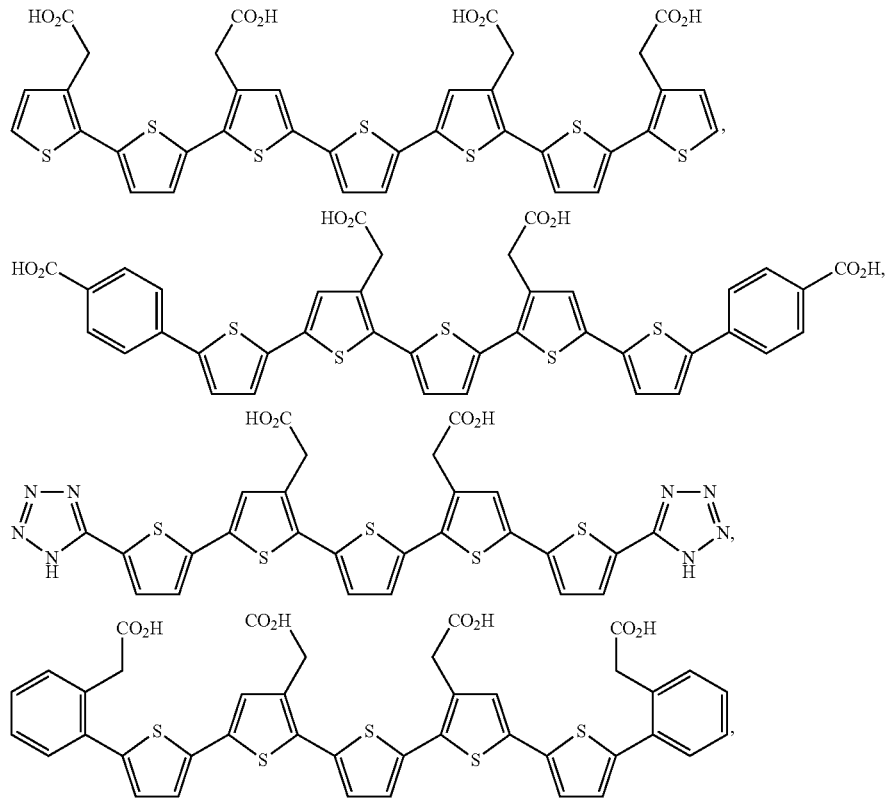

-continued
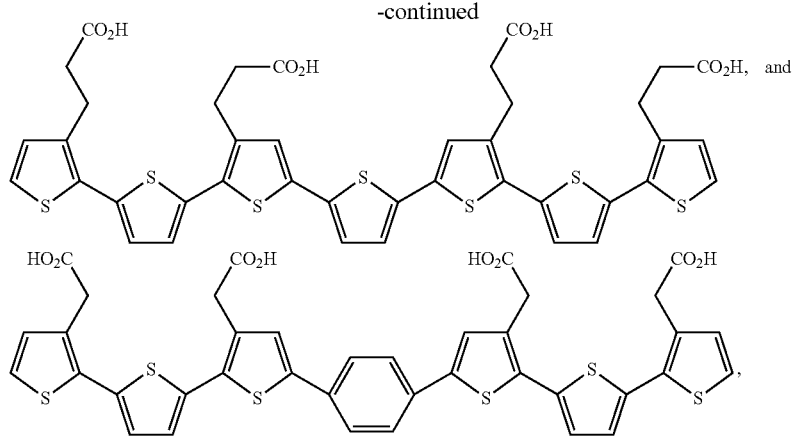
or a pharmaceutically acceptable salt thereof.
8. A pharmaceutical composition comprising a compound according to claim 7, and optionally, pharmaceutically acceptable buffers, diluents, excipients and/or carriers.
* * * * *